US012690864B2

(12) United States Patent
Choi et al.

(10) Patent No.: US 12,690,864 B2
(45) Date of Patent: Jul. 28, 2026

(54) SURGICAL INSTRUMENT AND METHOD AND DEVICE FOR CONTROLLING ITS POSTURE

(71) Applicant: LIVSMED INC., Seongnam-si (KR)

(72) Inventors: Woo Jung Choi, Siheung-si (KR); Jin Hyuk Yoon, Seongnam-si (KR)

(73) Assignee: LIVSMED INC., Seongnam-si (KR)

( * ) Notice: Subject to any disclaimer, the term of this patent is extended or adjusted under 35 U.S.C. 154(b) by 0 days.

(21) Appl. No.: 19/010,528

(22) Filed: Jan. 6, 2025

(65) Prior Publication Data

US 2025/0221706 A1 Jul. 10, 2025

(30) Foreign Application Priority Data

Jan. 10, 2024 (KR) ........................ 10-2024-0004376

(51) Int. Cl.
A61B 17/068 (2006.01)
G16H 40/63 (2018.01)
*A61B 17/00* (2006.01)

(52) U.S. Cl.
CPC .......... *A61B 17/068* (2013.01); *G16H 40/63* (2018.01); *A61B 2017/00022* (2013.01); *A61B 2017/00371* (2013.01); *A61B 2017/00398* (2013.01); *A61B 2017/00477* (2013.01)

(58) Field of Classification Search
CPC ......... A61B 34/76; A61B 34/70; A61B 34/77; A61B 17/068; A61B 34/35; G16H 40/63
See application file for complete search history.

(56) References Cited

U.S. PATENT DOCUMENTS

| | | | | |
|---|---|---|---|---|
| 2021/0369366 | A1* | 12/2021 | Hwang | A61B 1/00045 |
| 2022/0175478 | A1* | 6/2022 | Kawabata | A61B 1/00045 |
| 2022/0233255 | A1* | 7/2022 | Kawabata | G16H 20/40 |
| 2022/0258333 | A1 | 8/2022 | Gao et al. | |
| 2022/0378455 | A1* | 12/2022 | Takahashi | A61B 34/71 |
| 2022/0384019 | A1* | 12/2022 | Shelton, IV | G16H 50/70 |
| 2022/0409317 | A1* | 12/2022 | Ichii | A61B 34/35 |

FOREIGN PATENT DOCUMENTS

| | | | |
|---|---|---|---|
| JP | 2015-213753 | A | 12/2015 |
| KR | 10-2013-0057249 | A | 5/2013 |
| KR | 10-2020-0068455 | A | 6/2020 |
| WO | 2022/219314 | A2 | 10/2022 |

* cited by examiner

*Primary Examiner* — Nathaniel C Chukwurah

(74) *Attorney, Agent, or Firm* — Bridgeway IP Law Group, PLLC; Sang Ho Lee; Hyun Woo Shin

(57) ABSTRACT

According to a surgical instrument and a method and device for controlling the posture thereof, a manipulation value according to user input to change a posture of an end tool included in the surgical instrument may be obtained, first posture information about a current posture of the end tool at the time of obtaining the user input may be obtained, and a motion of the end tool based on the manipulation value and the first posture information may be controlled so that a target posture according to the user input is implemented.

28 Claims, 78 Drawing Sheets

FIG. 35
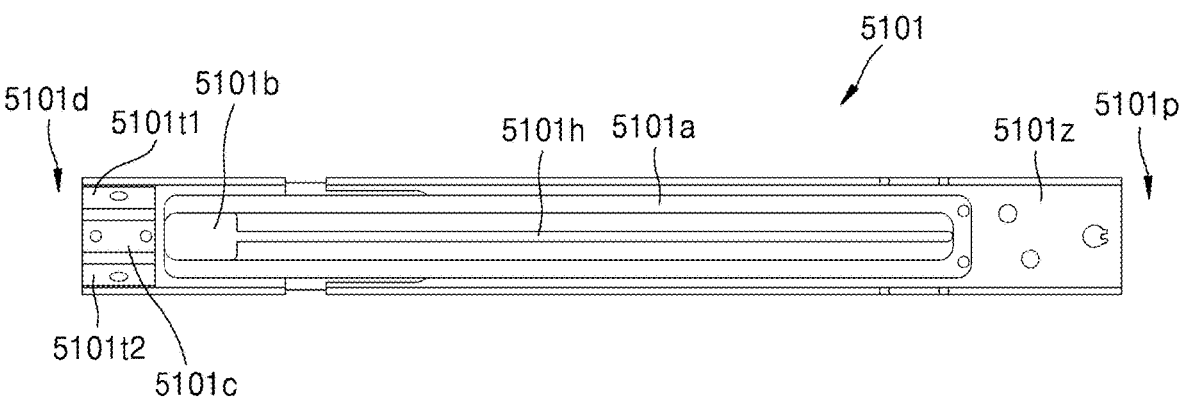
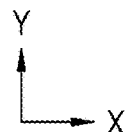

Figure 71:
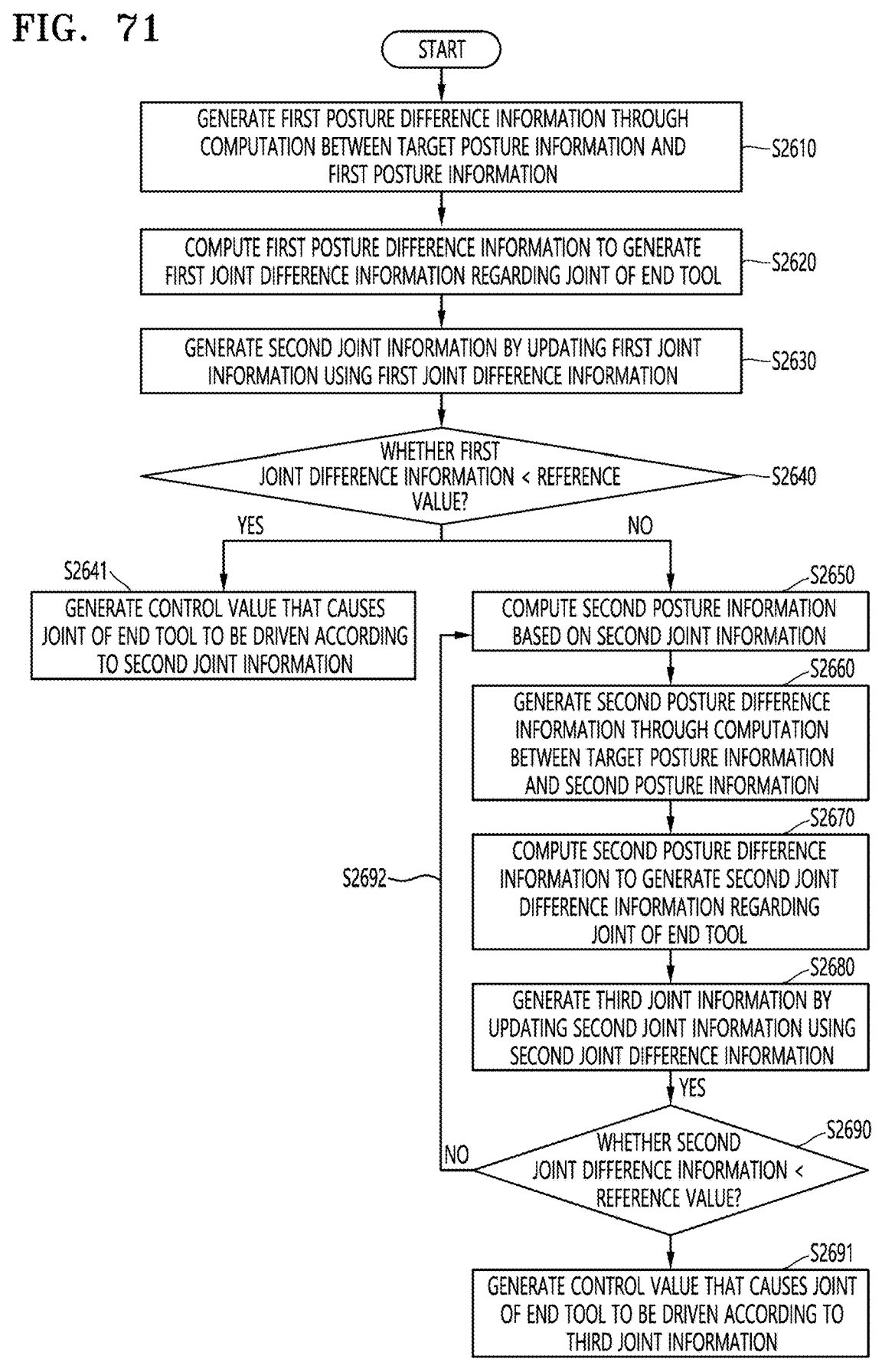

START

GENERATE FIRST POSTURE DIFFERENCE INFORMATION THROUGH COMPUTATION BETWEEN TARGET POSTURE INFORMATION AND FIRST POSTURE INFORMATION ——S2610

COMPUTE FIRST POSTURE DIFFERENCE INFORMATION TO GENERATE FIRST JOINT DIFFERENCE INFORMATION REGARDING JOINT OF END TOOL ——S2620

GENERATE SECOND JOINT INFORMATION BY UPDATING FIRST JOINT INFORMATION USING FIRST JOINT DIFFERENCE INFORMATION ——S2630

WHETHER FIRST JOINT DIFFERENCE INFORMATION < REFERENCE VALUE? ——S2640

YES     NO

S2641 — GENERATE CONTROL VALUE THAT CAUSES JOINT OF END TOOL TO BE DRIVEN ACCORDING TO SECOND JOINT INFORMATION

S2650 — COMPUTE SECOND POSTURE INFORMATION BASED ON SECOND JOINT INFORMATION

S2660 — GENERATE SECOND POSTURE DIFFERENCE INFORMATION THROUGH COMPUTATION BETWEEN TARGET POSTURE INFORMATION AND SECOND POSTURE INFORMATION

S2670 — COMPUTE SECOND POSTURE DIFFERENCE INFORMATION TO GENERATE SECOND JOINT DIFFERENCE INFORMATION REGARDING JOINT OF END TOOL

S2680 — GENERATE THIRD JOINT INFORMATION BY UPDATING SECOND JOINT INFORMATION USING SECOND JOINT DIFFERENCE INFORMATION

S2692

YES

S2690 — WHETHER SECOND JOINT DIFFERENCE INFORMATION < REFERENCE VALUE?

NO

S2691 — GENERATE CONTROL VALUE THAT CAUSES JOINT OF END TOOL TO BE DRIVEN ACCORDING TO THIRD JOINT INFORMATION

SURGICAL INSTRUMENT AND METHOD AND DEVICE FOR CONTROLLING ITS POSTURE

CROSS-REFERENCE TO RELATED APPLICATION

This application claims the benefit of Korean Patent Application Number 10-2024-0004376, filed on Jan. 10, 2024, with the Korean Intellectual Property Office (KIPO), the entire content of which is incorporated herein by reference.

TECHNICAL FIELD

The present disclosure relates to a surgical instrument and a method and device for controlling its posture.

BACKGROUND ART

Medically, surgery refers to the treatment of diseases by cutting, slitting, or manipulating the skin, mucous membranes, or other tissues using medical devices. In particular, open surgery in which the skin of the surgical site is incised and opened to treat, shape, remove organs or the like therein and the like cause problems such as bleeding, side effects, patient pain, scarring. Accordingly, recently, surgery performed by inserting only a medical device, for example, laparoscopic surgical instrument, microsurgical microscope, and the like by forming a predetermined hole in the skin or surgery using a robot has been spotlighted as an alternative.

Here, a surgical robot refers to a robot that has a function of replacing a surgical action performed by a surgeon. Advantageously, the surgical robot may operate more accurately and precisely as compared with a human and enable remote operation.

Surgical robots that are currently being developed worldwide may include a bone surgical robot, a laparoscopic surgical robot, a stereotactic surgical robot, and the like. Here, the laparoscopic surgical robot is a robot that performs minimum invasive surgery using a laparoscope and small surgical instruments.

Laparoscopic surgery is a cutting-edge surgery technique that involves perforating one or more small holes in the abdomen and inserting a laparoscope, which is an endoscope for looking inside the abdomen to perform the surgery, and is a field that is expected to advance in the future. Today's laparoscopes are mounted with computer chips and have been developed to the extent that magnified images, which are clearer than images seen with the naked eye, can be obtained and when used with specially-designed laparoscopic surgical tools while looking at a monitor screen, any type of surgery is possible.

Moreover, laparoscopic surgery offers the same range of surgical procedures as open surgery, but with several advantages including fewer complications, the ability to initiate treatment shortly after the procedure, and the capability to maintain the patient's stamina and immune functions. As a result, laparoscopic surgery is becoming increasingly recognized as the standard surgery for treating colorectal cancer or the like in places such as the United States and Europe.

Meanwhile, a surgical robot is generally composed of a master robot and a slave robot. When a surgical operator manipulates a control lever (e.g., a handle) equipped on the master robot, a surgical tool coupled to or held by a robot arm on the slave robot may be manipulated to perform surgery. The aforementioned background technology is technical information possessed by the inventor for derivation of the present disclosure or acquired by the inventor during the derivation of the present disclosure, and is not necessarily prior art disclosed to the public before the application of the present disclosure.

Disclosure Technical Problem

Some embodiments according to the present disclosure provide a surgical instrument and a method and device for controlling its posture. The problem to be solved by the present disclosure is not limited to the problems mentioned above, and other problems and advantages of the present disclosure, which are not mentioned, will be understood by the following description, and will be more clearly understood by the embodiments of the present disclosure. In addition, it will be appreciated that the problems and advantages to be solved by the present disclosure may be realized by means and combinations thereof indicated in the claims.

Additional aspects will be set forth in part in the description which follows and, in part, will be apparent from the description, or may be learned by practice of the presented embodiments of the disclosure.

Technical Solution

According to a first aspect of the present disclosure, there is provided a method of controlling a posture of a surgical instrument, the method including obtaining a manipulation value according to user input to change a posture of an end tool included in the surgical instrument, obtaining first posture information about a current posture of the end tool at the time of obtaining the user input, and controlling a motion of the end tool based on the manipulation value and the first posture information, so that a target posture according to the user input is implemented.

In the first aspect, the user input may include an input for at least one of a roll rotation, a pitch rotation, and a yaw rotation.

In the first aspect, the controlling of the motion of the end tool may include generating target orientation information about a target orientation of the end tool based on the user input, and generating target posture information according to the user input based on the target orientation information of the end tool and a change in position of the surgical instrument.

In the first aspect, the obtaining of the first posture information may include obtaining first joint information, which is information about a current joint of the end tool at the time of obtaining the user input, and computing the first posture information based on the first joint information.

In the first aspect, the controlling of the motion of the end tool may include generating first posture difference information corresponding to a difference between the target posture information according to the user input and the first posture information, generating first joint difference information regarding a joint of the end tool by computing the first posture difference information, generating second joint information by updating first joint information, which is information about a current joint of the end tool at the time of obtaining the user input, using the first joint difference information, and generating a control value to cause the joint of the end tool to be driven according to the second joint information.

In the first aspect, the method may further include computing second posture information based on the second joint information in response to the first joint difference information being greater than a preset reference value, and determining the joint information of the end tool for generating the control value by comparing the second posture information with the target posture information.

In the first aspect, the determining of the joint information may include generating second posture difference information corresponding to a difference between the target posture information and the second posture information, generating second joint difference information by computing the second posture difference information, generating third joint information by updating the second joint information using the second joint difference information in response to the second joint difference information being less than the preset reference value, and generating a control value to cause the joint of the end tool to be driven according to the third joint information. In the first aspect, the control value may include at least one of a first control value for controlling a roll rotation of the end tool, a second control value for controlling a pitch rotation of the end tool, and a third control value for controlling a yaw rotation of the end tool.

In the first aspect, the manipulation value according to user input may include at least one of a manipulation value for pitch rotation and a manipulation value for yaw rotation, and depending on the manipulation value, the control value may include a first control value for controlling a pitch rotation of the end tool and a second control value for controlling a yaw rotation of the end tool.

In the first aspect, the manipulation value according to user input may include at least one of a manipulation value for pitch rotation and a manipulation value for yaw rotation, and depending on the manipulation value, the control value may include a first control value for controlling a pitch rotation of the end tool, a second control value for controlling a yaw rotation of the end tool, and a third control value for controlling a roll rotation of the end tool.

In the first aspect, first posture change information of the end tool generated based on the user input and second posture change information of the end tool generated based on the control value may be pieces of information for implementing the target posture, wherein the first posture change information may be generated based on a first coordinate system defining a movement of a manipulation part configured to receive the user input, and the second posture change information may be generated based on a second coordinate system defining a movement of the end tool.

In the first aspect, even when a roll rotation angle included in the first posture information is not an angle in an initial state, the target posture may be implemented in the end tool to intuitively correspond to a movement of the manipulation part.

In the first aspect, the manipulation value according to user input may be a manipulation value for roll rotation, and depending on the manipulation value, the control value may include a first control value for controlling a roll rotation of the end tool, a second control value for controlling a pitch rotation of the end tool, and a third control value for controlling a yaw rotation of the end tool.

In the first aspect, first posture change information of the end tool generated based on the user input and second posture change information of the end tool generated based on the control value may be pieces of information for implementing the target posture, wherein the first posture change information may be generated based on a first coordinate system defining a movement of a manipulation part configured to receive the user input, and the second posture change information may be generated based on a second coordinate system defining a movement of the end tool.

In the first aspect, when the end tool performs a motion according to the second posture change information, an axis of the end tool before the roll rotation is performed and an axis of the end tool after the roll rotation is performed may be parallel to each other.

According to a second aspect of the present disclosure, there is provided a device for controlling a posture of a surgical instrument, the device including a memory in which at least one program is stored, and a processor configured to execute the at least one program, wherein the processor is configured to obtain a manipulation value according to user input to change a posture of an end tool included in the surgical instrument, obtain first posture information, which is information about a current posture of the end tool at the time of obtaining the user input, and control a motion of the end tool based on the manipulation value and the first posture information, so that a target posture according to the user input is implemented.

According to a third aspect of the present disclosure, there is provided a computer-readable recording medium having recorded thereon a program for executing the method of the first aspect on a computer.

According to a fourth aspect of the present disclosure, there is provided a surgical instrument including an end tool configured to perform a surgical operation, a manipulation part configured to receive user input to change a posture of the end tool, a power generation part configured to generate power to control the end tool in response to receiving the user input, a power transmission part configured to transmit the generated power to the end tool, a connection part configured to connect the manipulation part to the end tool by being coupled to the power transmission part at one end portion thereof and coupled to the end tool at another end portion thereof, and a control part configured to control a motion of the end tool based on a manipulation value according to user input, so that a target posture is implemented, wherein the control part is configured to obtain the manipulation value according to user input to change the posture of the end tool included in the surgical instrument, obtain first posture information, which is information about a current posture of the end tool at the time of obtaining the user input, and control a motion of the end tool based on the manipulation value and the first posture information, so that the target posture according to the user input is implemented.

In the fourth aspect, the manipulation part may be implemented in a form including one or more user interfaces configured to receive one of the user input for a roll rotation of the end tool, the user input for a pitch rotation of the end tool, and the user input for a yaw rotation of the end tool.

In the fourth aspect, the manipulation part may be implemented to include a first user interface configured to receive the user input for a pitch rotation and a yaw rotation of the end tool, and a second user interface configured to receive the user input for a roll rotation of the end tool.

In the fourth aspect, the first user interface may be implemented in the form of a joystick, and receives the user input for the pitch rotation and the yaw rotation of the end tool over a range of 360 degrees.

In the fourth aspect, the first user interface may be attached to the manipulation part on an imaginary surface perpendicular to a direction in which the connection part extends.

In the fourth aspect, the first user interface may be attached to a front surface portion or a rear surface portion of the manipulation part.

In the fourth aspect, the second user interface may be attached to the manipulation part on an imaginary surface parallel to a direction in which the connection part extends.

In the fourth aspect, the second user interface may be implemented to include two switches capable of receiving the user input, and is attached to a side surface portion of the manipulation part.

In the fourth aspect, of the two switches included in the second user interface, one switch may be disposed on one side surface portion of the manipulation part, and another switch may be disposed symmetrically with the one switch on another side surface portion of the manipulation part.

According to a fifth aspect of the present disclosure, there is provided a surgical instrument including a manipulation part configured to receive user input to change a posture of an end tool, a control part configured to control a motion of the end tool based on a manipulation value according to user input, so that a target posture is implemented, a power generation part configured to generate power for changing the posture of the end tool based on a control value of the control part, a power transmission part configured to transmit the generated power to the end tool, a connection part configured to connect the manipulation part to the end tool by being coupled to the power transmission part at one end portion thereof and coupled to the end tool at another end portion thereof, and the end tool configured to perform a motion for changing a posture thereof by using the power, wherein the end tool performs a motion so that a target posture according to the user input is implemented independently of a current posture of the end tool at the time of obtaining the user input.

In the fifth aspect, even when a roll rotation angle included in the current posture of the end tool is not an angle in an initial state, the target posture may be implemented in the end tool to intuitively correspond to a movement of the manipulation part.

In the fifth aspect, even when a pitch rotation angle or a yaw rotation angle included in the current posture of the end tool is not an angle in an initial state, the target posture may be implemented in the end tool to intuitively correspond to a movement of the manipulation part.

In the fifth aspect, when the end tool performs a motion according to second posture change information to implement the target posture based on the control value, an axis of the end tool before a roll rotation is performed and an axis of the end tool after the roll rotation is performed may be parallel to each other.

In addition, other methods and systems for implementing the present disclosure, and a computer-readable recording medium having recorded thereon a program for executing the method may be further provided.

Other aspects, features, and advantages other than those described above will become apparent from the following drawings, claims, and detailed description of the disclosure.

Advantageous Effects

According to an embodiment of the present disclosure, a control value for changing a posture of an end tool can be generated based on user input to change the posture of the end tool, in consideration of a transformation between a coordinate system used by a manipulation part and a coordinate system used by the end tool. Accordingly, a user's intended change in the posture of the end tool can correspond one-to-one with an actual change in the posture of the end tool, so that the user can control the posture intuitively and efficiently.

The effects of the present disclosure are not limited to those mentioned above, and other effects not mentioned may be clearly understood by those of ordinary skill in the art from the following description.

DESCRIPTION OF DRAWINGS

FIG. 2 is a side view of the surgical instrument of FIG. 1.

FIG. 23 is a view for describing a roll motion of a surgical instrument according to an embodiment of the present disclosure.

FIGS. 24 and 25 are views for describing a coupling structure of the surgical instrument according to an embodiment of the present disclosure.

FIG. 35 is a plan view schematically illustrating the first jaw of the end tool of FIG. 27.

FIGS. 58 to 62 are views illustrating a yaw rotation motion of the surgical instrument according to an embodiment of the present disclosure.

FIG. 71 is a flowchart for describing another example of a method of controlling a posture of the surgical instrument according to an embodiment.

MODE FOR INVENTION

Figure 1:
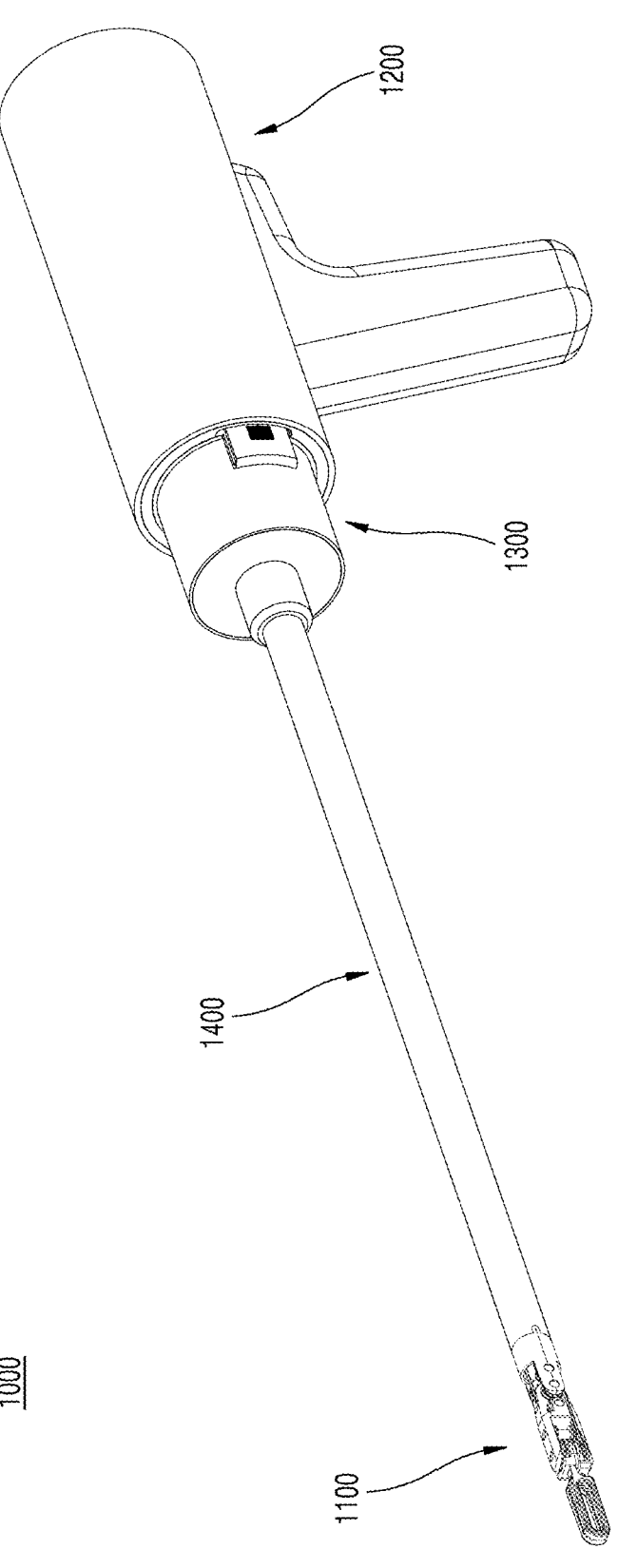
FIG. 1 is a perspective view illustrating a surgical instrument according to an embodiment of the present disclosure.

While the present disclosure is susceptible to various modifications and alternative forms, specific embodiments thereof are shown by way of example in the drawings and will herein be described in detail. Advantages and features of the present disclosure and methods for accomplishing the same will be more clearly understood from embodiments described below with reference to the drawings. However, the present disclosure is not limited to the embodiments disclosed below but may be implemented in various forms.

Hereinafter, the embodiments of the present disclosure will be described in detail with reference to the accompanying drawings, but when describing with reference to the drawings, equal or corresponding components will be referred to as the same reference numerals, and repeated descriptions thereof will be omitted.

In the following embodiments, the terms "first," "second," and the like have been used to distinguish one component from another and are not intended to impose any limitations.

In the following embodiments, singular forms are intended to include plural forms as well, unless the context clearly indicates otherwise.

In the following embodiments, terms such as "include" or "have" means that the features or components described in the specification are present, and the possibility that one or more other features or components will be added is not excluded in advance.

Sizes of components in the drawings may be exaggerated or reduced for convenience of description. For example, the size and thickness of each component shown in the drawings are arbitrarily represented for convenience of description, and thus, the present disclosure is not necessarily limited thereto.

In the following embodiments, an x-axis, a y-axis, and a z-axis are not limited to three axes of the rectangular coordinate system, and may be interpreted in a broader sense. For example, the x-axis, the y-axis, and the z-axis may be perpendicular to one another, or may represent different directions that are not perpendicular to one another.

In cases where certain embodiments may be implemented otherwise, a specific process sequence may be performed differently from the described sequence. For example, two consecutively described processes may be performed substantially at the same time or performed in an order opposite to the described order.

Hereinafter, based on the above principle, a surgical instrument according to the present disclosure will be described in detail with reference to the drawings.

Figure 2:
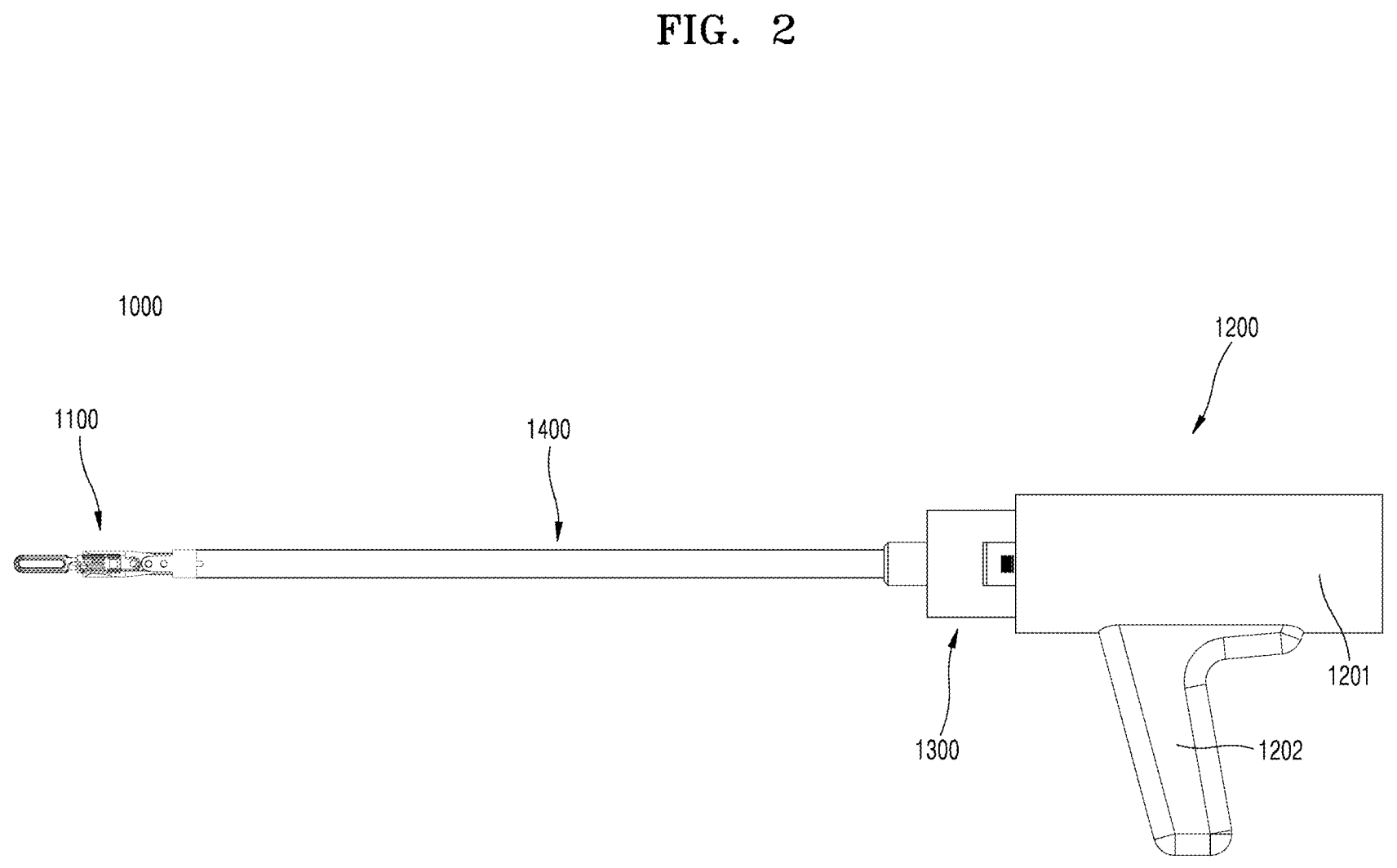

FIG. 1 is a perspective view illustrating a surgical instrument according to an embodiment of the present disclosure, and FIG. 2 is a side view of the surgical instrument of FIG. 1.

Referring to FIGS. 1 and 2, a surgical instrument 1000 according to an embodiment of the present disclosure may include an end tool 1100, a manipulation part 1200, a power transmission part 1300, and a connection part 1400.

The end tool 1100 is formed on one end portion of the connection part 1400, and performs necessary motions for surgery by being inserted into a surgical site. As an example of the above-described end tool 1100, a pair of jaws (not shown) for performing a grip motion may be used. The above-described end tool 1100 is connected to the manipulation part 1200 by the power transmission part 1300 and the connection part 1400, which will be described later, and receives a driving force of the manipulation part 1200 through the power transmission part 1300 to perform a motion necessary for surgery, such as gripping, cutting, suturing, or the like. However, the concept of the present disclosure is not limited thereto, and various devices for performing surgery may be used as the end tool 1100. For example, hereinafter, for convenience of description, the end tool 1100 used as a surgical clamp and an end tool used as a stapler are described by way of example, but the present disclosure is not limited thereto, and configurations such as a surgical grasper, a vessel sealer, and a one-armed cautery may also be used as the end tool.

The manipulation part 1200 may control motions of the end tool 1100. For example, the manipulation part 1200 is a configuration for a user to input signals to control the motions of the end tool 1100. Here, the signals for controlling the motions of the end tool 1100 may correspond to mechanical manipulations such as pressing a button or switch, or rotating or moving a particular member, and may also be electrical signals generated by such mechanical manipulations, but the present disclosure is not limited thereto. The manipulation part 1200 is provided as an interface to be directly controlled by a medical doctor, for example, provided in a gun shape, a tongs shape, a stick shape, a lever shape, or the like, and when the medical doctor controls the manipulation part 1200, the end tool 1100, which is connected to the corresponding interface and inserted into the body of a surgical patient, performs a certain motion, thereby performing surgery. Here, the manipulation part 1200 is illustrated in FIG. 1 as being formed in a gun shape, but the concept of the present disclosure is not limited thereto, and various types of manipulation parts that can be connected to the end tool 1100 and manipulate the end tool 1100 may be possible.

The power transmission part 1300 may be formed on another end portion of the connection part 1400 and may serve to transmit power generated from a power generation part to be described later to the end tool 1100. For example, the power transmission part 1300 may be disposed between the end tool 1100 and the manipulation part 1200. As will be described later, when a user such as a medical doctor manipulates the manipulation part 1200, the power generation part generates power to control the end tool 1100, and the generated power may be transmitted to the end tool 1100 through the power transmission part 1300. The power transmission part 1300 may include a plurality of wires, a plurality of pulleys, a plurality of links, a plurality of joints, a plurality of gears, and the like.

The connection part 1400 is formed in the shape of a hollow shaft, and one or more wires and electric wires may be accommodated therein. The connection part 1400 has one end portion to which the end tool 1100 is coupled and another end portion to which the power transmission part 1300 is coupled, and the power transmission part 1300 may be connected to the manipulation part 1200. That is, it may be said that the connection part 1400 may serve to connect the manipulation part 1200 to the end tool 1100.

Meanwhile, a connector (not shown) may be formed on the manipulation part 1200. The connector (not shown) may be connected to an external power source (not shown), and the connector (not shown) may also be connected to the end tool 1100 via an electric wire, and may transmit, to the end tool 1100, electrical energy supplied from the external power source (not shown). In addition, the electrical energy, which is transmitted to the end tool 1100 as described above, may provide a driving force for performing a yaw rotation motion, a pitch rotation motion, an actuation motion, a staple motion, and the like of the end tool 1100 to be described later. Alternatively, the electrical energy transmitted to the end tool 1100 may provide a driving force for performing cutting and cauterizing functions of the end tool 1100, such as with a monopolar/bipolar or ultrasonic blade. In addition, the electrical energy may be supplied to drive the power transmission part 1300. Of course, a built-in battery may be used.

The manipulation part 1200 may include a housing 1201 forming the exterior of the manipulation part 1200. As will be described later, at least a portion of the power generation part configured to generate power to control the end tool 1100 may be accommodated inside the housing 1201. In addition, a circuit unit for controlling the operation of the power generation part and slip rings for supplying electrical energy to the power generation part or for connecting communication may be accommodated inside the housing 1201.

A handle 1202 may be formed on the manipulation part 1200. The handle 1202 is a part for a user to grip. Thus, the user can use the surgical instrument 1000 according to the present disclosure while gripping the handle 1202 of the manipulation part 1200.

Meanwhile, although not shown in the drawings, a button, a switch, a lever, and the like for controlling various motions of the end tool 1100 may be further formed in the manipulation part.

Hereinafter, an embodiment of the manipulation part of the surgical instrument illustrated in FIGS. 1 and 2 will be described in more detail.

Figure 3:
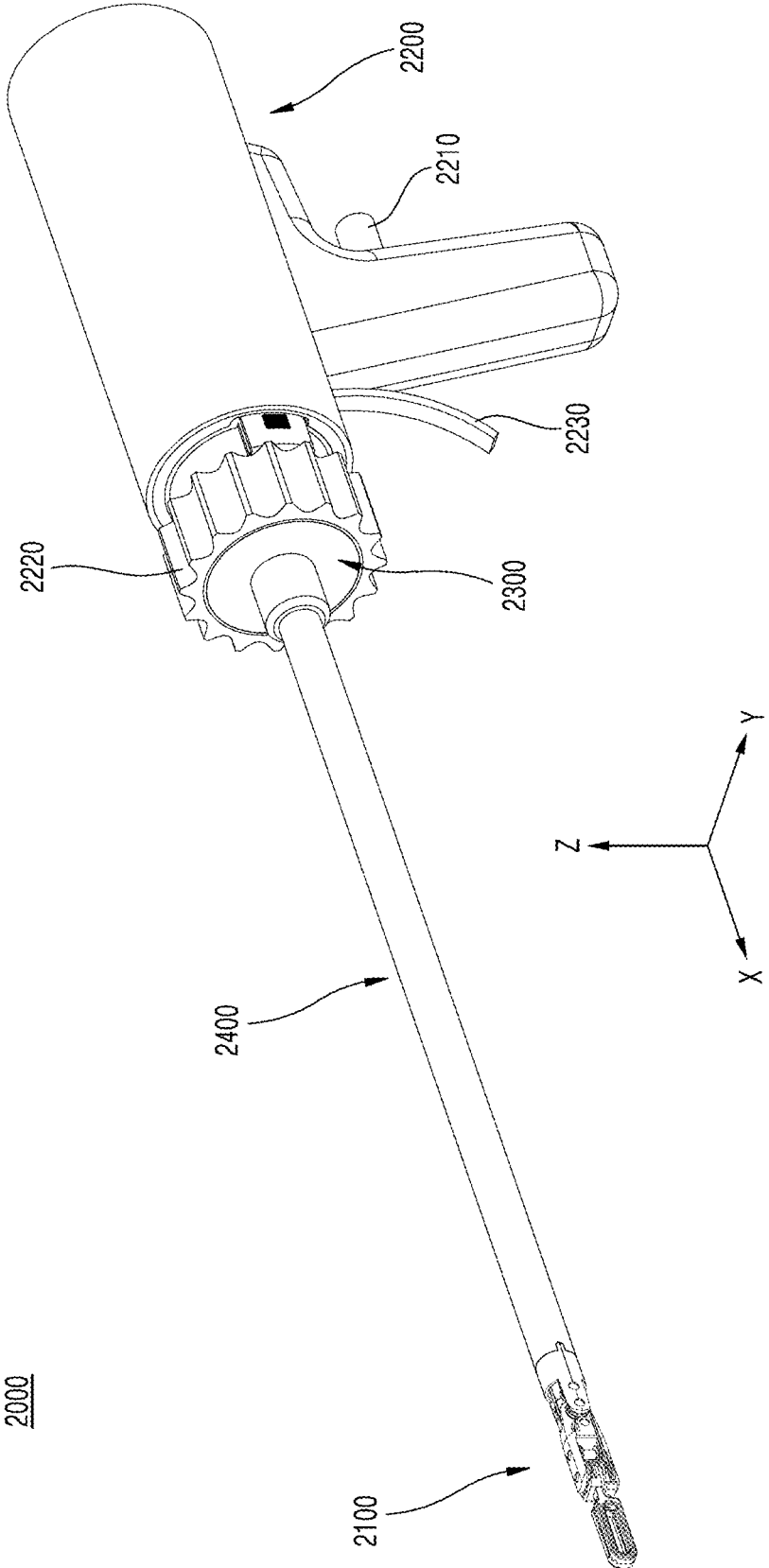
FIG. 3 is a perspective view illustrating an example of a manipulation part of a surgical instrument according to an embodiment.
Figure 4:
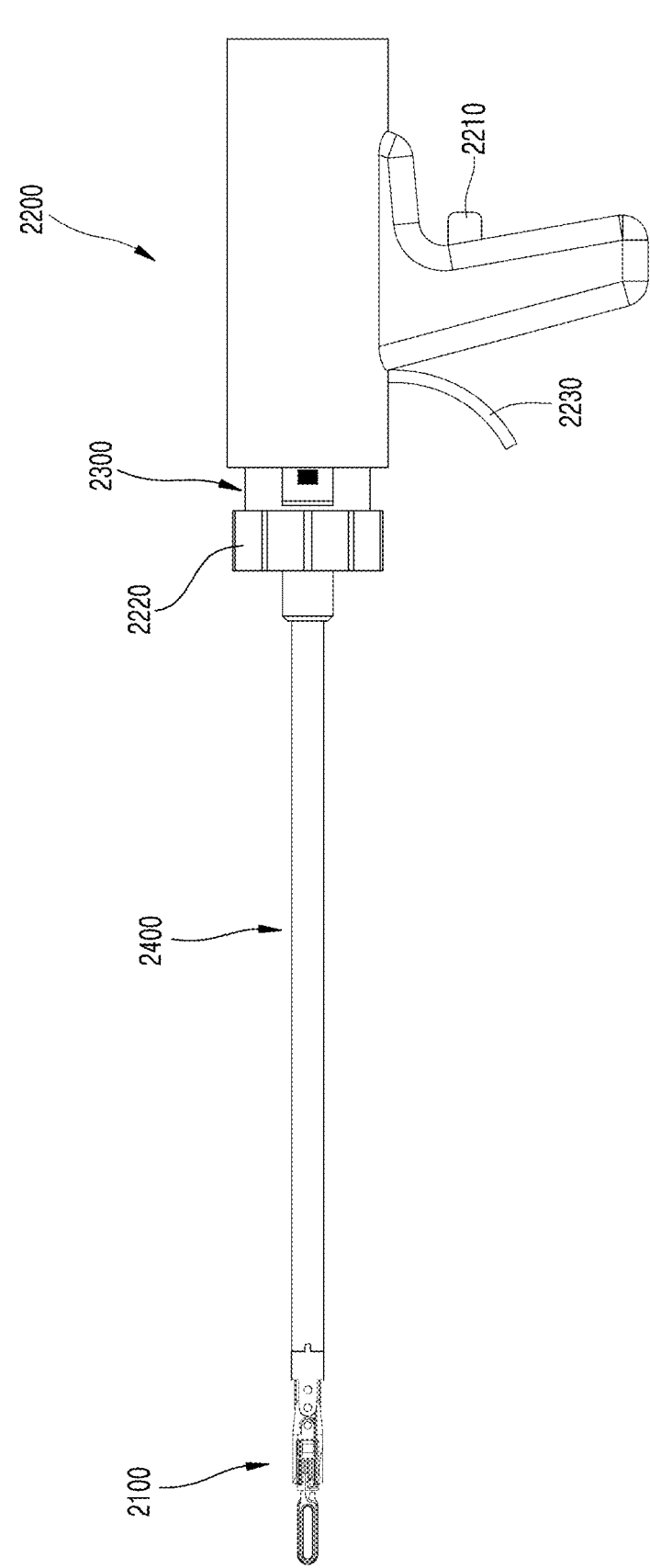
FIG. 4 is a side view of the surgical instrument of FIG. 3.

FIG. 3 is a perspective view illustrating an example of a manipulation part of a surgical instrument according to an embodiment, and FIG. 4 is a side view of the surgical instrument of FIG. 3.

Referring to FIGS. 3 and 4, a surgical instrument 2000 according to an embodiment of the present disclosure may include an end tool 2100, a manipulation part 2200, a power transmission part 2300, and a connection part 2400.

According to an embodiment, the manipulation part 2200 may be a configuration for a user to input to control motions of the end tool 2100. As an example, the user may input a signal for controlling (or changing) a posture of the end tool 2100 via the manipulation part 2200. In other words, the manipulation part 2200 may receive user input to change the posture of the end tool 2100. Here, a posture is defined as the expression of an object's spatial state, which may be expressed as a combination of an orientation and a position. As another example, the user may input signals for the end tool 2100 to perform motions, such as clamping, stapling, and firing, through the manipulation part 2200. In other words, the manipulation part 2200 may receive input signals of a user for the end tool 2100 to perform motions such as clamping, stapling, firing, and the like.

Meanwhile, in the present disclosure, the end tool 2100 may have a plurality of degrees of freedom. For example, the end tool 2100 may have various combinations of degrees of freedom, such as two displacement degrees of freedom, one displacement degree of freedom, one rotational degree of freedom, and two rotational degrees of freedom. However, since the displacement degrees of freedom of the end tool 2100 may be manipulated by a user through repositioning of the surgical instrument 2000 via the manipulation part 2200, in the present disclosure, the degrees of freedom of the end tool 2100 related to the manipulation part 2200 are described as rotational degrees of freedom.

In this regard, the end tool 2100 may have two or more rotational degrees of freedom. As an example, the end tool 2100 may have two rotational degrees of freedom for a pitch rotation and a yaw rotation. Alternatively, the end tool 2100 may have two rotational degrees of freedom for a pitch rotation and a roll rotation or two rotational degrees of freedom for a yaw rotation and a roll rotation. As another example, the end tool 2100 may have three rotational degrees of freedom, i.e., a roll rotational degree of freedom, a pitch rotational degree of freedom, and a yaw rotational degree of freedom.

The end tool 2100 having three rotational degrees of freedom means that a user can control each rotation. That is, user input received by the manipulation part 2200 may refer to user input for at least one of a roll rotation, a pitch rotation, and a yaw rotation of the end tool 2100.

Meanwhile, the manipulation part 2200 may be implemented in a form including one or more user interfaces that receive user input for controlling motions of the end tool 2100. For example, the manipulation part 2200 may include a plurality of independently implemented user interfaces, each of which may receive user input for controlling at least one rotational motion from among a roll rotation, a yaw rotation, and a pitch rotation of the end tool 2100. The user interface may be implemented in a form capable of obtaining (or receiving) user manipulation or input, such as a joystick, a button, a keypad, a trackball, a foot pedal, a touch screen, but the present disclosure is not be limited to the above form.

According to an embodiment, the manipulation part 2200 may be implemented to include a user interface (not shown) capable of receiving user input for a roll rotation, a pitch rotation, and a yaw rotation of the end tool 2100. In other words, the user may input signals for controlling a roll rotation, a pitch rotation, and a yaw rotation of the end tool 2100 via the user interface. As an example, the user interface may separately receive user input for each of a roll rotation, a pitch rotation, and a yaw rotation according to the user input method (e.g., the region of the user interface that receives the input, the time (or, period) at which the input is received, the method of receiving the input, and the like). As another example, the user interface may receive at least one user input for a roll rotation, a pitch rotation, and a yaw rotation based on the user input.

According to another embodiment, the manipulation part 2200 may be implemented to include a first user interface 2210 capable of receiving user input for a pitch rotation and a yaw rotation of the end tool 2100, and a second user interface 2220 capable of receiving user input for a roll rotation of the end tool 2100. For example, the first user interface 2210 may be implemented in the form of a joystick, and the second user interface 2220 may be implemented in the form of a dial, thereby receiving user input over a range of 360 degrees for the pitch rotation, the yaw rotation, and the roll rotation. However, the form (e.g., a joystick) of the first user interface 2210 and the form (e.g., a dial) of the second user interface 2220 are not limited to those illustrated in FIGS. 3 and 4.

According to another embodiment, the manipulation part 2200 may be implemented to include a third user interface 2230 capable of receiving user input for controlling motions of the end tool 2100, such as clamping, stapling, and firing. For example, the third user interface 2230 may be implemented in the form of a button or a switch to receive a push input from a user. However, the form (e.g., a button or a switch) of the third user interface 2230 is not limited to that illustrated in FIGS. 3 and 4.

According to another embodiment, the manipulation part 2200 may be implemented to include a fourth user interface (not shown) capable of receiving user input such that a target posture according to the user input may be considered and selected in controlling the motion of the end tool. For example, the fourth user interface may be implemented in the form of a button or a switch to receive a push input from a user. For example, when the switch is turned on in response to user input, a control part to be described later may control a motion of the end tool such that a target posture according to the user input is implemented. In contrast, when the switch is turned off in response to user input, the control part to be described later may control a motion of the end tool independently of the target posture. When controlling the motion of the end tool independently of the target posture, the control part may control the motion of the end tool according to a manipulation value according to user input, taking into account current posture information about a current posture of the end tool. This is similar to posture control method 2510 of FIG. 70 to be described later.

Meanwhile, the positions to which the first user interface 2210, the second user interface 2220, and the third user interface 2230 are attached on the manipulation part 2200 are not limited to those illustrated in FIGS. 3 and 4. For example, the attachment positions of the first user interface 2210, the second user interface 2220, and the third user interface 2230 may be determined in consideration of an intuitive use by a user.

For example, for the intuitive use by a user, the first user interface 2210 may be attached to a front surface portion or a rear surface portion of the manipulation part 2200 such that an imaginary surface including a point of the manipulation part 2200 to which the first user interface 2210 is attached is perpendicular to a direction (an x-axis direction in FIG. 3) in which the connection part 2400 extends. In other words, an axis along the direction in which the connection part 2400 extends may be oriented perpendicular to the imaginary surface. In other words, the first user interface 2210 may be attached to the front or rear surface portion of the manipulation part 2200 such that a direction in which the point of the manipulation part 2200 to which the first user interface 2210 is attached extends is parallel to the direction in which the connection part 2400 extends (the x-axis direction in FIG. 3).

For example, for the intuitive use by a user, the second user interface 2220 may be attached to a region where the manipulation part 2200 is connected to the power transmission part 2300 or a region adjacent to the power transmission part 2300, as illustrated in FIGS. 3 and 4. Alternatively, for the intuitive use by a user, the second user interface 2220 may be attached to a side surface portion of the manipulation part 2200. In this case, the second user interface 2220 may be attached to the side surface portion of the manipulation part 2200 such that the imaginary surface including a point of the manipulation part 2200 to which the second user interface 2220 is attached is parallel to the direction in which the connection part 2400 extends (the x-axis direction in FIG. 3). In other words, an axis along the direction in which the connection part 2400 extends may be oriented in a direction parallel to the imaginary surface. In other words, the second user interface 2220 may be attached to the side surface portion of the manipulation part 2200 such that a direction in which the point of the manipulation part 2200 to which the second user interface 2220 is attached extends is perpendicular to the direction in which the connection part 2400 extends (the x-axis direction in FIG. 3).

According to another embodiment, the second user interface may be implemented in the form of a button (or, a switch) or the like to receive a push input from a user. For example, the second user interface is implemented to include two switches such that one switch may receive user input for a roll rotation in a clockwise direction and another switch may receive user input for a roll rotation in a counterclockwise direction. As an example, the two switches included in the second user interface may be disposed above and below the position of the manipulation part 2200 to which the second user interface is attached (such as, a left or right side surface of the manipulation part). As another example, one of the two switches included in the second user interface is disposed on one side surface of the manipulation part, and another one thereof may be disposed on another side surface of the manipulation part to be symmetrical thereto. As another example, the second user interface 2220 may be implemented in a form in which switch sets each including two switches are attached to different positions of the manipulation part 2200, respectively. For example, a first switch set included in the second user interface 2220 may be disposed on one side surface of the manipulation part, and a second switch set may be disposed on another side surface of the manipulation part.

For example, for the intuitive use by a user, the third user interface 2230 may be attached to the front surface portion of the manipulation part 2200, as illustrated in FIGS. 3 and 4. For example, when the manipulation part 2200 is formed in a gun shape as illustrated in FIGS. 3 and 4, the third user interface 2230 may be formed in the shape of a trigger and attached to the front surface portion of the manipulation part 2200.

Meanwhile, in a coordinate system used by the manipulation part 2200 and a coordinate system used by the end tool 2100, in an initial state, which is a state before the user manipulates the manipulation part 2200 to change the posture of the end tool 2100, reference points (or, origins) in each coordinate system may be different, but reference axes (e.g., a roll rotation axis, a pitch rotation axis, and a yaw direction rotation axis) in each coordinate system may all be oriented in the same direction. In other words, in the initial state, the reference axes in the coordinate system used by the manipulation part 2200 and the coordinate system used by the end tool 2100 may be either parallel or perpendicular to each other. That is, in the initial state, user input in the coordinate system used by the manipulation part 2200 corresponding to the user's intent may be equivalent to an actual pose change of the end tool 2100 in the coordinate system used by the end tool 2100.

In contrast, when a user manipulates the manipulation part 2200 to change the posture of the end tool 2100, the orientation of the reference axis in the coordinate system used by the end tool 2100 may be different from that in the coordinate system used by the manipulation part 2200. In this case, the user input in the coordinate system used by the manipulation part 2200 corresponding to the user's intent may be different from the actual pose change of the end tool 2100 in the coordinate system used by the end tool 2100, making it difficult for the user to intuitively manipulate the end tool 2100. For example, when the connection part 2400 is rotated (e.g., the end tool 2100 changes a posture thereof according to roll rotation), and in that state, the user subsequently inputs a signal for a pitch rotation into the manipulation part 2200, the end tool 2100 may actually perform a yaw rotation contrary to the user's intention.

In another example, when the user manipulates the manipulation part 2200 with the intention of performing a roll rotation, due to the difference between the coordinate system used by the manipulation part 2200 and the coordinate system used by the end tool 2100, in the end tool 2100, not only a roll direction posture but also a pitch direction posture and a yaw direction posture may be changed. In this case, in the end tool 2100, the pitch rotation axis and the yaw direction rotation axis are changed due to user's signal input for a roll rotation, and thus, information about the orientation related to the pitch rotation and the yaw rotation of the end tool 2100 aligned with the surgical site to perform a surgical operation may be changed.

In other words, the difficulty experienced by the user in the above-described examples may result from the end tool 2100 that operates according to a signal input by a user through the manipulation part 2200. In other words, when a motion control signal is generated based on a signal input by the user through the manipulation part 2200 taking into consideration of a transformation between the coordinate system used by the manipulation part 2200 and the coordinate system used by the end tool 2100, and the generated motion control signal is transmitted to the end tool 2100, a posture change of the end tool 2100 intended by the user may be the same as an actual posture change of the end tool 2100, thereby reducing inconvenience to the user and allowing the user to change the posture of the end tool 2100 conveniently and intuitively.

Accordingly, the present disclosure describes a method and device for generating a control value (or a control signal) based on a signal input by a user through the manipulation part 2200 to change a posture of an end tool 2100. A more detailed description thereof will be provided below with reference to FIGS. 68 to 72.

Hereinafter, the end tool, the manipulation part, the power transmission part, the power generation part, and the like of each of the surgical instruments of FIGS. 1, 2, 3, and 4 will be described in more detail.

Figure 5:
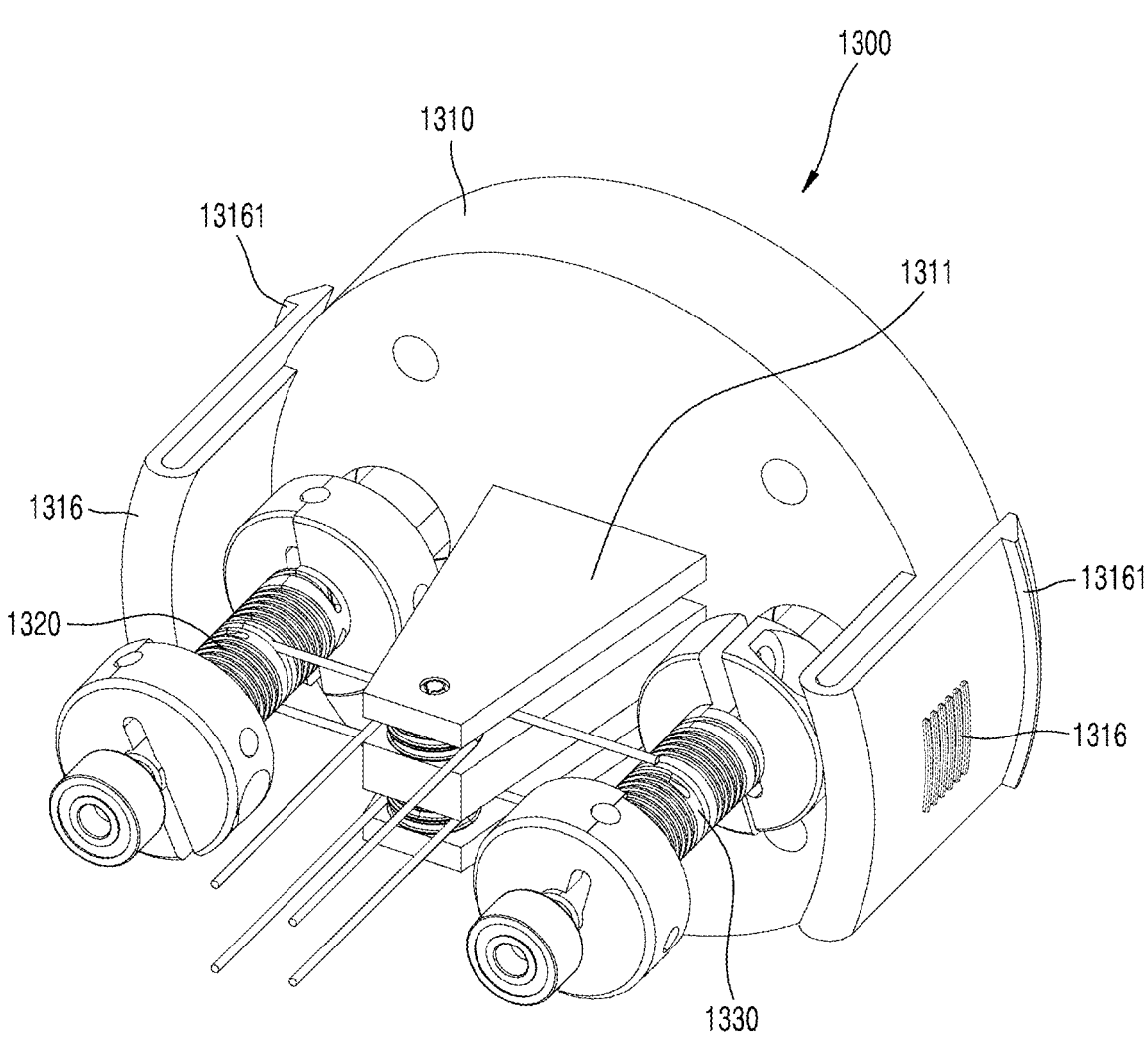
FIG. 5 is a view for describing an internal structure of a power transmission part according to an embodiment of the present disclosure.
Figure 6:
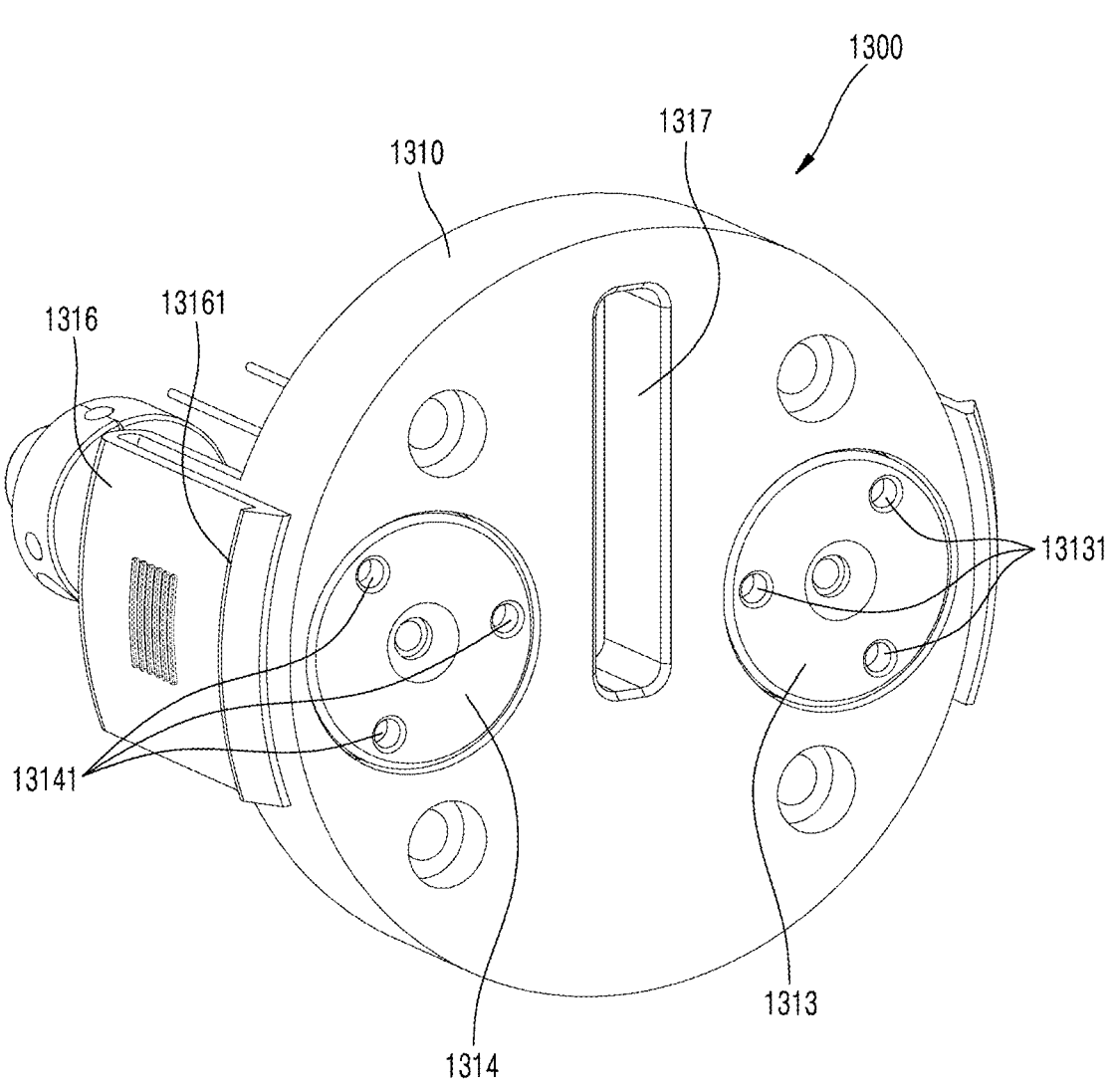
FIG. 6 is a rear view of the power transmission part of FIG. 5.
Figure 7:
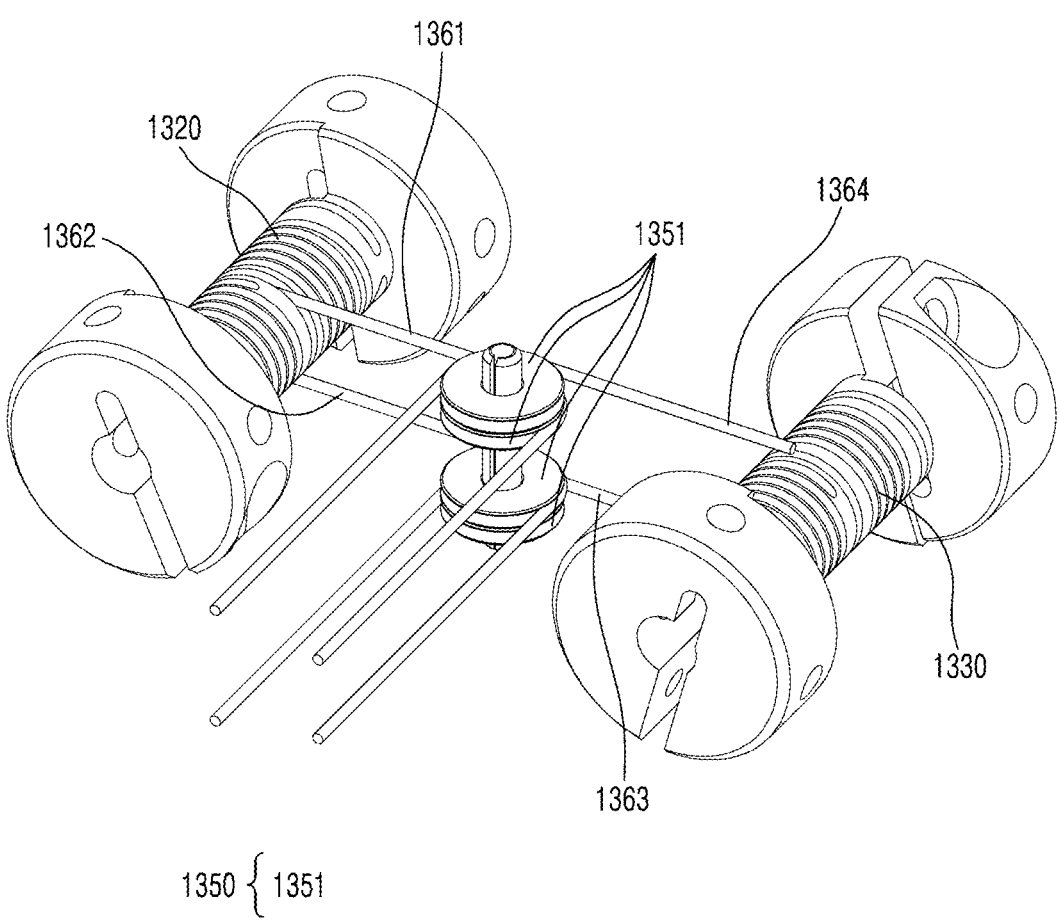
FIG. 7 is a view for describing the arrangement of pulleys and wires of the power transmission part of FIG. 5.

FIG. 5 is a view for describing an internal structure of the power transmission part according to an embodiment of the present disclosure, FIG. 6 is a rear view of the power transmission part of FIG. 5, and FIG. 7 is a view for describing the arrangement of pulleys and wires of the power transmission part of FIG. 5.

Referring to FIGS. 5 to 7, the power transmission part 1300 according to an embodiment of the present disclosure may include a pulley frame 1310, at least one pulley, and at least one wire.

The pulley frame 1310 may form the overall framework of the power transmission part 1300.

At least one pulley may be disposed in the pulley frame 1310. Here, disposing a pulley should be interpreted in a broad sense. For example, disposing a pulley may mean connecting the pulley directly to the pulley frame 1310, or may also mean installing a rotation shaft in the pulley frame 1310 and connecting the pulley to the rotation shaft. Alternatively, disposing a pulley may also mean proving a separate member in the pulley frame 1310, connecting a rotation shaft to the separate member, and connecting the pulley to the rotation shaft. Alternatively, disposing a pulley may also mean forming a hole in the pulley frame 1310, disposing a rotation shaft to pass through the hole, and installing the pulley on the rotation shaft.

The power transmission part 1300 may include at least one pulley.

The pulley is a member around which a wire is wound, and a groove around which a wire may be wound may be formed in the pulley.

In an embodiment, the power transmission part 1300 may include a yaw pulley 1320 and a pitch pulley 1330. In addition, the power transmission part 1300 may include at least one or more yaw wires 1361 and 1362 and at least one or more pitch wires 1363 and 1364.

The yaw pulley 1320 is a pulley associated with a yaw rotation of the end tool 1100, and the yaw wires 1361 and 1362 are wires associated with the yaw rotation of the end tool 1100. The yaw pulley 1320 may be disposed in one region of the pulley frame 1310.

The yaw wires 1361 and 1362 may be wires extending toward the yaw pulley 1320 from a pulley disposed in the end tool 1100 and associated with a yaw rotation of the end tool 1100.

In an embodiment, the yaw wires 1361 and 1362 may be provided in a pair. As will be described later, the yaw wires 1361 and 1362 may be connected to upper and lower sides of the yaw pulley 1320, respectively.

As a specific embodiment, the yaw wires 1361 and 1362 may include a first yaw wire 1361 and a second yaw wire 1362. The first yaw wire 1361 may extend to the upper side of the yaw pulley 1320 based on FIG. 7 to be connected to the yaw pulley 1320. The second yaw wire 1362 may extend to the lower side of the yaw pulley 1320 based on FIG. 7 to be connected to the yaw pulley 1320.

The yaw wires 1361 and 1362 may be connected to the yaw pulley 1320, and then, may be wound around the yaw pulley 1320 or unwound therefrom when the yaw pulley 1320 rotates. That is, when the yaw pulley 1320 rotates in one direction, one yaw wire is wound around the yaw pulley 1320, and another yaw wire is unwound from the yaw pulley 1320. For example, when the yaw pulley 1320 rotates in the clockwise direction based on FIG. 7, the first yaw wire 1361 is unwound from the yaw pulley 1320, and the second yaw wire 1362 is wound around the yaw pulley 1320. On the contrary, when the yaw pulley 1320 rotates in a counter-clockwise direction based on FIG. 7, the first yaw wire 1361 is wound around the yaw pulley 1320, and the second yaw wire 1362 is unwound from the yaw pulley 1320.

In other words, it may be said that, when the yaw pulley 1320 rotates, the pair of yaw wires 1361 and 1362 may move in opposite directions to each other with respect to the yaw pulley 1320.

As described above, when the yaw pulley 1320 rotates to move the pair of yaw wires 1361 and 1362 in different directions, the pulley on the end tool 1100 side, which is connected to the yaw wires 1361 and 1362, is rotated in a direction corresponding thereto. Thus, as the pulley on the end tool 1100 side, which is connected to the yaw wires 1361 and 1362, rotates in one direction, a yaw rotation of the end tool 1100 may be implemented.

The pitch pulley 1330 is a pulley associated with a pitch rotation of the end tool 1100, and the pitch wires 1363 and 1364 are wires associated with the pitch rotation of the end tool 1100.

The pitch pulley 1330 may be disposed in one region of the pulley frame 1310.

In an embodiment, the pitch pulley 1330 may be disposed on the opposite side of the yaw pulley 1320. In an exemplary embodiment, the pitch pulley 1330 and the yaw pulley 1320 may be symmetrically disposed on both sides of the center of the pulley frame 1310. Accordingly, as will be described later, the yaw wires 1361 and 1362 and the pitch wires 1363 and 1364, which extend via auxiliary pulleys 1350, may approach the yaw pulley 1320 and the pitch pulley 1330 to be nearly perpendicular thereto.

The pitch wires 1363 and 1364 may extend toward the pitch pulley 1330 from a pulley disposed in the end tool 1100 and associated with the pitch rotation of the end tool 1100.

In an embodiment, the pitch wires 1363 and 1364 may be provided in a pair. As will be described later, the pitch wires 1363 and 1364 may be connected to upper and lower sides of the pitch pulley 1330, respectively.

As a specific embodiment, the pitch wires 1363 and 1364 may include a first pitch wire 1363 and a second pitch wire 1364. The first pitch wire 1363 may extend to the lower side of the pitch pulley 1330 based on FIG. 7 to be connected to the pitch pulley 1330. The second pitch wire 1364 may extend to the upper side of the pitch pulley 1330 based on FIG. 7 to be connected to the pitch pulley 1330.

The pitch wires 1363 and 1364 may be connected to the pitch pulley 1330, and then may be wound around the pitch pulley 1330 or unwound therefrom when the pitch pulley 1330 rotates. That is, when the pitch pulley 1330 rotates in one direction, one pitch wire is wound around the pitch pulley 1330, and another pitch wire is unwound from the pitch pulley 1330. For example, when the pitch pulley 1330 rotates in the clockwise direction based on FIG. 7, the first pitch wire 1363 is unwound from the pitch pulley 1330, and the second pitch wire 1364 is wound around the pitch pulley 1330. On the contrary, when the pitch pulley 1330 rotates in the counterclockwise direction based on FIG. 7, the first pitch wire 1363 is wound around the pitch pulley 1330, and the second pitch wire 1364 is unwound from the pitch pulley 1330.

In other words, it may be said that, when the pitch pulley 1330 rotates, the pair of pitch wires 1363 and 1364 may move in opposite directions to each other with respect to the pitch pulley 1330.

As described above, when the pitch pulley 1330 rotates to move the pair of pitch wires 1363 and 1364 in different directions, the pulley on the end tool 1100 side, which is connected to the pitch wires 1363 and 1364, rotates in a direction corresponding thereto. Thus, as the pulley on the end tool 1100 side, which is connected to the pitch wires 1363 and 1364, rotates in one direction, a pitch rotation of the end tool 1100 may be implemented.

In an embodiment, the power transmission part 1300 may further include at least one or more auxiliary pulleys 1350. For example, the auxiliary pulleys 1350 may include a first auxiliary pulley 1351 connected to the yaw wires 1361 and 1362 and the pitch wires 1363 and 1364 and configured to reroute the yaw wires 1361 and 1362 and the pitch wires 1363 and 1364.

The first auxiliary pulley 1351 may be disposed in the power transmission part 1300, and may serve to reroute the yaw wires 1361 and 1362 and the pitch wires 1363 and 1364 extending from the end tool 1100 to the power transmission part 1300 through the connection part 1400.

An auxiliary pulley fixing part 1311 may be formed in the pulley frame 1310. The auxiliary pulley fixing part 1311 is a part in which a first auxiliary pulley 1351 is installed. For example, the auxiliary pulley fixing part 1311 may be integrally formed with the pulley frame 1310. Alternatively, the auxiliary pulley fixing part 1311 may be formed as a separate member, and may be coupled or assembled to the pulley frame 1310.

In an embodiment, the auxiliary pulley fixing part 1311 may include at least one or more through holes, and a rotation shaft of the first auxiliary pulley 1351 may be disposed to pass through the through holes. In other words, the first auxiliary pulley 1351 may be disposed parallel to the through holes formed in the auxiliary pulley fixing part 1311 so as to overlap therewith, and the rotation shaft may be disposed to simultaneously pass through the first auxiliary pulley 1351 and the auxiliary pulley fixing part 1311.

The auxiliary pulley fixing part 1311 may be formed in a shape protruding in a direction toward the connection part 1400 from the pulley frame 1310. For example, it may be said that the auxiliary pulley fixing part 1311 is formed to protrude in a direction toward the connection part 1400 from one surface of the pulley frame 1310. In an exemplary embodiment, the auxiliary pulley fixing part 1311 may be disposed in the center of the pulley frame 1310.

In this case, the yaw pulley 1320 and the pitch pulley 1330 may be disposed on both sides of the auxiliary pulley fixing part 1311, respectively. In an exemplary embodiment, the yaw pulley 1320 and the pitch pulley 1330 may be disposed in positions symmetrical to each other with respect to the auxiliary pulley fixing part 1311. In other words, the yaw wires 1361 and 1362 and the pitch wires 1363 and 1364 entering the first auxiliary pulley 1351 may be distributed to opposite sides while passing through the auxiliary pulley fixing part 1311. Accordingly, it may be said that the yaw wires 1361 and 1362 extend toward the yaw pulley 1320, and the pitch wires 1363 and 1364 extend toward the pitch pulley 1330.

Accordingly, the yaw wires 1361 and 1362 may approach the yaw pulley 1320 to be nearly perpendicular thereto, and the pitch wires 1363 and 1364 may approach the pitch pulley 1330 to be nearly perpendicular thereto. The yaw wires 1361 and 1362 may perpendicularly approach the yaw pulley 1320, and the pitch wires 1363 and 1364 may perpendicularly approach the pitch pulley 1330. In other words, it may be said that the yaw wires 1361 and 1362 may approach the yaw pulley 1320 to form a tangent therewith, and the pitch wires 1363 and 1364 may approach the pitch pulley 1330 to form a tangent therewith.

The first auxiliary pulley 1351 may be disposed in the auxiliary pulley fixing part 1311 and may reroute paths along which the pitch wires 1363 and 1364 and the yaw wires 1361 and 1362 extend to the power transmission part 1300.

Specifically, the first auxiliary pulley 1351 may be disposed between the yaw pulley 1320 and the pitch pulley 1330 as shown in FIG. 7.

A plurality of first auxiliary pulleys 1351 may be provided. The first auxiliary pulleys 1351 may be provided in a number corresponding to at least the number of wires entering the power transmission part 1300.

As an example, the yaw wires 1361 and 1362 may be provided in a pair so as to respectively enter the upper and lower sides of the yaw pulley 1320. In addition, the pitch wires 1363 and 1364 may be provided in a pair so as to respectively enter the upper and lower sides of the pitch pulley 1330. That is, when there are four wires entering the power transmission part 1300, four first auxiliary pulleys 1351 may be provided.

In an optional embodiment, the plurality of first auxiliary pulleys 1351 may be disposed parallel to each other. This is to ensure that the wires 1361, 1362, 1363, and 1364 emerging from being wound around the first auxiliary pulleys 1351 extend to the yaw pulley 1320 and/or the pitch pulley 1330 parallel or nearly parallel to each other.

Specifically, the wires 1361, 1362, 1363, and 1364 extending from the end tool 1100 to the power transmission part 1300 extend parallel to each other. Thus, by disposing the plurality of first auxiliary pulleys 1351 parallel to each other, the wires 1361, 1362, 1363, and 1364 emerging from being wound around the respective first auxiliary pulleys 1351 may extend to the yaw pulley 1320 and/or the pitch pulley 1330 parallel to each other, or at least nearly parallel to each other.

In an optional embodiment, in relation to the yaw pulley 1320 and the pitch pulley 1330, the first auxiliary pulleys 1351 may be disposed such that the wires 1361, 1362, 1363, and 1364 are wound in directions nearly perpendicular to each other, and preferably perpendicular to each other. When further describing with reference to FIG. 7, the direction in which the wires 1361, 1362, 1363, and 1364 are wound around the first auxiliary pulley 1351 and the direction in which the wires 1361, 1362, 1363, and 1364 are wound the yaw pulley 1320 and the pitch pulley 1330 may be perpendicular to each other. In other words, it may be described that the first auxiliary pulley 1351 changes an advancing direction of the wires 1361, 1362, 1363, and 1364 entering the first auxiliary pulley 1351 by 90°. In other words, it may be described that a groove formed in the first auxiliary pulley 1351 is perpendicular to grooves formed in the yaw pulley 1320 and the pitch pulley 1330.

With this configuration, the wires 1361, 1362, 1363, and 1364 entering the power transmission part 1300 may be rerouted through the first auxiliary pulley 1351, and may approach the yaw pulley 1320 and the pitch pulley 1330 perpendicular or nearly perpendicular thereto.

Figure 8:
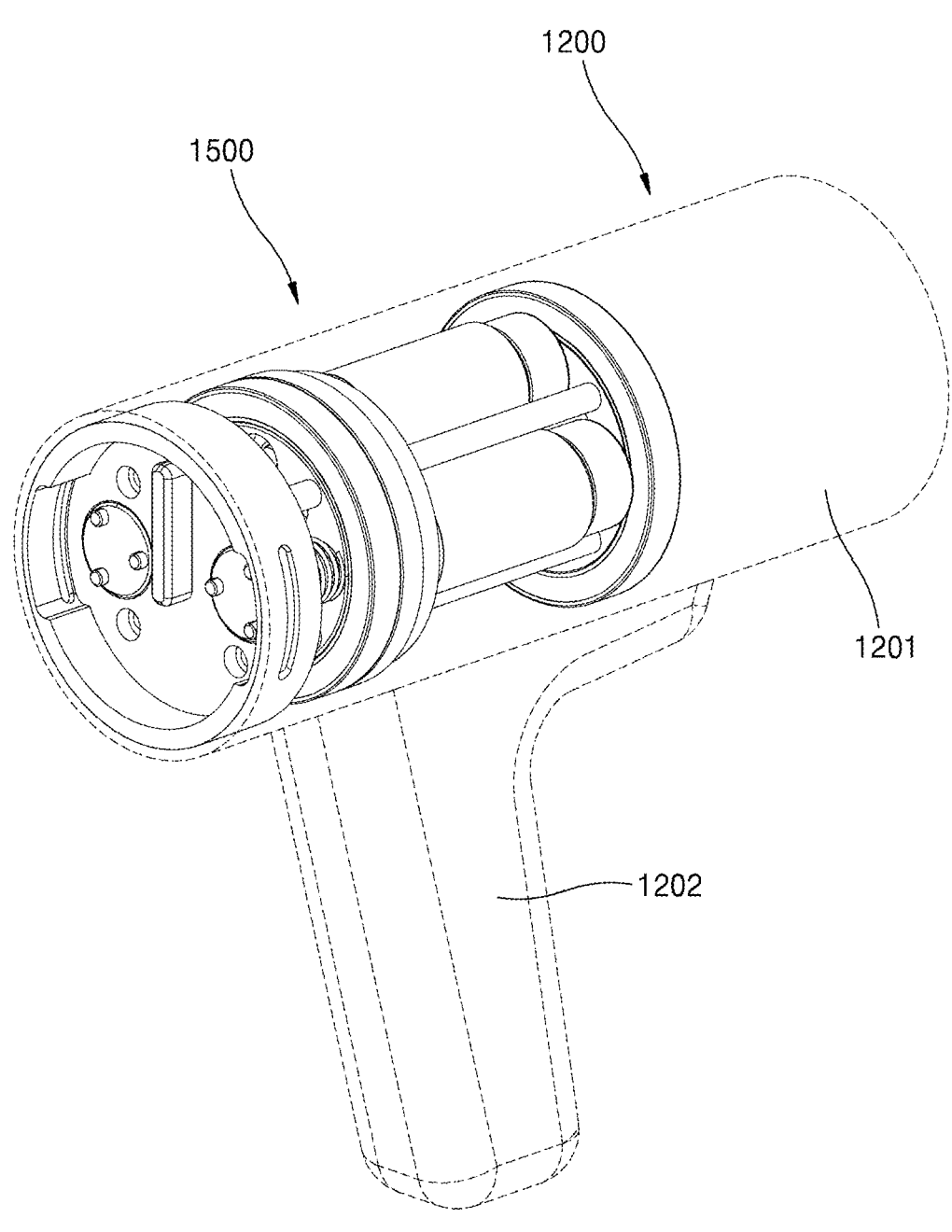
FIG. 8 is a view illustrating the manipulation part and a power generation part according to an embodiment of the present disclosure.
Figure 9:
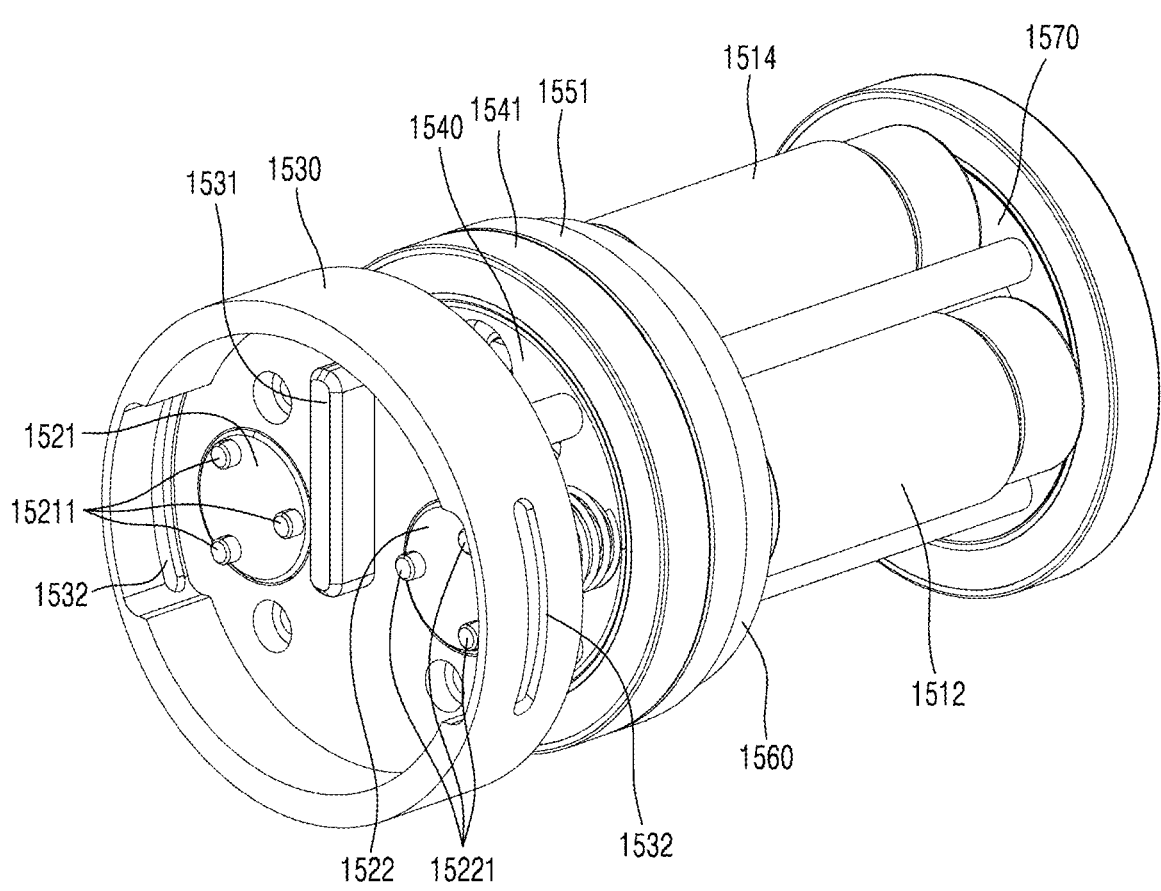
FIG. 9 is a perspective view illustrating the power generation part of FIG. 8.
Figure 10:
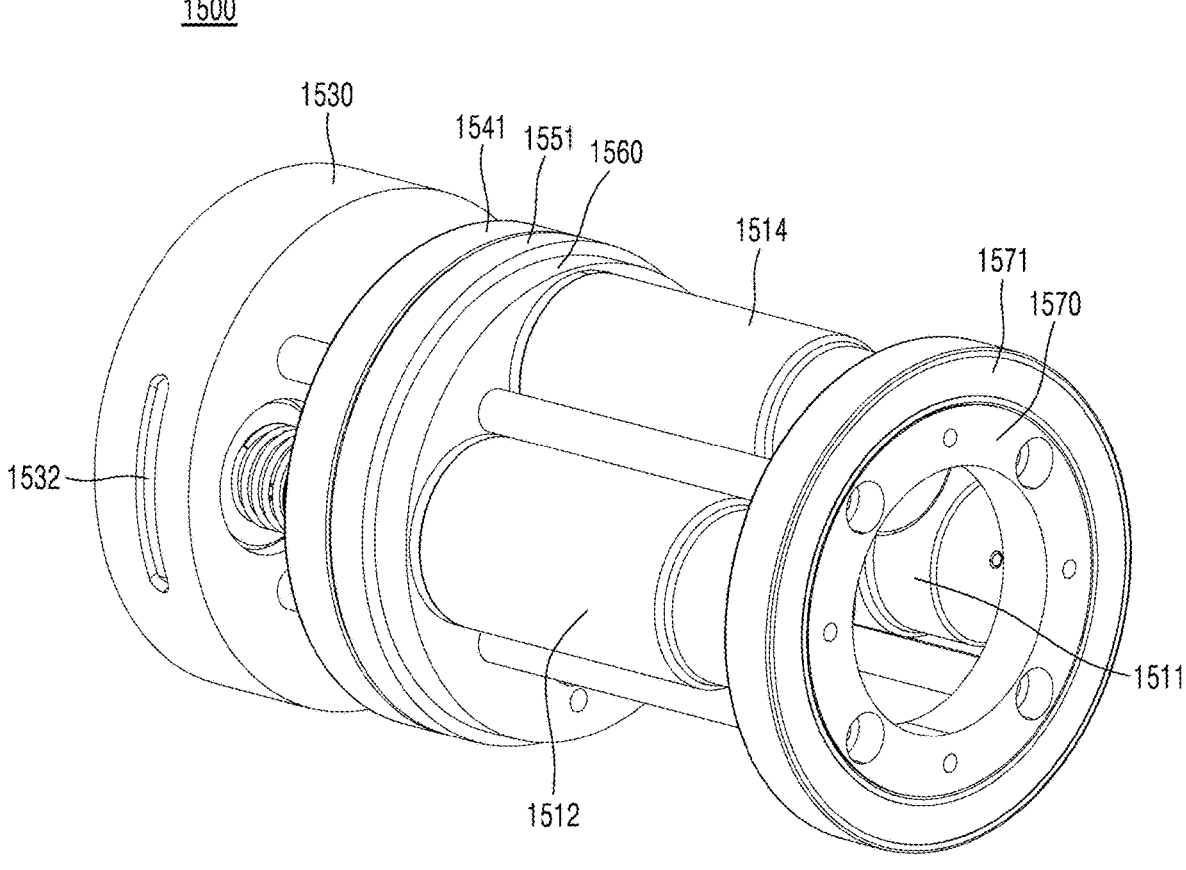
FIG. 10 is a view illustrating the power generation part of FIG. 9 as viewed from the rear side.
Figure 11:
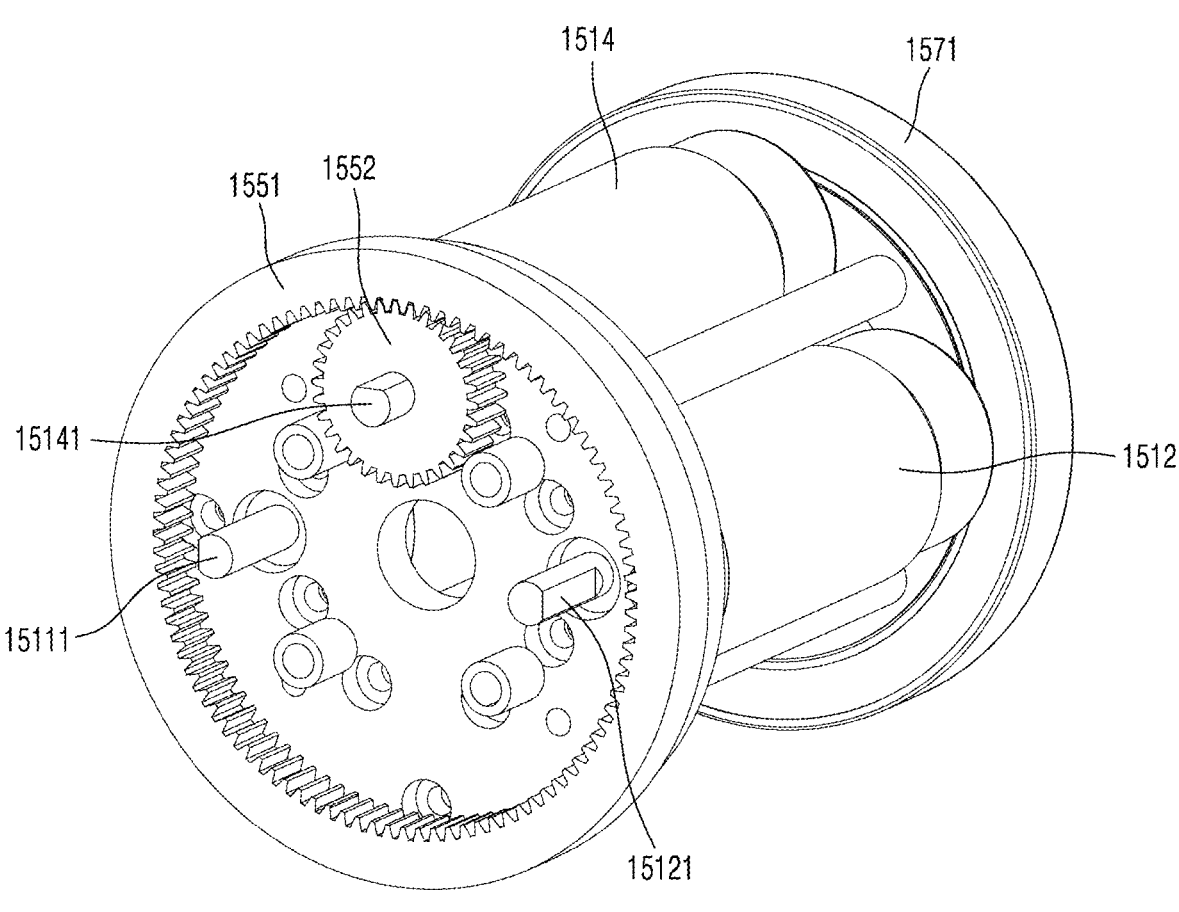
FIG. 11 is a view for describing a gear structure of the power generation part of FIG. 9.
Figure 12:
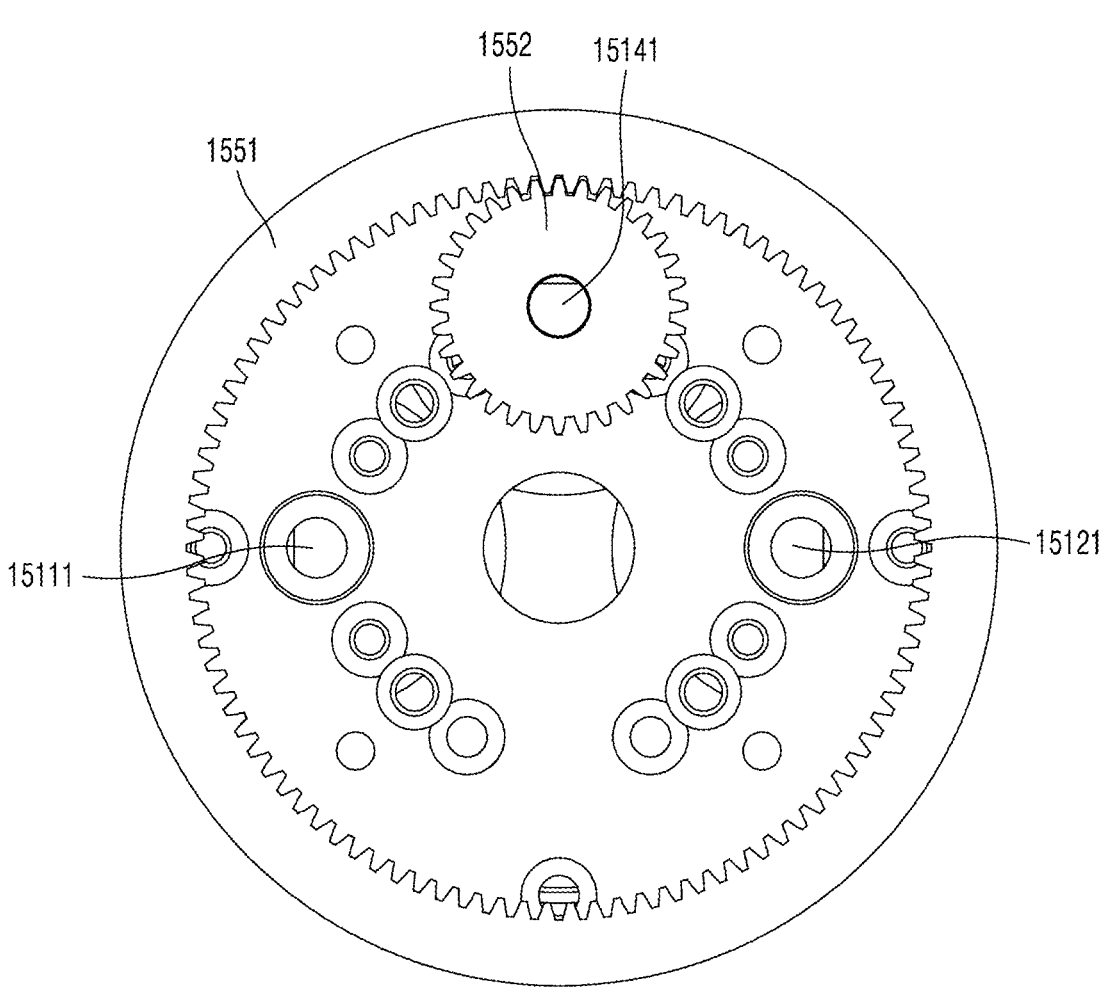
FIG. 12 is a front view of FIG. 11.
Figure 13:
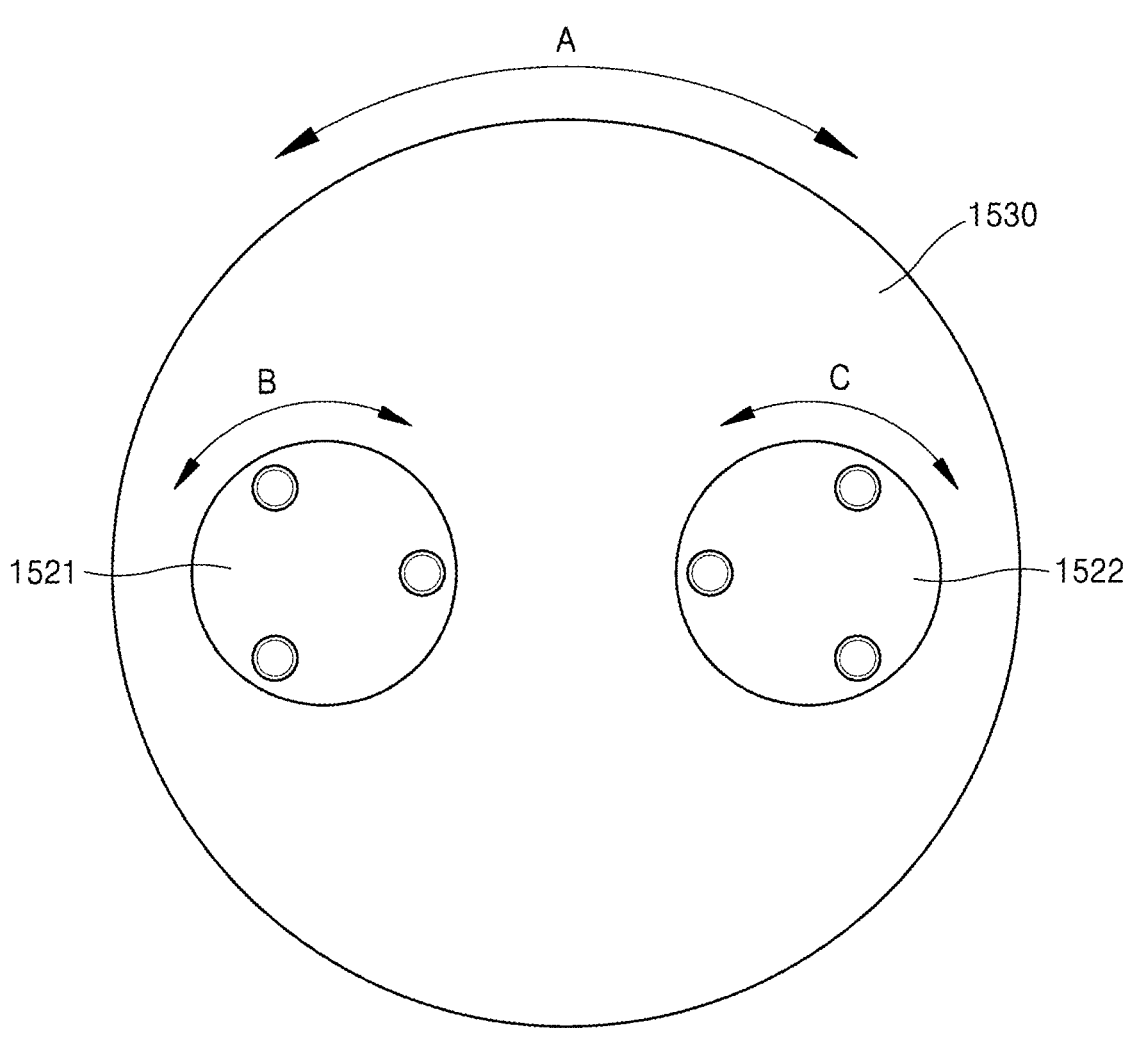
FIG. 13 is a view for describing rotation of the power generation part of FIG. 9.

FIG. 8 is a view illustrating the manipulation part and the power generation part according to an embodiment of the present disclosure, FIG. 9 is a perspective view illustrating the power generation part of FIG. 8, and FIG. 10 is a view illustrating the power generation part of FIG. 9 as viewed from the rear side. FIG. 11 is a view for describing a gear structure of the power generation part of FIG. 9, FIG. 12 is a front view of FIG. 11, and FIG. 13 is a view for describing rotation of the power generation part of FIG. 9.

Referring to FIGS. 8 to 13, the surgical instrument 1000 according to an embodiment of the present disclosure may include a power generation part 1500 configured to generate power to control the end tool 1100.

The power generation part 1500 may be disposed to be at least partially accommodated in the housing 1201 of the manipulation part 1200.

When a user manipulates the manipulation part 1200, the power generation part 1500 may generate power to control the end tool 1100 based on the manipulation.

The power generation part 1500 may include a motor pack including at least one motor.

The motor pack 1510 may roll-rotate in a direction in which the connection part 1400 extends.

Here, a roll motion as used herein is defined as follows.

A roll motion refers to a motion in which the end tool 1100, the connection part 1400, the motor pack 1510, and the like, which constitute the surgical instrument 1000, rotate around an axis formed in the direction in which a connection part 1400 extends. In other words, the roll motion refers to a motion of rotating around an axis formed in an extension direction (the X-axis direction in FIG. 3) of the connection part 1400 without bending in a Y-axis direction of FIG. 3 or a Z-axis direction of FIG. 3.

Referring to FIG. 8 again, at least a portion of the power generation part 1500 may be accommodated in the housing 1201 of the manipulation part 1200. In this case, the motor pack 1510 is accommodated in the housing 1201 of the manipulation part 1200. Here, the phrase "the motor pack 1510 roll-rotates" may mean that the motor pack 1510 rotates inside the housing 1201 along an inner circumferential surface of the housing 1201. In other words, when a user performs a manipulation to roll-rotate the manipulation part 1200 while grasping the handle 1202 of the manipulation part 1200, the motor pack 1510 may rotate around the axis, which is formed in the direction in which the connection part 1400 extends, inside the housing 1201 while the housing 1201 and the handle 1202 of the manipulation part 1200 are fixed in place. In other words, it may be said that the housing 1201 and the handle 1202 rotate when the user performs a manipulation for a roll motion while grasping connection part 1400.

The motor pack 1510 may include at least one motor.

The motor pack 1510 may include a yaw drive motor 1511. The yaw drive motor 1511 may generate power to yaw-rotate the end tool 1100. For example, when a user manipulates the manipulation part 1200 to yaw-rotate the end tool 1100, the yaw drive motor 1511 may generate a driving force to yaw-rotate the end tool 1100.

The driving force generated by the yaw drive motor 1511 may be transmitted to the power transmission part 1300 to rotate the yaw pulley 1320, and as the yaw wires 1361 and 1362 are moved by the rotation of the yaw pulley 1320, the end tool 1100 may yaw-rotate.

The yaw drive motor 1511 may include a yaw motor rotation shaft 15111 formed to extend in one direction. The yaw motor rotation shaft 15111 is a part that rotates when the yaw drive motor 1511 starts driving. For example, the yaw motor rotation shaft 15111 may be formed to extend in a direction toward the power transmission part 1300 from a body of the yaw drive motor 1511. As will be described later, a yaw motor plate 1521 may be disposed at one end of the yaw motor rotation shaft 15111, and the yaw motor plate 1521 may rotate together with the yaw motor rotation shaft 15111 when the yaw motor rotation shaft 15111 rotates. The yaw motor plate 1521 may be connected to the yaw pulley 1320, and the driving force may be transmitted to the yaw pulley 1320 as the yaw motor plate 1521 rotates.

The motor pack 1510 may include a pitch drive motor 1512. The pitch drive motor 1512 may generate power to pitch-rotate the end tool 1100. For example, the pitch drive motor 1512 may generate a driving force to pitch-rotate the end tool 1100 when a user manipulates the manipulation part 1200 to pitch-rotate the end tool 1100.

The driving force generated by the pitch drive motor 1512 may be transmitted to the power transmission part 1300 to rotate the pitch pulley 1330, and as the pitch wires 1363 and 1364 are moved by the rotation of the pitch pulley 1330, the end tool 1100 may pitch-rotate.

The pitch drive motor 1512 may include a pitch motor rotation shaft 15121 formed to extend in one direction. The pitch motor rotation shaft 15121 is a part that rotates when the pitch drive motor 1512 starts driving. For example, the pitch motor rotation shaft 15121 may be formed to extend in a direction toward the power transmission part 1300 from a body of the pitch drive motor 1512. As will be described later, a pitch motor plate 1522 may be disposed at one end of the pitch motor rotation shaft 15121, and the pitch motor plate 1522 may rotate together with the pitch motor rotation shaft 15121 when the pitch motor rotation shaft 15121 rotates. The pitch motor plate 1522 may be connected to the pitch pulley 1330, and as the pitch motor plate 1522 rotates, the driving force may be transmitted to the pitch pulley 1330.

The motor pack 1510 may include a roll drive motor 1514. The roll drive motor 1514 may generate power to roll-rotate the motor pack 1510. For example, the roll drive motor 1514 may generate a driving force to roll-rotate the motor pack 1510 when a user manipulates the manipulation part 1200 to rotate the motor pack 1510.

The motor pack 1510 may include a base plate 1560. The base plate 1560 may be disposed in front of the yaw drive motor 1511, the pitch drive motor 1512, and the roll drive motor 1514. The base plate 1560 may be connected to the roll drive motor 1514, the yaw drive motor 1511, and the pitch drive motor 1512. In other words, it may be said that the roll drive motor 1514, the yaw drive motor 1511, and the pitch drive motor 1512 are connected to the base plate 1560. In other words, the base plate 1560 may connect the roll drive motor 1514, the yaw drive motor 1511, and the pitch drive motor 1512 to each other such that the roll drive motor 1514, the yaw drive motor 1511, and the pitch drive motor 1512 move or rotate together as one body.

Thus, when the base plate 1560 rotates due to the driving force of the roll drive motor 1514, the roll drive motor 1514, the yaw drive motor 1511, and the pitch drive motor 1512 connected to the base plate 1560 may rotate simultaneously. That is, when the roll drive motor 1514 is driven, the base plate 1560 is rotated, and when the base plate 1560 rotates, the roll drive motor 1514, the yaw drive motor 1511, and the pitch drive motor 1512 connected to the base plate 1560 are rotated together with the base plate 1560. Here, since the base plate 1560 rotates around the axis formed in the direction in which the connection part 1400 extends, the motor pack 1510 including the base plate 1560, the roll drive motor 1514, the yaw drive motor 1511, and the pitch drive motor 1512 roll-rotates around the axis formed in the direction in which the connection part 1400 extends.

In an embodiment, the roll drive motor 1514, the yaw drive motor 1511, and the pitch drive motor 1512 may be disposed parallel to each other. In addition, the roll drive motor 1514, the yaw drive motor 1511, and the pitch drive motor 1512 may be disposed to form a circular pattern.

As described above, the motor pack 1510 may roll-rotate inside the housing 1201 of the manipulation part 1200. In this case, since the motor pack 1510 includes a plurality of motors, by disposing the roll drive motor 1514, the yaw drive motor 1511, and the pitch drive motor 1512 to form a circular pattern with each other, when the motor pack 1510 rotates, a diameter of a space occupied by the rotation of the motor pack 1510 may be minimized. That is, by disposing the roll drive motor 1514, the yaw drive motor 1511, and the pitch drive motor 1512 to form a circular pattern, an inner diameter inside the housing 1201 necessary for the rotation of the motor pack 1510 may be designed to be small, which may contribute to miniaturization and lightweighting of the surgical instrument 1000.

Meanwhile, disposing the roll drive motor 1514, the yaw drive motor 1511, and the pitch drive motor 1512 to form a circular pattern does not mean that the roll drive motor 1514, the yaw drive motor 1511, and the pitch drive motor 1512 are disposed to be equally spaced from each other, but rather it is sufficient when outer circumferential surfaces of the roll drive motor 1514, the yaw drive motor 1511, and the pitch drive motor 1512 are disposed within a single circle.

In an embodiment, the roll drive motor 1514, the yaw drive motor 1511, and the pitch drive motor 1512 may be provided to have different performance. For example, the magnitudes of driving forces that the roll drive motor 1514, yaw drive motor 1511, and pitch drive motor 1512 must generate to perform their respective roles may be different from each other. To this end, the roll drive motor 1514, the yaw drive motor 1511, and the pitch drive motor 1512 may have different outputs or sizes as necessary.

At least one through hole may be formed in the base plate 1560. For example, the base plate 1560 may have at least one corresponding through hole for each motor included in the motor pack 1510. The through hole is a part through which the rotation shaft of each motor passes.

For example, the yaw motor rotation shaft 15111 extends from the body of the yaw drive motor 1511, and may be formed to extend through the base plate 1560 (or through the through hole). In addition, the pitch motor rotation shaft 15121 extends from the body of the pitch drive motor 1512, and may be formed to extend through the base plate 1560 (or through the through hole).

Meanwhile, the roll drive motor 1514 may include a roll motor rotation shaft 15141 formed to extend in one direction. The roll motor rotation shaft 15141 is a part that rotates when the roll drive motor 1514 starts driving. For example, the roll motor rotation shaft 15141 may be formed to extend in a forward-facing direction from a body of the roll drive motor 1514. That is, the roll motor rotation shaft 15141 extends forward from the body of the roll drive motor 1514, and may be formed to extend through the base plate 1560.

Hereinafter, the principle of rotation of the motor pack 1510 will be described in detail. Referring to FIGS. 11 and 12, the power generation part 1500 may include a first gear 1551 formed in the shape of a circle and a second gear 1552 engaged with the first gear 1551.

The first gear 1551 may be formed in the shape of a hollow circle, and gear teeth may be formed on an inner circumferential surface of the circle. That is, the first gear 1551 may be a kind of ring gear with gear teeth formed on an inner circumferential surface thereof.

The second gear 1552 is a gear having gear teeth formed on an outer circumferential surface thereof, and may be engaged with the first gear 1551. The second gear 1552 may be disposed on the roll motor rotation shaft 15141. That is, the roll motor rotation shaft 15141 is formed to extend forward to pass through the base plate 1560 from the body of the roll drive motor 1514, and the second gear 1552 may be disposed in the extending portion of the roll motor rotation shaft 15141. In this case, the second gear 1552 is coupled to the roll motor rotation shaft 15141, and the second gear 1552 may rotate together with the roll motor rotation shaft 15141 when the roll motor rotation shaft 15141 rotates.

The first gear 1551 may be disposed in front of the base plate 1560. In addition, the first gear 1551 may be fixed to the inner circumferential surface of the housing 1201. Accordingly, when the roll drive motor 1514 is driven, the motor pack 1510 may roll-rotate inside the housing 1201.

Specifically, when the roll drive motor 1514 is driven, the roll motor rotation shaft 15141 may rotate, and the second gear 1552 disposed on the roll motor rotation shaft 15141 may rotate together with the roll motor rotation shaft 15141. In this case, since the first gear 1551 engaged with the second gear 1552 is fixed to the inner circumferential surface of the housing 1201, when the second gear 1552 rotates, the second gear 1552 moves along the gear teeth of the first gear 1551. That is, when the roll drive motor 1514 starts driving, the first gear 1551 and the second gear 1552 rotate with respect to each other, and in this case, since the first gear 1551 is fixed to the housing 1201, the second gear 1552 relatively moves along the first gear 1551. In addition, the second gear 1552 is connected to the roll motor rotation shaft 15141, the roll drive motor 1514 is connected to the base plate 1560, and the base plate 1560 is connected to the yaw drive motor 1511 and the pitch drive motor 1512. Accordingly, the motor pack 1510 may rotate with respect to the housing 1201 by the operation of the first gear 1551 and the second gear 1552.

More specifically, the base plate 1560 may rotate with respect to the housing 1201. That is, since the second gear 1552 is connected to the base plate 1560 by the roll motor rotation shaft 15141, when the second gear 1552 moves, the base plate 1560 rotates with respect to the housing 1201 as the second gear 1552 moves along the first gear 1551. Here, since the roll motor rotation shaft 15141 is eccentric with respect to the rotation shaft of the base plate 1560, when the second gear 1552 moves along the first gear 1551, the base plate 1560 may rotate with respect to the housing 1201, rather than change in position along the second gear 1552.

Meanwhile, as will be described later, a bearing plate 1540 may be similarly connected to the second gear 1552 by the roll motor rotation shaft 15141. Thus, when the second gear 1552 rotates, the bearing plate 1540 may rotate with respect to the housing 1201 as the second gear 1552 moves along the first gear 1551. In this case, as will be described later, a first bearing 1541 may be disposed to be in contact with the inner circumferential surface of the housing 1201, coaxially with the bearing plate 1540, to reduce rotational friction of the bearing plate 1540. Accordingly, the bearing plate 1540 may be easily rotated.

Meanwhile, the gear teeth of the first gear 1551 and the second gear 1552 are illustrated in the drawings as spur gears, but the present disclosure is not limited thereto, and it is of course possible that the gear teeth may have various shapes such as a helical gear, a herringbone gear, and the like.

In an embodiment, the power generation part 1500 may further include the bearing plate 1540 and the first bearing 1541. The bearing plate 1540 and the first bearing 1541 may reduce rotational friction between the motor pack 1510 and the housing 1201 when the motor pack 1510 roll-rotates.

The bearing plate 1540 may be disposed in front of the first gear 1551.

At least one or more through holes may be formed in the bearing plate 1540. The through holes are parts through which the rotation shafts of each motor pass.

For example, the yaw motor rotation shaft 15111 may be formed to extend from the body of the yaw drive motor 1511 to pass through the base plate 1560 and the bearing plate 1540. In addition, the pitch motor rotation shaft 15121 may be formed to extend from the body of the pitch drive motor 1512 to pass through the base plate 1560 and the bearing plate 1540. In this case, the roll motor rotation shaft 15141 is formed to extend from the body of the roll drive motor 1514 to pass through the base plate 1560, but may not extend to the bearing plate 1540.

As such, since the yaw motor rotation shaft 15111 and the pitch motor rotation shaft 15121 are formed to extend through the bearing plate 1540, when the motor pack 1510 rotates, the base plate 1560 and the bearing plate 1540 may rotate together.

The first bearing 1541 may be disposed on an outer circumferential surface of the bearing plate 1540. For example, the first bearing 1541 may be disposed to cover the outer circumferential surface of the bearing plate 1540. Thus, when the motor pack 1510 roll-rotates, the bearing plate 1540 rotates together with the motor pack 1510, and in this case, the bearing plate 1540 and the first bearing 1541 may reduce the rotational friction between the motor pack 1510 and the housing 1201.

In an embodiment, the power generation part 1500 may further include a circuit plate 1570 and a second bearing 1571. The circuit plate 1570 and the second bearing 1571 may reduce the rotational friction between the motor pack 1510 and the housing 1201 when the motor pack 1510 roll-rotates.

The circuit plate 1570 may be disposed at the rear of the motor pack 1510.

As will be described later, the circuit plate 1570 is a part to which the circuit unit is connected.

The circuit plate 1570 is connected to the motor pack 1510, and may rotate together with the motor pack 1510 when the motor pack 1510 rotates.

A second bearing 1571 may be disposed on an outer circumferential surface of the circuit plate 1570. Thus, when the motor pack 1510 roll-rotates, the circuit plate 1570 rotates together with the motor pack 1510, and in this case, the circuit plate 1570 and the second bearing 1571 may reduce the rotational friction between the motor pack 1510 and the housing 1201.

The power generation part 1500 may further include a pulley coupling plate 1530.

The pulley coupling plate 1530 is a part to which the power transmission part 1300 is connected.

In an embodiment, the power transmission part 1300 may be detachably fastened to the power generation part 1500. For example, the power transmission part 1300 may be detachably fastened to the pulley coupling plate 1530. Thus, after using components (such as, the power transmission part 1300, the connection part 1400, and the end tool 1100) in a direction from the power transmission part 1300 toward the distal end, the user may discard these components and connect new products for these components to the manipulation part 1200, which accommodates the power generation part 1500, to use the surgical instrument 1000.

In an embodiment, at least one coupling member 1316 may be formed in the pulley frame 1310 of the power transmission part 1300 (See FIG. 6). A hook 13161 may be formed in the coupling member 1316. In addition, the pulley coupling plate 1530 may include an internal space for accommodating at least a portion of the pulley frame 1310, and a wall surface formed along a circumference of the pulley coupling plate 1530 to define the internal space. At this time, a hook groove 1532 to which the hook 13161 is caught and fixed may be formed in the wall surface. Thus, when the pulley frame 1310 is inserted into the internal space of the pulley coupling plate 1530, the hook 13161 may be inserted into the hook groove 1532 and coupled and fixed thereto.

In an embodiment, the pulley coupling plate 1530 may include a coupling block 1531 that is formed to protrude, and the pulley frame 1310 may include an insertion groove formed to allow the coupling block 1531 to be inserted therein. Thus, when the pulley coupling plate 1530 is coupled to the pulley frame 1310, the coupling block 1531 is inserted into the insertion groove, so that the pulley coupling plate 1530 and the pulley frame 1310 may be coupled to each other at a predetermined position. In addition, since the coupling block 1531 is inserted into the insertion groove, a roll rotational force of the pulley coupling plate 1530 may be transmitted to the pulley frame 1310 by the coupling block 1531 and the insertion groove. In an optional embodiment, the coupling block 1531 may be formed in the shape of an elongated bar, and in this case, the insertion groove may be formed in a shape corresponding thereto.

In an embodiment, although not shown in the drawings, the surgical instrument 1000 according to the present disclosure may further include a waterproof structure.

As a specific embodiment, at least one O-ring may be provided inside the housing 1201.

For example, a first O-ring may be provided between the housing 1201 and an outer circumferential surface of the pulley coupling plate 1530. The first O-ring is disposed between the outer circumferential surface of the pulley coupling plate 1530 and the housing 1201 to be in close contact therewith, thereby preventing water or the like from penetrating between the power generation part 1500 and the housing 1201.

As another example, a second O-ring may be provided at least one of between the yaw motor plate 1521 and the pulley coupling plate 1530 and between the pitch motor plate 1522 and the pulley coupling plate 1530. The second O-ring is disposed between the yaw or pitch motor plate 1521 or 1522 and the pulley coupling plate 1530 to be in close contact therewith, thereby preventing water or the like from penetrating between the yaw or pitch motor plate 1521 or 1522 and the pulley coupling plate 1530.

In an embodiment, the pulley coupling plate 1530 may be fastened to the bearing plate 1540 by at least one bolt. In this case, a bolt hole into which the bolt is inserted may have at least one seal washer disposed below the bolt. The seal washer may prevent water or the like from penetrating through the bolt hole.

At least one or more through holes may be formed in the pulley coupling plate 1530. For example, two through holes may be formed in the pulley coupling plate 1530.

The yaw motor plate 1521 and the pitch motor plate 1522 may be disposed in the through hole formed in the pulley coupling plate 1530.

The yaw motor plate 1521 may be rotated by a driving force generated from the yaw drive motor 1511. The yaw motor plate 1521 may be disposed at one end of the yaw motor rotation shaft 15111. For example, when the yaw motor rotation shaft 15111 rotates, the yaw motor plate 1521 may rotate together therewith. In other words, the yaw motor plate 1521 may be referred to as a member that transmits the driving force generated from the yaw drive motor 1511 to the power transmission part 1300.

At least one first protrusion 15211 may be formed on the yaw motor plate 1521. The first protrusion 15211 is a part that protrudes outward from the yaw motor plate 1521. As will be described later, the first protrusion 15211 may be inserted into a first insertion hole 13131 formed in a yaw pulley plate 1313 (See FIG. 6).

The pitch motor plate 1522 may be rotated by a driving force generated from the pitch drive motor 1512. The pitch motor plate 1522 may be disposed at one end of the pitch motor rotation shaft 15121. For example, when the pitch motor rotation shaft 15121 rotates, the pitch motor plate 1522 may rotate together therewith. In other words, the pitch motor plate 1522 may be referred to as a member that transmits the driving force generated from the pitch drive motor 1512 to the power transmission part 1300.

At least one second protrusion 15221 may be formed in the pitch motor plate 1522. The second protrusion 15221 is a part that protrudes outward from the pitch motor plate 1522. As will be described later, the second protrusion 15221 may be inserted into a second insertion hole 13141 formed in a pitch pulley plate 1314 (See FIG. 6).

The yaw pulley plate 1313 and the pitch pulley plate 1314 may be disposed on the pulley frame 1310.

The yaw pulley plate 1313 may be formed to be rotatable. Specifically, the yaw pulley plate 1313 may be fastened to the yaw motor plate 1521 and may rotate together with the yaw motor plate 1521 when the yaw motor plate 1521 rotates. The yaw pulley plate 1313 is a part connected to the yaw pulley 1320, and when the yaw pulley plate 1313 rotates, the yaw pulley 1320 may rotate together with the yaw pulley plate 1313. In other words, when power transmitted from the outside causes the yaw pulley plate 1313 to rotate, the yaw pulley 1320 may rotate together with the yaw pulley plate 1313. In other words, the yaw pulley plate 1313 may be referred to as a part that receives a driving force generated from the yaw drive motor 1511 and transmits the driving force to the yaw pulley 1320.

The yaw pulley plate 1313 may include at least one first insertion hole 13131. The first insertion hole 13131 is a part into which the first protrusion 15211 of the yaw motor plate 1521 is inserted. As described above, the yaw motor plate 1521 and the yaw pulley plate 1313 may be stably coupled to each other by the coupling of the at least one first protrusion 15211 and the at least one first insertion hole 13131, and the driving force of the yaw drive motor 1511 may be efficiently transmitted to the yaw pulley 1320.

The pitch pulley plate 1314 may be formed to be rotatable. Specifically, the pitch pulley plate 1314 may be fastened to the pitch motor plate 1522, and may rotate together with the pitch motor plate 1522 when the pitch motor plate 1522 rotates. The pitch pulley plate 1314 is a part connected to the pitch pulley 1330, and when the pitch pulley plate 1314 rotates, the pitch pulley 1330 may rotate together with the pitch pulley plate 1314. In other words, when power transmitted from the outside causes the pitch pulley plate 1314 to rotate, the pitch pulley 1330 may rotate together with the pitch pulley plate 1314. In other words, the pitch pulley plate 1314 may be referred to as a part that receives a driving force generated from the pitch drive motor 1512 and transmits the driving force to the pitch pulley 1330.

The pitch pulley plate 1314 may include at least one second insertion hole 13141. The second insertion hole 13141 is a part into which the second protrusion 15221 of the pitch motor plate 1522 is inserted. As such, the pitch motor plate 1522 and the pitch pulley plate 1314 may be stably coupled to each other by the coupling of the at least one second protrusion 15221 and the at least one second insertion hole 13141, and the driving force of the pitch drive motor 1512 may be efficiently transmitted to the pitch pulley 1330.

In an embodiment, the yaw drive motor 1511, the pitch drive motor 1512, and the roll drive motor 1514 may be driven independently of each other. Accordingly, the yaw drive motor 1511, the pitch drive motor 1512, and the roll drive motor 1514 may independently perform a yaw rotation of the end tool 1100, a pitch rotation of the end tool 1100, and a roll rotation of the motor pack 1510.

When further describing with reference to FIG. 13 again, as the roll drive motor 1514 is driven, the pulley coupling plate 1530 may rotate in an A direction. At this time, the yaw drive motor 1511 may be driven independently, and thus may rotate the yaw motor plate 1521 in a B direction by being independently driven regardless of the driving of the roll drive motor 1514. In addition, the pitch drive motor 1512 may be driven independently, and thus may rotate the pitch motor plate 1522 in a C direction by being independently driven regardless of the driving of the roll drive motor 1514 and the yaw drive motor 1511. In other words, the end tool 1100 may perform any one of a pitch rotation, a yaw rotation, and a roll rotation, and may also perform all of the rotations simultaneously.

Figure 14:
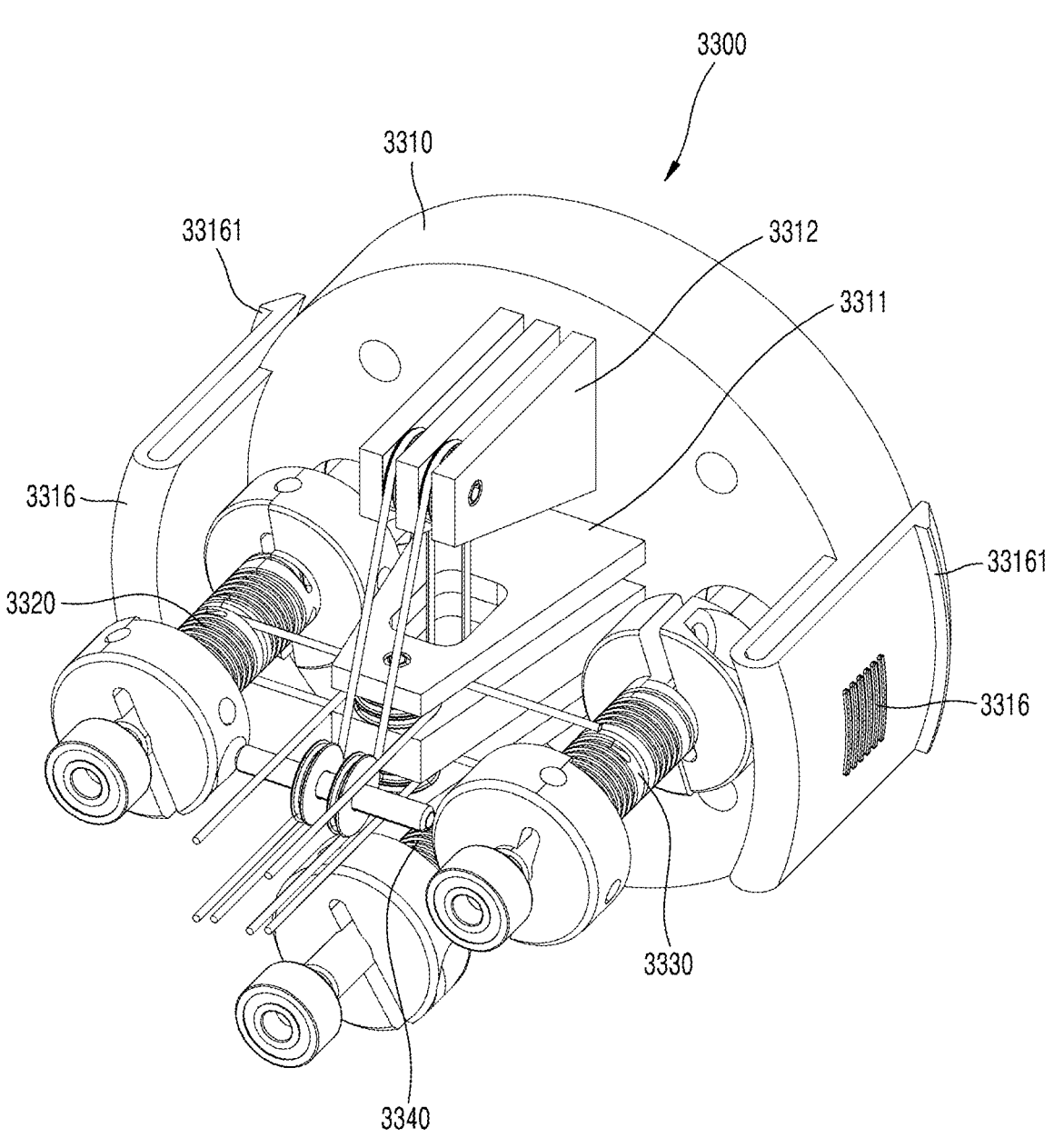
FIG. 14 is a view for describing an internal structure of a power transmission part according to another embodiment of the present disclosure.
Figure 15:
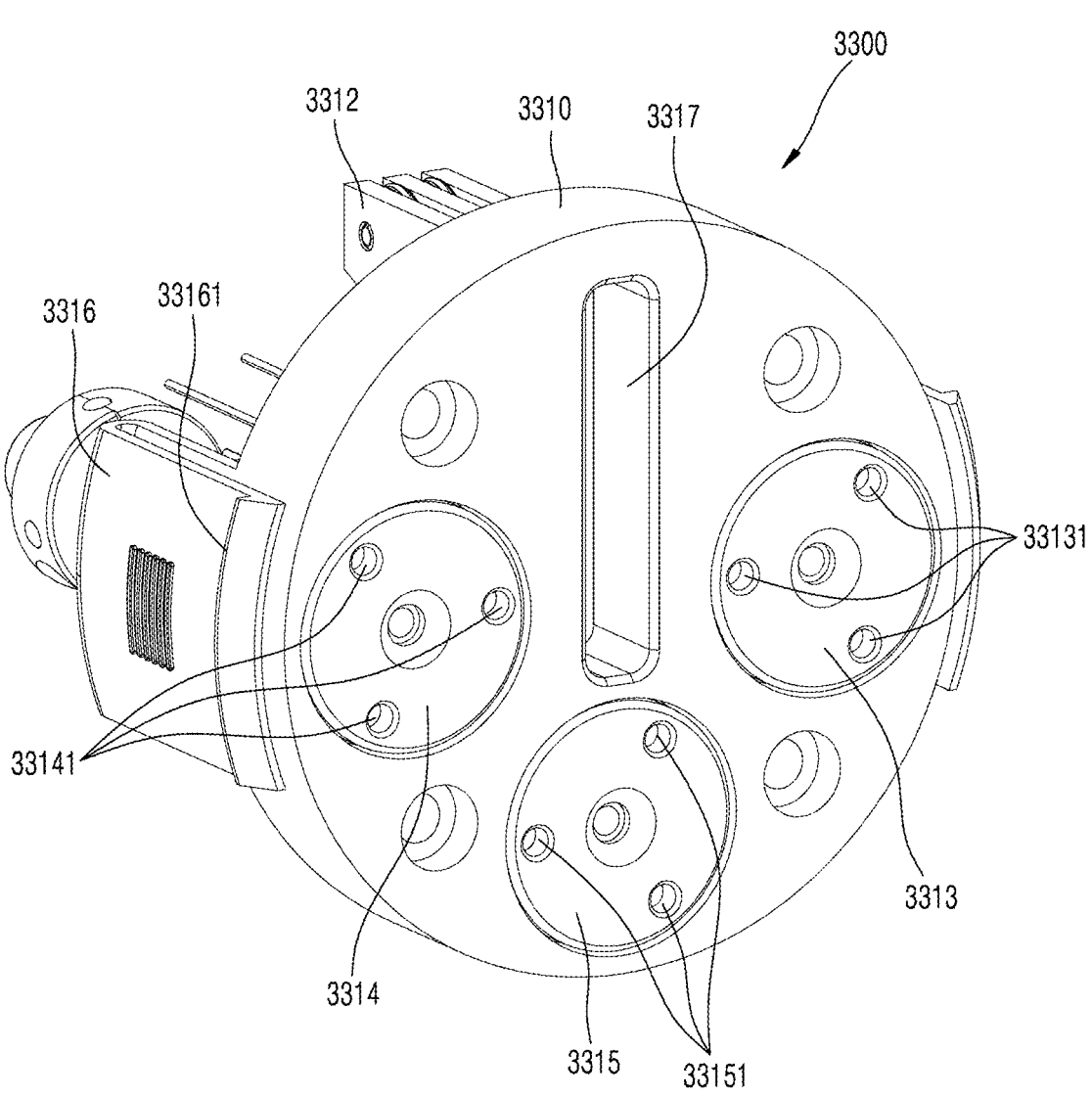
FIG. 15 is a rear view of the power transmission part of FIG. 14.
Figure 16:
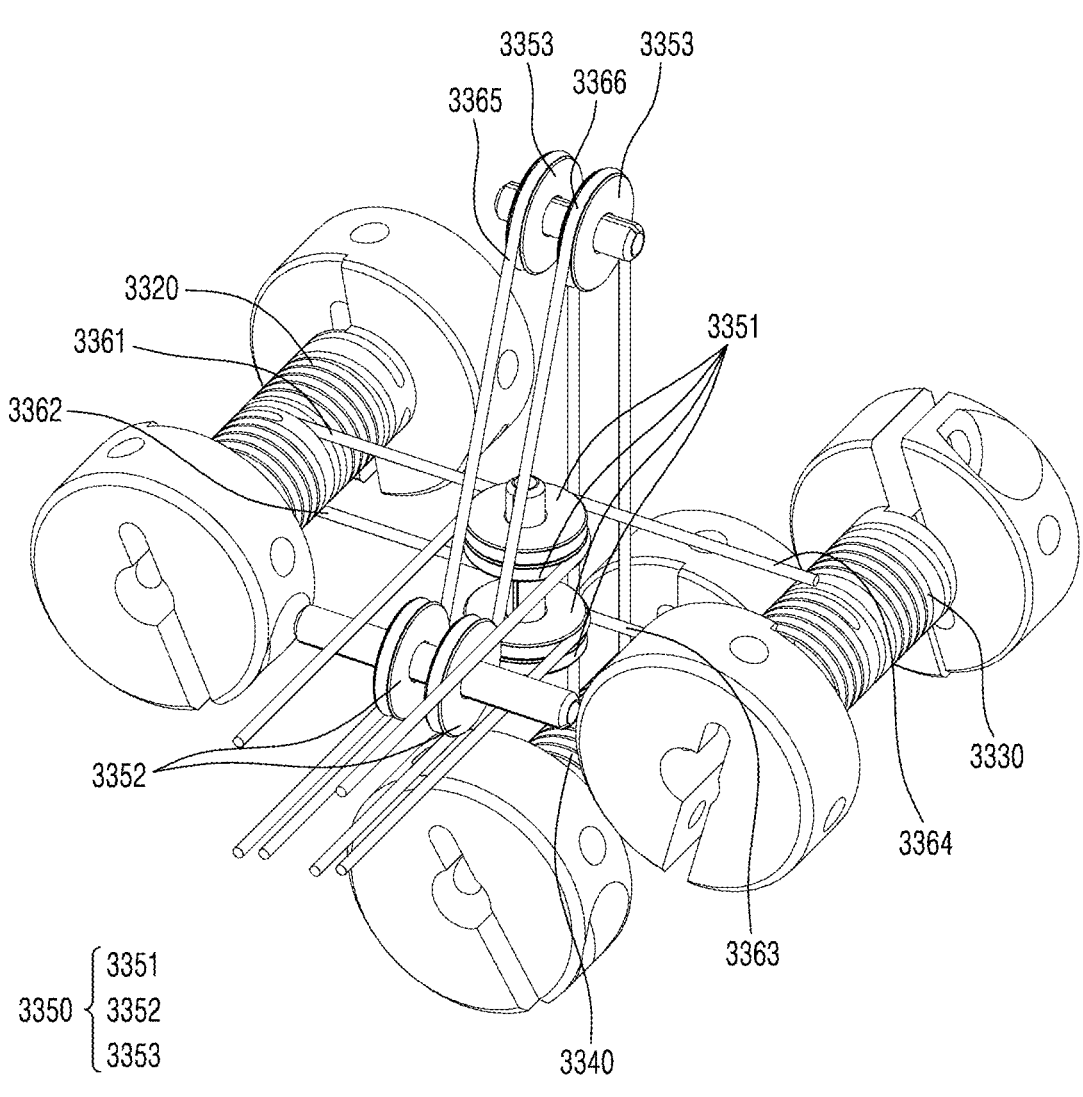
FIG. 16 is a view for describing the arrangement of pulleys and wires of the power transmission part of FIG. 14.

FIG. 14 is a view for describing an internal structure of a power transmission part according to another embodiment of the present disclosure, FIG. 15 is a rear view of the power transmission part of FIG. 14, and FIG. 16 is a view for describing the arrangement of pulleys and wires of the power transmission part of FIG. 14.

Referring to FIGS. 14 to 16, a power transmission part 3300 according to an embodiment of the present disclosure may include a pulley frame 3310, at least one pulley, and at least one wire.

The pulley frame 3310 may form the overall framework of the power transmission part 3300.

At least one pulley may be disposed in the pulley frame 3310. Here, disposing a pulley should be interpreted in a broad sense. For example, disposing a pulley may mean connecting the pulley directly to the pulley frame 3310, or may also mean installing a rotation shaft in the pulley frame 3310 and connecting the pulley to the rotation shaft. Alternatively, disposing a pulley may also mean proving a separate member in the pulley frame 3310, connecting a rotation shaft to the separate member, and connecting the pulley to the rotation shaft. Alternatively, disposing a pulley may also mean forming a hole in the pulley frame 3310, disposing a rotation shaft to pass through the hole, and installing the pulley on the rotation shaft.

The power transmission part 3300 may include at least one pulley.

The pulley is a member around which a wire is wound, and a groove around which a wire may be wound may be formed in the pulley.

In an embodiment, the power transmission part 3300 may include a yaw pulley 3320, a pitch pulley 3330, and a firing pulley 3340. In addition, the power transmission part 3300 may include at least one or more yaw wires 3361 and 3362, at least one or more pitch wires 3363 and 3364, and at least one or more firing wires 3365 and 3366.

The yaw pulley 3320 is a pulley associated with a yaw rotation of the end tool, and the yaw wires 3361 and 3362 are wires associated with the yaw rotation of the end tool.

The yaw pulley 3320 may be disposed in one region of the pulley frame 3310.

The yaw wires 3361 and 3362 may be wires extending toward the yaw pulley 3320 from a pulley disposed in the end tool and associated with a yaw rotation of the end tool.

In an embodiment, the yaw wires 3361 and 3362 may be provided in a pair. As will be described later, the yaw wires 3361 and 3362 may be connected to upper and lower sides of the yaw pulley 3320, respectively.

As a specific embodiment, the yaw wires 3361 and 3362 may include a first yaw wire 3361 and a second yaw wire 3362. The first yaw wire 3361 may extend to the upper side of the yaw pulley 3320 based on FIG. 16 to be connected to the yaw pulley 3320. The second yaw wire 3362 may extend to the lower side of the yaw pulley 3320 based on FIG. 16 to be connected to the yaw pulley 3320.

The yaw wires 3361 and 3362 may be connected to the yaw pulley 3320, and then, may be wound around the yaw pulley 3320 or unwound therefrom when the yaw pulley 3320 rotates. That is, when the yaw pulley 3320 rotates in one direction, one yaw wire is wound around the yaw pulley 3320, and another yaw wire is unwound from the yaw pulley 3320. For example, when the yaw pulley 3320 rotates in a clockwise direction based on FIG. 16, the first yaw wire 3361 is unwound from the yaw pulley 3320, and the second yaw wire 3362 is wound around the yaw pulley 3320. On the contrary, when the yaw pulley 3320 rotates in a counterclockwise direction based on FIG. 16, the first yaw wire 3361 is wound around the yaw pulley 3320, and the second yaw wire 3362 is unwound from the yaw pulley 3320.

In other words, it may be said that, when the yaw pulley 3320 rotates, the pair of yaw wires 3361 and 3362 may move in opposite directions to each other with respect to the yaw pulley 3320.

As described above, when the yaw pulley 3320 rotates to move the pair of yaw wires 3361 and 3362 in different directions, the pulley on the end tool side, which is connected to the yaw wires 3361 and 3362, is rotated in a direction corresponding thereto. Thus, as the pulley on the end tool side, which is connected to the yaw wires 3361 and 3362, rotates in one direction, a yaw rotation of the end tool may be implemented.

The pitch pulley 3330 is a pulley associated with a pitch rotation of the end tool, and the pitch wires 3363 and 3364 are wires associated with the pitch rotation of the end tool.

The pitch pulley 3330 may be disposed in one region of the pulley frame 3310.

In an embodiment, the pitch pulley 3330 may be disposed on the opposite side of the yaw pulley 3320. In an exemplary embodiment, the pitch pulley 3330 and the yaw pulley 3320 may be symmetrically disposed on both sides of the center of the pulley frame 3310. Accordingly, as will be described later, the yaw wires 3361 and 3362 and the pitch wires 3363 and 3364, which extend via auxiliary pulleys 3350, may approach the yaw pulley 3320 and the pitch pulley 3330 to be nearly perpendicular thereto.

The pitch wires 3363 and 3364 may extend toward the pitch pulley 3330 from a pulley disposed in the end tool and associated with a pitch rotation of the end tool.

In an embodiment, the pitch wires 3363 and 3364 may be provided in a pair. As will be described later, the pitch wires 3363 and 3364 may be connected to upper and lower sides of the pitch pulley 3330, respectively.

As a specific embodiment, the pitch wires 3363 and 3364 may include a first pitch wire 3363 and a second pitch wire 3364. The first pitch wire 3363 may extend to the lower side of the pitch pulley 3330 based on FIG. 16 to be connected to the pitch pulley 3330. The second pitch wire 3364 may extend to the upper side of the pitch pulley 3330 based on FIG. 16 to be connected to the pitch pulley 3330.

The pitch wires 3363 and 3364 may be connected to the pitch pulley 3330, and then may be wound around the pitch pulley 3330 or unwound therefrom when the pitch pulley 3330 rotates. That is, when the pitch pulley 3330 rotates in one direction, one pitch wire is wound around the pitch pulley 3330, and another pitch wire is unwound from the pitch pulley 3330. For example, when the pitch pulley 3330 rotates in the clockwise direction based on FIG. 16, the first pitch wire 3363 is unwound from the pitch pulley 3330, and the second pitch wire 3364 is wound around the pitch pulley 3330. On the contrary, when the pitch pulley 3330 rotates in the counterclockwise direction based on FIG. 16, the first pitch wire 3363 is wound around the pitch pulley 3330, and the second pitch wire 3364 is unwound from the pitch pulley 3330.

In other words, it may be said that, when the pitch pulley 3330 rotates, the pair of pitch wires 3363 and 3364 may move in opposite directions to each other with respect to the pitch pulley 3330.

As described above, when the pitch pulley 3330 rotates to move the pair of pitch wires 3363 and 3364 in different directions, the pulley on the end tool side, which is connected to the pitch wires 3363 and 3364, rotates in a direction corresponding thereto. Thus, as the pulley on the end tool side, which is connected to the pitch wires 3363 and 3364, rotates in one direction, a pitch rotation of the end tool may be implemented.

The firing pulley 3340 is a pulley associated with the movement of an operation member provided in the end tool, and the firing wires 3365 and 3366 are wires associated with the movement of the operation member provided in the end tool.

The firing pulley 3340 may be disposed in one region of the pulley frame 3310.

As a specific embodiment, the firing pulley 3340 may be disposed at a position not in line with the yaw pulley 3320 and the pitch pulley 3330 of the pulley frame 3310, and may be disposed, for example, below the yaw pulley 3320 and the pitch pulley 3330. For example, as shown in FIG. 14, the yaw pulley 3320 and the pitch pulley 3330 may be disposed side by side with each other on the pulley frame 3310, and the firing pulley 3340 may be disposed below the yaw pulley 3320 and the pitch pulley 3330.

In an embodiment, the firing wires 3365 and 3366 may be connected to a moving member 3155 of the end tool, and in this case, the firing wires 3365 and 3366 may extend toward the firing pulley 3340 from the moving member 3155. In another embodiment, the firing wires 3365 and 3366 may be directly connected to the operation member, in which case the firing wires 3365 and 3366 may extend toward the firing pulley 3340 from the operation member. In another embodiment, when a pulley associated with a translational motion of the operation member is separately provided in the end tool, the firing wires 3365 and 3366 may be connected to the pulley, and the firing wires 3365 and 3366 may extend toward the firing pulley 3340 from the pulley.

In an embodiment, the firing wires 3365 and 3366 may be provided in a pair. As will be described later, the firing wires 3365 and 3366 may be connected to left and right sides of the firing pulley 3340, respectively.

As a specific embodiment, the firing wires 3365 and 3366 may include a first firing wire 3365 and a second firing wire 3366. The first firing wire 3365 may extend to the left side of the firing pulley 3340 based on FIG. 16 to be connected to the firing pulley 3340. The second firing wire 3366 may extend to the right side of the firing pulley 3340 based on FIG. 16 to be connected to the firing pulley 3340.

The firing wires 3365 and 3366 may be connected to the firing pulley 3340, and then, may be wound around the firing pulley 3340 or unwound therefrom when the firing pulley 3340 rotates. That is, when the firing pulley 3340 rotates in one direction, one of the firing wires 3365 and 3366 is wound around the firing pulley 3340, and another one of the firing wires 3365 and 3366 is unwound from the firing pulley 3340. For example, when the firing pulley 3340 rotates in the clockwise direction based on FIG. 16, the first firing wire 3365 is unwound from the firing pulley 3340, and the second firing wire 3366 is wound around the firing pulley 3340. On the contrary, when the firing pulley 3340 rotates in the counterclockwise direction based on FIG. 16, the first firing wire 3365 is wound around the firing pulley 3340, and the second firing wire 3366 is unwound from the firing pulley 3340.

In other words, it may be said that, when the firing pulley 3340 rotates, the pair of firing wires 3365 and 3366 may move in opposite directions to each other with respect to the firing pulley 3340.

As described above, when the firing pulley 3340 rotates to move the pair of firing wires 3365 and 3366 in different directions from each other, the operation member provided in the end tool may move forward or backward in response thereto. As an example, when the operation member is formed to move dependently on the movement of the moving member 3155, the rotation of the firing pulley 3340 may cause the pair of firing wires 3365 and 3366 to move the moving member 3155 forward or backward, thereby causing the operation member to move forward or backward. As another example, when the operation member is connected to the firing wires 3365 and 3366 and formed to move forward or backward directly from the firing wires 3365 and 3366, the rotation of the firing pulley 3340 may directly cause the pair of firing wires 3365 and 3366 to move the operation member forward or backward. However, the present disclosure is not limited thereto, and when the end tool is formed such that a pulley associated with the translational motion of the operation member is separately provided therein, by connecting the firing wires 3365 and 3366 to the pulley and rotating the pulley, the operation member may be moved forward or backward.

In an embodiment, the power transmission part 3300 may further include at least one or more auxiliary pulleys 3350. The auxiliary pulleys 3350 may serve to reroute the wires entering the power transmission part 3300.

In an embodiment, the auxiliary pulleys 3350 may include a first auxiliary pulley 3351 connected to the yaw wires 3361 and 3362 and the pitch wires 3363 and 3364 and configured to reroute the yaw wires 3361 and 3362 and the pitch wires 3363 and 3364. In addition, the auxiliary pulleys 3350 may include a second auxiliary pulley 3352 and a third auxiliary pulley 3353 connected to the firing wires 3365 and 3366 and configured to reroute the firing wires 3365 and 3366.

The first auxiliary pulley 3351 may be disposed in the power transmission part 3300, and may serve to reroute the yaw wires 3361 and 3362 and the pitch wires 3363 and 3364, which extend from the end tool to the power transmission part 3300, through a connection part 3400.

A first auxiliary pulley fixing part 3311 may be formed on the pulley frame 3310. The first auxiliary pulley fixing part 3311 is a part in which the first auxiliary pulley 3351 is installed. For example, the first auxiliary pulley fixing part 3311 may be integrally formed with the pulley frame 3310. Alternatively, the first auxiliary pulley fixing part 3311 may be formed as a separate member, and may be coupled or assembled to the pulley frame 3310.

In an embodiment, the first auxiliary pulley fixing part 3311 may include at least one or more through holes, and a rotation shaft of the first auxiliary pulley 3351 may be disposed to pass through the through holes. In other words, the first auxiliary pulley 3351 may be disposed parallel to the through holes formed in the first auxiliary pulley fixing part 3311 so as to overlap therewith, and the rotation shaft may be disposed to simultaneously pass through the first auxiliary pulley 3351 and the first auxiliary pulley fixing part 3311.

The first auxiliary pulley fixing part 3311 may be formed in a shape at least partially extending in a direction toward the connection part 3400 from the pulley frame 3310. For example, it may be said that the first auxiliary pulley fixing part 3311 is formed to extend in a direction toward the connection part 3400 from one surface of the pulley frame 3310. In an exemplary embodiment, the first auxiliary pulley fixing part 3311 may be disposed in the center of the pulley frame 3310.

In this case, the yaw pulley 3320 and the pitch pulley 3330 may be disposed on both sides of the first auxiliary pulley fixing part 3311, respectively. In an exemplary embodiment, the yaw pulley 3320 and the pitch pulley 3330 may be disposed in positions symmetrical to each other with respect to the first auxiliary pulley fixing part 3311. In other words, the yaw wires 3361 and 3362 and the pitch wires 3363 and 3364 entering the first auxiliary pulley 3351 may be distributed to opposite sides while passing through the first auxiliary pulley fixing part 3311. Accordingly, it may be said that the yaw wires 3361 and 3362 extend toward the yaw pulley 3320, and the pitch wires 3363 and 3364 extend toward the pitch pulley 3330.

Accordingly, the yaw wires 3361 and 3362 may approach the yaw pulley 3320 to be nearly perpendicular thereto, and the pitch wires 3363 and 3364 may approach the pitch pulley 3330 to be nearly perpendicular thereto. The yaw wires 3361 and 3362 may perpendicularly approach the yaw pulley 3320, and the pitch wires 3363 and 3364 may perpendicularly approach the pitch pulley 3330. In other words, it may be said that the yaw wires 3361 and 3362 may approach the yaw pulley 3320 to form a tangent therewith, and the pitch wires 3363 and 3364 may approach the pitch pulley 3330 to form a tangent therewith.

The first auxiliary pulley 3351 may be disposed in the first auxiliary pulley fixing part 3311 and may reroute paths along which the pitch wires 3363 and 3364 and the yaw wires 3361 and 3362 extend to the power transmission part 3300.

Specifically, the first auxiliary pulley 3351 may be disposed between the yaw pulley 3320 and the pitch pulley 3330 as shown in FIG. 16.

A plurality of first auxiliary pulleys 3351 may be provided. The first auxiliary pulleys 3351 may be provided in a number corresponding to at least the number of wires entering the power transmission part 3300.

As an example, the yaw wires 3361 and 3362 may be provided in a pair so as to respectively enter the upper and lower sides of the yaw pulley 3320. In addition, the pitch wires 3363 and 3364 may be provided in a pair so as to respectively enter the upper and lower sides of the pitch pulley 3330. That is, when there are four wires entering the power transmission part 3300, four first auxiliary pulleys 3351 may be provided.

In an optional embodiment, the plurality of first auxiliary pulleys 3351 may be disposed side by side with each other. For example, the plurality of first auxiliary pulleys 3351 may be disposed parallel to each other. This is to ensure that the wires emerging from being wound around the first auxiliary pulley 3351 extend to the yaw pulley 3320 and the pitch pulley 3330 parallel or nearly parallel to each other.

Specifically, the wires extending from the end tool to the power transmission part 3300 extend parallel to each other. Thus, as the plurality of first auxiliary pulleys 3351 are disposed side by side with each other, the wires respectively emerging from being wound around the first auxiliary pulleys 3351 may extend to the yaw pulley 3320 and/or the pitch pulley 3330 parallel or at least nearly parallel to each other.

In an optional embodiment, in relation to the yaw pulley 3320 and the pitch pulley 3330, the first auxiliary pulleys 3351 may be disposed such that the wires are wound in directions nearly perpendicular to each other, and preferably perpendicular to each other. When further describing with reference to FIG. 16, the direction in which the wire is wound around the first auxiliary pulley 3351 and the direction in which the wire is wound around the yaw pulley 3320 and the pitch pulley 3330 may be perpendicular to each other. In other words, it may be described that the first auxiliary pulley 3351 changes an advancing direction of the wire entering the first auxiliary pulley 3351 by 90°. In other words, it may be described that the groove formed in the first auxiliary pulley 3351 is perpendicular to the grooves formed in the yaw pulley 3320 and the pitch pulley 3330.

With this configuration, the wires entering the power transmission part 3300 may be rerouted through the first auxiliary pulley 3351, and may approach the yaw pulley 3320 and the pitch pulley 3330 perpendicular or nearly perpendicular thereto.

The second auxiliary pulley 3352 may be disposed in the power transmission part 3300 and may serve to reroute the firing wires 3365 and 3366, which extend from the end tool to the power transmission part 3300, through the connection part 3400.

The third auxiliary pulley 3353 may be disposed in the power transmission part 3300, and may serve to reroute the firing wires 3365 and 3366 extending from the second auxiliary pulley 3352.

Referring to FIG. 14 again, the second auxiliary pulley 3352 may guide the firing wires 3365 and 3366, which enter the power transmission part 3300 from the end tool through the connection part 3400, in an upward direction. Specifically, the second auxiliary pulley 3352 may guide the firing wires 3365 and 3366 in a direction opposite to the direction in which the firing pulley 3340 is located by rerouting the firing wires 3365 and 3366 entering the power transmission part 3300. The third auxiliary pulley 3353 may guide the firing wires 3365 and 3366 toward the firing pulley 3340 by rerouting the firing wires 3365 and 3366 extending from the second auxiliary pulley 3352.

Accordingly, the firing wires 3365 and 3366 may extend in a direction away from the firing pulley 3340 by the second auxiliary pulley 3352 and then extend back toward the firing pulley 3340.

As described above, the firing pulley 3340 and the firing wires 3365 and 3366 are associated with the movement of the operation member of the end tool. At this time, the firing wires 3365 and 3366 may be wound around the firing pulley 3340 a greater number of times than the yaw wires 3361 and 3362 or the pitch wires 3363 and 3364. This relates to the movement of the operation member. For example, this is due to the fact that the lengths of the yaw wires 3361 and 3362 and the pitch wires 3363 and 3364 wound and unwound for the yaw and pitch motions of the end tool are longer than the lengths of the firing wires 3365 and 3366 wound and unwound for the movement of the operation member.

At this time, a groove formed in the firing pulley 3340 is formed in the shape of a screw valley, and thus, as the firing wires 3365 and 3366 are wound around the firing pulley 3340 multiple times, the firing wires 3365 and 3366 move in an axial direction of the firing pulley 3340. This means that the firing wires 3365 and 3366 form a larger angle as the firing wires 3365 and 3366 extend from the third auxiliary pulley 3353 to the firing pulley 3340 (forming an oblique connection). In this case, a relatively strong stress may be applied to the firing wires 3365 and 3366.

Thus, the second auxiliary pulley 3352 guides the firing wires 3365 and 3366 in the opposite direction of the firing pulley 3340, and the third auxiliary pulley 3353 guides the firing wires 3365 and 3366 again in a direction toward the firing pulley 3340. Thus, the length of the firing wires 3365 and 3366 extending from the third auxiliary pulley 3353 to the firing pulley 3340 may be secured, and as a result, the change in angle at which the firing wires 3365 and 3366 enter the firing pulley 3340 may be reduced.

A fixing part 3312 for the second auxiliary pulley 3352 may be formed on the pulley frame 3310. The fixing part

3312 for the second auxiliary pulley 3352 is a part in which the third auxiliary pulley 3353 is installed. For example, the fixing part 3312 for the second auxiliary pulley 3352 may be integrally formed with the pulley frame 3310. Alternatively, the fixing part 3312 for the second auxiliary pulley 3352 may be formed as a separate member, and may be coupled or assembled to the pulley frame 3310.

In an embodiment, the fixing part 3312 for the second auxiliary pulley 3352 may include at least one or more through holes, and a rotation shaft of the third auxiliary pulley 3353 may be disposed to pass through the through holes. In other words, the third auxiliary pulley 3353 may be disposed parallel to the through holes formed in the fixing part 3312 of the second auxiliary pulley 3352 so as to overlap therewith, and the rotation shaft may be disposed to simultaneously pass through the third auxiliary pulley 3353 and the fixing part 3312 for the second auxiliary pulley 3352.

The fixing part 3312 for the second auxiliary pulley 3352 may be formed in a shape protruding in a direction toward the connection part 3400 from the pulley frame 3310. For example, it may be said that the fixing part 3312 for the second auxiliary pulley 3352 may be formed to protrude in a direction toward the connection part 3400 from one surface of the pulley frame 3310.

In an exemplary embodiment, the fixing part 3312 for the second auxiliary pulley 3352 may be disposed on an upper side of the pulley frame 3310, and may be disposed, for example, on the opposite side of the firing pulley 3340 based on the center of the pulley frame 3310.

In an embodiment, each of the second auxiliary pulley 3352 and the third auxiliary pulley 3353 may be provided as a pair. For example, the second auxiliary pulleys 3352 may include a pulley to which the first firing wire 3365 is connected and a pulley to which the second firing wire 3366 is connected. In addition, the third auxiliary pulleys 3353 may include a pulley to which the first firing wire 3365 is connected and a pulley to which the second firing wire 3366 is connected.

In an optional embodiment, the two second auxiliary pulleys 3352 may be disposed parallel to each other. This is to ensure that the wires 3365 and 3366 emerging from being wound around the second auxiliary pulley 3352 extend to the third auxiliary pulley 3353 parallel or nearly parallel to each other.

Specifically, the wires 3365 and 3366 extending from the end tool to the power transmission part 3300 extend parallel to each other. Thus, by disposing the two second auxiliary pulleys 3352 parallel to each other, the wires 3365 and 3366 emerging from being wound around the second auxiliary pulley 3352 may extend to the third auxiliary pulley 3353 parallel to each other, or at least nearly parallel to each other.

In an optional embodiment, the two third auxiliary pulleys 3353 may be disposed parallel to each other. This is to ensure that the wires 3365 and 3366 emerging from being wound around the third auxiliary pulley 3353 extend to the firing pulley 3340 parallel or nearly parallel to each other.

Specifically, the wires 3365 and 3366 extending from the second auxiliary pulley 3352 to the third auxiliary pulley 3353 extend parallel to each other. Thus, by disposing the two third auxiliary pulleys 3353 parallel to each other, the wires 3365 and 3366 respectively emerging from being wound around the third auxiliary pulleys 3353 may extend to the firing pulley 3340 parallel to each other, or at least nearly parallel to each other.

In an optional embodiment, in relation to the firing pulley 3340, the second auxiliary pulley 3352 and the third auxiliary pulley 3353 may be disposed such that the wires 3365 and 3366 are wound in directions nearly perpendicular to each other, and preferably perpendicular to each other. When further describing with reference to FIG. 14, the direction in which the wires 3365 and 3366 are wound around the second auxiliary pulley 3352 and the third auxiliary pulley 3353 and the direction in which the wires 3365 and 3366 are wound around the firing pulley 3340 may be perpendicular to each other. In other words, it may be described that grooves formed in the second auxiliary pulley 3352 and the third auxiliary pulley 3353 are perpendicular to a groove formed in the firing pulley 3340.

With this configuration, the wires 3365 and 3366 emerging from being wound around the second auxiliary pulley 3352 and the third auxiliary pulley 3353 are rerouted, and may approach the firing pulley 3340 perpendicular or nearly perpendicular thereto.

Figure 17:
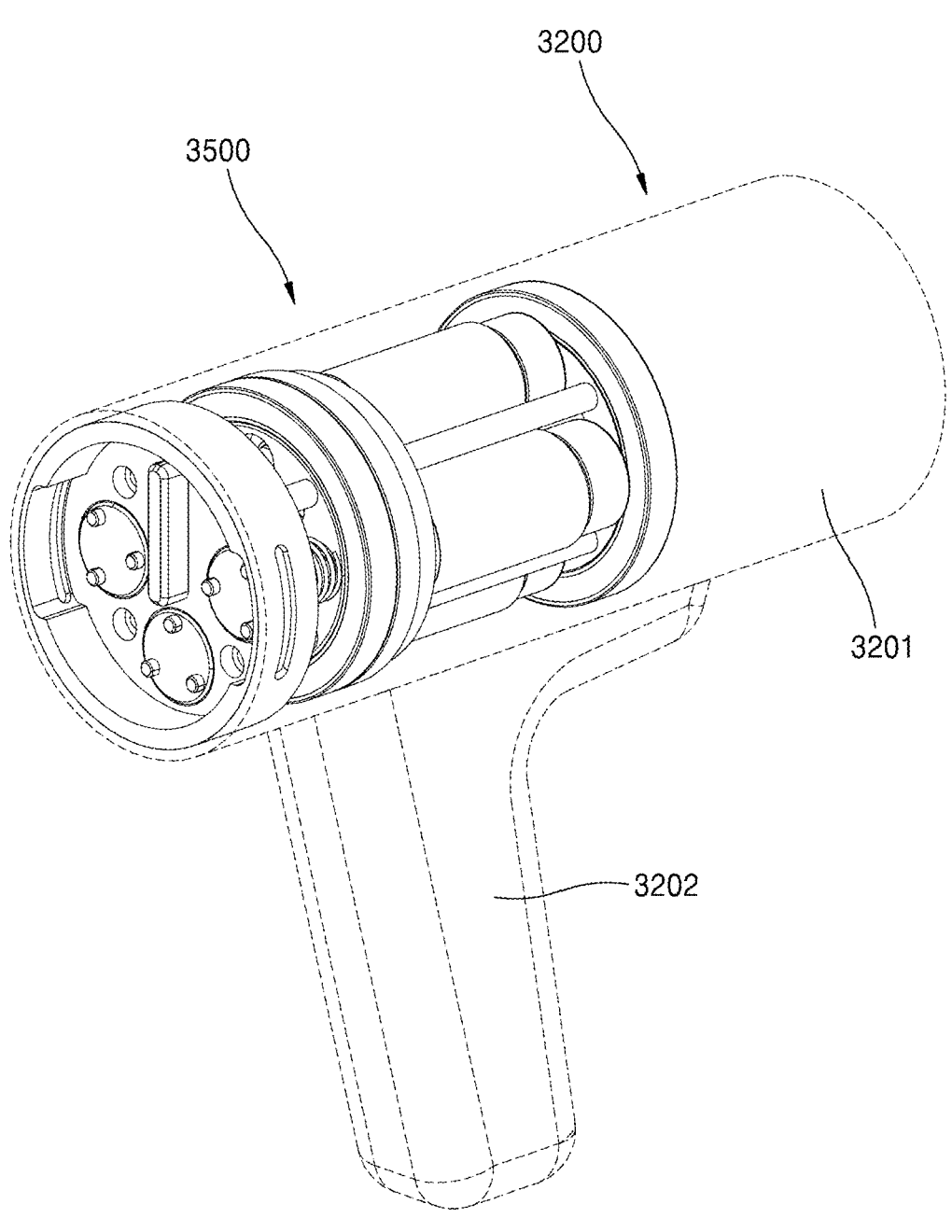
FIG. 17 is a view illustrating a manipulation part and a power generation part according to another embodiment of the present disclosure.
Figure 18:
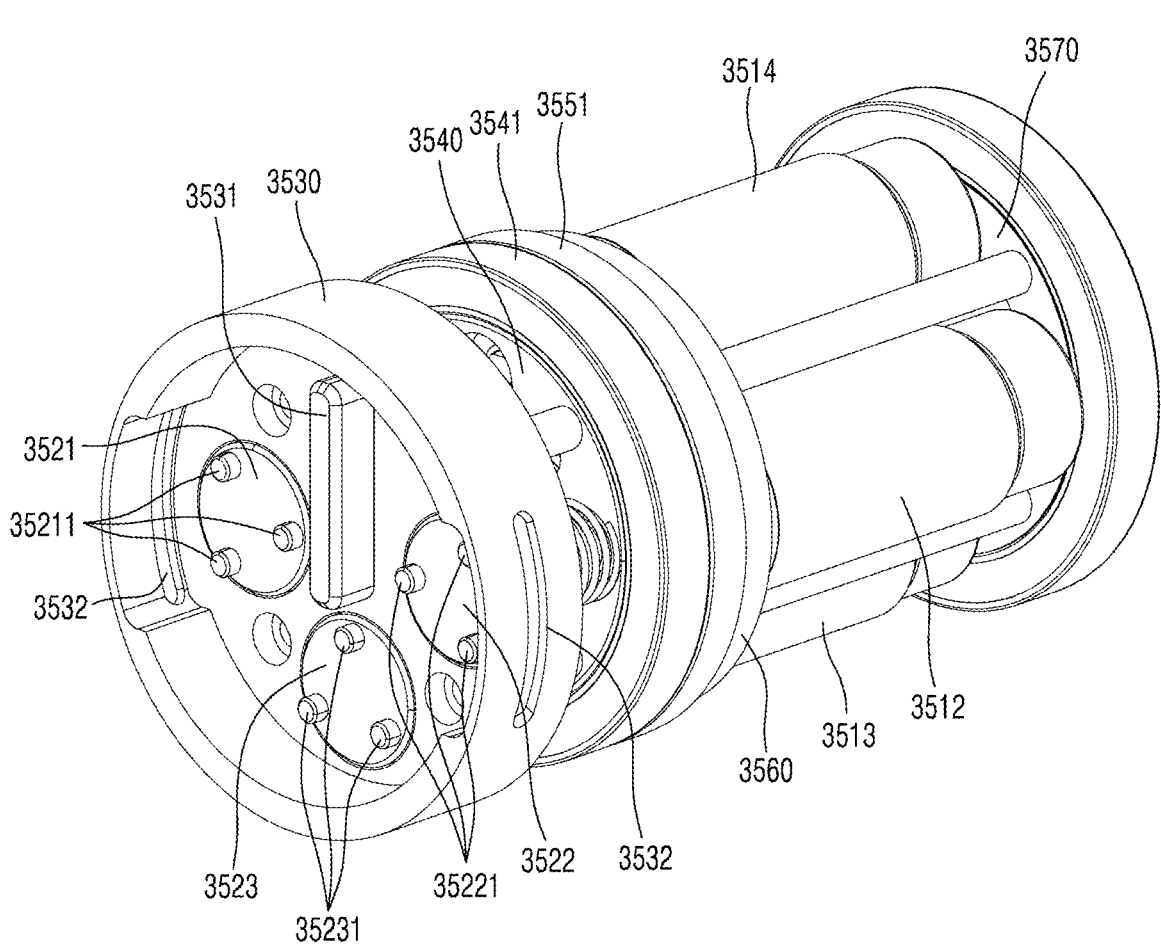
FIG. 18 is a perspective view illustrating the power generation part of FIG. 17.
Figure 19:
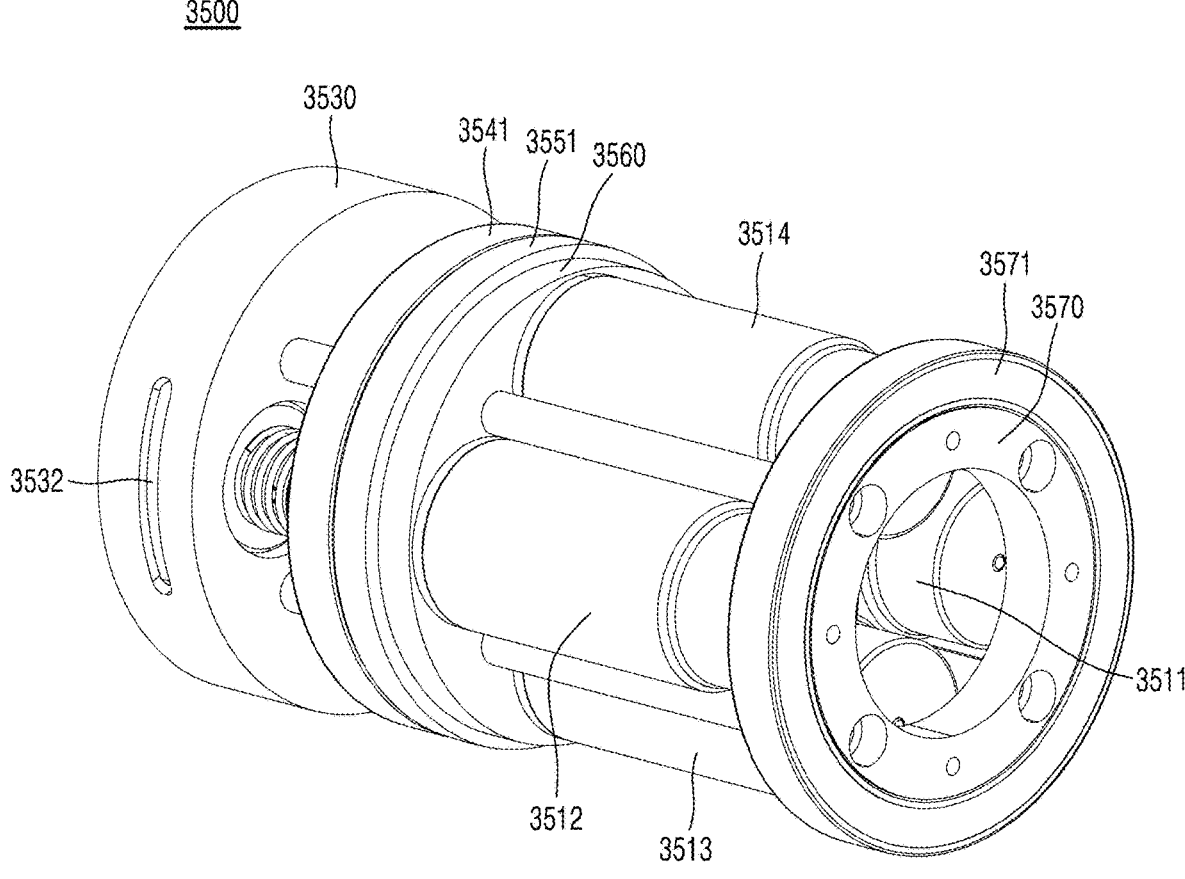
FIG. 19 is a view illustrating the power generation part of FIG. 18 as viewed from the rear side.
Figure 20:
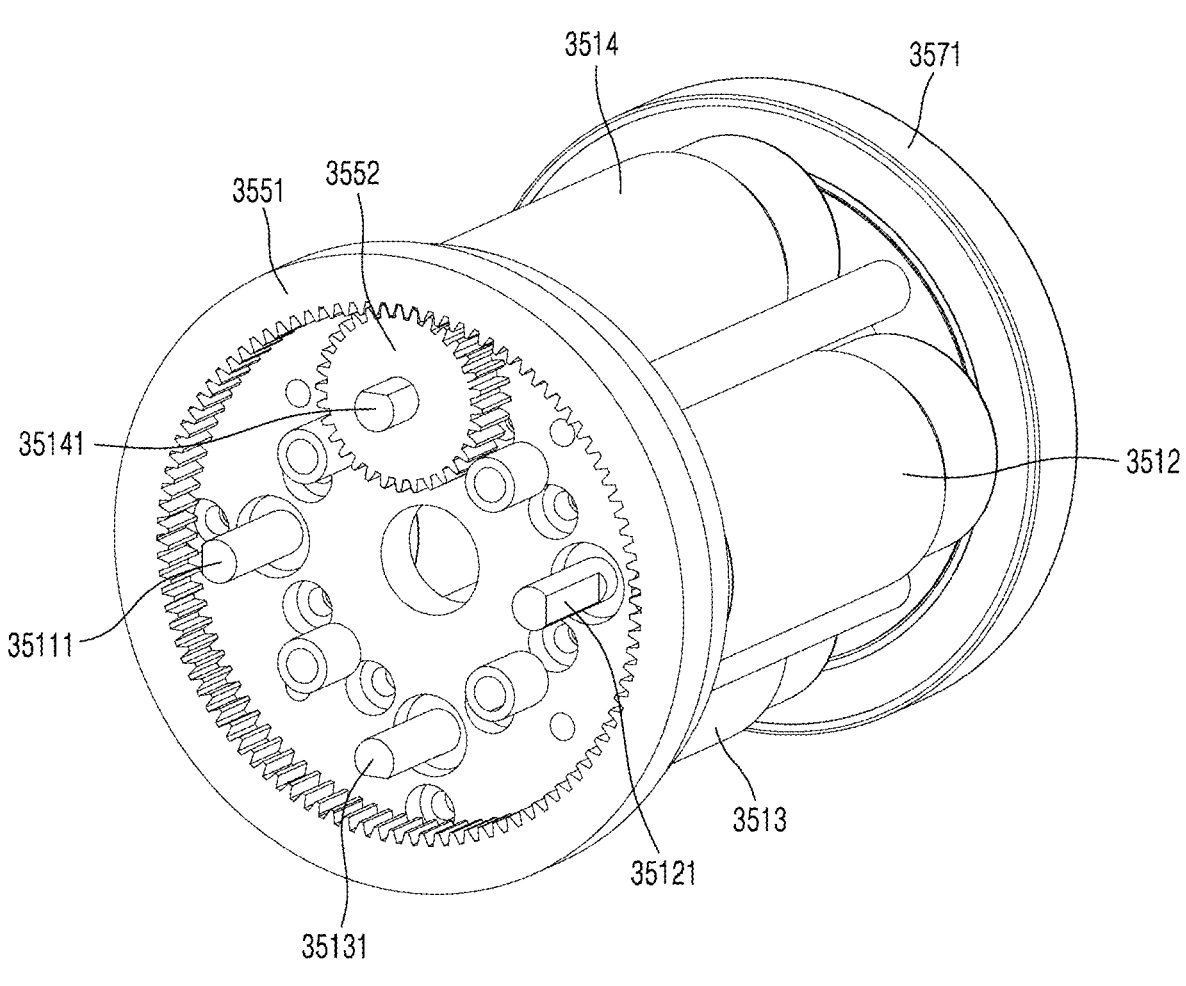
FIG. 20 is a view for describing a gear structure of the power generation part of FIG. 18.
Figure 21:
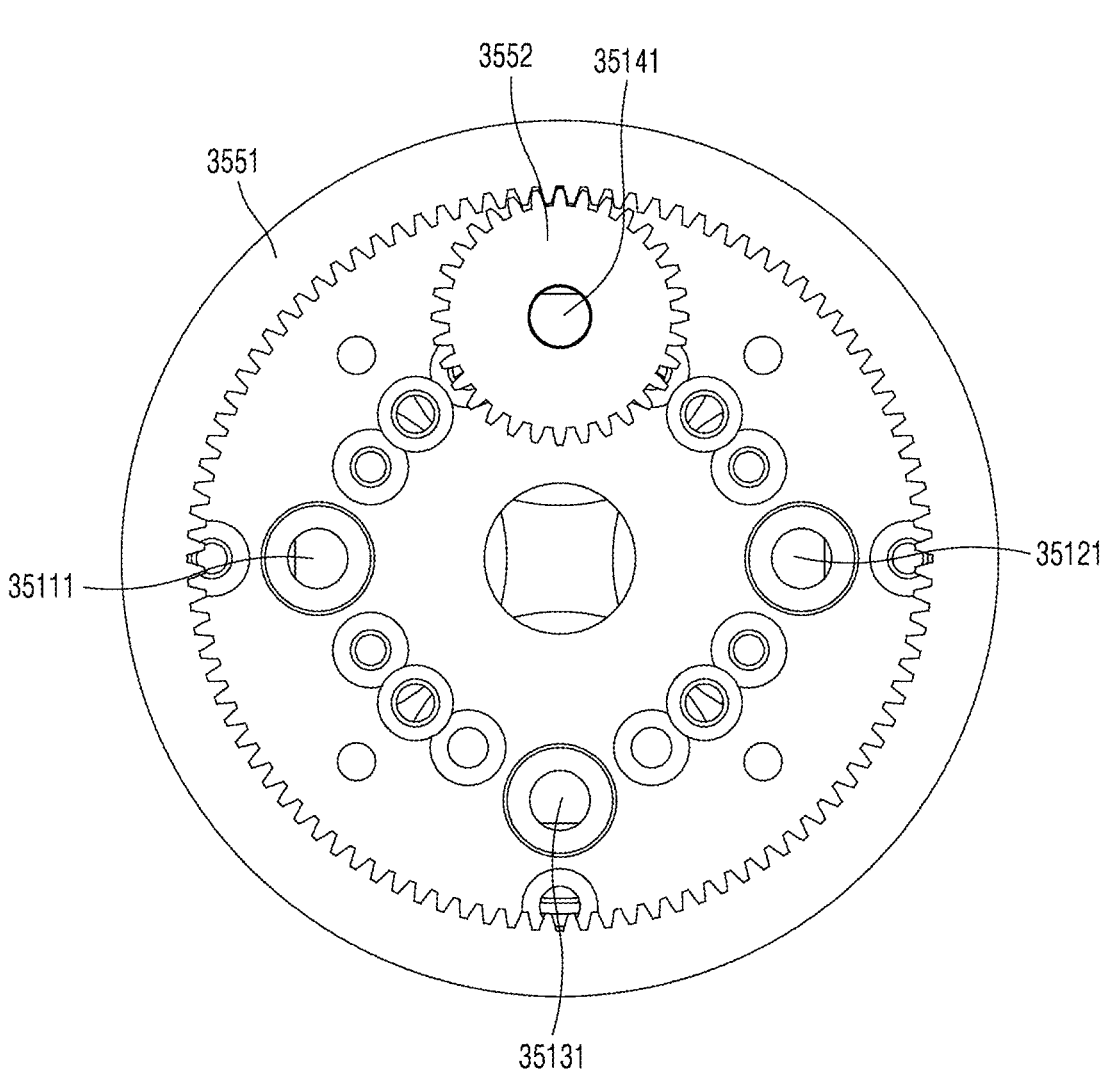
FIG. 21 is a front view of FIG. 20.
Figure 22:
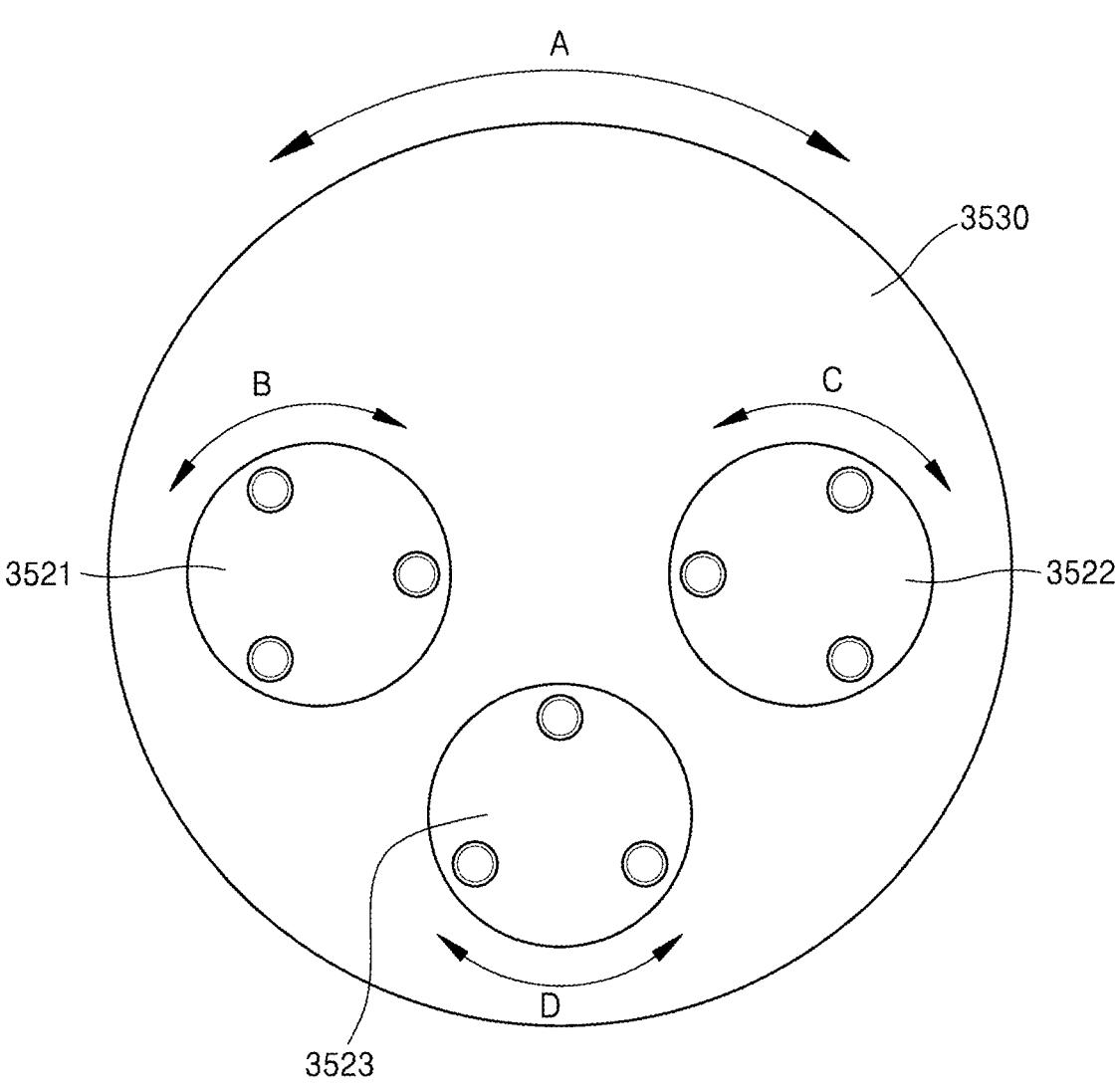
FIG. 22 is a view for describing rotation of the power generation part of FIG. 18.

FIG. 17 is a view illustrating a manipulation part and a power generation part according to another embodiment of the present disclosure, FIG. 18 is a perspective view illustrating the power generation part of FIG. 17, and FIG. 19 is a view illustrating the power generation part of FIG. 18 as viewed from the rear side. FIG. 20 is a view for describing a gear structure of the power generation part of FIG. 18, FIG. 21 is a front view of FIG. 20, and FIG. 22 is a view for describing rotation of the power generation part of FIG. 18.

Referring to FIGS. 17 to 22, the surgical instrument according to an embodiment of the present disclosure may include a power generation part 3500 configured to generate power to control the end tool.

The power generation part 3500 may be disposed to be at least partially accommodated in a housing 3201 of a manipulation part 3200.

When a user manipulates the manipulation part 3200, the power generation part 3500 may generate power to control the end tool based on the manipulation.

The power generation part 3500 may include a motor pack including at least one motor.

The motor pack 3510 may roll-rotate in a direction in which the connection part 3400 extends.

Here, a roll motion as used herein is defined as follows.

A roll motion refers to a motion in which the end tool, the connection part 3400, the motor pack 3510, and the like, which constitute a surgical instrument 3000, rotate around an axis formed in a direction in which a connection part 3400 extends. In other words, the roll motion refers to a motion of rotating around an axis formed in an extension direction (the X-axis direction in FIG. 3) of the connection part 3400 without bending in the Y-axis direction of FIG. 3 or the Z-axis direction of FIG. 3.

Referring to FIG. 17 again, at least a portion of the power generation part 3500 may be accommodated in the housing 3201 of the manipulation part 3200. In this case, the motor pack 3510 is accommodated in the housing 3201 of the manipulation part 3200. Here, the phrase "the motor pack 3510 roll-rotates" may mean that the motor pack 3510 rotates inside the housing 3201 along an inner circumferential surface of the housing 3201. In other words, when a user performs a manipulation to roll-rotate the manipulation part 3200 while grasping a handle 3202 of the manipulation part 3200, the motor pack 3510 may rotate around the axis, which is formed in the direction in which the connection part 3400 extends, inside the housing 3201 while the housing 3201 and the handle 3202 of the manipulation part 3200 are fixed in place. In other words, it may be described that the housing 3201 and the handle 3202 rotate when the user performs a manipulation for a roll motion while grasping the connection part 3400.

The motor pack 3510 may include at least one motor.

The motor pack 3510 may include a yaw drive motor 3511. The yaw drive motor 3511 may generate power to yaw-rotate the end tool. For example, when a user manipulates the manipulation part 3200 to yaw-rotate the end tool, the yaw drive motor 3511 may generate a driving force to yaw-rotate the end tool.

The driving force generated by the yaw drive motor 3511 may be transmitted to the power transmission part 3300 to rotate the yaw pulley 3320, and as the yaw wires 3361 and 3362 are moved by the rotation of the yaw pulley 3320, the end tool may yaw-rotate.

The yaw drive motor 3511 may include a yaw motor rotation shaft 35111 formed to extend in one direction. The yaw motor rotation shaft 35111 is a part that rotates when the yaw drive motor 3511 is driven. For example, the yaw motor rotation shaft 35111 may be formed to extend in a direction toward the power transmission part 3300 from a body of the yaw drive motor 3511. As will be described later, a yaw motor plate 3521 may be disposed at one end of the yaw motor rotation shaft 35111, and the yaw motor plate 3521 may rotate together with the yaw motor rotation shaft 35111 when the yaw motor rotation shaft 35111 rotates. The yaw motor plate 3521 may be connected to the yaw pulley 3320, and the driving force may be transmitted to the yaw pulley 3320 as the yaw motor plate 3521 rotates.

The motor pack 3510 may include a pitch drive motor 3512. The pitch drive motor 3512 may generate power to pitch-rotate the end tool. For example, the pitch drive motor 3512 may generate a driving force to pitch-rotate the end tool when a user manipulates the manipulation part 3200 to pitch-rotate the end tool.

The driving force generated by the pitch drive motor 3512 may be transmitted to the power transmission part 3300 to rotate the pitch pulley 3330, and as the pitch wires 3363 and 3364 are moved by the rotation of the pitch pulley 3330, the end tool may pitch-rotate.

The pitch drive motor 3512 may include a pitch motor rotation shaft 35121 formed to extend in one direction. The pitch motor rotation shaft 35121 is a part that rotates when the pitch drive motor 3512 is driven. For example, the pitch motor rotation shaft 35121 may be formed to extend in a direction toward the power transmission part 3300 from a body of the pitch drive motor 3512. As will be described later, a pitch motor plate 3522 may be disposed at one end of the pitch motor rotation shaft 35121, and the pitch motor plate 3522 may rotate together with the pitch motor rotation shaft 35121 when the pitch motor rotation shaft 35121 rotates. The pitch motor plate 3522 may be connected to the pitch pulley 3330, and as the pitch motor plate 3522 rotates, the driving force may be transmitted to the pitch pulley 3330.

The motor pack 3510 may include a roll drive motor 3514. The roll drive motor 3514 may generate power to roll-rotate the motor pack 3510. For example, the roll drive motor 3514 may generate a driving force to roll-rotate the motor pack 3510 when a user manipulates the manipulation part 3200 to rotate the motor pack 3510.

The motor pack 3510 may include a firing drive motor 3513. The firing drive motor 3513 may generate power to linearly move the operation member of the end tool. For example, the firing drive motor 3513 may generate a driving force to linearly move the operation member when a user manipulates the manipulation part 3200 to linearly move the operation member of the end tool.

The firing drive motor 3513 may include a firing motor rotation shaft 35131 formed to extend in one direction. The firing motor rotation shaft 35131 is a part that rotates when the firing drive motor 3513 is driven. For example, the firing motor rotation shaft 35131 may be formed to extend in a direction toward the power transmission part 3300 from a body of the firing drive motor 3513. As will be described later, a firing motor plate 3523 may be disposed at one end of the firing motor rotation shaft 35131, and the firing motor plate 3523 may rotate together with the firing motor rotation shaft 35131 when the firing motor rotation shaft 35131 rotates. The firing motor plate 3523 may be connected to the firing pulley 3340, and as the firing motor plate 3523 rotates, the driving force may be transmitted to the firing pulley 3340.

The motor pack 3510 may include a base plate 3560. The base plate 3560 may be disposed in front of the yaw drive motor 3511, the pitch drive motor 3512, the roll drive motor 3514, and the firing drive motor 3513. The base plate 3560 may be connected to the roll drive motor 3514, the yaw drive motor 3511, the pitch drive motor 3512, and the firing drive motor 3513. In other words, it may be said that the roll drive motor 3514, the yaw drive motor 3511, the pitch drive motor 3512, and the firing drive motor 3513 are connected to the base plate 3560. In other words, the base plate 3560 may connect the roll drive motor 3514, the yaw drive motor 3511, the pitch drive motor 3512, and the firing drive motor 3513 to each other such that the roll drive motor 3514, the yaw drive motor 3511, the pitch drive motor 3512, and the firing drive motor 3513 move or rotate together as one body.

Accordingly, when the base plate 3560 rotates, the roll drive motor 3514, the yaw drive motor 3511, the pitch drive motor 3512, and the firing drive motor 3513 connected to the base plate 3560 may rotate simultaneously. Here, since the base plate 3560 rotates around the axis formed in the direction in which the connection part 3400 extends, the motor pack 3510 including the base plate 3560, the roll drive motor 3514, the yaw drive motor 3511, the pitch drive motor 3512, and the firing drive motor 3513 roll-rotates around the axis formed in the direction in which the connection part 3400 extends.

In an embodiment, the roll drive motor 3514, the yaw drive motor 3511, the pitch drive motor 3512, and the firing drive motor 3513 may be disposed parallel to each other. In addition, the roll drive motor 3514, the yaw drive motor 3511, the pitch drive motor 3512, and the firing drive motor 3513 may be disposed to form a circular pattern.

As described above, the motor pack 3510 may roll-rotate inside the housing 3201 of the manipulation part 3200. In this case, since the motor pack 3510 includes a plurality of motors, by disposing the roll drive motor 3514, the yaw drive motor 3511, the pitch drive motor 3512, and the firing drive motor 3513 to form a circular pattern with each other, when the motor pack 3510 rotates, a diameter of a space occupied by the rotation of the motor pack 3510 may be minimized. That is, by disposing the roll drive motor 3514, the yaw drive motor 3511, the pitch drive motor 3512, and the firing drive motor 3513 to form a circular pattern, an inner diameter inside the housing 3201 which is required for the motor pack 3510 to rotate may be designed to be small, which may contribute to the miniaturization and light-weighting of the surgical instrument 3000.

Meanwhile, here, disposing the roll drive motor 3514, the yaw drive motor 3511, the pitch drive motor 3512, and the firing drive motor 3513 to form a circular pattern does not imply equal spacing therebetween. Instead, it is sufficient when outer circumferential surfaces of the roll drive motor 3514, the yaw drive motor 3511, the pitch drive motor 3512, and the firing drive motor 3513 are disposed within a circle.

In an embodiment, the roll drive motor 3514, the yaw drive motor 3511, the pitch drive motor 3512, and the firing drive motor 3513 may be provided to have different performance. For example, the magnitudes of driving forces that the roll drive motor 3514, the yaw drive motor 3511, the pitch drive motor 3512, and the firing drive motor 3513 must generate to perform their respective roles may be different from each other. To this end, the roll drive motor 3514, the yaw drive motor 3511, the pitch drive motor 3512, and the firing drive motor 3513 may have different outputs or sizes as necessary.

At least one through hole may be formed in the base plate 3560. For example, the base plate 3560 may have at least one corresponding through hole for each motor included in the motor pack 3510. The through hole is a part through which the rotation shaft of each motor passes.

For example, the yaw motor rotation shaft 35111 extends from the body of the yaw drive motor 3511, and may be formed to extend through the base plate 3560 (or through the through hole). In addition, the pitch motor rotation shaft 35121 extends from the body of the pitch drive motor 3512, and may be formed to extend through the base plate 3560 (or through the through hole). In addition, the firing motor rotation shaft 35131 extends from the body of the firing drive motor 3513, and may be formed to extend through the base plate 3560 (or through the through hole).

Meanwhile, the roll drive motor 3514 may include a roll motor rotation shaft 35141 formed to extend in one direction. The roll motor rotation shaft 35141 is a part that rotates when the roll drive motor 3514 starts driving. For example, the roll motor rotation shaft 35141 may be formed to extend in a forward-facing direction from a body of the roll drive motor 3514. That is, the roll motor rotation shaft 35141 extends forward from the body of the roll drive motor 3514, and may be formed to extend through the base plate 3560.

Hereinafter, the principle of rotation of the motor pack 3510 will be described in detail.

Referring to FIGS. 20 and 21, the power generation part 3500 may include a first gear 3551 formed in the shape of a circle and a second gear 3552 engaged with the first gear 3551.

The first gear 3551 may be formed in the shape of a hollow circle, and gear teeth may be formed on an inner circumferential surface of the circle. That is, the first gear 3551 may be a kind of ring gear with gear teeth formed on an inner circumferential surface thereof.

The second gear 3552 is a gear having gear teeth formed on an outer circumferential surface thereof, and may be engaged with the first gear 3551. The second gear 3552 may be disposed on the roll motor rotation shaft 35141. That is, the roll motor rotation shaft 35141 is formed to extend forward to pass through the base plate 3560 from the body of the roll drive motor 3514, and the second gear 3552 may be disposed in the extending portion of the roll motor rotation shaft 35141. In this case, the second gear 3552 is coupled to the roll motor rotation shaft 35141, and the second gear 3552 may rotate together with the roll motor rotation shaft 35141 when the roll motor rotation shaft 35141 rotates.

The first gear 3551 may be disposed in front of the base plate 3560. In addition, the first gear 3551 may be fixed to the inner circumferential surface of the housing 3201.

Accordingly, when the roll drive motor 3514 is driven, the motor pack 3510 may roll-rotate inside the housing 3201.

Specifically, when the roll drive motor 3514 is driven, the roll motor rotation shaft 35141 may rotate, and the second gear 3552 disposed on the roll motor rotation shaft 35141 may rotate together with the roll motor rotation shaft 35141. In this case, since the first gear 3551 engaged with the second gear 3552 is fixed to the inner circumferential surface of the housing 3201, when the second gear 3552 rotates, the second gear 3552 moves along the gear teeth of the first gear 3551. That is, when the roll drive motor 3514 starts driving, the first gear 3551 and the second gear 3552 rotate with respect to each other, and in this case, since the first gear 3551 is fixed to the housing 3201, the second gear 3552 relatively moves along the first gear 3551. In addition, the second gear 3552 is connected to the roll motor rotation shaft 35141, the roll drive motor 3514 is connected to the base plate 3560, and the base plate 3560 is connected to the yaw drive motor 3511 and the pitch drive motor 3512. Accordingly, the motor pack 3510 may rotate with respect to the housing 3201 by the operation of the first gear 3551 and the second gear 3552.

More specifically, the base plate 3560 may rotate with respect to the housing 3201. That is, since the second gear 3552 is connected to the base plate 3560 by the roll motor rotation shaft 35141, when the second gear 3552 moves, the base plate 3560 rotates with respect to the housing 3201 as the second gear 3552 moves along the first gear 3551. Here, since the roll motor rotation shaft 35141 is eccentric with respect to the rotation shaft of the base plate 3560, when the second gear 3552 moves along the first gear 3551, the base plate 3560 may rotate with respect to the housing 3201, rather than change in position along the second gear 3552.

Meanwhile, as will be described later, a bearing plate 3540 may be similarly connected to the second gear 3552 by the roll motor rotation shaft 35141. Thus, when the second gear 3552 rotates, the bearing plate 3540 may rotate with respect to the housing 3201 as the second gear 3552 moves along the first gear 3551. In this case, as will be described later, a first bearing 3541 may be disposed to be in contact with the inner circumferential surface of the housing 3201, coaxially with the bearing plate 3540, to reduce rotational friction of the bearing plate 3540. Accordingly, the bearing plate 3540 may be easily rotated.

Meanwhile, the gear teeth of the first gear 3551 and the second gear 3552 are illustrated in the drawings as spur gears, but the present disclosure is not limited thereto, and it is of course possible that the gear teeth may have various shapes such as a helical gear, a herringbone gear, and the like.

In an embodiment, the power generation part 3500 may further include the bearing plate 3540 and the first bearing 3541. The bearing plate 3540 and the first bearing 3541 may reduce rotational friction between the motor pack 3510 and the housing 3201 when the motor pack 3510 roll-rotates.

The bearing plate 3540 may be disposed in front of the first gear 3551.

At least one or more through holes may be formed in the bearing plate 3540. The through holes are parts through which the rotation shafts of each motor pass.

For example, the yaw motor rotation shaft 35111 may be formed to extend from the body of the yaw drive motor 3511 to pass through the base plate 3560 and the bearing plate 3540. In addition, the pitch motor rotation shaft 35121 may be formed to extend from the body of the pitch drive motor 3512, passing through the base plate 3560 and the bearing plate 3540. In addition, the firing motor rotation shaft 35131 may be formed to extend from the body of the firing drive motor 3513 to pass through the base plate 3560 and the bearing plate 3540. In this case, the roll motor rotation shaft 35141 is formed to extend from the body of the roll drive motor 3514 to pass through the base plate 3560, but may not extend to the bearing plate 3540.

As such, since the yaw motor rotation shaft 35111, the pitch motor rotation shaft 35121, and the firing motor rotation shaft 35131 are formed to extend through the bearing plate 3540, when the motor pack 3510 rotates, the base plate 3560 and the bearing plate 3540 may rotate together the motor pack 3510.

The first bearing 3541 may be disposed on an outer circumferential surface of the bearing plate 3540. For example, the first bearing 3541 may be disposed to cover the outer circumferential surface of the bearing plate 3540. Thus, when the motor pack 3510 roll-rotates, the bearing plate 3540 rotates together with the motor pack 3510, and in this case, the bearing plate 3540 and the first bearing 3541 may reduce the rotational friction between the motor pack 3510 and the housing 3201.

In an embodiment, the power generation part 3500 may further include a circuit plate 3570 and a second bearing 3571. The circuit plate 3570 and the second bearing 3571 may reduce the rotational friction between the motor pack 3510 and the housing 3201 when the motor pack 3510 roll-rotates.

The circuit plate 3570 may be disposed at the rear of the motor pack 3510.

As will be described later, the circuit plate 3570 is a part to which a circuit unit 3600 is connected.

The circuit plate 3570 is connected to the motor pack 3510, and may rotate together with the motor pack 3510 when the motor pack 3510 rotates.

The second bearing 3571 may be disposed on an outer circumferential surface of the circuit plate 3570. Thus, when the motor pack 3510 roll-rotates, the circuit plate 3570 rotates together with the motor pack 3510, and in this case, the circuit plate 3570 and the second bearing 3571 may reduce the rotational friction between the motor pack 3510 and the housing 3201.

The power generation part 3500 may further include a pulley coupling plate 3530.

The pulley coupling plate 3530 is a part to which the power transmission part 3300 is connected.

Figure 24:
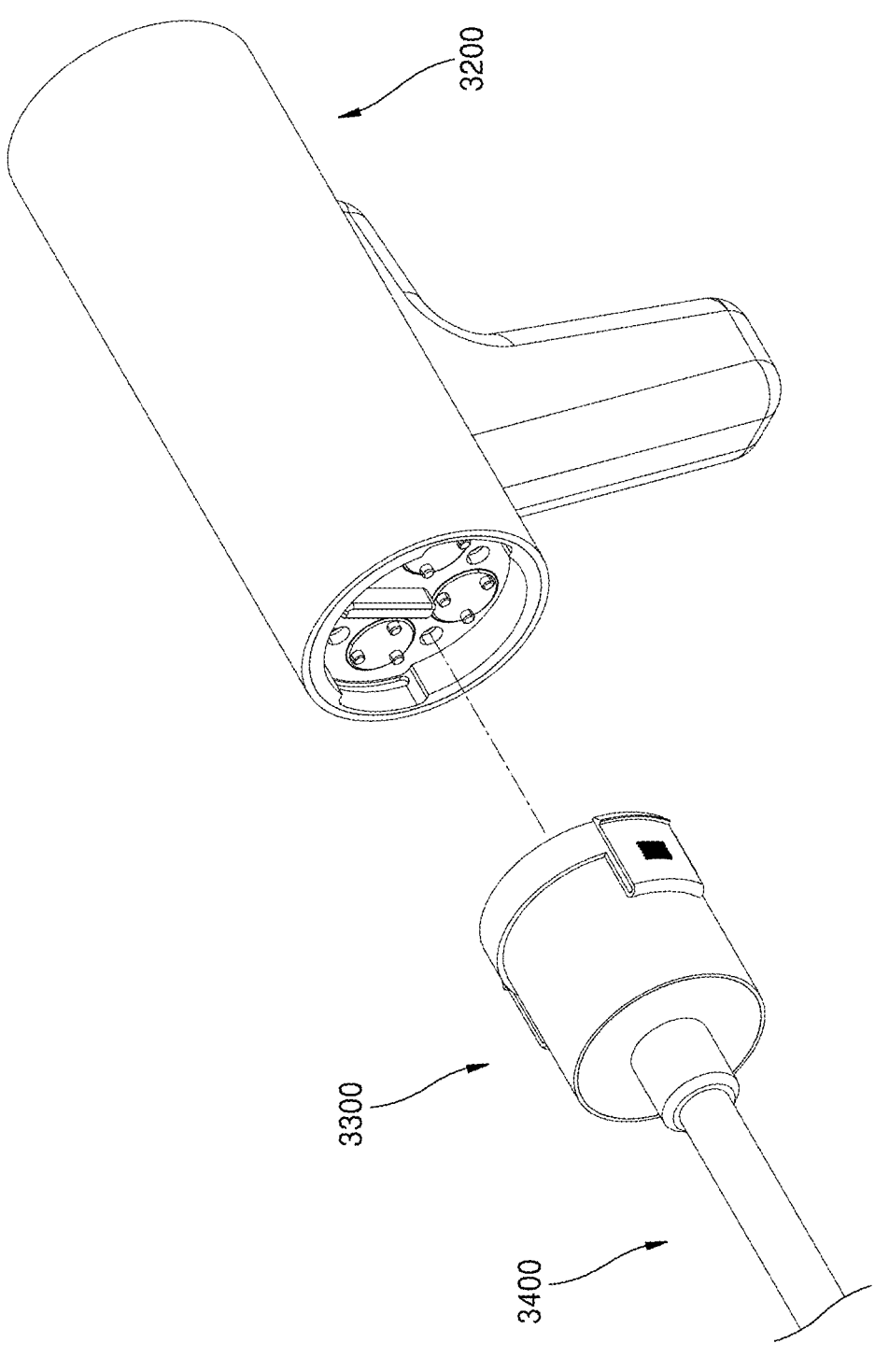
Figure 25:
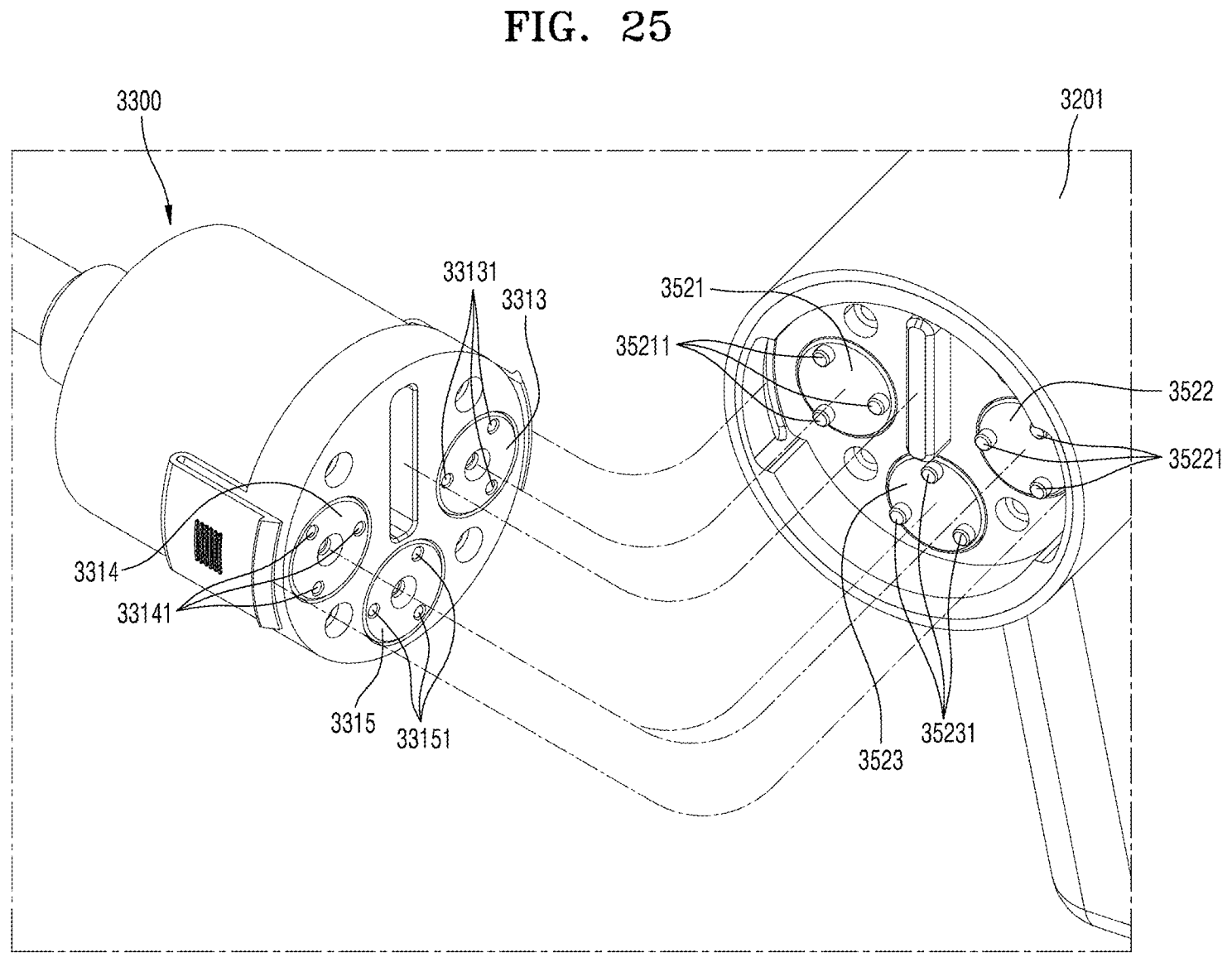

FIGS. 24 and 25 are views for describing a coupling structure of the surgical instrument according to an embodiment of the present disclosure. Referring to FIGS. 24 and 25 together, in an embodiment, the power transmission part 3300 may be detachably fastened to the power generation part 3500. For example, the power transmission part 3300 may be detachably fastened to the pulley coupling plate 3530. Thus, after using components (such as, the power transmission part 3300, the connection part 3400, and the end tool) in a direction from the power transmission part 3300 toward the distal end, the user may discard these components and connect new products for these components to the manipulation part 3200, which accommodates the power generation part 3500, to use the surgical instrument 3000.

In an embodiment, at least one coupling member 3316 may be formed in the pulley frame 3310 of the power transmission part 3300. A hook 33161 may be formed in the coupling member 3316 (See FIG. 15). In addition, the pulley coupling plate 3530 may include an internal space for accommodating at least a portion of the pulley frame 3310, and a wall surface formed along a circumference of the pulley coupling plate 3530 to define the internal space. At this time, a hook groove 3532 to which the hook 33161 is caught and fixed may be formed in the wall surface. Thus, when the pulley frame 3310 is inserted into the internal space of the pulley coupling plate 3530, the hook 33161 may be inserted into the hook groove 3532 and coupled and fixed thereto.

In an embodiment, the pulley coupling plate 3530 may include a coupling block 3531 that is formed to protrude, and the pulley frame 3310 may include an insertion groove formed to allow the coupling block 3531 to be inserted therein. Thus, when the pulley coupling plate 3530 is coupled to the pulley frame 3310, the coupling block 3531 is inserted into the insertion groove, so that the pulley coupling plate 3530 and the pulley frame 3310 may be coupled to each other at a predetermined position. In addition, since the coupling block 3531 is inserted into the insertion groove, a roll rotational force of the pulley coupling plate 3530 may be transmitted to the pulley frame 3310 by the coupling block 3531 and the insertion groove. In an optional embodiment, the coupling block 3531 may be formed in the shape of an elongated bar, and in this case, the insertion groove may be formed in a shape corresponding thereto.

In an embodiment, although not shown in the drawings, the surgical instrument 3000 according to the present disclosure may further include a waterproof structure.

As a specific embodiment, at least one O-ring may be provided inside the housing 3201. For example, a first O-ring may be provided between the housing 3201 and an outer circumferential surface of the pulley coupling plate 3530. The first O-ring is disposed between the outer circumferential surface of the pulley coupling plate 3530 and the housing 3201 to be in close contact therewith, thereby preventing water or the like from penetrating between the power generation part 3500 and the housing 3201.

As another example, a second O-ring may be provided at least one of between the yaw motor plate 3521 and the pulley coupling plate 3530 and between the pitch motor plate 3522 and the pulley coupling plate 3530. The second O-ring is disposed between the yaw or pitch motor plate 3521 or 3522 and the pulley coupling plate 3530 to be in close contact therewith, thereby preventing water or the like from penetrating between the yaw or pitch motor plate 3521 or 3522 and the pulley coupling plate 3530.

In an embodiment, the pulley coupling plate 3530 may be fastened to the bearing plate 3540 by at least one bolt. In this case, a bolt hole into which the bolt is inserted may have at least one seal washer disposed below the bolt. The seal washer may prevent water or the like from penetrating through the bolt hole.

At least one or more through holes may be formed in the pulley coupling plate 3530. For example, three through holes may be formed in the pulley coupling plate 3530.

The yaw motor plate 3521, the pitch motor plate 3522, and the firing motor plate 3523 may be disposed in the through holes formed in the pulley coupling plate 3530.

The yaw motor plate 3521 may be rotated by a driving force generated from the yaw drive motor 3511. The yaw motor plate 3521 may be disposed at one end of the yaw motor rotation shaft 35111. For example, when the yaw motor rotation shaft 35111 rotates, the yaw motor plate 3521 may rotate together therewith. In other words, the yaw motor plate 3521 may be referred to as a member that transmits the driving force generated from the yaw drive motor 3511 to the power transmission part 3300.

At least one first protrusion 35211 may be formed on the yaw motor plate 3521. The first protrusion 35211 is a part that protrudes outward from the yaw motor plate 3521. As will be described later, the first protrusion 35211 may be inserted into a first insertion hole 33131 formed in a yaw pulley plate 3313.

The pitch motor plate 3522 may be rotated by a driving force generated from the pitch drive motor 3512. The pitch motor plate 3522 may be disposed at one end of the pitch motor rotation shaft 35121. For example, when the pitch motor rotation shaft 35121 rotates, the pitch motor plate 3522 may rotate together therewith. In other words, the pitch motor plate 3522 may be referred to as a member that transmits the driving force generated from the pitch drive motor 3512 to the power transmission part 3300.

At least one second protrusion 35221 may be formed in the pitch motor plate 3522. The second protrusion 35221 is a part that protrudes outward from the pitch motor plate 3522. As will be described later, the second protrusion 35221 may be inserted into a second insertion hole 33141 formed in a pitch pulley plate 3314.

The firing motor plate 3523 may be rotated by a driving force generated from the firing drive motor 3513. The firing motor plate 3523 may be disposed at one end of the firing motor rotation shaft 35131. For example, when the firing motor rotation shaft 35131 rotates, the firing motor plate 3523 may rotate together therewith. In other words, the firing motor plate 3523 may be referred to as a member that transmits the driving force generated from the firing drive motor 3513 to the power transmission part 3300.

At least one third protrusion 35231 may be formed on the firing motor plate 3523. The third protrusion 35231 is a part that protrudes outward from the firing motor plate 3523. As will be described later, the third protrusion 35231 may be inserted into a third insertion hole 33151 formed in a firing pulley plate 3315.

The yaw pulley plate 3313, the pitch pulley plate 3314, and the firing pulley plate 3315 may be disposed on the pulley frame 3310.

The yaw pulley plate 3313 may be formed to be rotatable. Specifically, the yaw pulley plate 3313 may be fastened to the yaw motor plate 3521 and may rotate together with the yaw motor plate 3521 when the yaw motor plate 3521 rotates. The yaw pulley plate 3313 is a part connected to the yaw pulley 3320, and when the yaw pulley plate 3313 rotates, the yaw pulley 3320 may rotate together with the yaw pulley plate 3313. In other words, when power transmitted from the outside causes the yaw pulley plate 3313 to rotate, the yaw pulley 3320 may rotate together with the yaw pulley plate 3313. In other words, the yaw pulley plate 3313 may be referred to as a part that receives a driving force generated from the yaw drive motor 3511 and transmits the driving force to the yaw pulley 3320.

The yaw pulley plate 3313 may include at least one first insertion hole 33131. The first insertion hole 33131 is a part into which the first protrusion 35211 of the yaw motor plate 3521 is inserted. As described above, the yaw motor plate 3521 and the yaw pulley plate 3313 may be stably coupled to each other by the coupling of the at least one first protrusion 35211 and the at least one first insertion hole 33131, and the driving force of the yaw drive motor 3511 may be efficiently transmitted to the yaw pulley 3320.

The pitch pulley plate 3314 may be formed to be rotatable. Specifically, the pitch pulley plate 3314 may be fastened to the pitch motor plate 3522, and may rotate together with the pitch motor plate 3522 when the pitch motor plate 3522 rotates. The pitch pulley plate 3314 is a part connected to the pitch pulley 3330, and when the pitch pulley plate 3314 rotates, the pitch pulley 3330 may rotate together with the pitch pulley plate 3314. In other words, when power transmitted from the outside causes the pitch pulley plate 3314 to rotate, the pitch pulley 3330 may rotate together with the pitch pulley plate 3314. In other words, the pitch pulley plate 3314 may be referred to as a part that receives a driving force generated from the pitch drive motor 3512 and transmits the driving force to the pitch pulley 3330.

The pitch pulley plate 3314 may include at least one second insertion hole 33141. The second insertion hole 33141 is a part into which the second protrusion 35221 of the pitch motor plate 3522 is inserted. As such, the pitch motor plate 3522 and the pitch pulley plate 3314 may be stably coupled to each other by the coupling of the at least one second protrusion 35221 and the at least one second insertion hole 33141, and the driving force of the pitch drive motor 3512 may be efficiently transmitted to the pitch pulley 3330.

The firing pulley plate 3315 may be formed to be rotatable. Specifically, the firing pulley plate 3315 may be fastened to the firing motor plate 3523, and may rotate together with the firing motor plate 3523 when the firing motor plate 3523 rotates. The firing pulley plate 3315 is a part connected to the firing pulley 3340, and when the firing pulley plate 3315 rotates, the firing pulley 3340 may rotate together with the firing pulley plate 3315. In other words, when power transmitted from the outside causes the firing pulley plate 3315 to rotate, the firing pulley 3340 may rotate together with the firing pulley plate 3315. In other words, the firing pulley plate 3315 may be referred to as a part that receives a driving force generated from the firing drive motor 3513 and transmits the driving force to the firing pulley 3340.

The firing pulley plate 3315 may include at least one third insertion hole 33151. The third insertion hole 33151 is a part into which the third protrusion 35231 of the firing motor plate 3523 is inserted. As described above, the firing motor plate 3523 may be stably coupled to the firing pulley plate 3315 due to the coupling of the at least one third protrusion 35231 and the at least one third insertion hole 33151, and the driving force of the firing drive motor 3513 may be efficiently transmitted to the firing pulley 3340.

In an embodiment, the yaw drive motor 3511, the pitch drive motor 3512, the roll drive motor 3514, the firing drive motor 3513 may be driven independently of each other. Accordingly, the yaw drive motor 3511, the pitch drive motor 3512, the roll drive motor 3514, and the firing drive motor 3513 may independently perform a yaw rotation of the end tool, a pitch rotation of the end tool, a roll rotation of the motor pack 3510, and a linear movement of the operation member.

When further describing with reference to FIG. 22 again, as the roll drive motor 3514 is driven, the pulley coupling plate 3530 may rotate in an A direction. At this time, the yaw drive motor 3511 may be driven independently, and thus may rotate the yaw motor plate 3521 in a B direction by being independently driven regardless of the driving of the roll drive motor 3514. In addition, the pitch drive motor 3512 may be driven independently, and thus may rotate the pitch motor plate 3522 in a C direction by being independently driven regardless of the driving of the roll drive motor 3514 and the yaw drive motor 3511. In addition, the firing drive motor 3513 may be driven independently, and thus may rotate the firing motor plate 3523 in a D direction by being independently driven regardless of the driving of the roll drive motor 3514, the yaw drive motor 3511, and the pitch drive motor 3512. In other words, the end tool may perform any one of a pitch rotation, a yaw rotation, a roll rotation, and a linear movement of the operation member and may also perform all of the rotations simultaneously.

Figure 23:
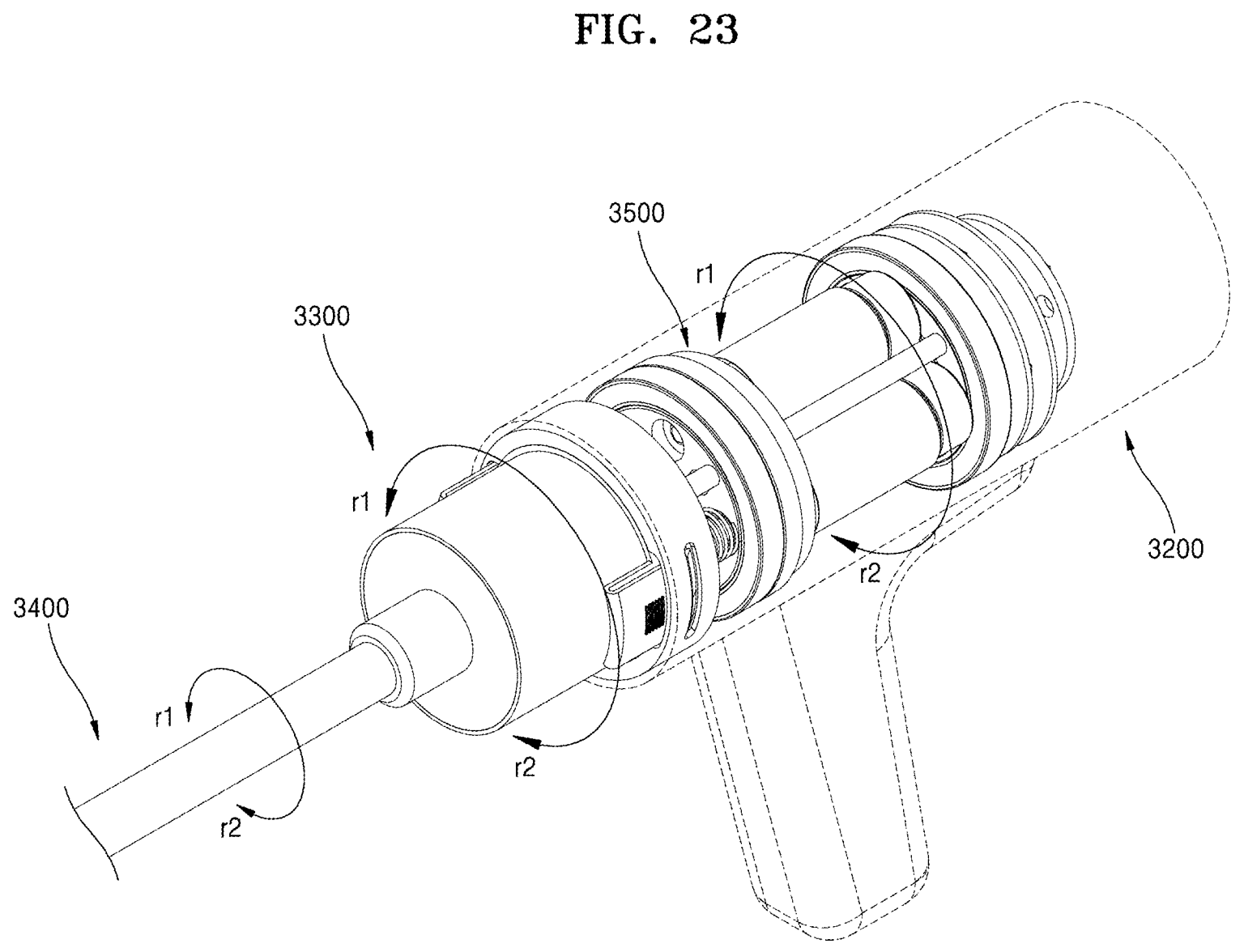

FIG. 23 is a view for describing a roll motion of the surgical instrument according to an embodiment of the present disclosure.

Referring to FIG. 23, the surgical instrument according to an embodiment of the present disclosure may be formed such that the motor pack 3510 is roll-rotatable.

Here, the power generation part including the motor pack 3510 may include the pulley frame 3310, which is coupled to the power transmission part, at the frontmost position. The pulley frame 3310 may be coupled to the power transmission part. Thus, the power transmission part 3300 may roll-rotate together with the pulley coupling plate 3530 while being fastened to the pulley coupling plate 3530.

In addition, the connection part 3400 may be connected to the power transmission part 3300. Thus, the connection part 3400 may roll-rotate together with the power transmission part 3300 by the roll rotation of the power transmission part 3300.

In addition, the end tool 1100 disposed at one side of the connection part 3400 may be connected to the connection part 3400. Thus, the end tool 1100 may roll-rotate together with the connection part 3400 by the rotation of the connection part 3400.

As a result, according to the present disclosure, when a user manipulates the manipulation part 3200 to drive the roll drive motor 3514, the components excluding the manipulation part 3200 may roll-rotate around an axis extending in a longitudinal direction of the connection part 3400.

Figure 26:
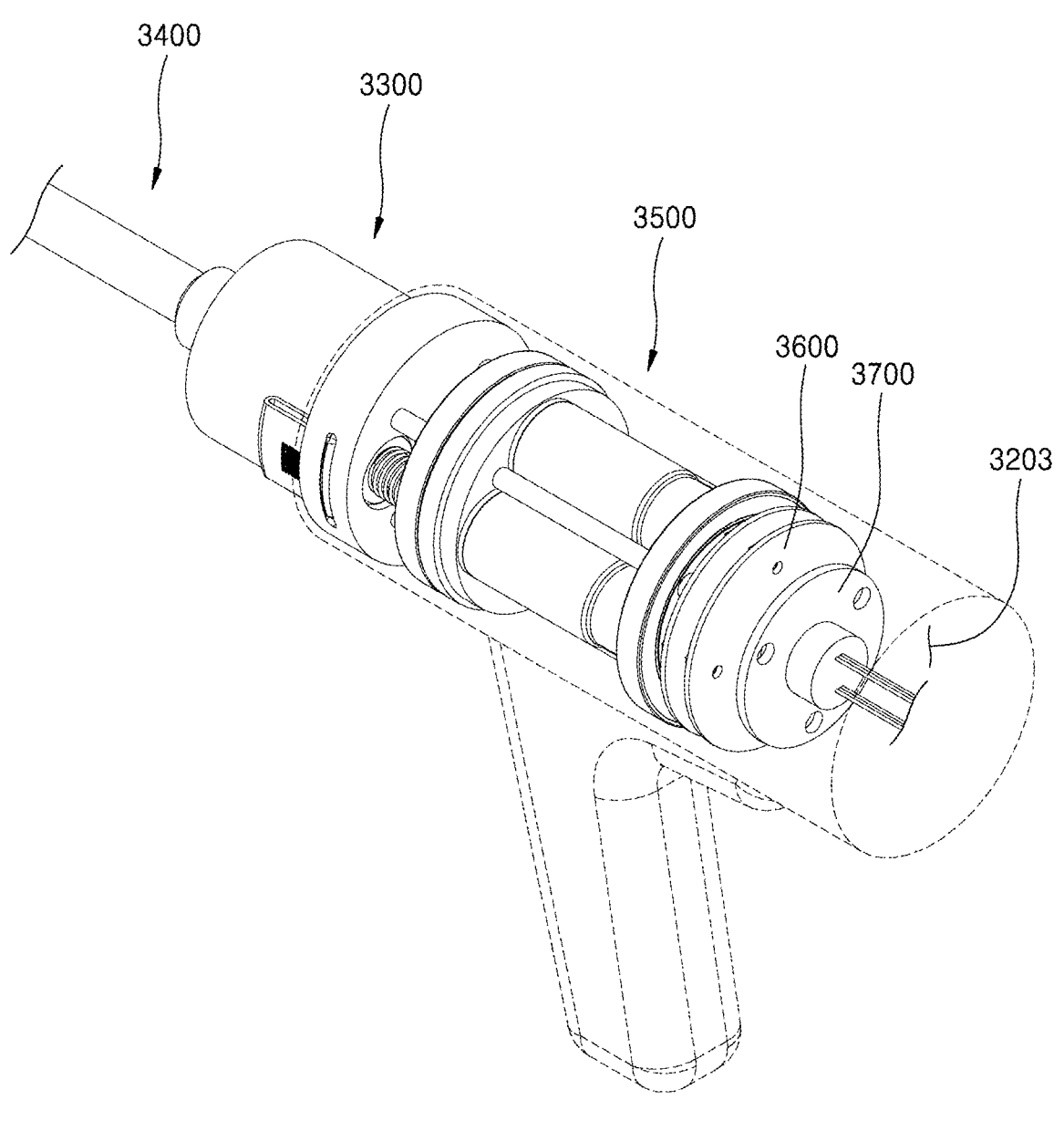
FIG. 26 is a view illustrating an internal structure of a surgical instrument according to another embodiment of the present disclosure.

FIG. 26 is a view illustrating an internal structure of the surgical instrument according to another embodiment of the present disclosure.

Referring to FIG. 26, a manipulation part internal space 3203 may be provided inside the manipulation part 3200.

The circuit unit 3600 may be disposed in the manipulation part internal space 3203.

The circuit unit 3600 is a configuration including an electronic circuit for controlling the driving of the motor pack 3510. As an example, the circuit unit 3600 may include a motor driver, a motor controller, and a microcontroller unit, but the present disclosure is not limited thereto, and any component may be used as the circuit unit 3600 as long as it can drive the motor pack 3510.

The circuit unit 3600 may be disposed at the rear of the motor pack 3510. In more detail, the circuit unit 3600 may be connected to the circuit plate 3570 of the power generation part 3500. Thus, when the motor pack 3510 roll-rotates, the circuit unit 3600 may rotate together with the motor pack 3510.

Although not shown in the drawings, in order to drive the motor pack 3510, the circuit unit 3600 and the motor pack 3510 may be connected to each other through a plurality of electric wires. Thus, as the motor pack 3510 roll-rotates, the circuit unit 3600 also rotates together with the motor pack 3510, so that a problem of twisting the plurality of electric wires connecting the motor pack 3510 to the circuit unit 3600 can be prevented.

In an embodiment, a slip ring 3700 may be disposed on one side of the circuit unit 3600. The slip ring 3700 is a component for connecting various electrical/electronic elements or connecting communication with the circuit unit 3600 that controls the driving of the motor pack 3510 or the motor pack 3510. For example, the slip ring 3700 may electrically connect the circuit unit, which controls the driving of the motor pack 3510 or the motor pack 3510, to a power supply, a switch, a button, an organic light-emitting diode (OLED) screen, and other circuit units. Here, the power supply, the switch, the button, the OLED screen, and other circuit units may be disposed inside the surgical instrument 3000 according to the present disclosure or may be disposed outside the surgical instrument 3000. In addition, the slip ring 3700 may connect communication between various elements for the operation of the surgical instrument 3000. For example, the slip ring 3700 may connect communication between at least some of the manipulation part 3200, the power transmission part 3300, the power generation part 3500, and the circuit unit 3600. In this case, the type of communication is not limited, and any type that can communicatively connect the various elements of the surgical instrument 3000 may be employed.

As described above, the motor pack 3510 and the circuit unit 3600 are formed to be roll-rotatable. In addition, the motor pack 3510 and/or the circuit unit 3600 may be electrically connected to various electrical/electronic elements. In this case, when the motor pack 3510 and/or the circuit unit 3600 are connected to the electrical/electronic elements through electric wires or the like, the electric wires may be twisted by the rotation of the motor pack 3510 and the circuit unit 3600.

Thus, by disposing the slip ring 3700 on one side of the circuit unit 3600, even when the circuit unit 3600 rotates, the electric wires connecting various electrical/electronic elements to the motor pack 3510 and/or the circuit unit 3600 may not be twisted. For example, since the electric wires are not twisted, the motor pack 3510 and the circuit unit 3600 may stably receive power from an external power supply.

In an embodiment, although not shown in the drawings, the surgical instrument may further include at least one sub-circuit unit. The sub-circuit unit may be disposed inside the manipulation part 3200. In an exemplary embodiment, the sub-circuit unit may be disposed on a portion of the handle 3202 (refer to FIG. 17) of the manipulation part 3200. In this case, the sub-circuit unit may not rotate even when the motor pack 3510 rotates.

The sub-circuit unit may primarily receive and process various signals for controlling the motor pack 3510. In addition, the sub-circuit unit may transmit a primarily processed signal to the circuit unit 3600. To this end, the circuit unit 3600 may be connected to the sub-circuit unit by serial communication or the like, but the present disclosure is not limited thereto, and the circuit unit 3600 may be connected to the sub-circuit unit in various ways. Thus, the number of electric wires that need to be connected to the circuit unit 3600 may be reduced by using the slip ring 3700.

As a specific example, when it is assumed that the manipulation part 3200 has four buttons for manipulation, and each button requires two electric wires (e.g., one electric wire for grounding and another electric wire for communication) to send and receive signals, at least five electric wires should be connected to the circuit unit 3600. That is, even when the electric wire for grounding is commonly used, at least one electric wire for grounding and four electric wires for communication are required for the manipulating electric wires in the manipulation part 3200. In this case, when the sub-circuit unit is included as in the present embodiment, and preprocesses signals from at least five electric wires simultaneously, through the communication connection function of the slip ring 3700, the four buttons of the circuit unit 3600 can be communicated with the manipulation part 3200 using only two electric wires. Thus, this configuration can simplify the arrangement of electric wires and further minimize the size of the slip ring 3700. However, this example represents just one of various functions of the sub-circuit unit, and in addition thereto, the sub-circuit unit can preprocess signals of various electric wires, and thus, the technical contents of the present disclosure are not limited to the description provided above.

In an embodiment, although not shown in the drawings, the surgical instrument may further include a component for setting a zero point of roll rotation of the motor pack 3510 or the like. For example, the surgical instrument may further include at least one encoder for measuring a roll rotation angle of the motor pack 3510 or the like. Alternatively, the surgical instrument may further include a touch sensor, a Hall effect sensor, a photo sensor, or the like to measure the roll rotation angle of the motor pack 3510. However, the present disclosure is not limited thereto, and any component capable of measuring the roll rotation angle of the motor pack 3510 or the like may be provided in the surgical instrument of the present disclosure.

Figure 27:
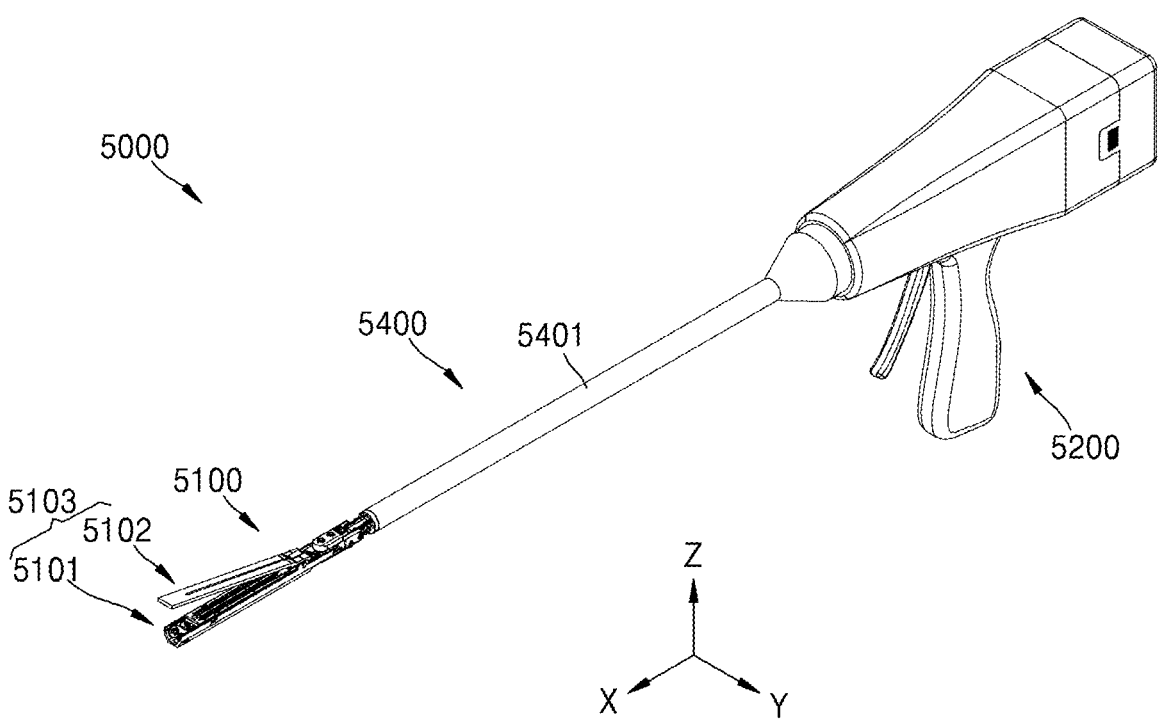
FIG. 27 is a schematic perspective view of a surgical instrument according to another embodiment of the present disclosure.
Figure 28:
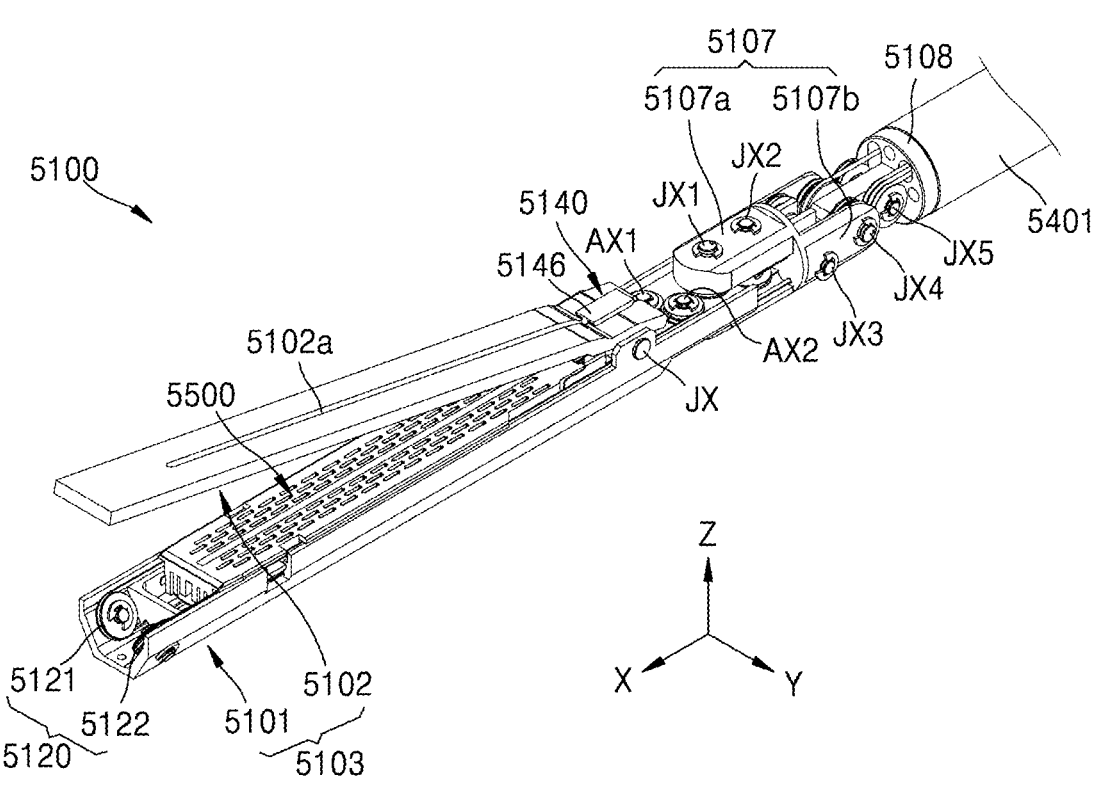
FIG. 28 is a schematic perspective view for describing an end tool of FIG. 27.
Figure 29:
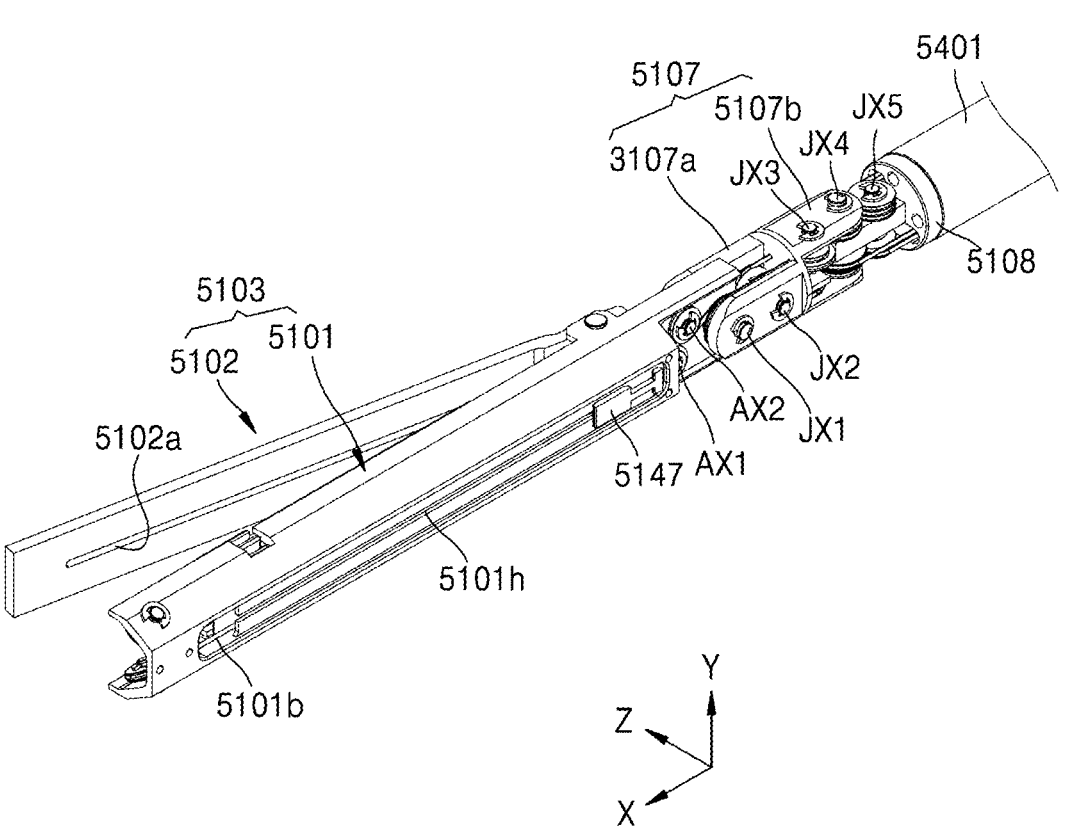
FIG. 29 is a perspective view of the end tool of FIG. 28 viewed from another direction.
Figure 30:
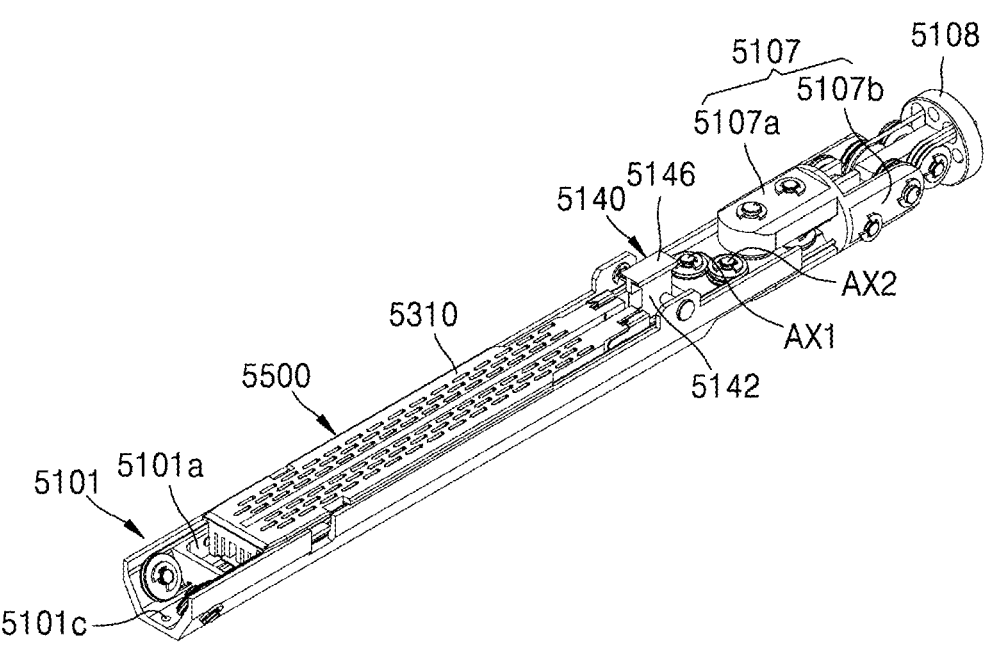
FIG. 30 is a schematic perspective view of the end tool of FIG. 27 with a second jaw removed.
Figure 31:
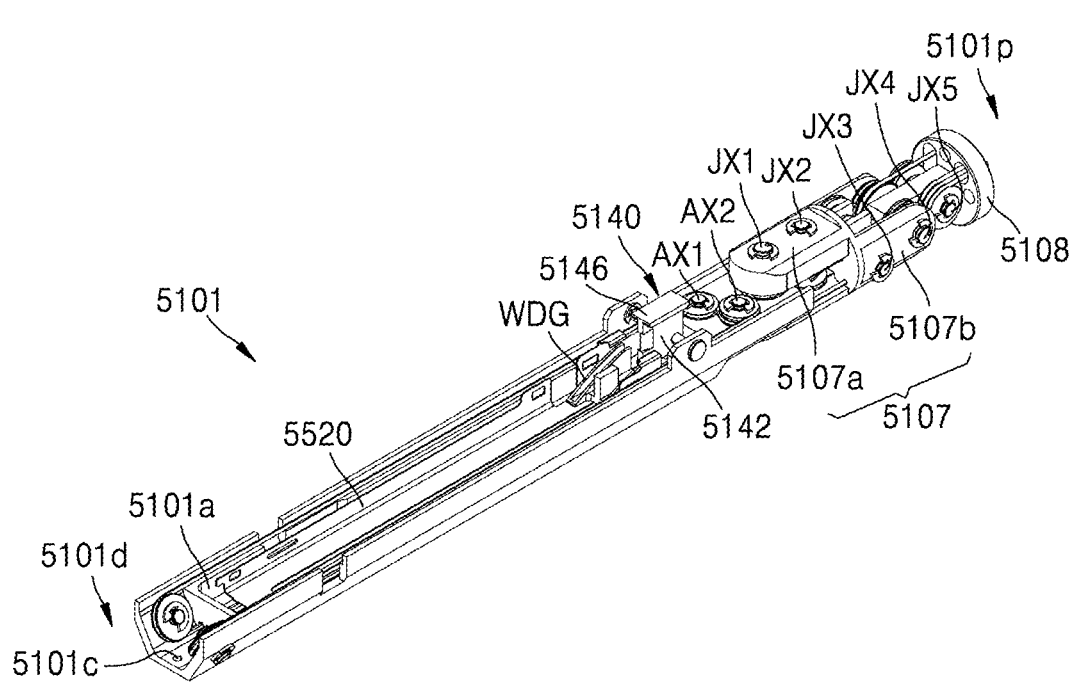
FIG. 31 is a schematic perspective view of the end tool of FIG. 30 with a cartridge removed.
Figure 32:
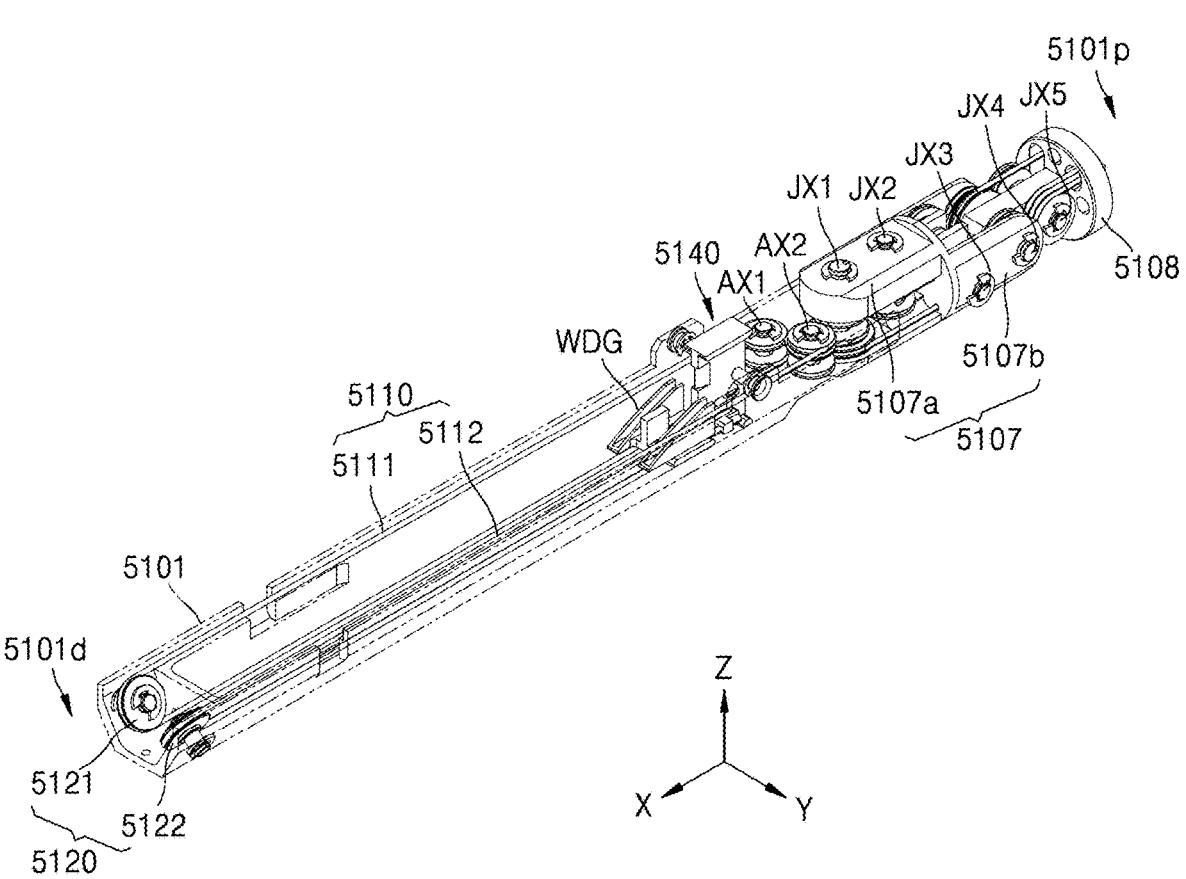
FIG. 32 is a transparent perspective view of FIG. 31.
Figure 33:
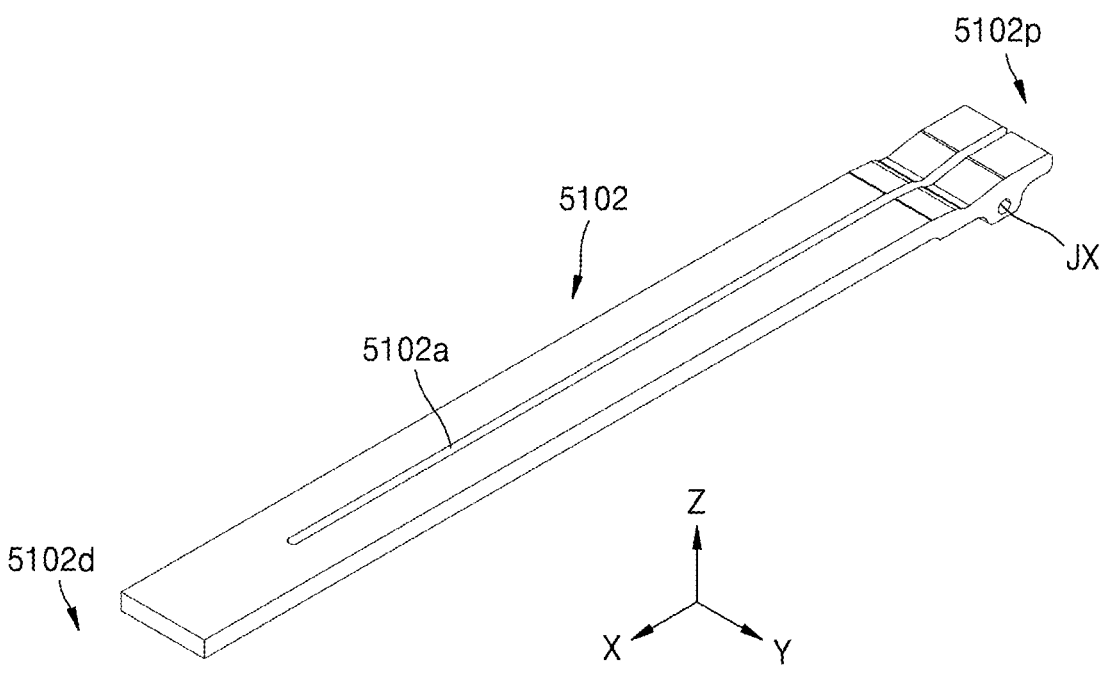
FIG. 33 is a perspective view schematically illustrating the second jaw of the end tool of FIG. 27.
Figure 34:
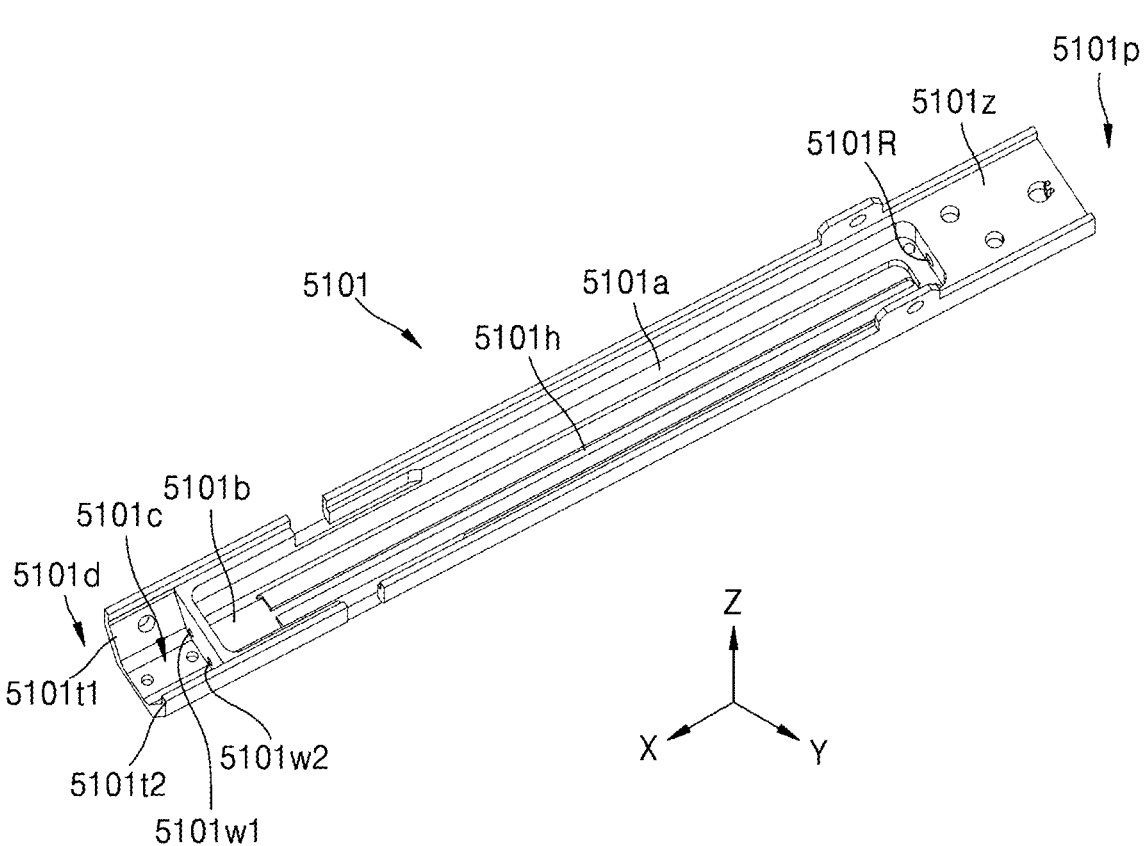
FIG. 34 is a perspective view schematically illustrating a first jaw of the end tool of FIG. 27.
Figure 36:
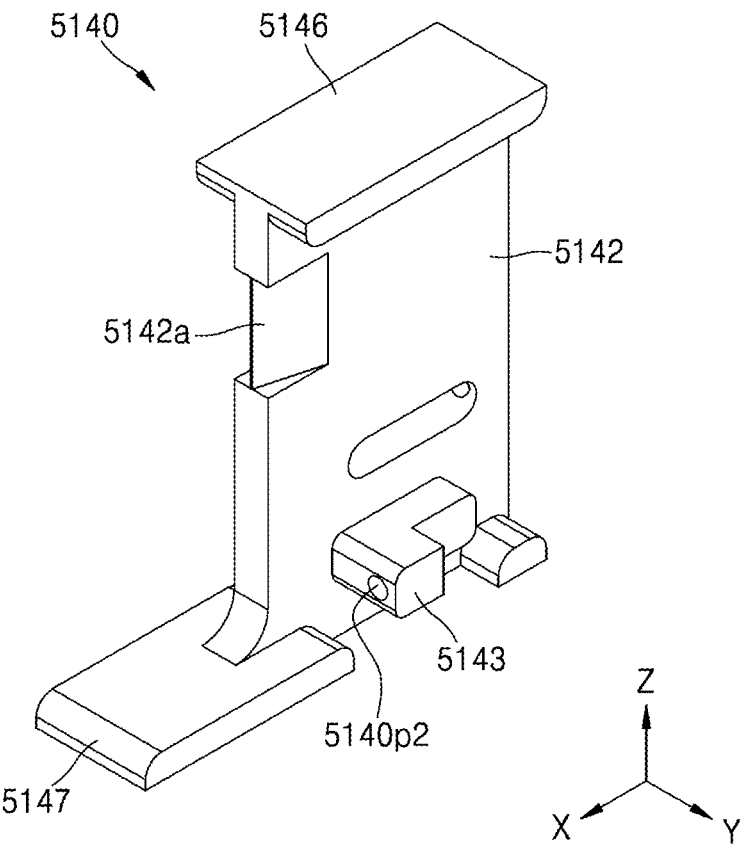
FIG. 36 is a perspective view illustrating an operation member of the end tool of FIG. 27.
Figure 37:
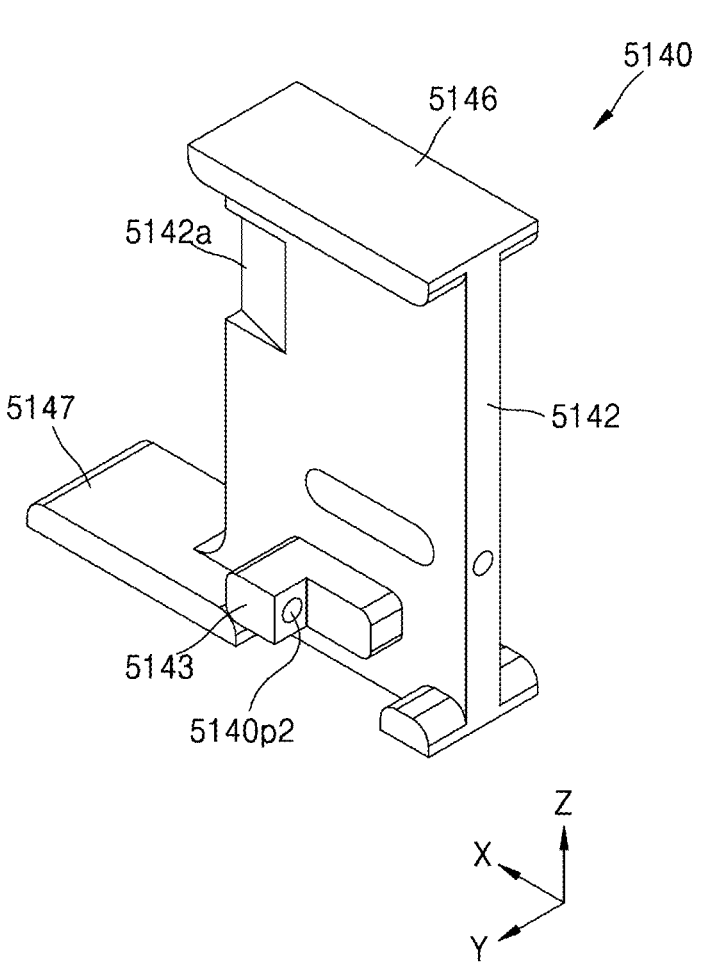
FIG. 37 is a perspective view of the operation member of FIG. 36 viewed from another direction.
Figure 38:
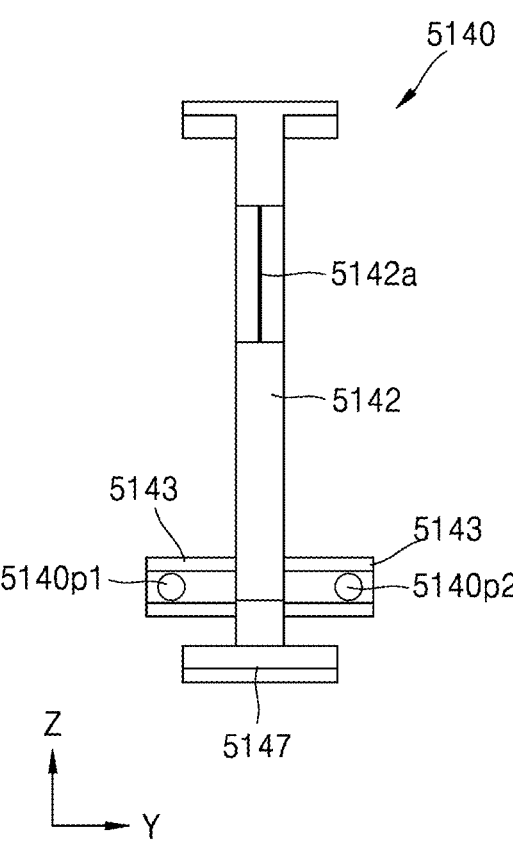
FIG. 38 is a front view of the operation member of FIG. 36 viewed in one direction.
Figure 39:
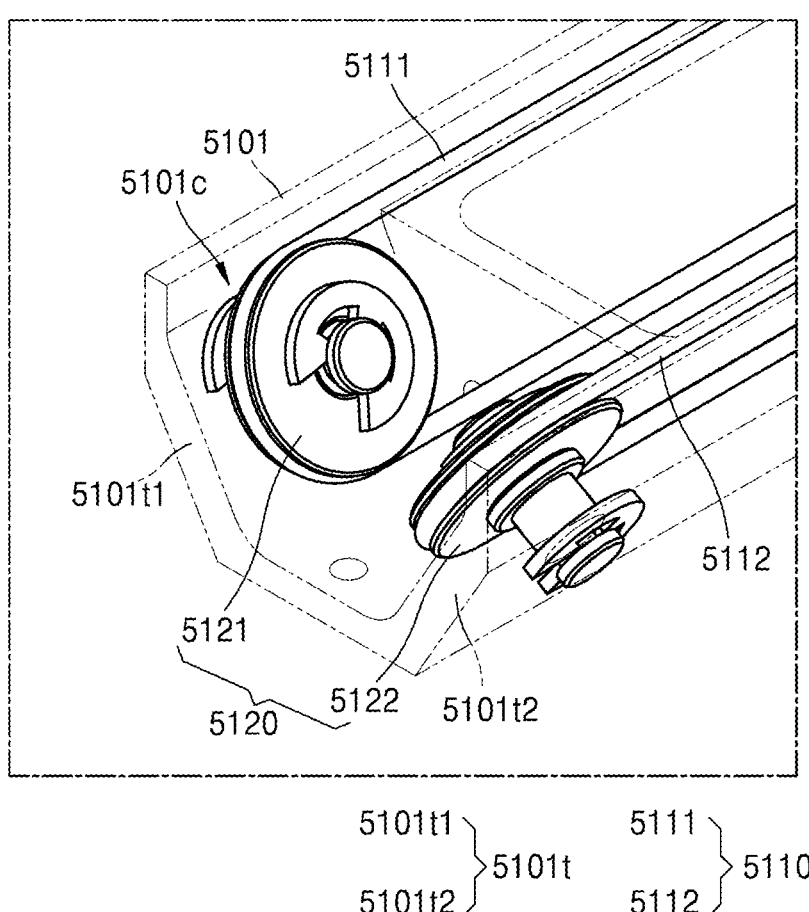
FIG. 39 is a schematic perspective view illustrating a portion of the end tool of FIG. 27.
Figure 40:
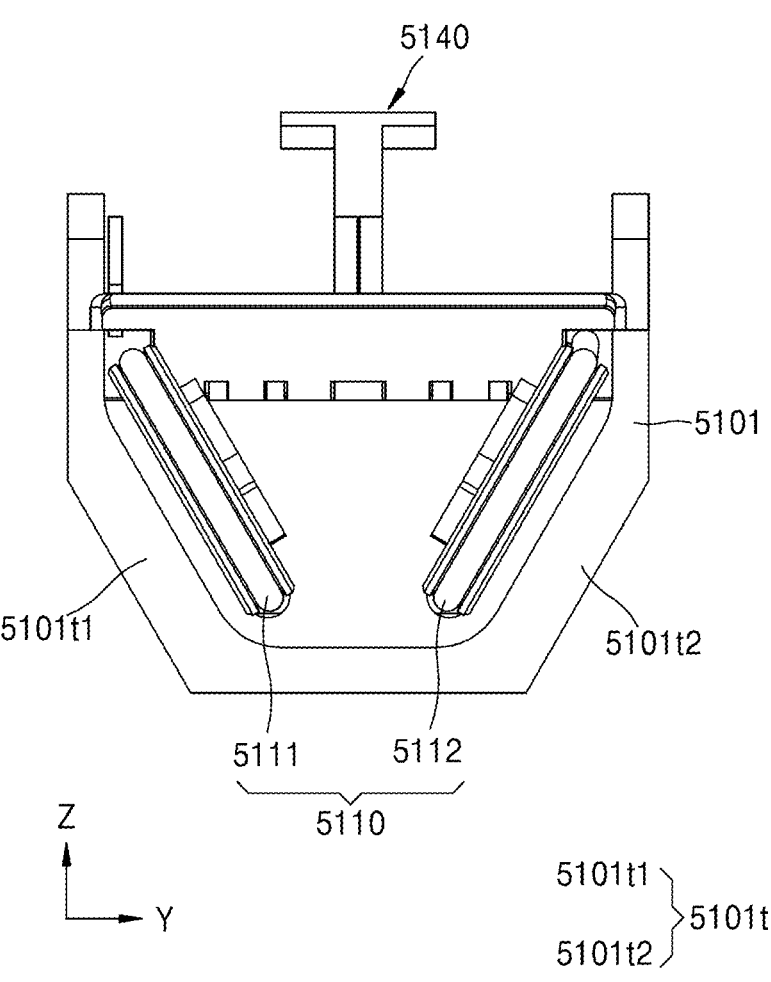
FIG. 40 is a front view of FIG. 39 viewed in one direction.
Figure 41:
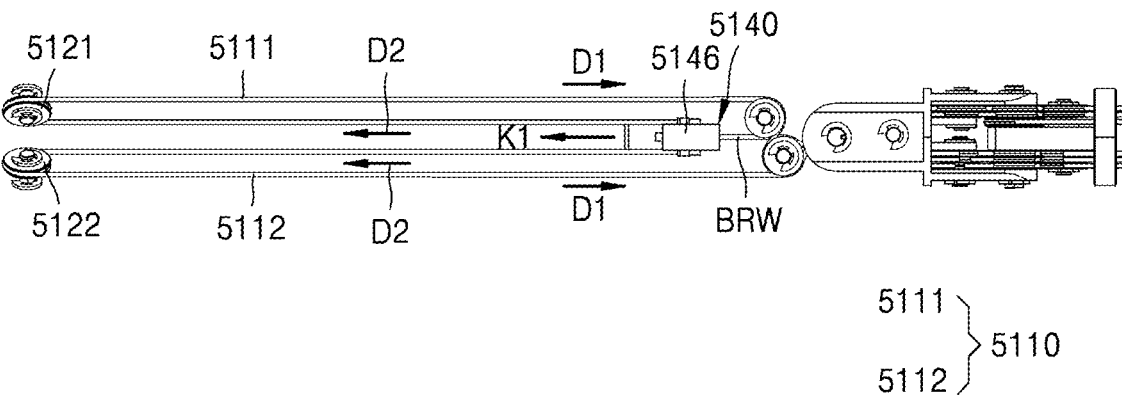
FIG. 41 is a schematic plan view for describing the operation member, a fixed pulley, and a forward-moving wire of the end tool of FIG. 27.
Figure 42:
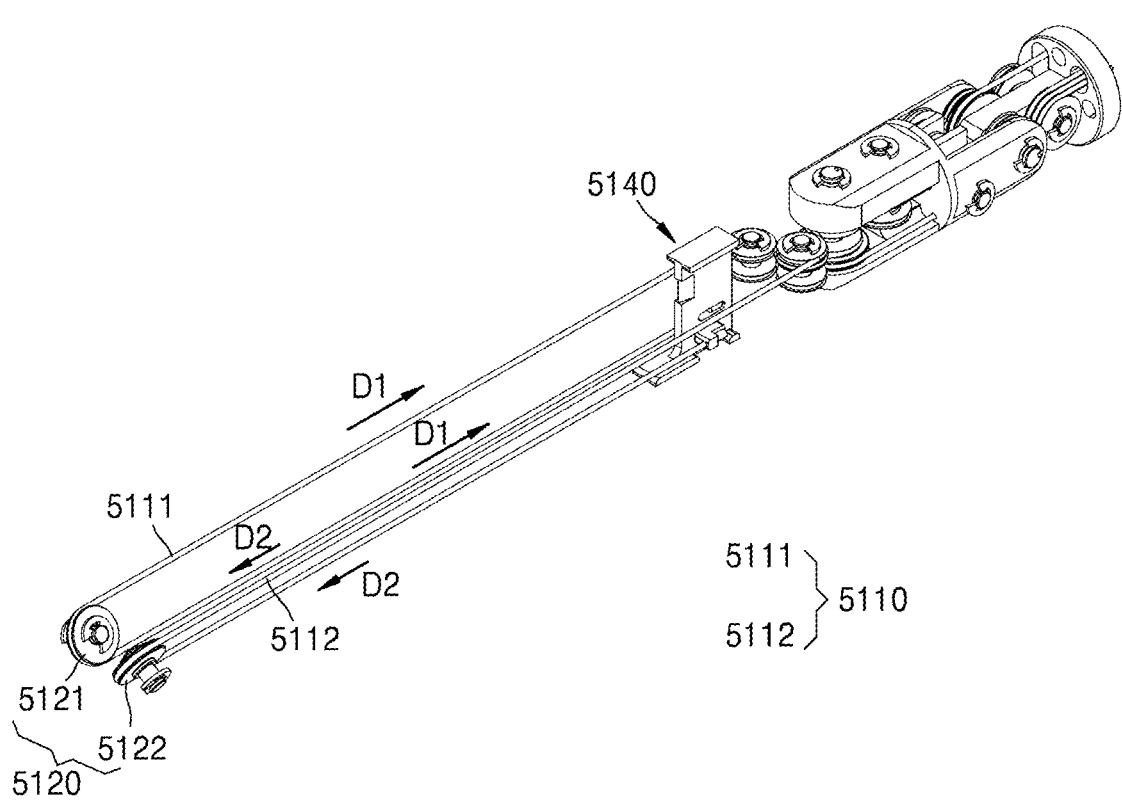
FIG. 42 is a schematic perspective view for describing the operation member, the fixed pulley, and the forward-moving wire of the end tool of FIG. 27.
Figure 43:
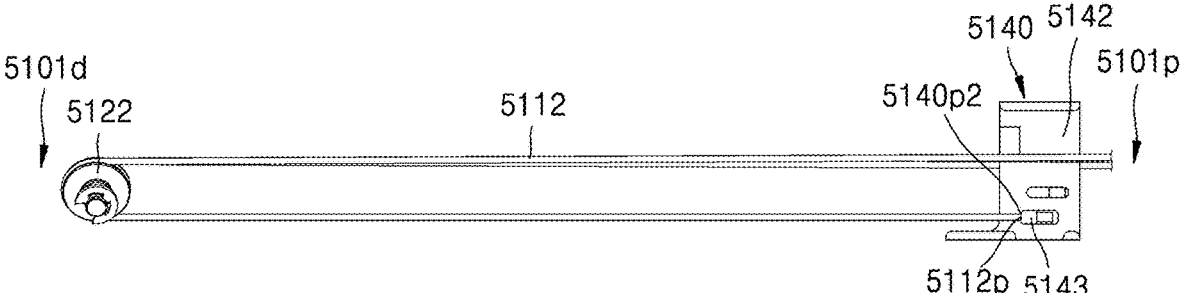
FIG. 43, and FIGS. 44A, 44B, and 44C are schematic views for describing an operation of the operation member of the end tool of FIG. 27.
Figure 47:
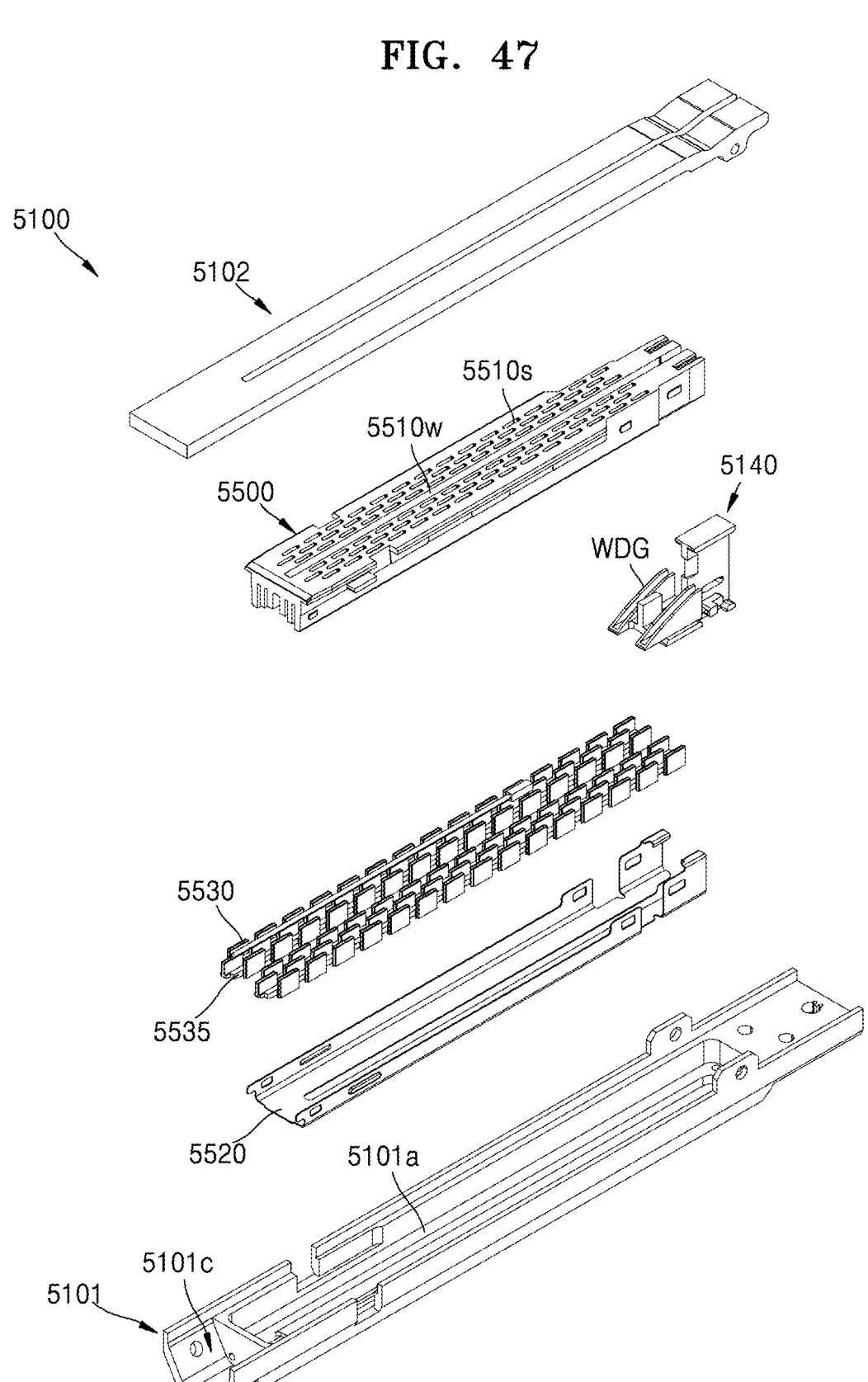
FIG. 47 is a perspective view illustrating the first jaw and the cartridge of the surgical instrument of FIG. 27.
Figure 48:
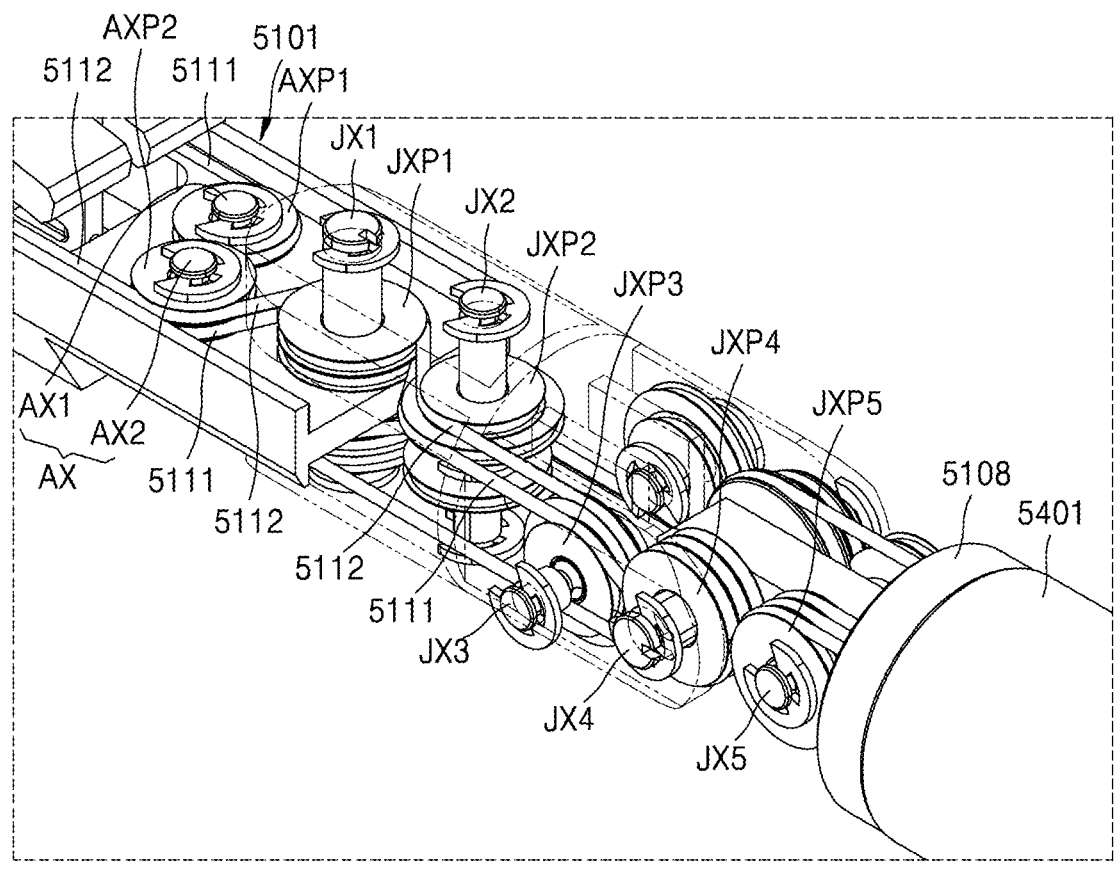
FIGS. 48 and 49 are views for describing a switching pulley, a yaw pulley, and a pitch pulley of the end tool of the surgical instrument of FIG. 27.
Figure 49:
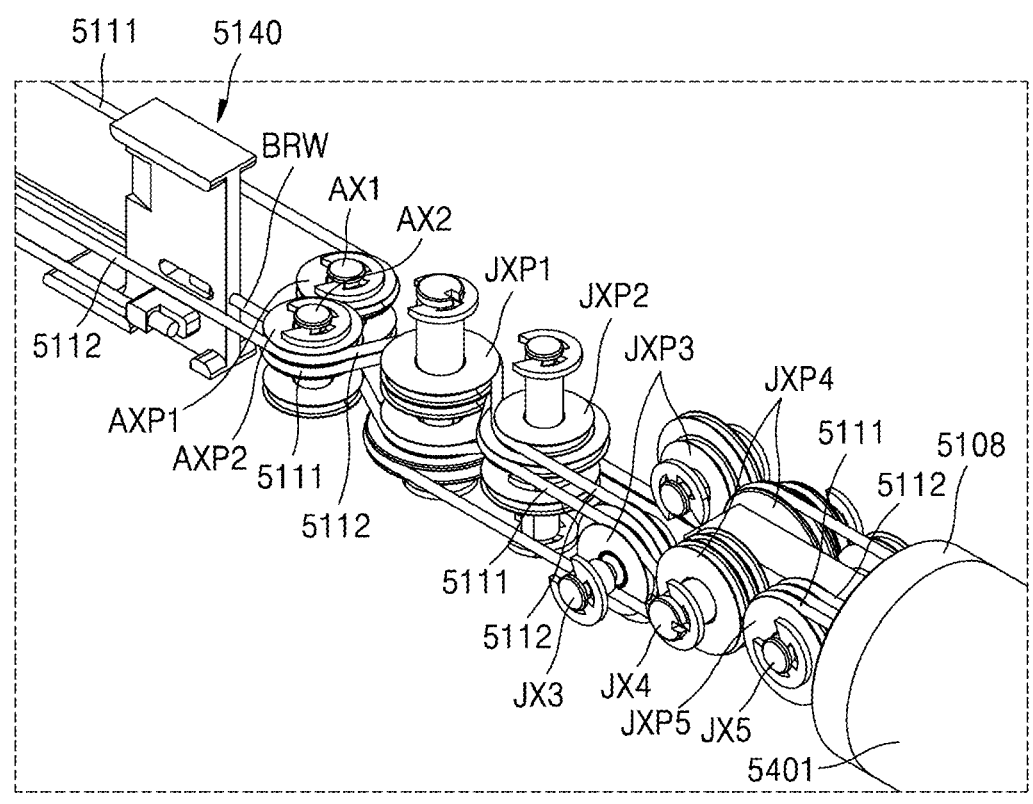

FIG. 27 is a schematic perspective view of a surgical instrument according to another embodiment of the present disclosure. FIG. 28 is a schematic perspective view for describing an end tool of FIG. 27. FIG. 29 is a perspective view of the end tool of FIG. 28 viewed from another direction. FIG. 30 is a schematic perspective view of the end tool of FIG. 27 with a second jaw removed. FIG. 31 is a schematic perspective view of the end tool of FIG. 30 with a cartridge removed. FIG. 32 is a transparent perspective view of FIG. 31. FIG. 33 is a perspective view schematically illustrating the second jaw of the end tool of FIG. 27. FIG. 34 is a perspective view schematically illustrating a first jaw of the end tool of FIG. 27. FIG. 35 is a plan view schematically illustrating the first jaw of the end tool of FIG. 27. FIG. 36 is a perspective view illustrating an operation member of the end tool of FIG. 27. FIG. 37 is a perspective view of the operation member of FIG. 36 viewed from another direction. FIG. 38 is a front view of the operation member of FIG. 36 viewed in one direction. FIG. 39 is a schematic perspective view illustrating a portion of the end tool of FIG. 27. FIG. 40 is a front view of FIG. 39 viewed in one direction. FIG. 41 is a schematic plan view for describing the operation member, a fixed pulley, and a forward-moving wire of the end tool of FIG. 27. FIG. 42 is a schematic perspective view for describing the operation member, the fixed pulley, and the forward-moving wire of the end tool of FIG. 27. FIGS. 43 and 44 are schematic views for describing an operation of the operation member of the end tool of FIG. 27. FIGS. 45 and 46 are views for describing an optional embodiment in which a backward-moving wire is added to the end tool of FIG. 27. FIG. 47 is a perspective view illustrating the first jaw and the cartridge of the surgical instrument of FIG. 27. FIGS. 48 and 49 are views for describing a switching pulley, a yaw pulley, and a pitch pulley of the end tool of the surgical instrument of FIG. 27.

A surgical instrument 5000 according to the present embodiment may include an end tool 5100, a manipulation part 5200, and a connection part 5400.

Here, the connection part 5400 is formed in the shape of a hollow shaft, and one or more wires and electric wires may be accommodated therein. The manipulation part 5200 is coupled to one end portion of the connection part 5400, the end tool 5100 is coupled to another end portion thereof, and the connection part 5400 may serve to connect the manipulation part 5200 to the end tool 5100. As an example, the connection part 5400 may include a straight part 5401, and although not shown in the drawings, the connection part

5400 may include one or more curved parts to increase case of use and control the arrangement of components for manipulation.

The manipulation part 5200 is formed at the one end portion of the connection part 5400 and provided as an interface to be directly controlled by a medical doctor, and may have, for example, a tongs shape, a stick shape, a lever shape, or the like, and when the medical doctor controls the manipulation part 5200, the end tool 5100, which is connected to the corresponding interface and inserted into the body of a surgical patient, performs a certain motion, thereby performing surgery. Here, the manipulation part 5200 is illustrated in FIG. 27 as being formed in a handle shape allowing user's fingers to come into close contact therewith and perform one or more motions, such as pulling or pushing, but the concept of the present disclosure is not limited thereto, and various types of manipulation parts that can be connected to the end tool 5100 and manipulate the end tool 5100 may be possible.

The end tool 5100 is formed on another end portion of the connection part 5400, and performs necessary motions for surgery by being inserted into a surgical site. As an example of the end tool 5100, a pair of jaws 5103 for performing a grip motion may be used. However, the concept of the present disclosure is not limited thereto, and various devices for performing surgery may be used as the end tool 5100. For example, a configuration of a cantilever cautery may also be used as the end tool. The end tool 5100 is connected to the manipulation part 5200 by a power transmission part (not shown, e.g., a wire or the like), and receives a driving force of the manipulation part 5200 through the power transmission part to perform a motion necessary for surgery, such as gripping, cutting, suturing, or the like.

Hereinafter, the end tool 5100 of the surgical instrument 5000 of FIG. 27 will be described in more detail.

FIG. 28 is a schematic perspective view for describing the end tool of FIG. 27. FIG. 29 is a perspective view of the end tool of FIG. 28 viewed from another direction. FIG. 30 is a schematic perspective view of the end tool of FIG. 27 with the second jaw removed. FIG. 31 is a schematic perspective view of the end tool of FIG. 30 with a cartridge removed. FIG. 32 is a transparent perspective view of FIG. 31.

The end tool 5100 may include the jaw 5103, a plurality of fixed pulleys 5120, and a plurality of forward-moving wires 5110. The plurality of fixed pulleys 5120 may include two or more pulleys, for example, a first fixed pulley 5121 and a second fixed pulley 5122. The plurality of forward-moving wires 5110 include two or more wires, and may include, for example, a first forward-moving wire 5111 and a second forward-moving wire 5112.

The jaw 5103 may perform various functions, for example, a grip motion, and may include a pair of jaws, e.g., a first jaw 5101 and a second jaw 5102 as a specific example. Here, each of the first jaw 5101 and the second jaw 5102, or a component encompassing the first jaw 5101 and the second jaw 5102 may be referred to as the jaw 5103.

The first jaw 5101 and the second jaw 5102 may be disposed to face each other, may move closer to or move away from each other, and may be formed to rotationally move around, for example, one shaft JX.

A cartridge 5500 may be disposed to be accommodated in the first jaw 5101, and a plurality of staples are disposed inside the cartridge 5500. When an operation member 5140 receives a force through the forward-moving wire 5110 while the first jaw 5101 and the second jaw 5102 are close to each other, such as when the first jaw 5101 and the second jaw 5102 are closed with the body tissue interposed therebetween, the operation member 5140 may push and raise the staples while moving toward a distal end 5101d of the first jaw 5101, so that stapling may be performed. At this point, one or more clamps 5146 and 5147 of the operation member 5140 may protrude to the outside of the first jaw 5101 and the second jaw 5102, allowing the operation member 5140 to move forward while applying pressure to an outer surface of the first jaw 5101 and the second jaw 5102, which facilitates the smooth progression of a stapling process. In an optional embodiment, the cartridge 5500 may include a case 5520 corresponding to the bottom, and the case 5520 is disposed in the first jaw 5101.

Meanwhile, the operation member 5140 may be used together with a wedge WDG. For example, the wedge WDG may be prepared separately from the operation member 5140 and then disposed adjacent to the operation member 5140 in the first jaw 5101. In addition, as another example, the operation member 5140 and the wedge WDG may be integrally formed. The wedge WDG may be disposed on at least one side of the body 5142 of the operation member 5140 and may be formed to have a predetermined inclined surface. That is, the wedge WDG may be formed to be inclined by a certain degree with respect to the extension direction of the end tool 5100. In other words, the wedge WDG may be formed to have a greater height at the proximal end 5101p side of the first jaw 5101 than the distal end 5101d side of the first jaw 5101.

The wedge WDG may be formed to be sequentially in contact with withdrawal members 5535 (refer to FIG. 47) or a plurality of staples 5530 (refer to FIG. 47) disposed in the cartridge 5500, and may serve to sequentially push and raise the staples 5530.

The plurality of fixed pulleys 5120 may be disposed in the first jaw 5101 to be closer to the front of the cartridge 5500, i.e., to the distal end 5101d of the first jaw 5101, than the cartridge 5500. For example, a plurality of fixed pulleys 5120 may be disposed in a front space 5101c of the first jaw 5101, and details thereof will be described below.

In addition, the end tool 5100 of the surgical instrument of the present embodiment may include one or more members, such as joint members, that connect the jaw 5103 to the connection part 5400. Further, in an optional embodiment, the end tool 5100 may include an end tool hub 5108 and a pitch hub 5107.

The end tool hub 5108 may be disposed to connect the end tool 5100 to the straight part 5401 of the connection part 5400.

As an example, the end tool hub 5108 may have a pulley shaft JX4 corresponding thereto, and the pulley shaft JX4 may be a pitch rotation shaft. As a specific example, the end tool 5100 may perform a vertical rotational motion around the pulley shaft JX4 based on the drawing. In addition, one or more pulleys may be disposed to be adjacent to the pulley shaft JX4.

The end tool hub 5108 may be in the form of a bar extending from the center of a surface thereof that corresponds to the connection part 5400, i.e., a bar extending from the center of a disk-shaped main region. The pulley shaft JX4 and a pulley shaft JX5 different from the pulley shaft JX4 may further correspond to a region of the bar.

The pitch hub 5107 is connected to the end tool hub 5108 and the jaw 5103. The pitch hub 5107 may be axially coupled to the end tool hub 5108 with respect to one pulley shaft, i.e., the pulley shaft JX4. The pitch hub 5107 may rotationally move around one pulley shaft, i.e., the pulley shaft JX4 while connected to the end tool hub 5108. That is, the end tool 5100 may perform a pitch motion as the pitch hub 5107 rotates around one pulley shaft, i.e., the pulley shaft JX4 with respect to the end tool hub 5108.

Further, the jaw 5103 of the end tool 5100 may be axially coupled to the pitch hub 5107 with respect to one pulley shaft, i.e., a pulley shaft JX1. The jaw 5103 may rotate around one pulley shaft, i.e., the pulley shaft JX1 while connected to the pitch hub 5107. That is, the jaw 5103 of the end tool 5100 may rotate around one pulley shaft, i.e., the pulley shaft JX1 with respect to the pitch hub 5107, thereby performing a yaw motion.

As a result, the yaw motion of the end tool 5100 includes a rotational motion of the jaw 5103 around one pulley shaft, i.e., the pulley shaft JX1 with respect to the pitch hub 5107, and the pitch motion of the end tool 5100 includes a rotational motion of the jaw 5103 coupled to the pitch hub 5107, which occurs as the pitch hub 5107 rotates around one pulley shaft, i.e., the pulley shaft JX4 together with the end tool hub 5108.

The pitch hub 5107 may include a first hub 5107a and a second hub 5107b.

The first hub 5107a of the pitch hub 5107 may be connected to the jaw 5103. As an example, the first hub 5107a may be elongated to connect to one region of the first jaw 5101, and specifically, may have two bars that are formed side by side to face each other and coupled to each other by placing one region of the first jaw 5101 therebetween.

The second hub 5107b of the pitch hub 5107 may be connected to the end tool hub 5108, for example, may have two bars that are formed side by side to face each other, and may be coupled to each other by placing one region of the end tool hub 5108 therebetween.

As described above, the pulley shaft JX5 is different from one pulley shaft, i.e., the pulley shaft JX4 may be disposed in the end tool hub 5108 to be spaced apart from the pulley shaft JX4 and closer to the connection part 5400 (refer to FIG. 27) than the pulley shaft JX4. The pulley shaft JX4 and the pulley shaft JX5 may have axes in directions parallel to each other.

A pulley shaft JX2, which is different from the pulley shaft JX1, is disposed in the pitch hub 5107 in a direction adjacent to and parallel to the pulley shaft JX1. In addition, a pulley shaft JX3 and the pulley shaft JX4 may be formed in a direction different from (for example, intersecting or orthogonal to) the direction in which the pulley shaft JX1 and the pulley shaft JX2 are disposed, and may be sequentially disposed in a direction toward (or away from the operation member) the connection part 5400.

The pulley shaft JX4 may be a pitch motion shaft of the end tool 5100, and the pulley shaft JX1 may be a yaw motion shaft.

The pulley shaft JX3 and the pulley shaft JX5 may be pitch auxiliary pulley shafts, and the pulley shaft JX2 may be a yaw auxiliary pulley shaft. One or more driving wires, such as a wire configured to transmit a driving force for a pitch motion or a yaw motion may have at least one region in contact with or wound around the pulley shafts JX1, JX2, JX3, JX4, and JX5.

The pulley shafts JX2, JX3, JX5 adjacent to the pulley shaft JX4, which is a pitch motion shaft, and the pulley shaft JX1, which is a yaw motion shaft, may control paths along which the driving wires are wound around the pulley shaft JX4 and the pulley shaft JX1 to secure the efficiency of the arrangement of the driving wires and stabilize the paths for transmitting forces through the driving wires.

In addition, at least one region of the forward-moving wire 5110 may be in contact with or wound around the pulley shafts JX1, JX2, JX3, JX4, and JX5.

A more detailed description of the arrangement of the pulley shafts JX1, JX2, JX3, JX4, and JX5 will be provided below.

One or more switching pulley shafts AX1 and AX2 may be disposed in the end tool 5100, and one or more pulleys corresponding to the switching pulley shafts AX1 and AX2 may be disposed.

For example, the switching pulley shafts AX1 and AX2 may be disposed in the jaw 5103, specifically, in a position toward the distal end 5101d of the first jaw 5101, and may be disposed closer to the distal end 5101d of the first jaw 5101 than at least the above-described pulley shafts JX1, JX2, JX3, JX4, and JX5.

The switching pulley shafts AX1 and AX2 may be shafts formed parallel to each other, and may be disposed to have different backward and forward positions with respect to each other such that the switching pulley shaft AX1 and the switching pulley shaft AX2 are sequentially disposed with respect to the distal end 5101d of the first jaw 5101 and some regions of the switching pulley shaft AX1 and the switching pulley shaft AX2 are overlap each other.

The switching pulley shafts AX1 and AX2 may be regions where at least one region of the forward-moving wires 5110 is wound or comes into contact to organize and guide the path of the forward-moving wire 5110 before entering the pulley shafts JX1, JX2, JX3, JX4, and JX5. A more detailed description of the arrangement of the switching pulley shafts AX1 and AX2 will be provided below.

As shown in FIG. 32, the first forward-moving wire 5111 and the second forward-moving wire 5112 may be correspondingly wound around the first fixed pulley 5121 and the second fixed pulley 5122 in the first jaw 5101 to be redirected, and connected to the rear of the end tool 5100 via at least one region of each of the switching pulley shafts AX1 and AX2 and the pulley shafts JX1, JX2, JX3, JX4, and JX5. Furthermore, the first forward-moving wire 5111 and the second forward-moving wire 5112 may further extend to the manipulation part 5200 (refer to FIG. 27) via the connection part 5400 to be precisely controlled. Accordingly, precise motion control of the operation member 5140 may be easily implemented, and details thereof will be described below.

The jaw 5103 of the end tool 5100 will be described in more detail.

FIG. 33 is a perspective view schematically illustrating the second jaw of the end tool of FIG. 27.

The second jaw 5102 may be formed in an elongated bar shape as a whole, and for example, the second jaw 5102 may be formed in a rod shape to correspond to the first jaw 5101 in at least one region. An anvil is formed at a distal end 5102d side of the second jaw 5102, and a region coupled to the first jaw 5101 may be included in a proximal end 5102p of the second jaw 5102. As an example, the proximal end 5102p is formed to be rotatable around a rotation shaft JX of the proximal end 5102p with respect to the first jaw 5101.

As a specific example, among surfaces of the second jaw 5102, the surface facing the first jaw 5101 may have the anvil formed thereon, may be formed in a flat plane shape, and may have shapes corresponding to the shapes of the staples 5530 to be described below. The anvil of the second jaw 5102 may serve as a support for supporting the staple 5130 on the opposite side of the operation member 5140 when the operation member 5140 pushes and raises the staple 5130 during a stapling motion, so that the staple 5130 is bent.

The second jaw 5102 includes a guide groove 5102a. The guide groove 5102a may have a shape elongated in a longitudinal direction of the second jaw 5102.

The guide groove 5102a may be formed to guide the operation member 5140, and may be a groove formed to pass through a region facing the operation member 5140. Through this, one region of the operation member 5140, such as at least one region of the body 5142 of the operation member 5140, or a first clamp 5146 connected thereto may pass through the guide groove 5102a to exit to the outside of the second jaw 5102. When the operation member 5140 moves forward, the first clamp 5146 may pass through the guide groove 5102a of the second jaw 5102 to be exposed to the outside of the second jaw 5102, and may come into contact with an upper surface of the second jaw 5102 or apply pressure thereto. As the operation member 5140 moves, the first clamp 5146 applies pressure on the upper surface of the second jaw 5102 and a second clamp 5147 to be described below applies pressure on a lower surface of the first jaw 5101 such that a gap between the second jaw 5102 and the first jaw 5101 decreases, allowing the second jaw 5102 to naturally remain in a closed state with respect to the first jaw 5101.

FIG. 34 is a perspective view schematically illustrating the first jaw of the end tool of FIG. 27. FIG. 35 is a plan view schematically illustrating the first jaw of the end tool of FIG. 27.

Referring to FIGS. 34 and 35 and the like, the first jaw 5101 is formed in an elongated bar shape as a whole, and a rotation shaft may be disposed in the proximal end such that the first jaw 5101 is rotationally movable, and such a rotation shaft may correspond to the rotation shaft JX formed in the second jaw 5102 described above. In addition, the cartridge 5500 (refer to FIG. 27) may be accommodated closer to the distal end 5101d side than the rotation shaft.

For example, the first jaw 5101 may be formed entirely in the form of a hollow box with one surface (upper surface) thereof is removed, such that a cartridge accommodation part 5101a capable of accommodating the cartridge 5500 may be formed inside the first jaw 5101. That is, the first jaw 5101 may be formed in a substantially "U" shape in cross section.

A guide groove 5101h may be formed in a bottom surface of the first jaw 5101, the bottom surface opposite to an upper open region formed by removing one surface. Specifically, the guide groove 5101h may be formed to guide a linear motion of the operation member 5140.

The guide groove 5101h may be formed to guide the operation member 5140, and may be a groove formed to pass through a region facing the operation member 5140. Through this, one region of the operation member 5140, such as at least one region of the body 5142 of the operation member 5140, or the second clamp 5147 connected thereto may pass through the guide groove 5101h to exit to the outside of the first jaw 5101. When the operation member 5140 moves forward, the second clamp 5147 may pass through the guide groove 5101h of the first jaw 5101 to be exposed to the outside of the first jaw 5101, and may come into contact with the lower surface of the first jaw 5101 or apply pressure thereto. As the operation member 5140 moves, the second clamp 5147 applies pressure on the lower surface of the first jaw 5101 and the first clamp 5146 applies pressure on the upper surface of the second jaw 5102 such that a gap between the second jaw 5102 and the first jaw 5101 decreases, allowing the second jaw 5102 to naturally remain in a closed state with respect to the first jaw 5101.

In an optional embodiment, the first jaw 5101 may include a window 5101b. After operating the operation member 5140 or using the end tool 5100, the second clamp 5147 of the operation member 5140 may be located corresponding to the window 5101b, and the coupled state of the first jaw 5101 and the operation member 5140 may be released.

The first jaw 5101 may include the front space 5101c located ahead of the cartridge accommodation part 5101a.

For example, the front space 5101c may be disposed closer to the distal end 5101d of the first jaw 5101 than the cartridge accommodation part 5101a. The plurality of fixed pulleys 5120 may be disposed in the front space 5101c, for example, the first fixed pulley 5121 and the second fixed pulley 5122 may be disposed in the front space 5101c (refer to, for example, FIGS. 28 to 32).

Two outer side surfaces of the front space 5101c include a first side surface 5101t1 and a second side surface 5101t2, and the first fixed pulley 5121 and the second fixed pulley 5122 may be disposed to correspond to the first side surface 5101t1 and the second side surface 5101t2, respectively.

Each of the first side surface 5101t1 and the second side surface 510112 may be formed to have an inclined shape. For example, the first side surface 5101t1 and the second side surface 5101t2 may be shaped such that a gap therebetween decreases as it moves downward, instead of being parallel to each other with the same gap. As a specific example, the gap between the first side surface 5101t1 and the second side surface 5101t2 may be formed to be smaller in a direction away from the second jaw 5102.

Since the first fixed pulley 5121 and the second fixed pulley 5122 are disposed to correspond to the first side surface 5101t1 and the second side surface 5101t2, respectively, the first fixed pulley 5121 and the second fixed pulley 5122 may be disposed to have an inclined shape such that a gap therebetween decreases in a direction away from the second jaw 5102 (refer to FIG. 28). The first fixed pulley 5121 and the second fixed pulley 5122 may be symmetrically shaped and may have the same size as each other.

In addition, a first path 5101w1 and a second path 5101w2 may be formed adjacent to the front space 5101c. For example, the first path 5101w1 and the second path 5101w2 may have the form of through holes formed in a barrier wall, and may be regions through which the first forward-moving wire 5111 and the second forward-moving wire 5112 pass, respectively.

In an optional embodiment, when a backward-moving wire (refer to, for example, FIG. 45) is disposed, the first jaw 5101 may include a rear side path 5101R corresponding to the backward-moving wire.

In addition, the first jaw 5101 may include a coupling region 5101z in a region adjacent to the proximal end 5101p. The coupling region 51012 is a region coupled to the pitch hub 5107 and may be in the form of a plate elongated to correspond to, for example, the first hub 5107a of the pitch hub 5107. The coupling region 5101z may be disposed and coupled between two bars formed on the first hub 5107a of the pitch hub 5107.

The operation member 5140 will be described in detail.

FIG. 36 is a perspective view illustrating an operation member of the end tool of FIG. 27. FIG. 37 is a perspective view of the operation member of FIG. 36 viewed from another direction. FIG. 38 is a front view of the operation member of FIG. 36 viewed in one direction.

The operation member 5140 may include the body 5142, the first clamp 5146, and the second clamp 5147. Meanwhile, the operation member 5140 may be used together with the wedge WDG (refer to FIGS. 31 and 32). For example, the wedge WDG may be prepared separately from the operation member 5140 and then disposed adjacent to the operation member 5140 in the first jaw 5101. In addition, as another example, the operation member 5140 and the wedge WDG may be integrally formed. In the present specification, for convenience of description, the operation member 5140 and the wedge WDG will be described and illustrated in the drawings with the assumption that the operation member 5140 and the wedge WDG are prepared separately.

The wedge WDG may be disposed on at least one side of the body 5142 and may be formed to have a predetermined inclined surface. That is, the wedge WDG may be formed to be inclined by a certain degree with respect to the extension direction of the end tool 5100. In other words, the wedge WDG may be formed to have a greater height at the proximal end 5101p side of the first jaw 5101 than the distal end 5101d side of the first jaw 5101.

The wedge WDG may be formed to be sequentially in contact with the withdrawal members 5535 (refer to FIG. 47) or the plurality of staples 5530 (refer to FIG. 47) and may serve to sequentially push and raise the staples 5530.

The body 5142 may be in the form of an elongated column, such as a plate-shaped column. In addition, a blade region 5142a may be formed in one region of the body 5142, and an edge sharply formed to cut tissue may be formed in the blade region 5142a. The tissue disposed between the first jaw 5101 and the second jaw 5102 may be cut as at least a portion of the edge formed in the blade region 5142a of the body 5142 is withdrawn to the outside of the first jaw 5101 and the cartridge 5500.

The first clamp 5146 may be formed in one region of the body 5142, and the second clamp 5147 may be formed in another region different from the one region. For example, the body 5142 may be disposed between the first clamp 5146 and the second clamp 5147.

The first clamp 5146 and the second clamp 5147 may be formed to have a region with a width at least greater than that of the body 5142. Accordingly, the first clamp 5146 may be inserted into and pass through the guide groove 5102a formed in the second jaw 5102 in the longitudinal direction to be disposed or brought into contact with the upper surface of the second jaw 5102 and, at the same time, the second clamp 5147 may be inserted into and pass through the guide groove 5101h formed in the first jaw 5101 in the longitudinal direction to be disposed or brought into contact with the lower surface of the first jaw 5101, so that the first clamp 5146 and the second clamp 5147 may move. Thus, when the operation member 5140 moves, the first clamp 5146 and the second clamp 5147 may apply forces in directions that bring the second jaw 5102 and the first jaw 5101 closer to each other.

As a result, when the operation member 5140 moves from the proximal end 5101p of the first jaw 5101 toward distal end 5101d of the first jaw 5101, a motion of decreasing a distance between the second jaw 5102 and the first jaw 5101, i.e., a closing motion of the jaw 5103, may be naturally implemented through the first clamp 5146 and the second clamp 5147.

The first clamp 5146 and the second clamp 5147 may be placed at different positions with respect to a forward-facing direction of the body 5142. For example, the second clamp 5147 may be located further forward than the first clamp 5146. For example, the second clamp 5147 may be located closer to the distal end 5101d of the first jaw 5101 than the first clamp 5146 when the operation member 5140 is disposed in the first jaw 5101. Accordingly, the operation member 5140 may move forward while the first jaw 5101 and second jaw 5102 are in the closed state, so that the first jaw 5101 and second jaw 5102 can be maintained with greater efficiency and stability while performing stapling.

A first connection region 5140p1 and a second connection region 5140p2 may be formed in one region of the body 5142, such as one region in a front side of the body 5142, specifically, a region of the body 5142 facing the distal end 5101d of the first jaw 5101.

The first connection region 5140p1 and the second connection region 5140p2 may be regions to which the first forward-moving wire 5111 and the second forward-moving wire 5112 are connected, respectively, and may each be in the form of a fixing groove such that respective one end portion region of the first forward-moving wire 5111 and the second forward-moving wire 5112 is accommodated or fixed thereto. When the first forward-moving wire 5111 and the second forward-moving wire 5112 are connected to the first connection region 5140p1 and the second connection region 5140p2 to pull the first forward-moving wire 5111 and the second forward-moving wire 5112, respectively, forces pulling the first forward-moving wire 5111 and the second forward-moving wire 5112 are transmitted to the operation member 5140 through the first connection region 5140p1 and the second connection region 5140p2 so that the operation member 5140 may move, i.e., move forward In an optional embodiment, the first connection region 5140p1 and the second connection region 5140p2 may be formed on side portions 5143 of the operation member 5140, respectively.

The side portions 5143 may be formed to protrude outward from both side surfaces of the body 5142, respectively. By forming the first connection region 5140p1 and the second connection region 5140p2 on the side portions 5143 formed to protrude from both sides of the body 5142, spaces for respectively connecting the first forward-moving wire 5111 and the second forward-moving wire 5112 to the first connection region 5140p1 and the second connection region 5140p2 can be easily secured.

Further, by forming the first connection region 5140p1 and the second connection region 5140p2 on the side portions 5143 formed on both sides of the body 5142, and connecting the first forward-moving wire 5111 and the second forward-moving wire 5112 to the first connection region 5140p1 and the second connection region 5140p2, the first forward-moving wire 5111 and the second forward-moving wire 5112 can be pulled from both sides of the body 5142, and also from symmetrical positions, so that the forward movement of the operation member 5140 can be precisely controlled.

In an optional embodiment, a connection region for the backward-moving wire may be formed in a rear side region of the body 5142.

FIG. 39 is a schematic perspective view illustrating a portion of the end tool of FIG. 27. FIG. 40 is a front view of FIG. 39 viewed in one direction.

Referring to FIGS. 39 and 40, the first fixed pulley 5121 and the second fixed pulley 5122 may be disposed to have an inclined shape without being disposed in parallel to each other. For example, as a specific example, based on the drawings, the first fixed pulley 5121 and the second fixed pulley 5122 may be disposed such that a gap therebetween decreases in a direction away from the second jaw 5102 (refer to FIG. 28).

Specifically, the first fixed pulley 5121 and the second fixed pulley 5122 may be disposed to face each other in the front space 5101c located further forward than the cartridge accommodation part 5101a of the first jaw 5101, and may be disposed symmetrically to each other as a specific example. In addition, the first fixed pulley 5121 and the second fixed pulley 5122 may be formed to have the same size.

Two outer side surfaces of the front space 5101c include the first side surface 5101t1 and the second side surface 510112, and the first fixed pulley 5121 and the second fixed pulley 5122 may be disposed to correspond to the first side surface 5101t1 and the second side surface 5101t2, respectively.

Each of the first side surface 5101t1 and the second side surface 510112 may be formed to have an inclined shape. For example, the first side surface 5101t1 and the second side surface 5101t2 may be shaped such that a gap therebetween decreases as it moves downward, instead of being parallel to each other with the same gap. As a specific example, the gap between the first side surface 5101t1 and the second side surface 5101t2 may be formed to be gradually smaller in a direction away from the second jaw 5102 (refer to FIG. 28). In addition, the first side surface 5101t1 and the second side surface 510112 may have shapes symmetrical to each other.

The first forward-moving wire 5111 and the second forward-moving wire 5112 may be correspondingly wound around the first fixed pulley 5121 and the second fixed pulley 5122, and the regions of the first forward-moving wire 5111 and the second forward-moving wire 5112 emerging from being wound around the lower sides of the first fixed pulley 5121 and the second fixed pulley 5122 may be directed to the first connection region 5140p1 and the second connection region 5140p2 of the operation member 5140 described above, respectively.

With such a shape, the characteristic of balanced arrangement of the first and second fixed pulleys 5121 and 5122 and the first and second forward-moving wires 5111 and 5112 with respect to the moving direction of the operation member 5140 may be improved, and for example, the symmetrical shape may be easily implemented. In addition, shaking or rotational moment generated when pulling the first forward-moving wire 5111 and the second forward-moving wire 5112 may be reduced, so that the end tool 5100 may be reduced or prevented from shaking.

In addition, the end tool 5100 may be shaped such that a width of, for example, one side of the first jaw 5101, which is one side of the jaw 5103, specifically, a width of a main region of the lower side is reduced, so that the end tool 5100 can be implemented in a compact structure as a whole.

The arrangement relationship of the operation member 5140, the plurality of forward-moving wires 5110, and the plurality of fixed pulleys 5120 will now be further described.

FIG. 41 is a schematic plan view for describing the operation member, the fixed pulley, and the forward-moving wire of the end tool of FIG. 27. FIG. 42 is a schematic perspective view for describing the operation member, the fixed pulley, and the forward-moving wire of the end tool of FIG. 27.

As described above, the first fixed pulley 5121 and second fixed pulley 5122 are disposed in the front space 5101c of the first jaw 5101, and each of the first fixed pulley 5121 and the second fixed pulley 5122 may be fixed to the first jaw 5101 and immobile, or fixed so as to be rotatable about one shaft.

The first forward-moving wire 5111 and the second forward-moving wire 5112 may be wound around outer circumferential surfaces of the first fixed pulley 5121 and the second fixed pulley 5122, respectively, and a groove may be formed in each of the outer circumferential surfaces of the first fixed pulley 5121 and the second fixed pulley 5122.

The first fixed pulley 5121 and the second fixed pulley 5122 may be disposed closer to the distal end 5101d of the first jaw 5101 at least than the operation member 5140.

The first forward-moving wire 5111 may extend to have a length in the longitudinal direction of the first jaw 5101, and one end portion region thereof may extend to the proximal end 5101p of the first jaw 5101, and pass through the switching pulley shafts AX1 and AX2 or switching pulleys coupled thereto and the pulley shafts JX1, JX2, JX3, JX4, and JX5 or pulleys coupled thereto to be connected to the inside of the driving part, such as the manipulation part 5200 (refer to FIG. 28), so that the first forward-moving wire 5111 can be pulled through manipulation of the manipulation part 5200.

Another end portion of the first forward-moving wire 5111 may extend in a direction toward the distal end 5101d of the first jaw 5101 along the longitudinal direction of the first jaw 5101, emerge from the lower side of the first fixed pulley 5121 after being wound around the upper side of the first fixed pulley 5121 while coming into contact therewith, and extend in a direction toward proximal end 5101p of the first jaw 5101 to be connected and fixed to the first connection region 5140p1 of the operation member 5140.

In an optional embodiment, among the regions of the first forward-moving wire 5111, the region extending to the distal end 5101d of the first jaw 5101 and being directed to the upper side of the first fixed pulley 5121 may be parallel to the region emerging from the lower side of the first fixed pulley 5121, extending toward the proximal end 5101p of the first jaw 5101, and being directed toward the first connection region 5140p1 of the operation member 5140.

Accordingly, a pulling force can be effectively transmitted to the operation member 5140 when pulling the first forward-moving wire 5111 toward the proximal end 5101p.

The second forward-moving wire 5112 may extend to have a length in the longitudinal direction of the first jaw 5101, and one end portion region thereof may extend to the proximal end 5101p of the first jaw 5101, and pass through the switching pulley shafts AX1 and AX2 or switching pulleys coupled thereto and the pulley shafts JX1, JX2, JX3, JX4, and JX5 or pulleys coupled thereto to be connected to the inside of the driving part, such as the manipulation part 5200 (refer to FIG. 58), so that the second forward-moving wire 5112 can be pulled through manipulation of the manipulation part 5200.

Another end portion of the second forward-moving wire 5112 may extend in a direction toward the distal end 5101d of the first jaw 5101 along the longitudinal direction of the first jaw 5101, emerge from the lower side of the second fixed pulley 5122 after being wound around the upper side of the second fixed pulley 5122 while coming into contact therewith, and extend in a direction toward proximal end 5101p of the first jaw 5101 to be connected and fixed to the second connection region 5140p2 of the operation member 5140.

In an optional embodiment, among the regions of the second forward-moving wire 5112, the region extending to the distal end 5101d of the first jaw 5101 and being directed to the upper side of the second fixed pulley 5122 may be parallel to the region emerging from the lower side of the second fixed pulley 5122, extending toward the proximal end 5101p of the first jaw 5101, and being directed toward the second connection region 5140p2 of the operation member 5140.

Accordingly, a pulling force can be effectively transmitted to the operation member 5140 when pulling the second forward-moving wire 5112 toward the proximal end 5101*p*.

As shown in FIGS. 41 and 42, when the first forward-moving wire 5111 and the second forward-moving wire 5112 are pulled in a first direction D1, one region of each of the first forward-moving wire 5111 and the second forward-moving wire 5112 may move in the first direction D1, and accordingly, the region of the forward-moving wire 5110 emerging from the lower sides of the first fixed pulley 5121 and the second fixed pulley 5122 after being wound around the upper sides thereof may move in a second direction D2, which is the opposite direction of the first direction D1. Accordingly, forces of the first forward-moving wire 5111 and the second forward-moving wire 5112 may be transmitted to the first connection region 5140*p*1 and the second connection region 5140*p*2 connected to the first forward-moving wire 5111 and the second forward-moving wire 5112, and the forces cause the operation member 5140 also move in a direction K1, which is the same direction as the second direction D2, i.e., move forward.

FIGS. 43 and 44 are schematic views for describing an operation of the operation member of the end tool of FIG. 27.

Figure 44A:
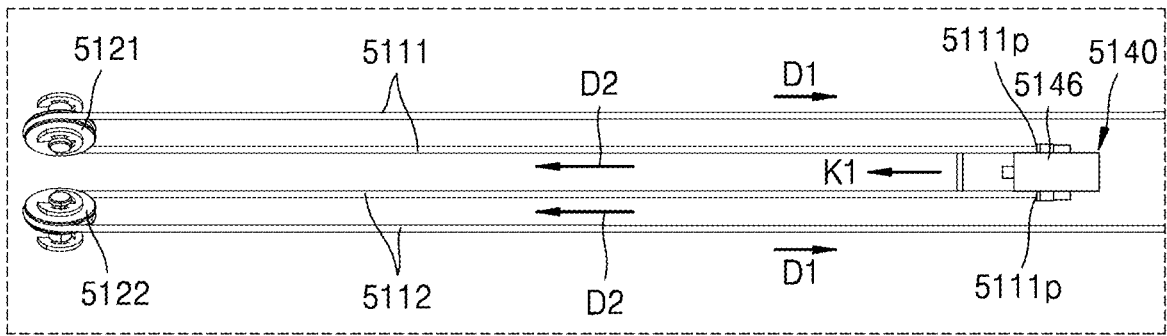
Figure 44B:
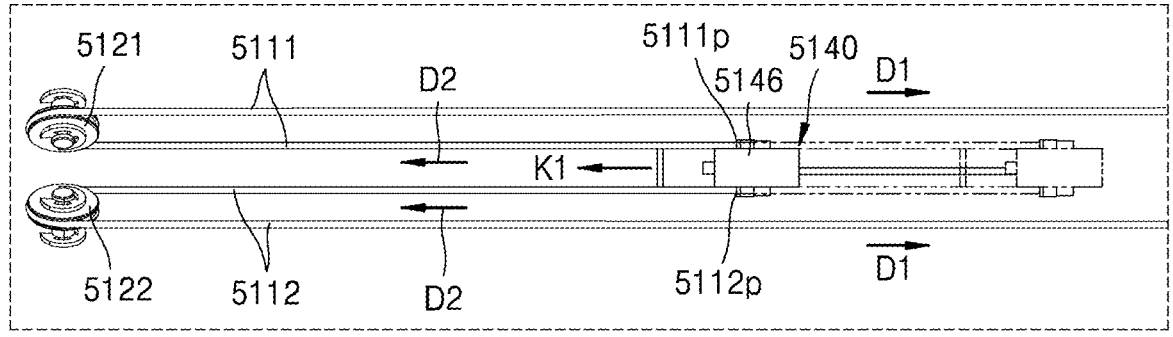
Figure 44C:
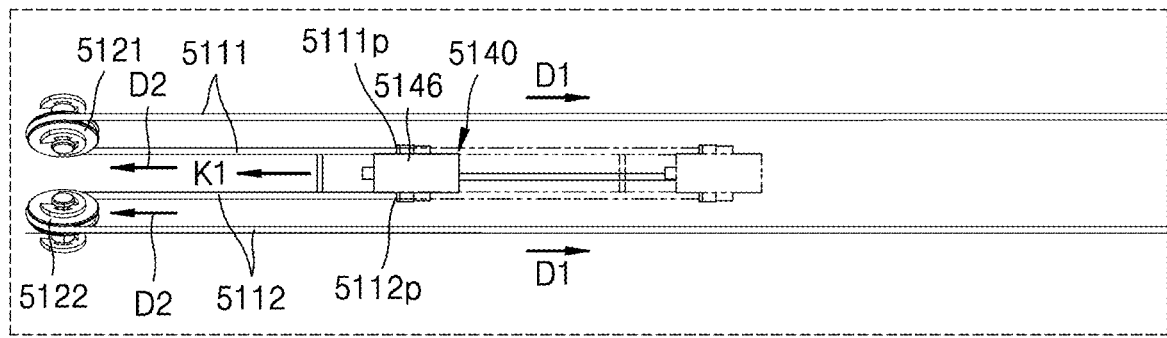
Figure 45:
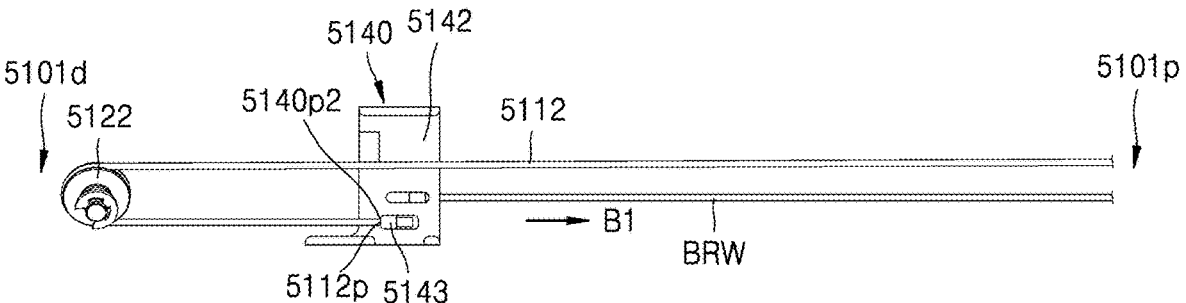
FIG. 45, and FIGS. 46A, 46B, and 46C are views for describing an optional embodiment in which a backward-moving wire is added to the end tool of FIG. 27.

Referring to FIGS. 43 and 44, for convenience of description, the first jaw 5101 is excluded, and the first forward-moving wire 5111, the second forward-moving wire 5112, the first fixed pulley 5121, the second fixed pulley 5122, and the operation member 5140 are illustrated. Based on FIG. 43, the operation member 5140 may move in a leftward direction, i.e., move forward toward the distal end 5101*d*, and this forward movement is illustrated sequentially in FIGS. 44A, 44B, and 44C.

As shown in FIG. 44A, when the first forward-moving wire 5111 and the second forward-moving wire 5112 are pulled in the first direction D1, one region of each of the first forward-moving wire 5111 and the second forward-moving wire 5112 is pulled in the first direction D1, and thus the regions of the first forward-moving wire 5111 and the second forward-moving wire 5112 emerging from the lower sides of the first fixed pulley 5121 and the second fixed pulley 5122 after being wound around the upper sides thereof move in the second direction D2, which is the opposite direction of the first direction D1. Accordingly, forces of the first forward-moving wire 5111 and the second forward-moving wire 5112 are transmitted respectively to the first connection region 5140*p*1 and the second connection region 5140*p*2 respectively connected to the first forward-moving wire 5111 and the second forward-moving wire 5112, and the forces cause the operation member 5140 to move in the direction K1, which is the same direction as the second direction D2, i.e., move forward, thereby positioning the operation member 5140 in an advanced position shown in FIG. 44B.

Thereafter, as shown in FIG. 44B, when the first forward-moving wire 5111 and the second forward-moving wire 5112 are pulled further in the first direction D1, one region of the first forward-moving wire 5111 and the second forward-moving wire 5112 is pulled further in the first direction D1, and thus the regions of the first forward-moving wire 5111 and the second forward-moving wire 5112 emerging from the lower sides of the first fixed pulley 5121 and the second fixed pulley 5122 after being wound around the upper sides thereof move further in the second direction D2, which is the opposite direction of the first direction D1. Accordingly, forces of the first forward-moving wire 5111 and the second forward-moving wire 5112 are transmitted respectively to the first connection region 5140*p*1 and the second connection region 5140*p*2 connected to the first forward-moving wire 5111 and the second forward-moving wire 5112, and the forces cause the operation member 5140 to move further in the direction K1, which is the same direction as the second direction D2, i.e., move forward to a further advanced position than in FIG. 44B, thereby positioning the operation member 5140 in the further advanced position shown in FIG. 44C.

Although not shown in the drawings, it will be appreciated of course that the form corresponding to the side view illustrating the operation of the operation member may be applied to the end tool 5100 of the present embodiment either as is or with appropriate modifications.

FIGS. 45 and 46 are views for describing an optional embodiment in which a backward-moving wire is added to the end tool of FIG. 27.

Referring to FIGS. 45 and 46, the end tool of the present embodiment may further include a backward-moving wire BRW.

For example, the structure of FIG. 45 may be the structure of FIG. 43 with the addition of the backward-moving wire BRW.

Referring to FIGS. 45 and 46, for convenience of description, the first jaw 5101 is excluded, and the first forward-moving wire 5111, the second forward-moving wire 5112, the first fixed pulley 5121, the second fixed pulley 5122, the operation member 5140, and the backward-moving wire BRW are illustrated.

Figure 46A:
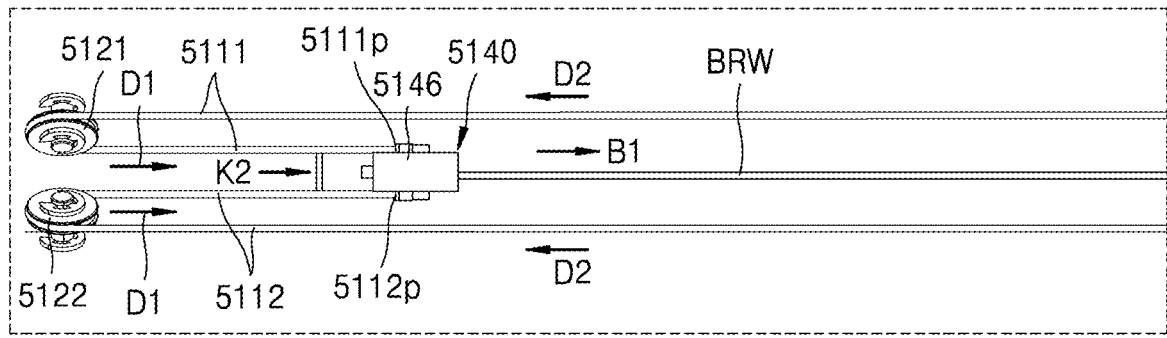
Figure 46B:
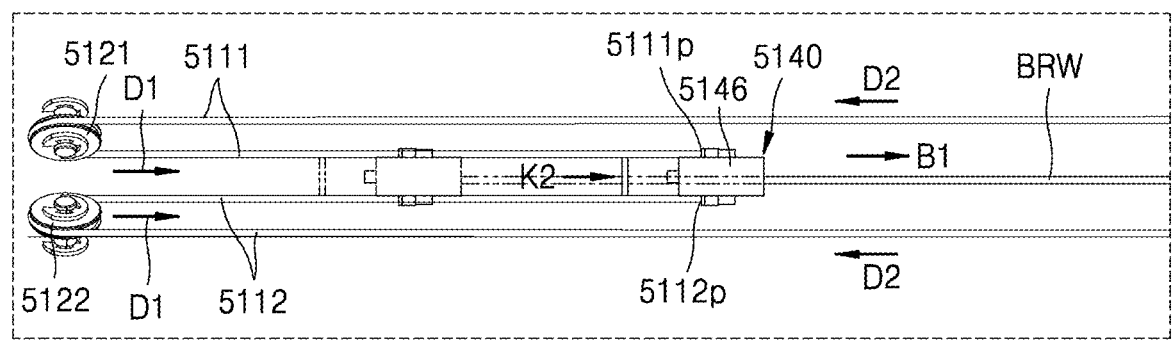
Figure 46C:
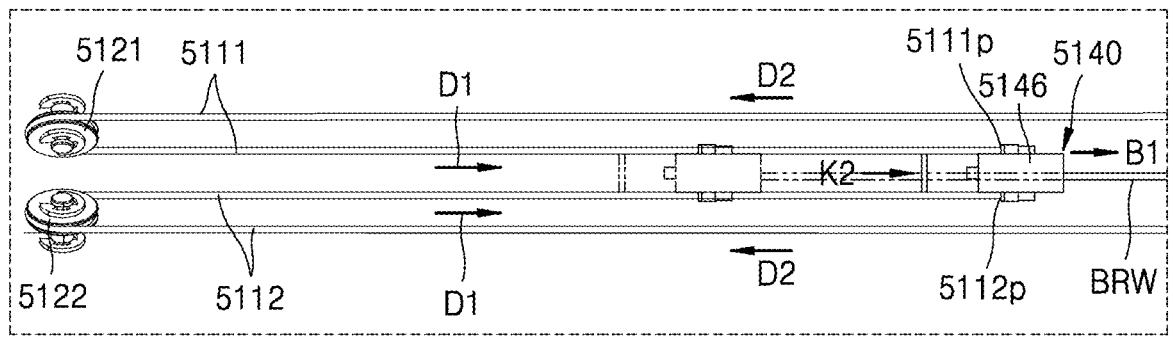

Based on FIG. 45, the operation member 5140 may move in a rightward direction, i.e., move backward toward the proximal end 5101*p*, and this backward movement is illustrated sequentially in FIGS. 46A, 46B, and 46C.

The backward-moving wire BRW may be connected to one region of the operation member 5140 and may be connected, for example, to a rear side of the operation member, specifically, to a region of the blade region 5142*a*, which is opposite to the region in which the edge of the blade region 5142*a* is formed, among regions of the body 5142.

A driving part or driving transmission part (e.g., a wire, a pulley, or the like) capable of pulling the backward-moving wire BRW may be connected to the backward-moving wire BRW, and the backward-moving wire BRW may be operated according to manual or automatic manipulation. For example, the backward-moving wire BRW may be pulled by the manipulation part 5200 (refer to FIG. 27).

By pulling the backward-moving wire BRW. the operation member 5140 may move backward.

For example, as shown in FIG. 46A, the backward-moving wire BRW is pulled in a reverse direction B1 in a state in which the operation member 5140 is located adjacent to the distal end 5101*d* of the first jaw 5101, the operation member 5140 connected to the backward-moving wire BRW moves backward in a direction K2, which is the same direction as the reverse direction B1.

At this point, the first forward-moving wire 5111 and the second forward-moving wire 5112 may be in a state in which a pulling force is not applied.

When the operation member 5140 moves backward (in the direction K2), the region of the first forward-moving wire 5111 and the second forward-moving wire 5112 connected to the first connection region 5140*p*1 and the second connection region 5140*p*2 of the operation member 5140 may move in the first direction D1, which is the same direction as the direction K2, and the regions of the first forward-moving wire 5111 and the second forward-moving wire 5112, which are wound around the lower sides of the first fixed pulley 5121 and the second fixed pulley 5122 and disposed on the upper sides thereof, may move in the second direction D2, which is the opposite direction of the direction K2. Accordingly, the operation member 5140 is in a position as shown in FIG. 46B, having moved backward to be closer to the proximal end 5101p compared to its position in FIG. 46A.

Thereafter, as shown in FIG. 46B, when the backward-moving wire BRW is pulled further in the reverse direction B1, the operation member 5140 connected to the backward-moving wire BRW moves backward in the direction K2, which is the same direction as the reverse direction B1. At this point, the first forward-moving wire 5111 and the second forward-moving wire 5112 may be in a state in which a pulling force is not applied. The regions of the first forward-moving wire 5111 and the second forward-moving wire 5112 connected to the first connection region 5140p1 and the second connection region 5140p2 of the operation member 5140 move in the first direction D1, which is the same direction as the direction K2, and the regions of the first forward-moving wire 5111 and the second forward-moving wire 5112, which are wound around the lower sides of the first fixed pulley 5121 and the second fixed pulley 5122 and disposed on the upper sides thereof, may move in the second direction D2, which is the opposite direction of the direction K2. Accordingly, the operation member 5140 is in a position as shown in FIG. 46C, having moved backward to be closer to the proximal end 5101p compared to its position in FIG. 46B.

Further, although not shown in the drawings, it is of course possible that the configuration of FIG. 27 described above may be optionally applied to the end tool 5100 of the present embodiment.

The cartridge 5500 accommodated in the end tool 5100 of FIG. 28 and a stapling motion will now be described in more detail.

FIG. 47 is a perspective view illustrating the first jaw and the cartridge of the surgical instrument of FIG. 27.

Referring to FIGS. 27, 28, 29, 30, and 47 and the like, the cartridge 5500 may be disposed in the first jaw 5101, and for example, the cartridge 5500 may be disposed by being coupled to the cartridge accommodation part 5101a of the first jaw 5101. For example, the cartridge 5500 may be integrally formed with the first jaw 5101 while the operation member 5140 is disposed in the first jaw 5101. In addition, in an optional embodiment, the cartridge 5500 may be formed to be mountable to and dismountable from the first jaw 5101.

The cartridge 5500 includes a plurality of staples 5530 therein to perform suturing of tissue, and performs cutting through the operation member 5140. Here, the cartridge 5500 may include the cover 5510 (See FIG. 50), the staples 5530, and the withdrawal members 5535.

The cover 5510 may be formed to cover the upper portion of the cartridge accommodation part 5101a of the first jaw 5101. Staple holes 5510s through which the plurality of staples 5530 may be ejected to the outside may be formed in the cover 5510. As the staples 5530, which are accommodated inside the cartridge accommodation part 5101a before a stapling operation, are pushed and raised upward by the operation member 5140 during a stapling motion, and pass through the staple holes 5510s of the cover 5510 to be withdrawn to the outside of the cartridge 5500, stapling may be performed.

Meanwhile, the slit 5510w may be formed in the cover 5510 along the longitudinal direction of the cover 5510. The blade region 5142a of the body 5142 of the operation member 5140 may protrude out of the cartridge 5500 through the slit 5510w. As the blade of the body 5142 of the operation member 5140 passes along the slit 5510w, staple-completed tissue may be cut.

In an optional embodiment, the cartridge 5500 may include a case 5520, and the cartridge 5500 may be disposed in the case 5520 after the case 5520 is disposed in the cartridge accommodation part 5101a of the first jaw 5101.

The plurality of staples 5530 may be disposed inside the cartridge accommodation part 5101a of the first jaw 5101. As the operation member 5140 linearly moves in one direction, the plurality of staples 5530 are sequentially pushed and raised from the inside of the cartridge accommodation part 5101a of the first jaw 5101 to the outside, thereby performing suturing, that is, stapling. Here, the staples 5530 may include a material that is durable and does not have an abnormal effect on the human body, such as titanium, stainless steel, or the like.

Meanwhile, the withdrawal members 5535 may be further disposed between the cartridge accommodation part 5101a of the first jaw 5101 and the staples 5530. In other words, it may be said that the staple 5530 is disposed above the withdrawal member 5535. In this case, the operation member 5140 linearly moves in one direction to push and raise the withdrawal member 5535, and the withdrawal member 5535 may push and raise the staple 5530.

As such, the operation member 5140 may be described as pushing and raising the staples 5530 in both the case in which the operation member 5140 directly pushes and raises the staples 5530 and the case in which the operation member 5140 pushes and raises the withdrawal members 5535 and the withdrawal members 5535 pushes and raises the staples 5530 (i.e., the operation member 5140 indirectly pushes and raises the staples 5530).

As described above, the operation member 5140 may be disposed inside the cartridge accommodation part 5101a of the first jaw 5101. In addition, the operation member 5140 may include the wedge WDG or may be used in conjunction with wedge WDG, and when the operation member 5140 moves, the wedge WDG may move together therewith so that the wedge WDG may directly push and raise the staple 5530, or the wedge WDG may push and raise the withdrawal member 5535 to push and raise the staple 5530.

As described above, the movement of the first forward-moving wire 5111 and the second forward-moving wire 5112, i.e., the pulling of the first forward-moving wire 5111 and the second forward-moving wire 5112 allows the operation member 5140 connected thereto to move forward toward the distal end 5101d of the first jaw 5101.

The forward movement of the operation member 5140 may cause the wedge WDG to push and raise the withdrawal member 5535, which may also cause the staple 5530 to rise, and at the same time, cutting using the blade region 5142a of the operation member 5140 may be performed. In addition, in an optional embodiment, in the case of the end tool in which the backward-moving wire BRW is connected to the operation member 5140, the backward-moving wire BRW may be pulled to cause the operation member 5140 to move toward the proximal end 5101p of the first jaw 5101.

FIGS. 48 and 49 are views for describing a switching pulley, a yaw pulley, and a pitch pulley of the end tool of the surgical instrument of FIG. 27.

As described above, the end tool 5100 may be connected to the connection part 5400, and the end tool 5100 may rotationally move around one shaft and also rotationally move around another shaft with respect to the connection part 5400.

For example, the end tool 5100 may perform a pitch motion, i.e., a vertical rotational motion based on FIGS. 28 to 47, and the end tool 5100 may perform a yaw motion, i.e., a horizontal rotational motion based on FIGS. 28 to 47. A rotation shaft of the pitch motion and a rotation shaft of the yaw motion may be located in directions that may intersect or be perpendicular to each other.

As an example, the end tool 5100 may include one or more members, such as joint members, that connect the jaw 5103 to the connection part 5400, and may include the end tool hub 5108 and the pitch hub 5107.

The end tool hub 5108 may be disposed to connect the end tool 5100 to the straight part 5401 of the connection part 5400. As an example, the end tool hub 5108 may have the pulley shaft JX4 corresponding thereto, and the pulley shaft JX4 may be a rotation shaft of the pitch motion. As a specific example, the end tool 5100 may rotationally move around the pulley shaft JX4, the pitch hub 5107 may rotationally move around the pulley shaft JX4, and the jaw 5103 may be connected to the pitch hub 5107 to perform a rotational motion, i.e., a pitch motion, around the pulley shaft JX4 integrally with the pitch hub 5107.

The pitch hub 5107 is connected to the end tool hub 5108 and the jaw 5103, and may rotationally move around the pulley shaft JX4 by being axially coupled to the end tool hub 5108 by the pulley shaft JX4. Further, the jaw 5103 may be axially coupled to the pitch hub 5107 with respect to one pulley shaft, i.e., the pulley shaft JX1. The jaw 5103 may perform a rotational motion, i.e., a yaw motion, around one pulley shaft, i.e., the pulley shaft JX1 while connected to the pitch hub 5107.

An auxiliary pulley shaft may be additionally disposed together with these rotation shafts, i.e., the pulley shafts for joint movement of the end tool 5100, such as the pulley shaft JX4 for pitch motion and the pulley shaft JX1 for yaw motion.

For example, the pulley shaft JX2 which is different from the pulley shaft JX1 is disposed in the pitch hub 5107 to be adjacent to and parallel to the pulley shaft JX1. The pulley shaft JX2 may have an axis oriented parallel to the pulley shaft JX1, and may be disposed further away from the operation member 5140 than the pulley shaft JX1, i.e., closer to the connection part 5400.

In addition, the pulley shaft JX3 may be disposed at a side of the pulley shaft JX4. In addition, the pulley shaft JX5 may be further disposed.

For example, the pulley shaft JX3 and the pulley shaft JX5 may be disposed on both sides of the pulley shaft JX4 interposed therebetween, and the pulley shaft JX3 and the pulley shaft JX5 may have axes oriented parallel to the pulley shaft JX4.

As a specific example, the pulley shaft JX3 may be disposed between the pulley shaft JX2 and the pulley shaft JX4, and may have an axis intersecting or orthogonal to the pulley shaft JX2 and the pulley shaft JX1. The pulley shaft JX5 may be disposed further away from the operation member 5140 than the pulley shaft JX4, i.e., closer to connection part 5400.

One or more switching pulley shafts AX1 and AX2, i.e., a first switching pulley shaft AX1 and a second switching pulley shaft AX2, may be disposed closer to the operation member 5140 than the pulley shafts JX1, JX2, JX3, JX4, and JX5

The first switching pulley shaft AX1 and the second switching pulley shaft AX2 may be shafts formed parallel to each other. The first switching pulley shaft AX1 and the second switching pulley shaft AX2 may be sequentially disposed in a direction toward the distal end 5101d of the first jaw 5101 so as to be offset from each other based on a width direction of the first jaw 5101, and may be disposed with some regions overlapping.

One or more pulleys may be disposed on the pulley shafts JX1, JX2, JX3, JX4, and JX5 and the switching pulley shafts AX1 and AX2.

When description is given in the order from the proximal end of the first jaw 5101 towards the connection part 5400, one or more switching pulleys AXP1 corresponding to the first switching pulley shaft AX1 and one or more switching pulleys AXP2 corresponding to the second switching pulley shaft AX2 are disposed.

The one or more switching pulleys AXP1 corresponding to the first switching pulley shaft AX1, and the one or more switching pulleys AXP2 corresponding to the second switching pulley shaft AX2 may all be disposed in a place overlapping the first jaw 5101, for example, may be disposed in one region of the coupling region 51012 of the first jaw 5101 so as not to overlap the pitch hub 5107.

The first forward-moving wire 5111 and the second forward-moving wire 5112 may come into contact with the switching pulleys AXP1 and the switching pulley AXP2, respectively, in at least one region, and thus may be guided in path.

For example, the first forward-moving wire 5111 may enter the switching pulleys AXP1 from the outside, wind inward, continue winding into one region of the switching pulleys AXP2 adjacent to the switching pulleys AXP1, and then exit from the switching pulleys AXP2.

The second forward-moving wire 5112 may come into contact with the switching pulleys AXP2 in at least one region, and may be guided in path. The first forward-moving wire 5111 and the second forward-moving wire 5112, which are collected in the switching pulley AXP2, may be wound together around one or more pulleys JXP1 corresponding to the pulley shaft JX1, which will be described below, in the same direction.

Accordingly, the first forward-moving wire 5111 and the second forward-moving wire 5112 can be moved in one direction, and can be organized on one side of the shaft and pulley for each joint movement, such as the pulley shaft and pulleys for pitch motion and the pulley shaft and pulleys for yaw motion, rather than on both sides of the shaft and pulley for each joint movement, thus facilitating precise implementation of simultaneous and straightforward control over the first forward-moving wire 5111 and the second forward-moving wire 5112.

In order to facilitate the path guidance for the first forward-moving wire 5111 and the second forward-moving wire 5112, the switching pulley AXP1 and the switching pulley AXP2 may have structures symmetrical to each other with respect to an extension line of the operation member 5140, that is, may have structures offset by the same distance with respect to the extension line of the operation member 5140. This allows the size of each of the switching pulley AXP1 and the switching pulley AXP2 to be increased, thereby improving the efficiency and stability of the path guidance for the first forward-moving wire 5111 and the second forward-moving wire 5112.

One or more pulleys JXP1 are disposed to correspond to the pulley shaft JX1, and one or more pulleys JXP2 corresponding to the pulley shaft JX2 are disposed adjacent to the one or more pulleys JXP1. The pulley JXP1 and the pulley JXP2 may have axes parallel to each other.

For example, the pulley JXP1 and the pulley JXP2 are disposed in the first hub 5107a (refer to FIG. 31) of the pitch hub 5107. One or more pulleys JXP2 guide the paths along which the wires, which are disposed to correspond to one or more pulleys JXP1, are driven, ensuring that the wires have a clear path to the pulley shaft JX4, or more closely, to the pulley shaft JX3 and a pulley JXP3 corresponding thereto.

Further, one or more pulleys JXP3 are disposed to correspond to the pulley shaft JX3, and one or more pulleys JXP4 corresponding to the pulley shaft JX4 are disposed adjacent to the one or more pulleys JXP4. For example, the pulley JXP3 and the pulley JXP4 are disposed in the second hub 5107*b* (refer to FIG. 31) of the pitch hub 5107. In addition, one or more pulleys JXP5 may be disposed to correspond to the pulley shaft JX5. The pulley JXP3, the pulley JXP4, and the pulley JXP5 may have axes that are parallel to each other and intersect or orthogonal to the axes of the pulley JXP1 and the pulley JXP2.

Meanwhile, by precisely controlling the paths of the first forward-moving wire 5111 and the second forward-moving wire 5112 as shown in FIGS. 48 and 49, the drive efficiency and control characteristics of the operation member 5140 can be maximized through the first forward-moving wire 5111 and the second forward-moving wire 5112.

As described above, the switching pulley AXP1 and the switching pulley AXP2 are disposed further forward than the pulley shaft JX4 and the pulley shaft JX1, which are respectively for two joint movements such as a pitch motion and a yaw motion of the end tool 5100, i.e., disposed closer to the operation member 5140 than the above pulleys.

As a specific example, the switching pulley AXP1 and the switching pulley AXP2 are disposed further forward than the pulley JXP4 corresponding to the pulley shaft JX4 for a pitch motion, the pulley JXP1 corresponding to the pulley shaft JX1 for a yaw motion, the pulley JXP3 and the pulley JXP5 corresponding to pitch auxiliary pulleys, and the pulley JXP2 that is a yaw auxiliary pulley, i.e., disposed closer to the operation member 5140 than the above pulleys.

As a result, the switching pulley AXP1 and the switching pulley AXP2 are disposed further forward than the pulley JXP1, the pulley JXP2, the pulley JXP3, the pulley JXP4, and the pulley JXP5, i.e., disposed closer to the operation member 5140 than the above pulleys.

Accordingly, the first forward-moving wire 5111 may enter the switching pulleys AXP1 from the outside, wind inward, continue winding into one region of the switching pulleys AXP2 adjacent to the switching pulleys AXP1, and then exit from the switching pulleys AXP2. In addition, the first forward-moving wire 5111 and the second forward-moving wire 5112 may be gathered together on one side (e.g., an outer side) of the switching pulley AXP2.

In addition, the first forward-moving wire 5111 and the second forward-moving wire 5112, which are gathered together on the outer side of the switching pulley AXP2, may be directed to the connection part 5400 after being simultaneously rerouted at an outer side of a pulley JXP1 corresponding to the pulley shaft JX1, which is a yaw pulley shaft, being wound around the pulley JXP2 corresponding to the pulley shaft JX2, which is a yaw auxiliary pulley shaft, to be rerouted, being controlled in path height by the pulley JXP3 corresponding to the pulley shaft JX3, being stably placed on a lower side of the pulley JXP4 corresponding to the pulley shaft JX4, which is a pitch shaft, and passing through the pulley JXP5.

That is, by first gathering the first forward-moving wire 5111 and the second forward-moving wire 5112 together through the switching pulley AXP1 and the switching pulley AXP2, the paths of the first forward-moving wire 5111 and the second forward-moving wire 5112 can be easily guided by simultaneously corresponding to the rotation shafts and the pulleys and their auxiliary pulleys for the joint movement of the end tool 5100, so that the accuracy and stability of the forward movement of the operation member 5140 can be improved.

In addition, by controlling heights of the paths of the first forward-moving wire 5111 and the second forward-moving wire 5112, which are gathered together, using the pulley JXP3 prior to directing to the pulley JXP4 corresponding to the pulley shaft JX4, which is a pitch shaft, the first forward-moving wire 5111 and the second forward-moving wire 5112 can be stability wound around the pulley JXP4 corresponding to the pulley shaft JX4, which is a pitch shaft, and the freedom of size, design and arrangement of the pulley JXP4 can be improved.

In an optional embodiment, the backward-moving wire BRW may be further disposed as described above, in which case the backward-moving wire BRW may pass between the switching pulley AXP1 and the switching pulley AXP2, or pass in contact with a common region of the switching pulley AXP1 and the switching pulley AXP2, and then pass while corresponding to the other pulleys JXP1, JXP2, JXP3, JXP4, and JXP5.

Meanwhile, the backward-moving wire BRW may be wound around the pulleys JXP1 and JXP2 in a direction opposite to the direction in which the first forward-moving wire 5111 and the second forward-moving wire 5112 are wound. For example, when the first forward-moving wire 5111 and the second forward-moving wire 5112 are wound around a rear side of the pulley JXP1 and wound around a front side of the pulley JXP2, the backward-moving wire BRW may be wound around a front side of the pulley JXP1 and wound around a rear side of the pulley JXP2. This allows the first forward-moving wire 5111 and the second forward-moving wire 5112 to be wound around one side of one or more pulley shafts, and the backward-moving wire BRW to be wound around anther side thereof, and when at least one of the first forward-moving wire 5111 and the second forward-moving wire 5112 and the backward-moving wire BRW form a close loop, tension of the entire wire can be easily maintained.

Meanwhile, pulling the first forward-moving wire 5111 and the second forward-moving wire 5112 of the present embodiment may cause some rotational force on the end tool 5100 due to the tension thereof, which may cause the jaw 5103 biting the body tissue to lose balance, or cause unnecessary external forces to be applied to the body tissue. In this case, the pulleys and the corresponding pulley shafts of the end tool 5100 may tilt or move slightly, as a result, inner diameter edges of the pulleys may dig into the pulley shafts, thereby increasing friction and tightening the coupling of the pulley and the pulley shaft. Accordingly, friction forces are generated to resist abnormal rotational forces on the end tool 5100, which can improve the reliability and usability of the end tool 5100. in addition, this is applicable even when the backward-moving wire BRW is used, and is applicable to the embodiments described below and the embodiments described above without change.

Meanwhile, when the tension applied to the first forward-moving wire 5111 and the second forward-moving wire 5112 or the backward-moving wire BRW is released, the frictional force may be eliminated together.

Figure 50:
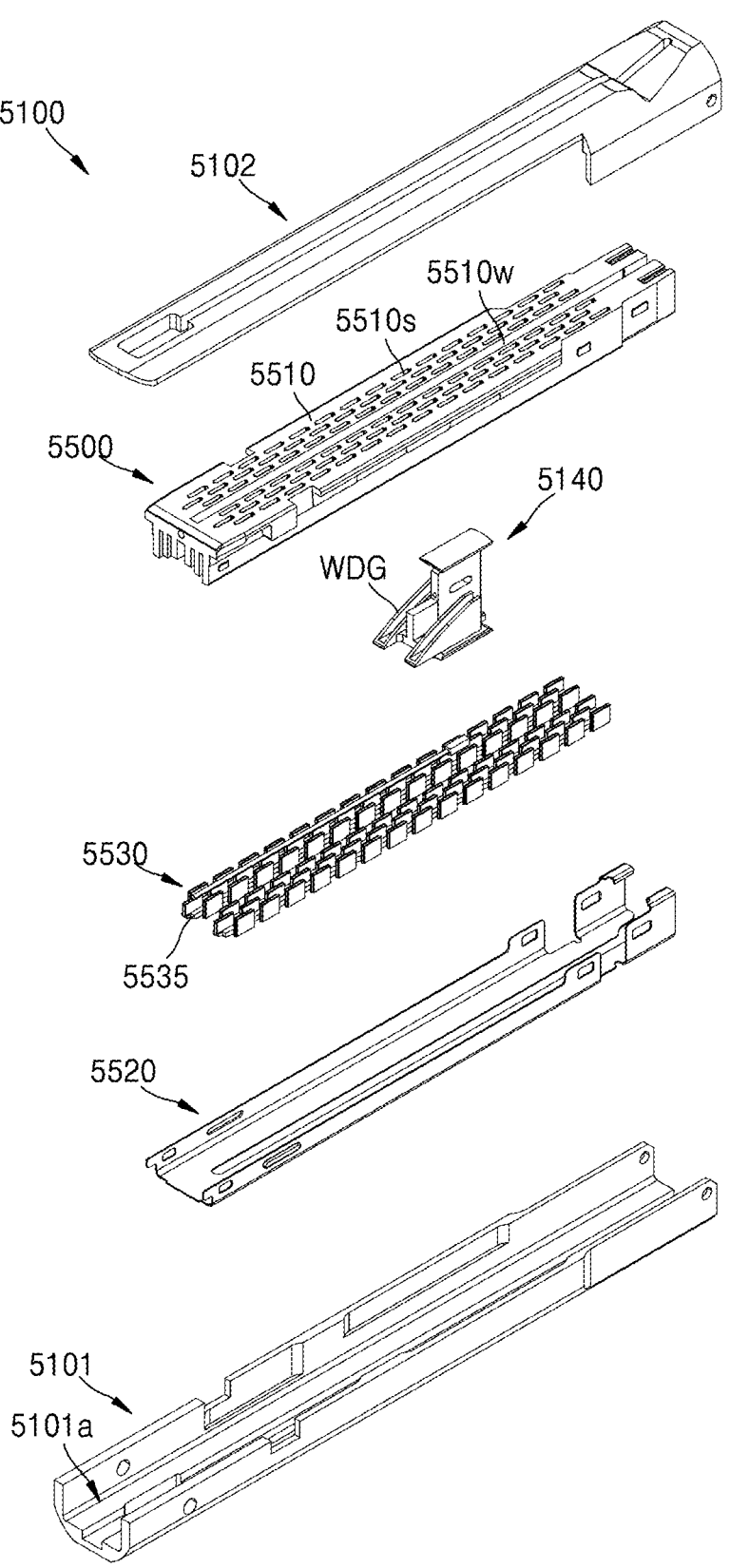
FIG. 50 is a perspective view illustrating the first jaw and the cartridge of the surgical instrument of FIG. 27.

FIG. 50 is a perspective view illustrating the first jaw and the cartridge of the surgical instrument of FIG. 28. FIGS. 51 and 52 are cross-sectional views illustrating a staple motion of the end tool of the surgical instrument of FIG. 28 as a whole.

Referring to FIGS. 27, 28, 29, and 50 and the like, the cartridge 5500 may be disposed in the first jaw 5101, and for example, the cartridge 5500 may be disposed by being coupled to the cartridge accommodation part 5101$a$ of the first jaw 5101. For example, the cartridge 5500 may be integrally formed with the first jaw 5101 while the operation member 5140 is disposed in the first jaw 5101. In addition, in an optional embodiment, the cartridge 5500 may be formed to be mountable to and dismountable from the first jaw 5101.

The cartridge 5500 includes a plurality of staples 5530 therein to perform suturing of tissue, and performs cutting through the operation member 5140. Here, the cartridge 5500 may include the cover 5510, the staples 5530, and the withdrawal members 5535.

The cover 5510 may be formed to cover the upper portion of the cartridge accommodation part 5101$a$ of the first jaw 5101. Staple holes 5510$s$ through which the plurality of staples 5530 may be ejected to the outside may be formed in the cover 5510. As the staples 5530, which are accommodated inside the cartridge accommodation part 5101$a$ before a stapling operation, are pushed and raised upward by the operation member 5140 during a stapling motion, and pass through the staple holes 5510$s$ of the cover 5510 to be withdrawn to the outside of the cartridge 5500, stapling may be performed.

Meanwhile, the slit 5510$w$ may be formed in the cover 5510 along the longitudinal direction of the cover 5510. The blade of the body 5142 of the operation member 5140 may protrude out of the cartridge 5500 through the slit 5510$w$. As the blade of the body 5142 of the operation member 5140 passes along the slit 5510$w$, staple-completed tissue may be cut.

In an optional embodiment, the cartridge 5500 may include a case 5520, and the cartridge 5500 may be disposed in the case 5520 after the case 5520 is disposed in the cartridge accommodation part 5101$a$ of the first jaw 5101.

The plurality of staples 5530 may be disposed inside the cartridge accommodation part 5101$a$ of the first jaw 5101. As the operation member 5140 linearly moves in one direction, the plurality of staples 5530 are sequentially pushed and raised from the inside of the cartridge accommodation part 5101$a$ of the first jaw 5101 to the outside, thereby performing suturing, that is, stapling. Here, the staples 5530 may include a material that is durable and does not have an abnormal effect on the human body, such as titanium, stainless steel, or the like.

Meanwhile, the withdrawal members 5535 may be further disposed between the cartridge accommodation part 5101$a$ of the first jaw 5101 and the staples 5530. In other words, it may be said that the staple 5530 is disposed above the withdrawal member 5535. In this case, the operation member 5140 linearly moves in one direction to push and raise the withdrawal member 5535, and the withdrawal member 5535 may push and raise the staple 5530.

As such, the operation member 5140 may be described as pushing and raising the staples 5530 in both the case in which the operation member 5140 directly pushes and raises the staples 5530 and the case in which the operation member 5140 pushes and raises the withdrawal members 5535 and the withdrawal members 5535 pushes and raises the staples 5530 (i.e., the operation member 5140 indirectly pushes and raises the staples 5530).

As described above, the operation member 5140 may be disposed inside the cartridge accommodation part 5101$a$ of the first jaw 5101. In addition, the operation member 5140 may include the wedge WDG or may be used in conjunction with wedge WDG, and when the operation member 5140 moves, the wedge WDG may move together therewith so that the wedge WDG may directly push and raise the staple 5530, or the wedge WDG may push and raise the withdrawal member 5535 to push and raise the staple 5530.

As described above, as the forward-moving wire 5110 moves, i.e., the forward-moving wire 5110 is pulled, the operation member 5140 connected thereto may move forward toward the distal end 5101$d$ of the first jaw 5101.

The forward movement of the operation member 5140 may cause the wedge WDG to push and raise the withdrawal member 5535, which may also cause the staple 5530 to rise, and at the same time, cutting using the blade region 5142$a$ of the operation member 5140 may be performed. In addition, in an optional embodiment, in the case of the end tool in which the backward-moving wire BRW is connected to the operation member 5140, the backward-moving wire BRW may be pulled to cause the operation member 5140 to move toward the proximal end 5101$p$ of the first jaw 5101.

Figure 51A:
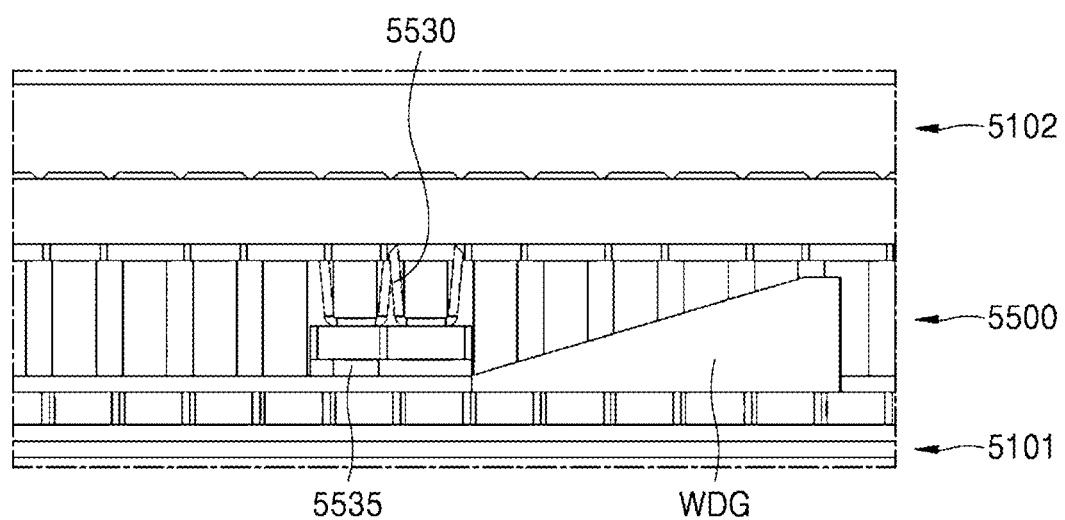
FIGS. 51A, 51B and 51C and FIG. 52 are cross-sectional views illustrating a staple motion of the end tool of the surgical instrument of FIG. 27 as a whole.
Figure 51B:
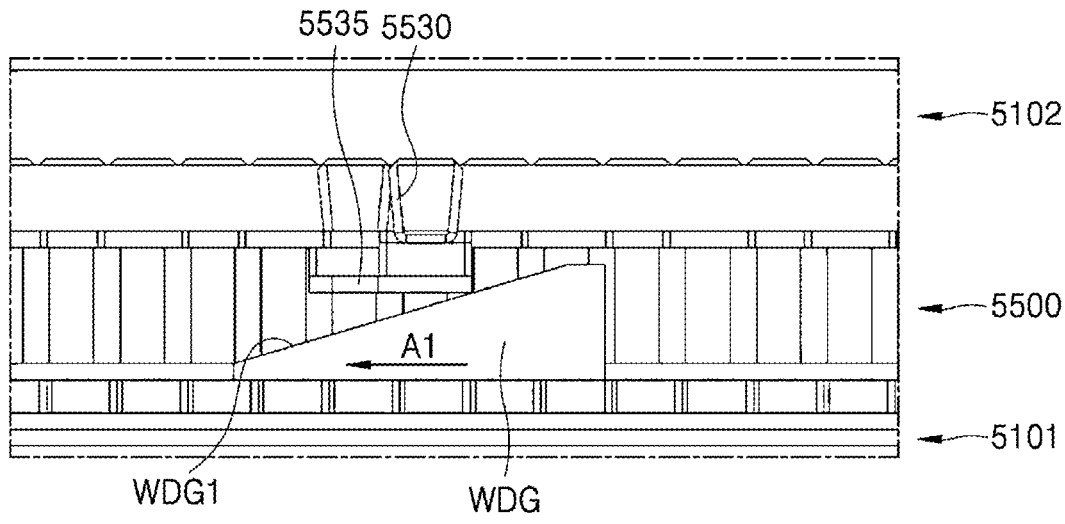
Figure 51C:
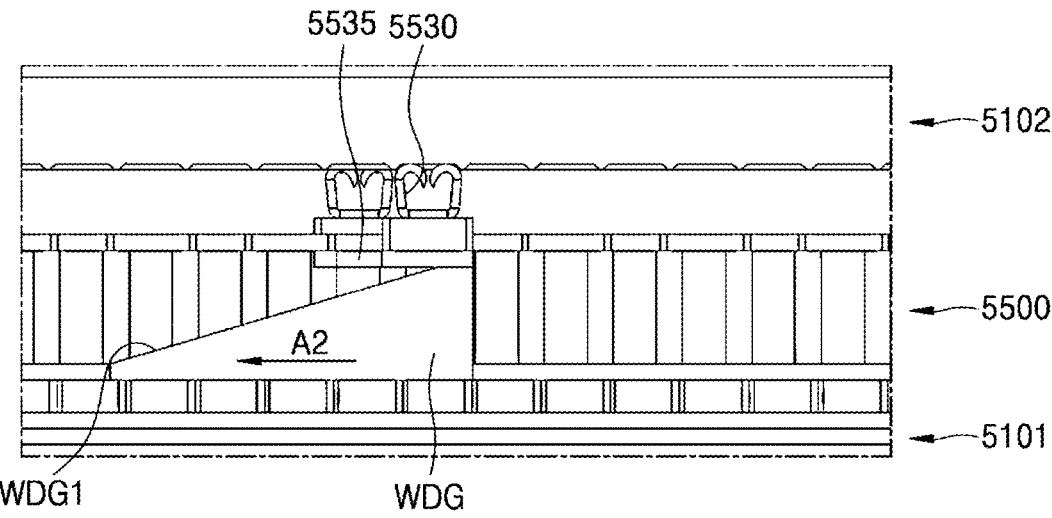
Figure 52:
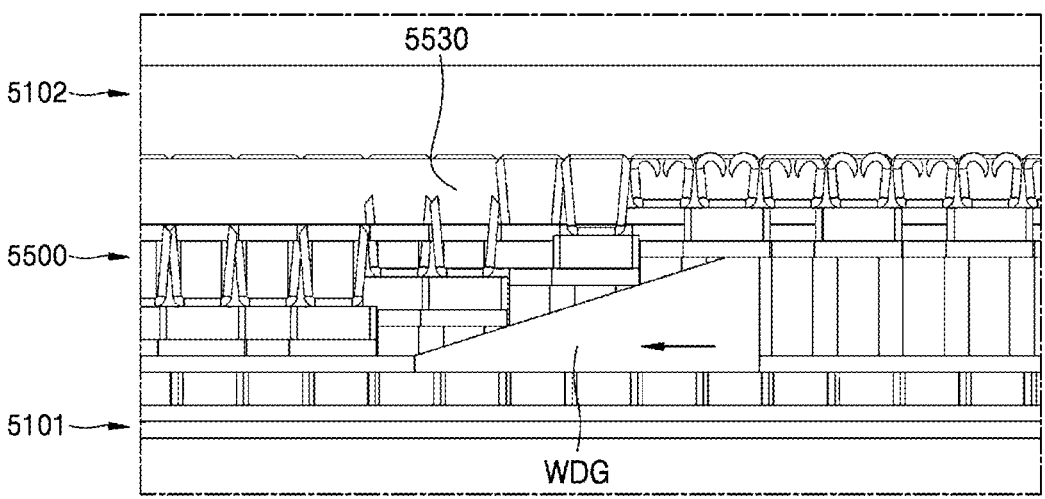

Referring to FIGS. 51 and 52, in the state as shown in FIG. 51A, as the operation member 5140 moves in the direction of an arrow A1 of FIG. 51B, the wedge WDG, specifically, an inclined surface WDG1 of the wedge WDG pushes and raises the withdrawal member 5535, and the withdrawal member 5535 pushes and raises one side of a lower portion of the staple 5530. In addition, due thereto, the staple 5530 is ejected to the outside of the first jaw 5101 and the cartridge 5500.

In this state, when the operation member 5140 further moves in the direction of an arrow A2 of FIG. 51C, the ejected staple 5530 is continuously pushed and raised by the operation member 5140 while in contact with the lower surface of the second jaw 5102, such as the anvil, so that stapling is performed while both end portions of the staple 5530 are bent.

FIGS. 53 to 57 are views illustrating a pitch rotation motion of a surgical instrument according to the present disclosure.

Figure 53:
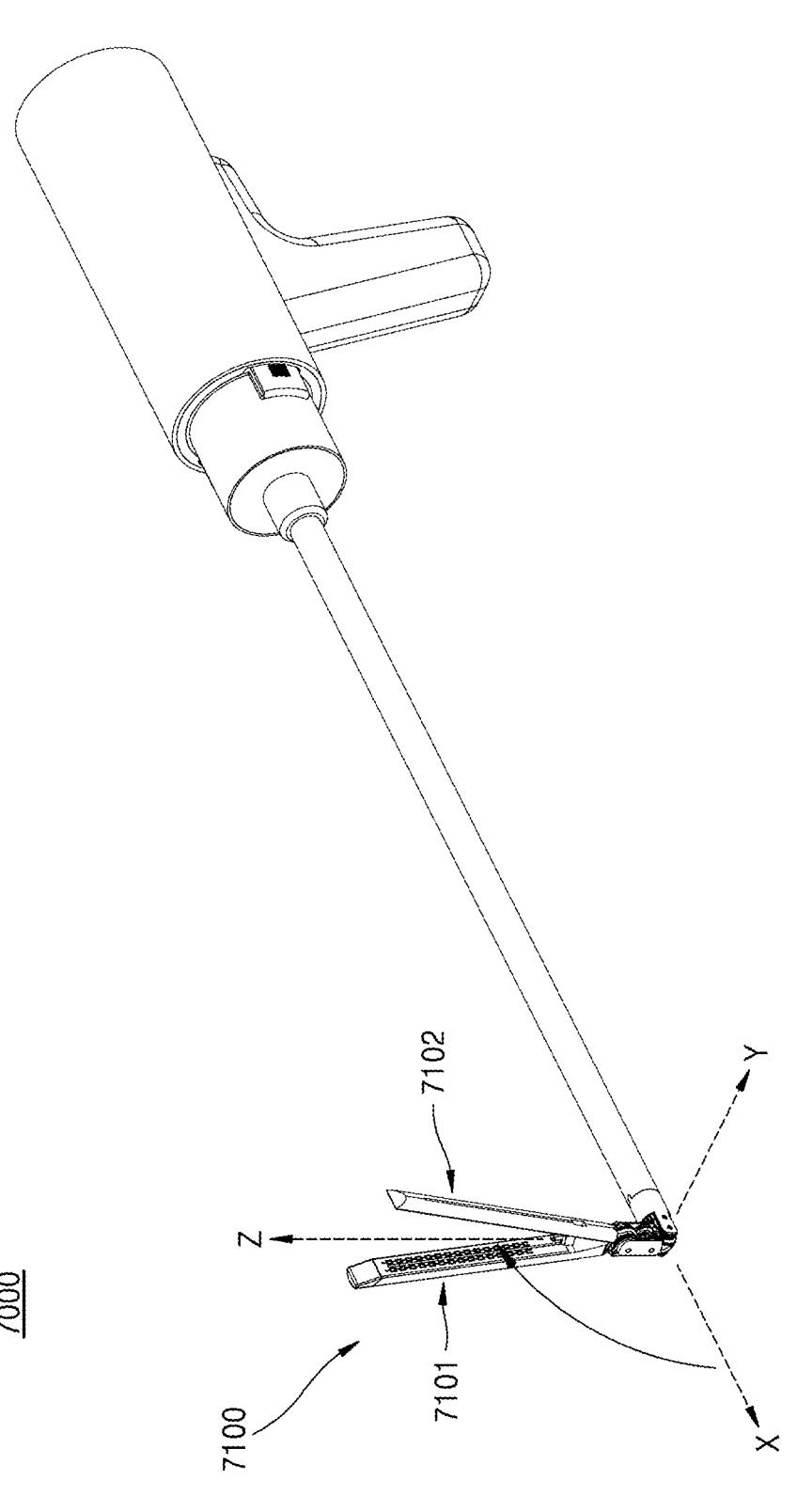
FIGS. 53 to 57 are views illustrating a pitch rotation motion of a surgical instrument according to an embodiment of the present disclosure.
Figure 54:
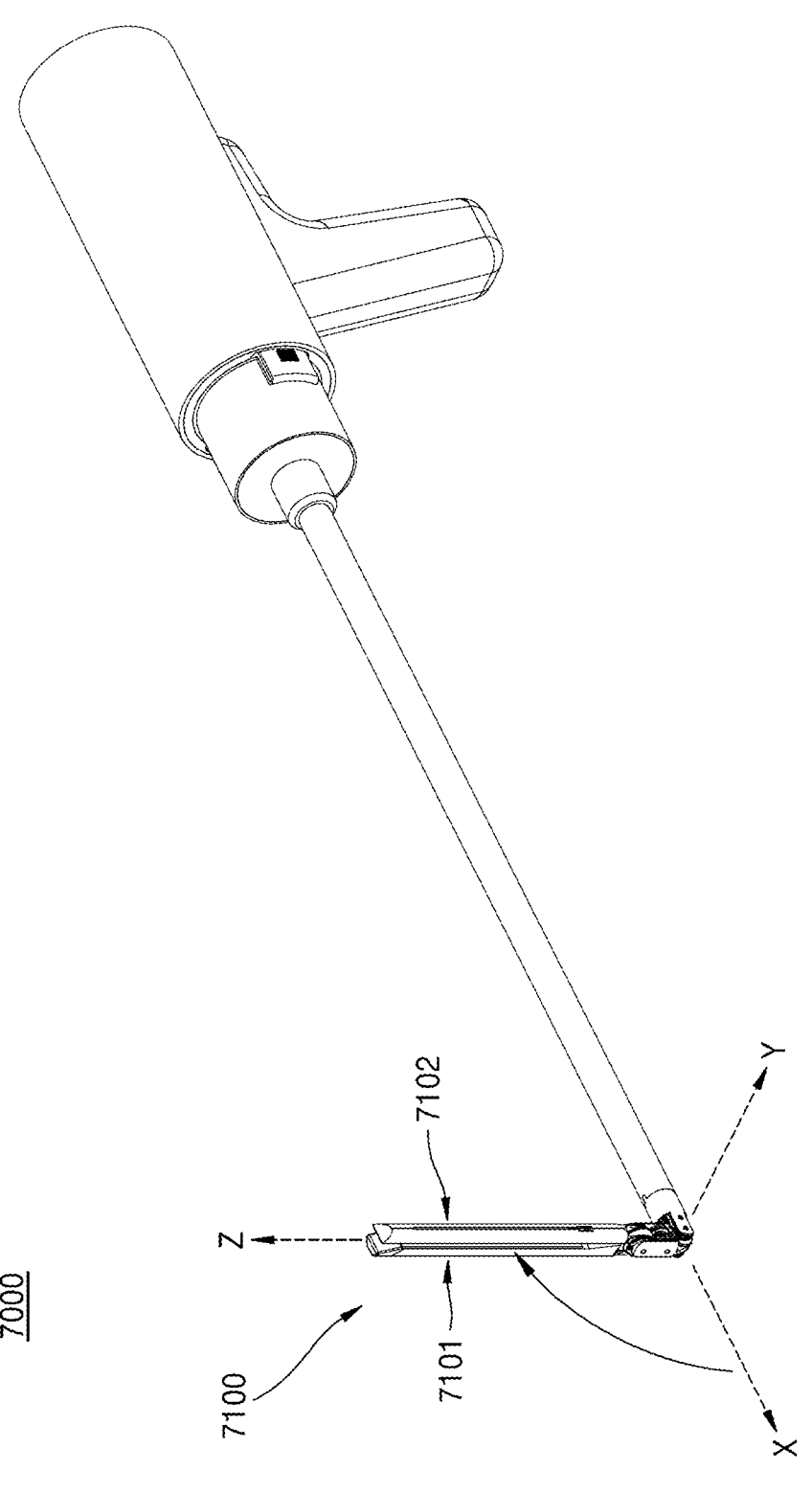
Figure 55:
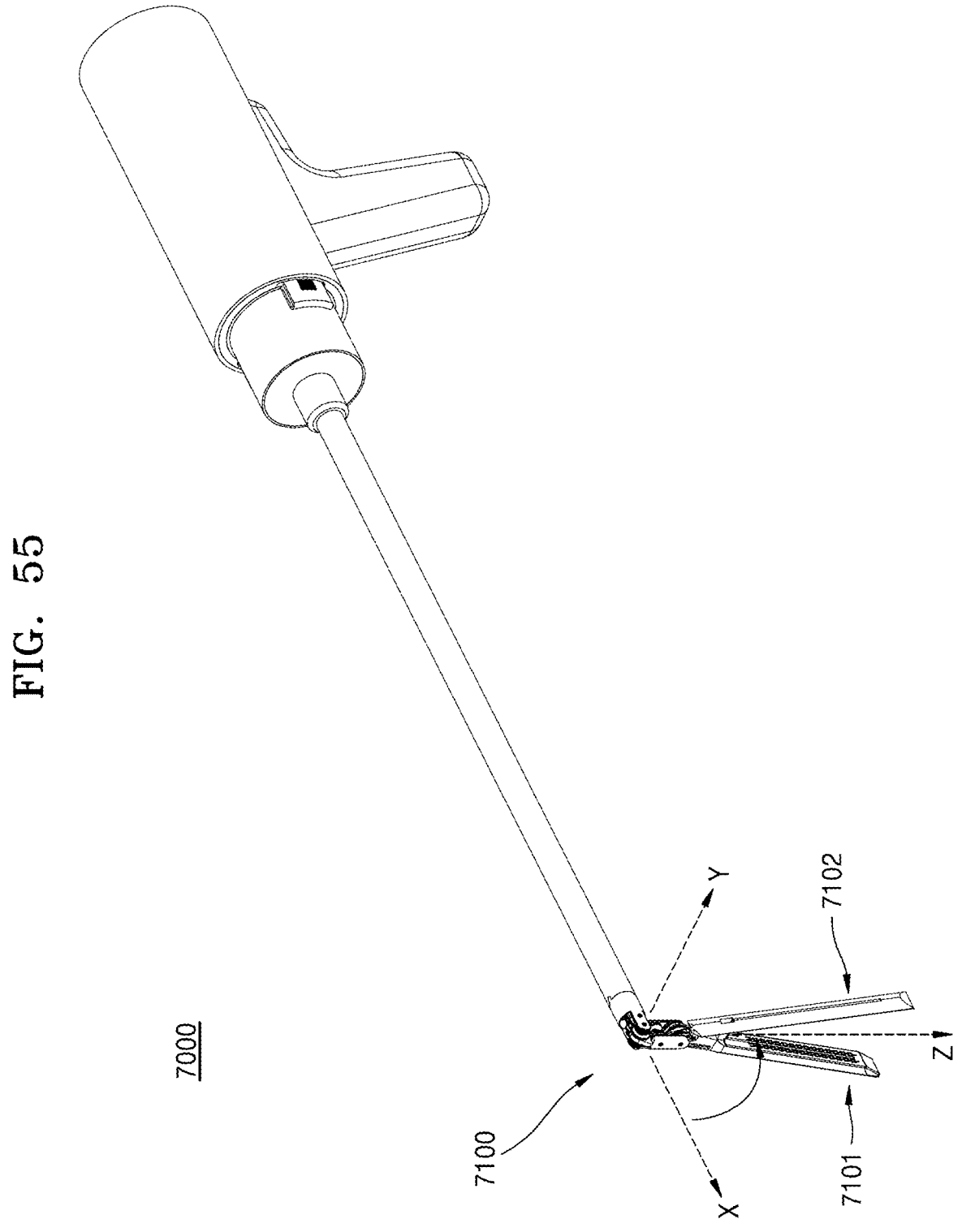
Figure 56:
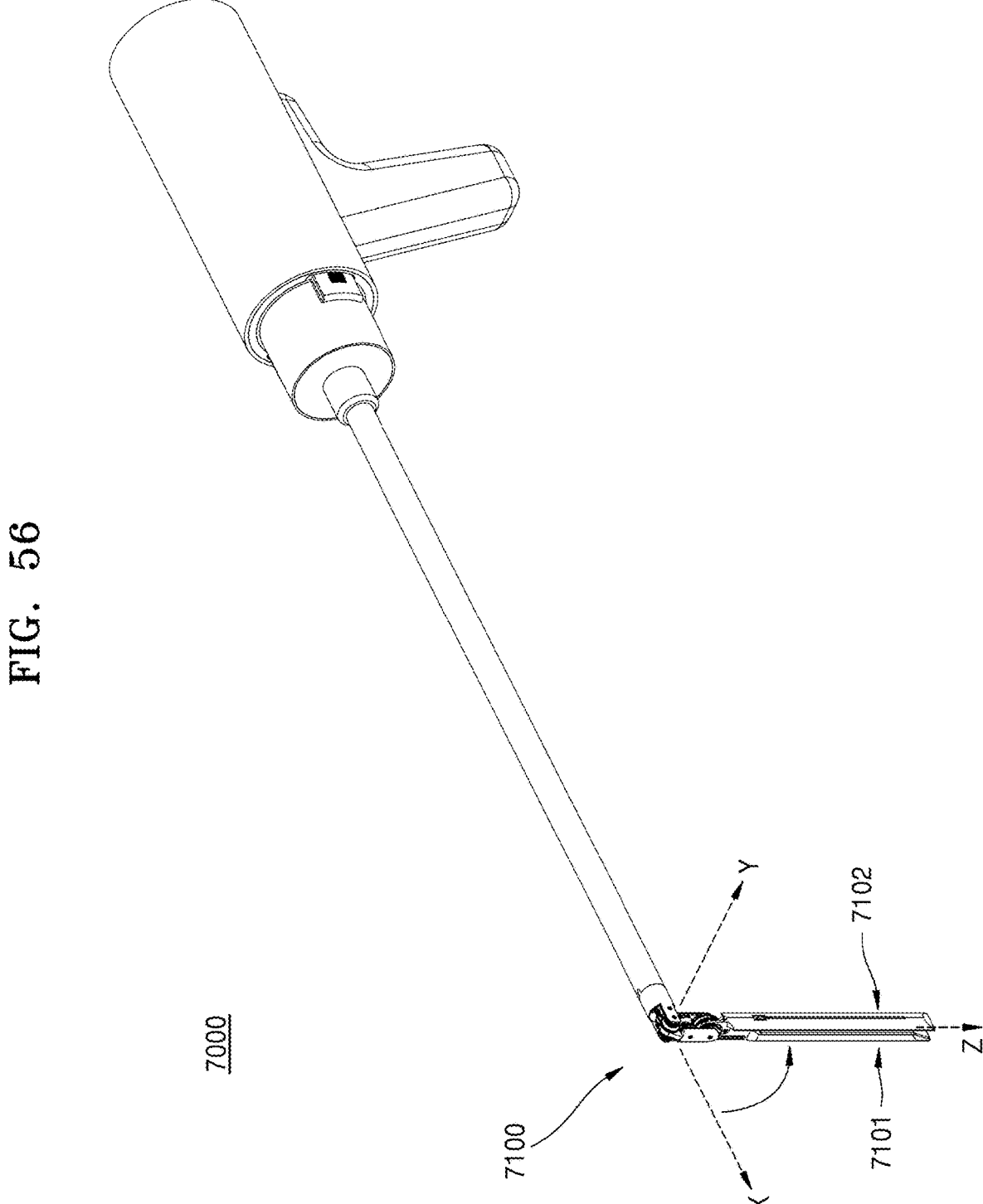
Figure 57:
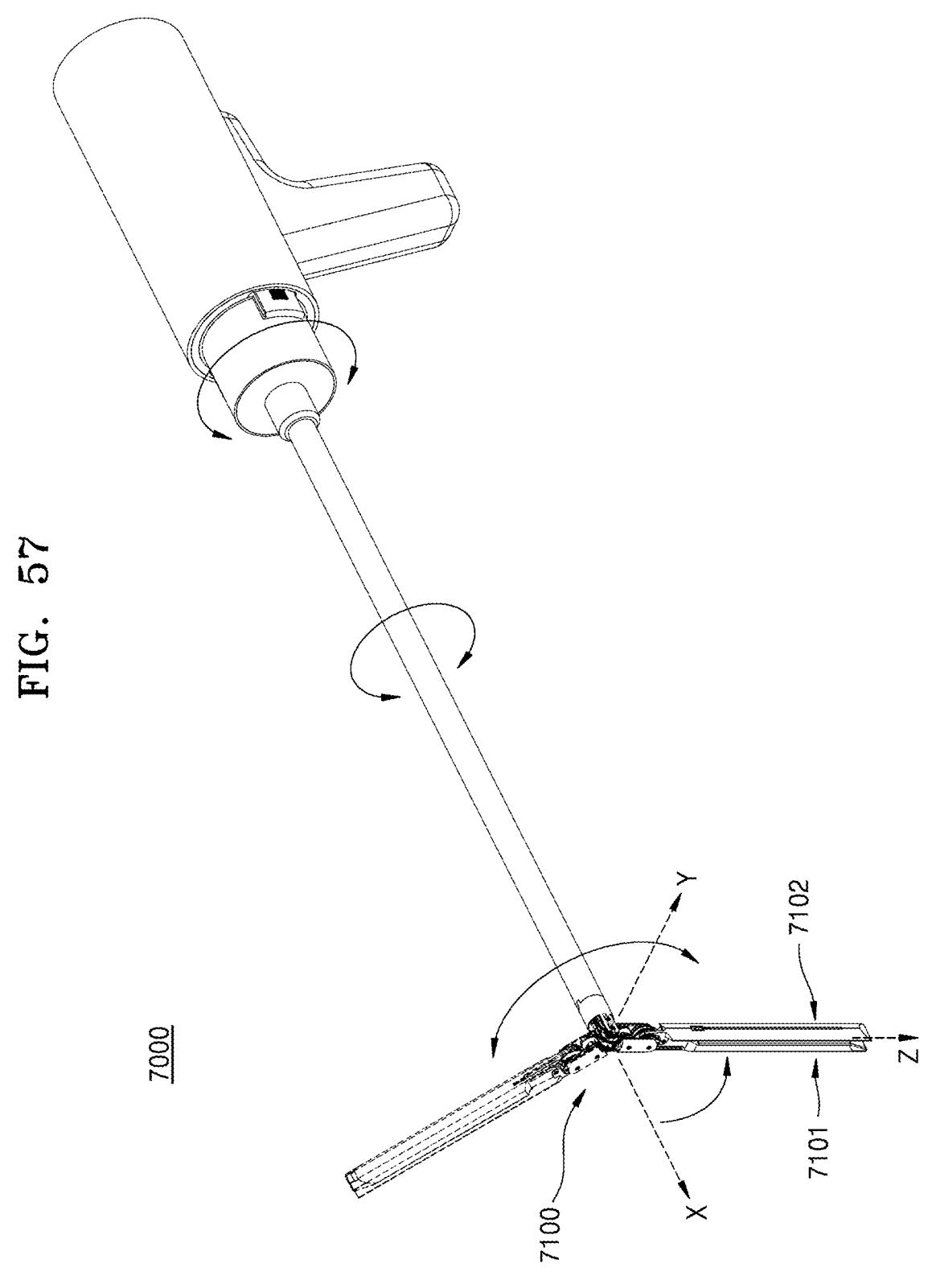

In detail, FIG. 53 is a view illustrating a state in which jaws are pitch-rotated by −90°, and FIG. 54 is a view illustrating a process of performing an actuation motion in a state in which the jaws are pitch-rotated by −90°. FIG. 55 is a view illustrating a state in which the jaws are pitch-rotated by +90°, FIG. 56 is a view illustrating a process of performing an actuation motion in a state in which the jaws are pitch-rotated by +90°, and FIG. 57 is a view illustrating a state in which a roll motion is performed in a state in which the jaws are pitch-rotated.

Referring to FIGS. 53 to 57, a surgical instrument 7000 according to the present disclosure may include an end tool 7100 including a first jaw 7101 and a second jaw 7102. Here, the end tool 7100 of the surgical instrument 7000 may be the end tool 5100 described with reference to FIG. 27. Alternatively, the end tool 7100 of the surgical instrument 7000 may be the end tool 5100 with at least some components changed or omitted.

The end tool 7100 of the surgical instrument 7000 may pitch-rotate in a positive (+) direction around a pitch rotation axis (Y-axis). In this case, the first jaw 7101 and the second jaw of the end tool 7100 may perform an actuation motion in a state in which the end tool 7100 pitch-rotates in the positive (+) direction around the pitch rotation axis (Y-axis).

Further, the end tool 7100 of the surgical instrument 7000 may pitch-rotate in a negative (−) direction around the pitch rotation axis (Y-axis). In this case, the first jaw 7101 and the second jaw of the end tool 7100 may perform an actuation motion in a state in which the end tool 7100 pitch-rotates in the negative (–) direction around the pitch rotation axis (Y-axis).

Here, a rotation angle of the end tool 7100 may be variously set according to the ratio of pulleys.

Meanwhile, the end tool 7100 of the surgical instrument 7000 may not rotate around the pitch rotation axis (Y-axis), but roll-rotate around a roll rotation axis (X-axis) while pitch-rotating in the positive (+) direction or negative (–) direction. At this time, the end tool 7100 may roll-rotate in a state in which the first jaw 7101 and the second jaw 7102 are spread apart from each other, and the first jaw 7101 and the second jaw 7102 may roll-rotate while performing an actuation motion.

Here, the end tool 7100 may rotate together with the rotation of a motor pack of a power generation part. When the motor pack of the power generation part roll-rotates, a power transmission part connected to the power generation part, a connection part connected to the power transmission part, and the end tool 7100 formed on one side of the connection part may rotate simultaneously.

FIGS. 58 to 62 are views illustrating a yaw rotation motion of the surgical instrument according to an embodiment of the present disclosure.

Figure 58:
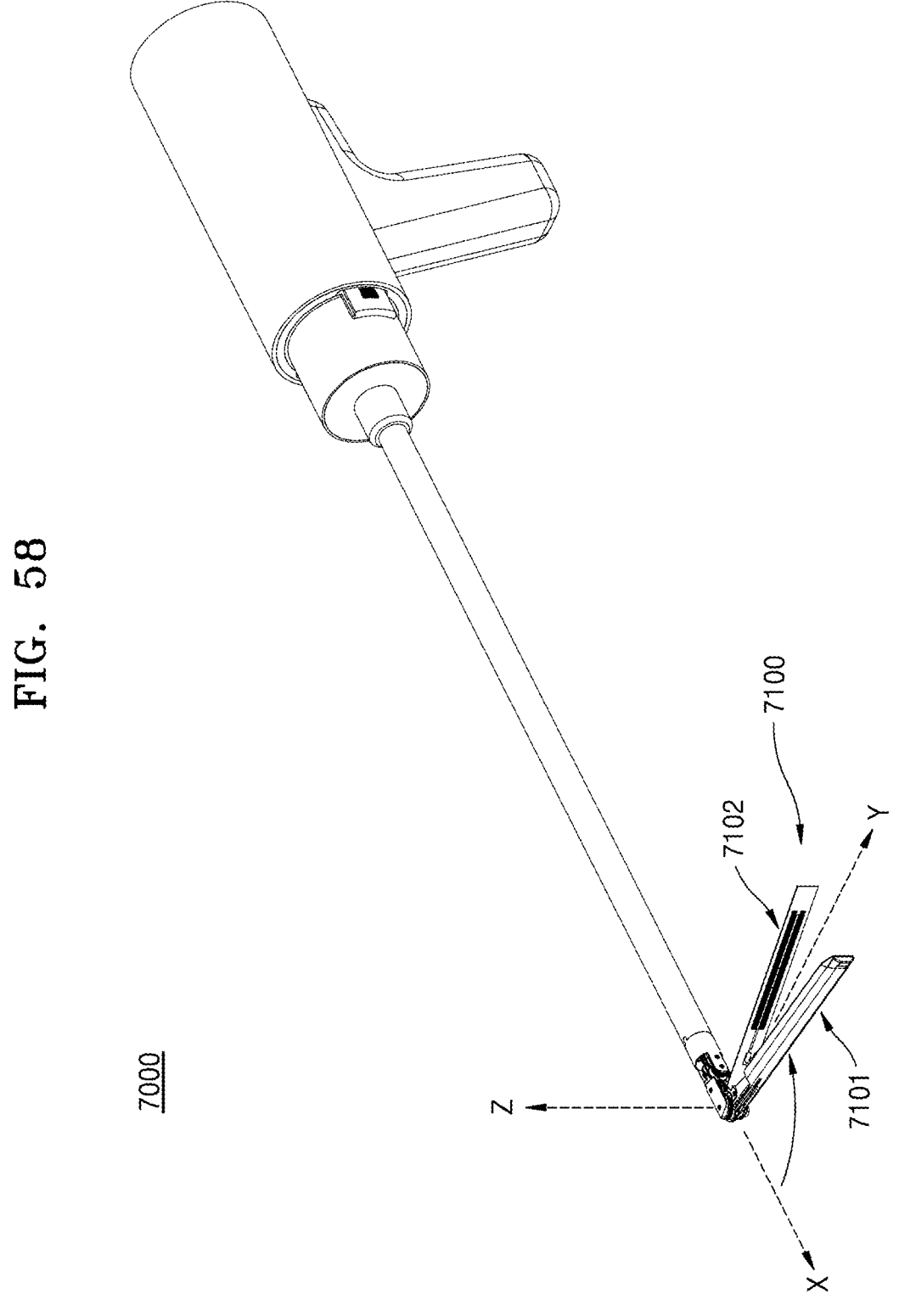
Figure 59:
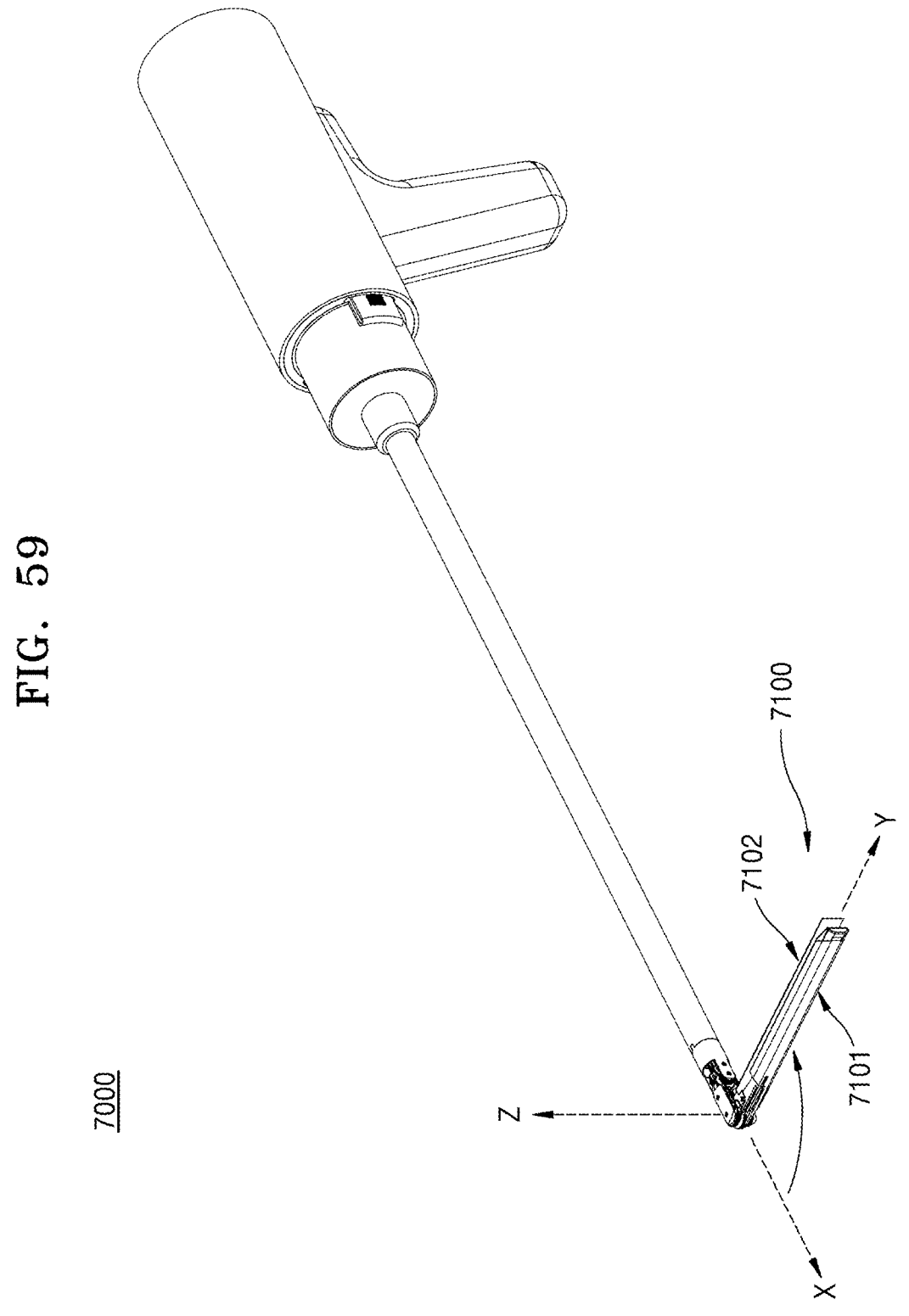
Figure 60:
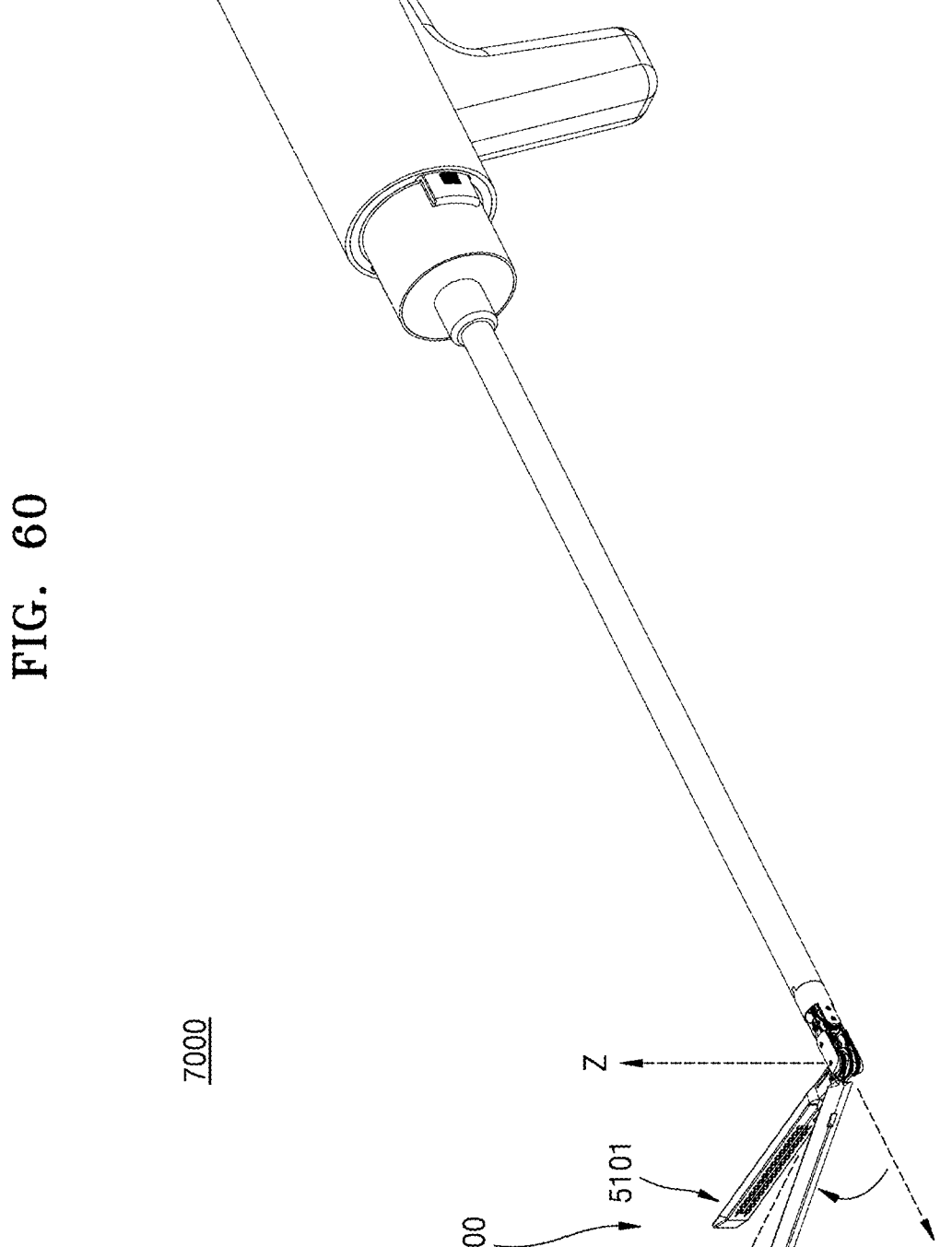
Figure 61:
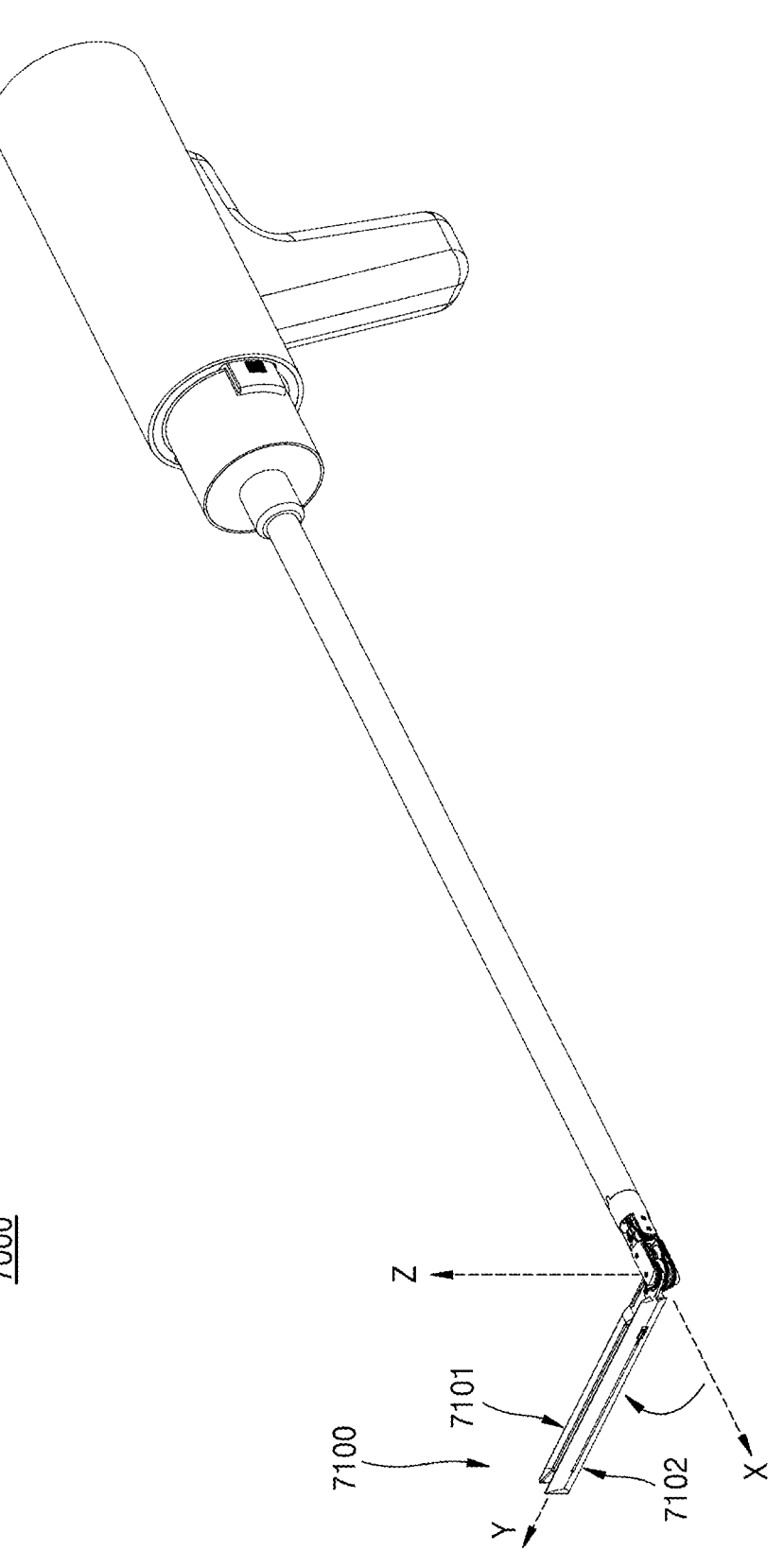
Figure 62:
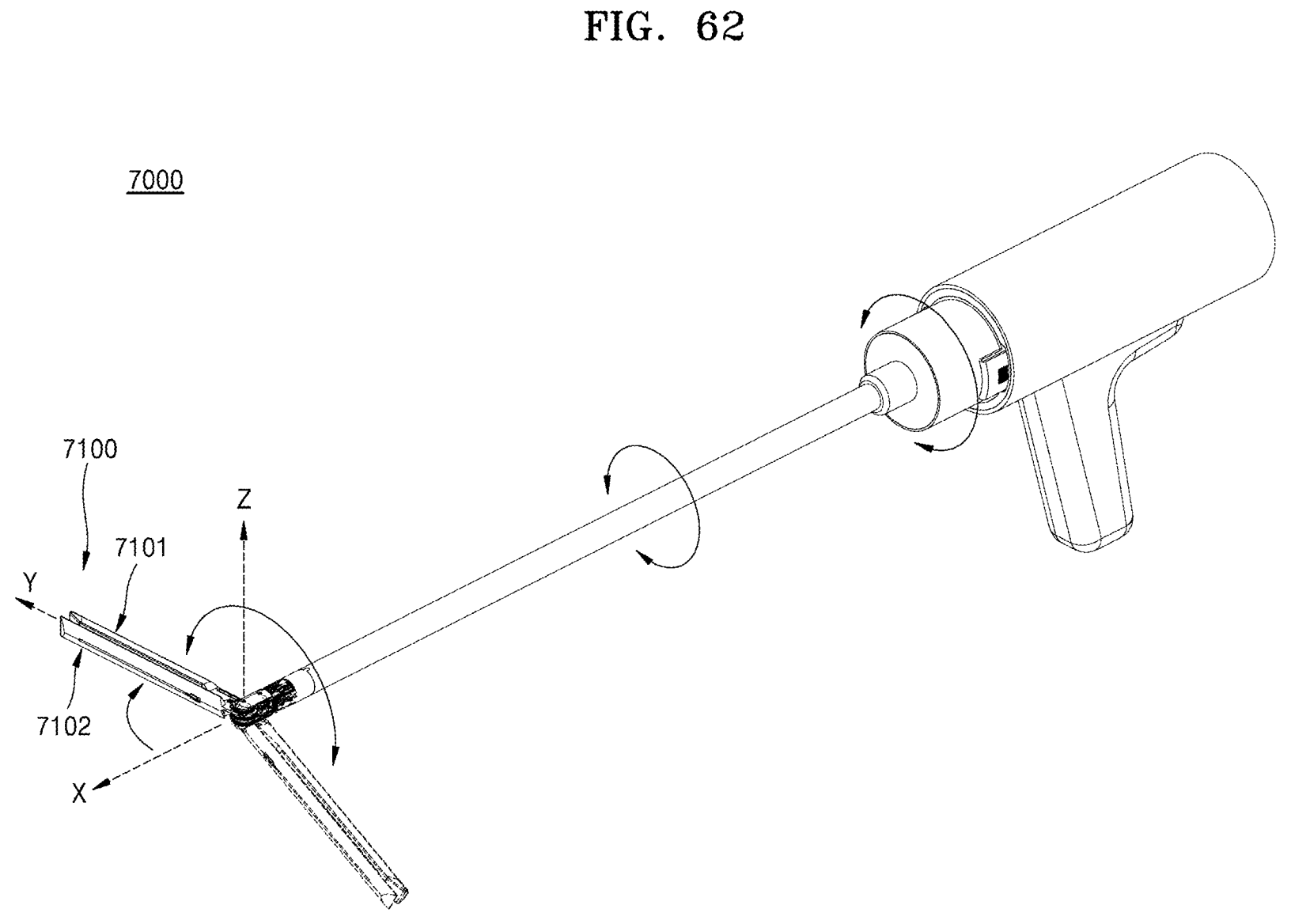

In detail, FIG. 58 is a view illustrating a state in which the jaws are yaw-rotated by –90°, and FIG. 59 is a view illustrating a process of performing an actuation motion in a state in which the jaws are yaw-rotated by –90°. FIG. 60 is a view illustrating a state in which the jaws are yaw-rotated by +90°, FIG. 61 is a view illustrating a process of performing an actuation motion in a state in which the jaws are yaw-rotated by +90°, and FIG. 62 is a view illustrating a state in which a roll motion is performed in a state in which the jaws are yaw-rotated.

Referring to FIGS. 58 to 62, the surgical instrument 7000 according to the present disclosure may include the end tool 7100 including the first jaw 7101 and the second jaw 7102. Here, the end tool 7100 of the surgical instrument 7000 may be the end tool 5100 described with reference to FIG. 27. Alternatively, the end tool 7100 of the surgical instrument 7000 may be the end tool 5100 with at least some components changed or omitted.

The end tool 7100 of the surgical instrument 7000 may yaw-rotate in a positive (+) direction around a yaw direction rotation axis (Z-axis). In this case, the first jaw 7101 and the second jaw of the end tool 7100 may perform an actuation motion in a state in which the end tool 7100 yaw-rotates in the positive (+) direction around the yaw direction rotation axis (Z-axis).

Further, the end tool 7100 of the surgical instrument 7000 may yaw-rotate in a negative (–) direction around the yaw direction rotation axis (Z-axis). In this case, the first jaw 7101 and the second jaw of the end tool 7100 may perform an actuation motion in a state in which the end tool 7100 yaw-rotates in the negative (–) direction around the yaw direction rotation axis (Z-axis).

Here, a rotation angle of the end tool 7100 may be variously set according to the ratio of pulleys.

Meanwhile, the end tool 7100 of the surgical instrument 7000 may not rotate around the yaw direction rotation axis (Z-axis), but roll-rotate around the roll rotation axis (X-axis) while roll-rotating in the positive (+) direction or negative (–) direction. At this time, the end tool 7100 may roll-rotate in a state in which the first jaw 7101 and the second jaw 7102 are spread apart from each other, and the first jaw 7101 and the second jaw 7102 may roll-rotate while performing an actuation motion.

Here, the end tool 7100 may rotate together with the rotation of the motor pack of the power generation part. When the motor pack of the power generation part roll-rotates, the power transmission part connected to the power generation part, the connection part connected to the power transmission part, and the end tool 7100 formed on one side of the connection part may rotate simultaneously.

FIGS. 63 to 67 are views illustrating a state in which the surgical instrument according to an embodiment of the present disclosure pitch-rotates and yaw-rotates.

Figure 63:
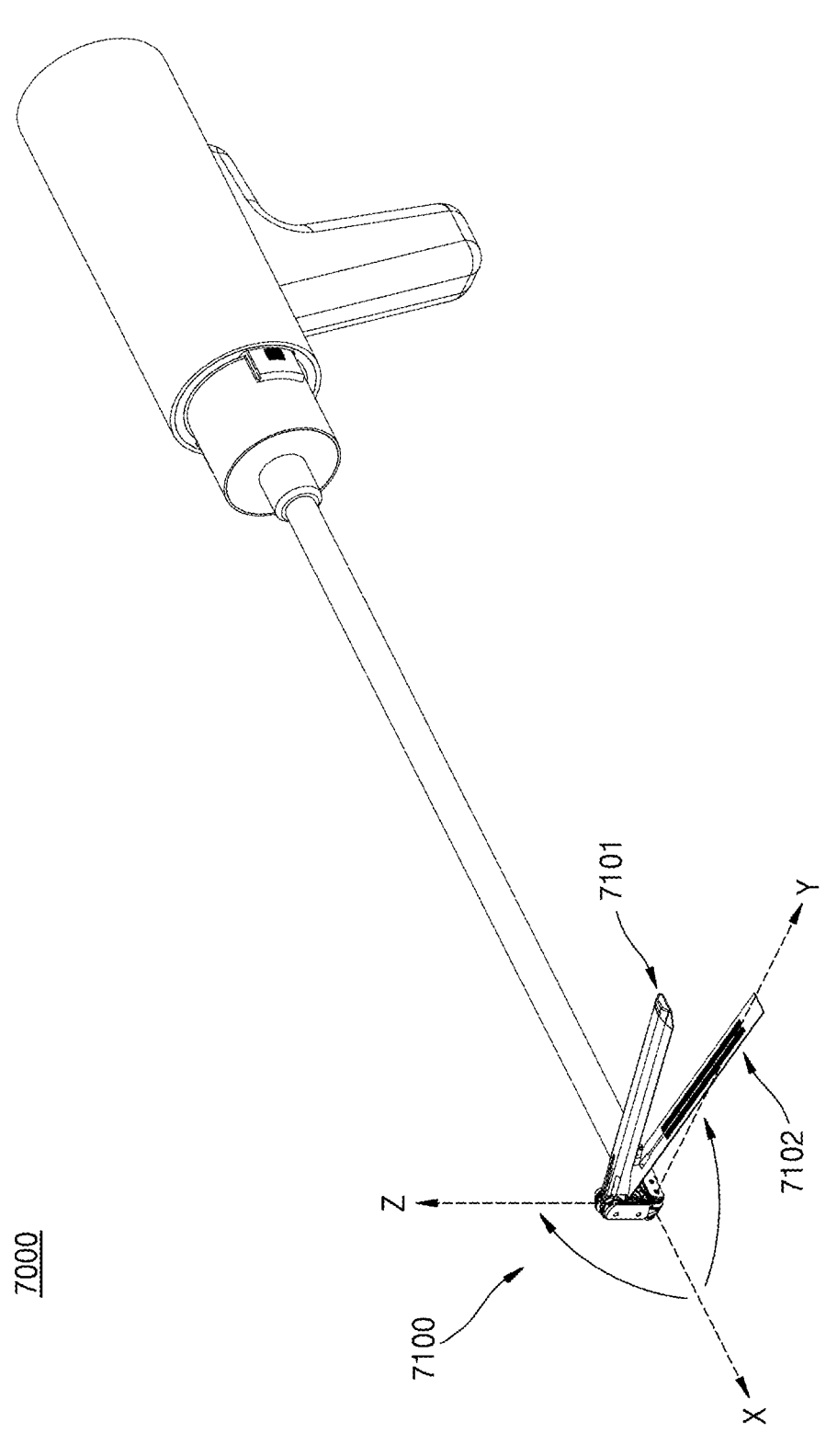
FIGS. 63 to 67 are views illustrating a state in which the surgical instrument according to an embodiment of the present disclosure performs a pitch rotation motion and a yaw rotation motion.
Figure 64:
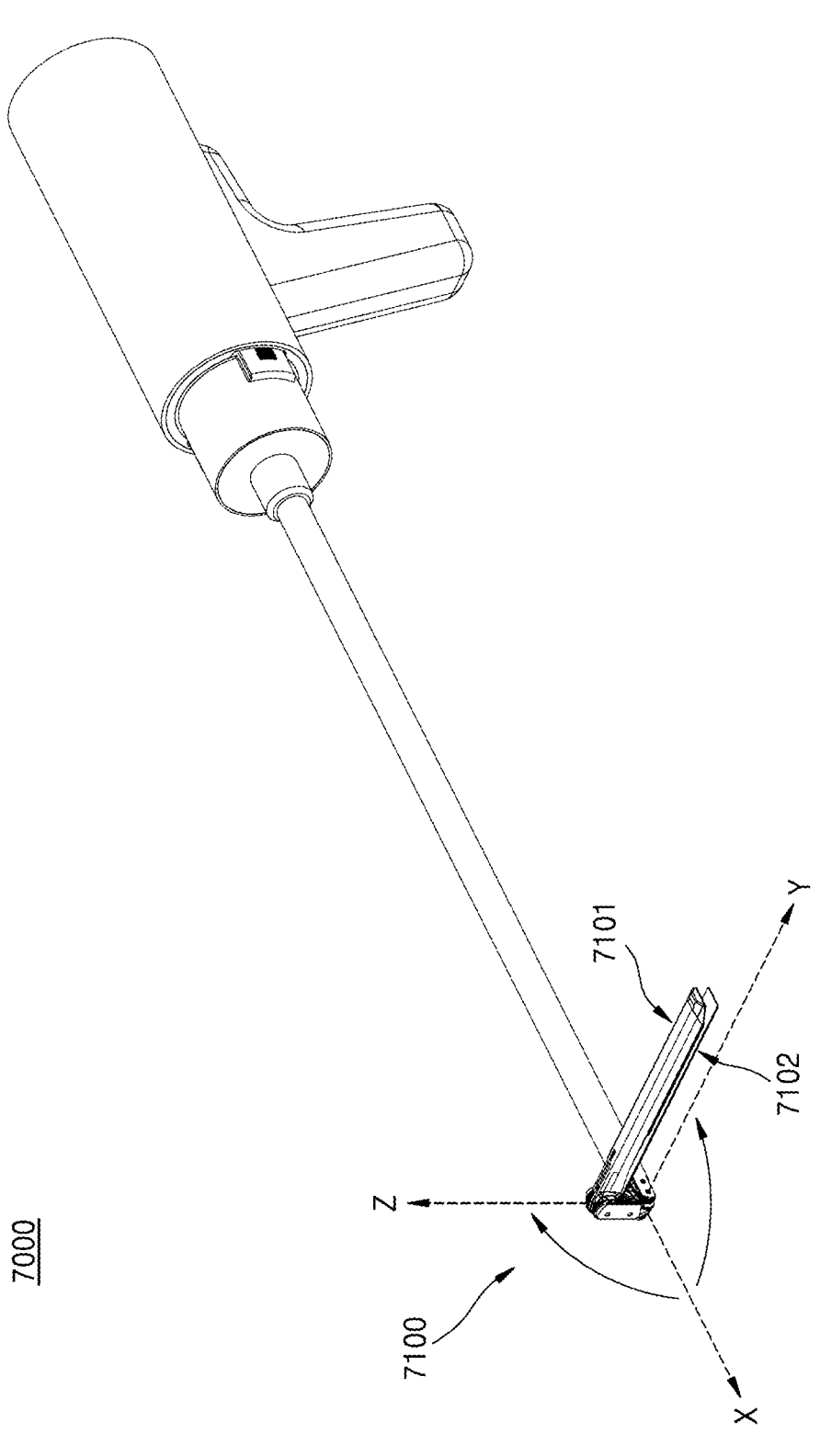
Figure 65:
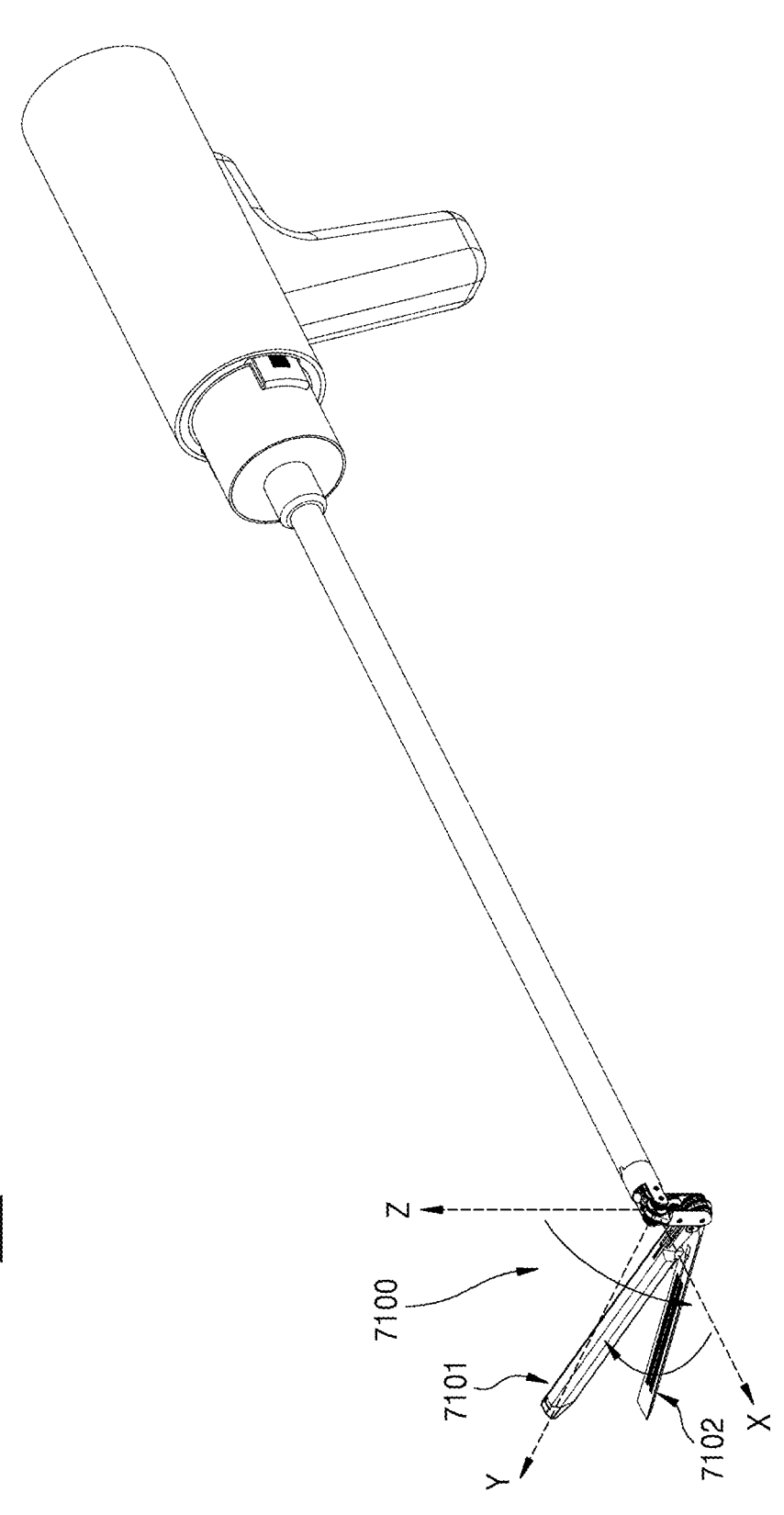
Figure 66:
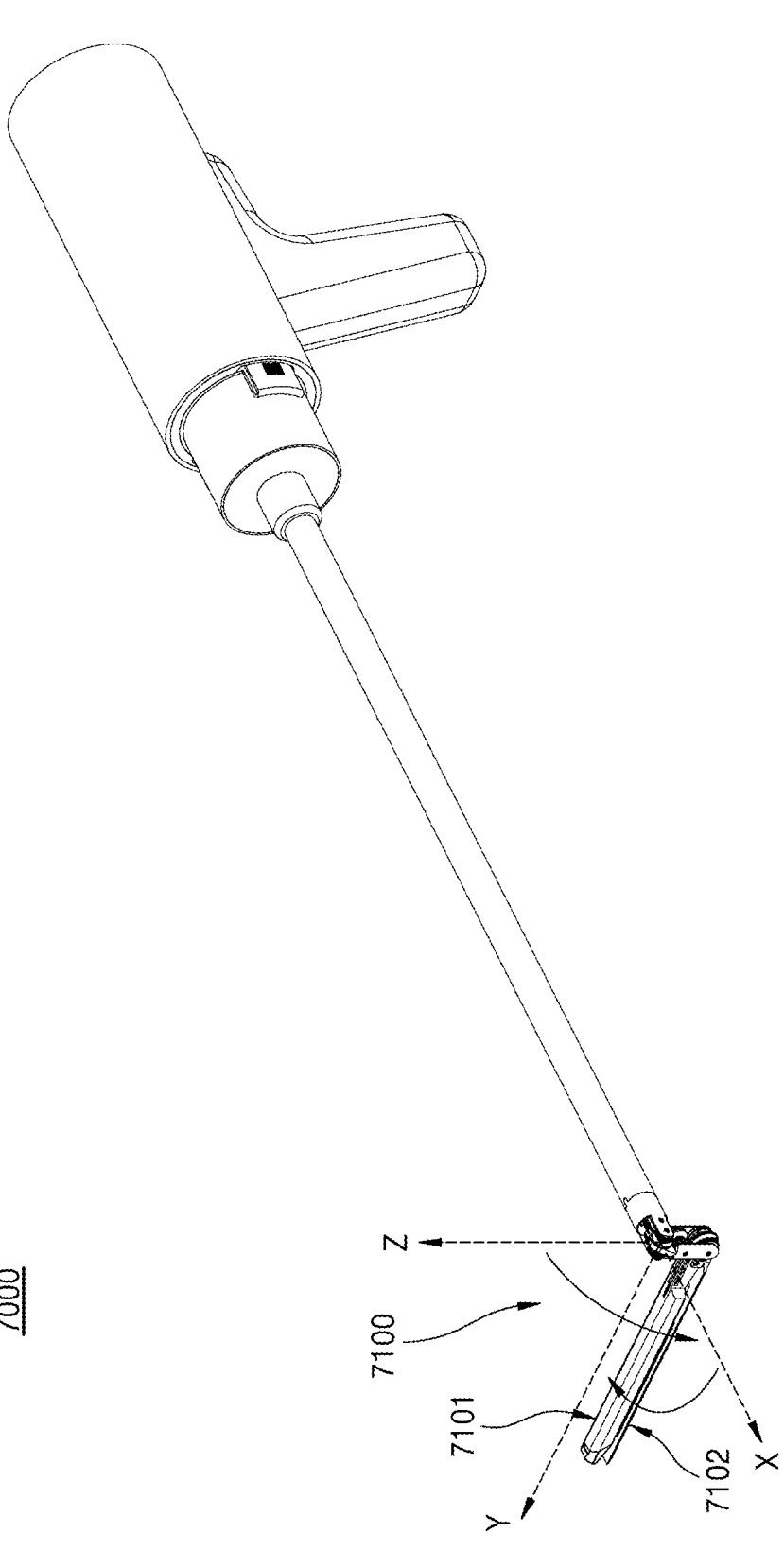
Figure 67:
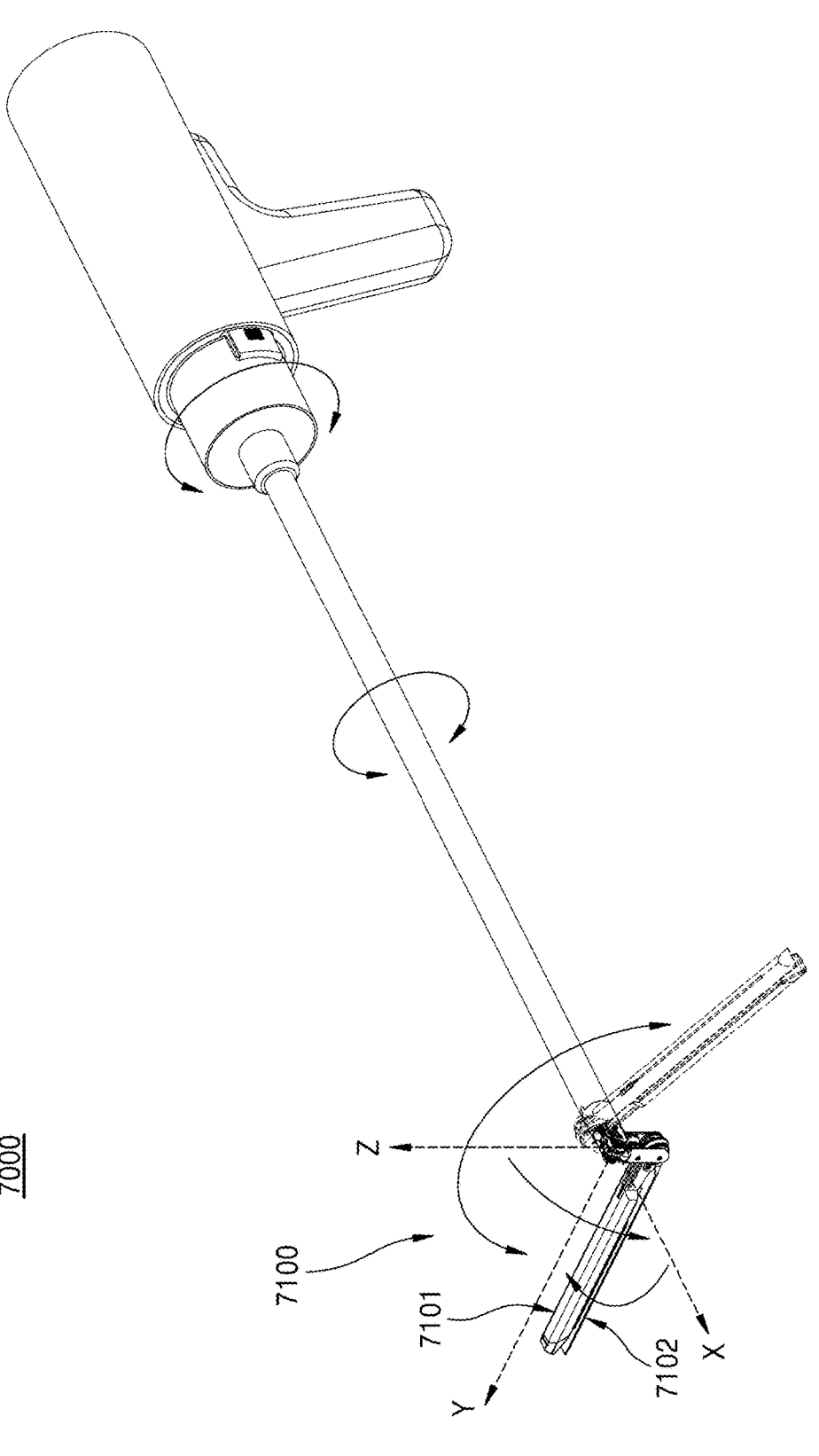

Specifically, FIG. 63 is a view illustrating a state in which the jaws are pitch-rotated by –90° and at the same time yaw-rotated by +90°, and FIG. 64 is a view illustrating a process of performing an actuation motion in the state in which the jaws are pitch-rotated by –90° and at the same time yaw-rotated by +90°, FIG. 65 is a view illustrating a state in which the jaws are pitch-rotated by +90° and simultaneously yaw-rotated by –90°, FIG. 66 is a view illustrating a process of performing an actuation motion in a state in which the jaws are pitch-rotated by +90° and simultaneously yaw-rotated by –90°, and FIG. 67 is a view illustrating a process of performing a roll motion in a state in which the jaws are pitch-rotated and yaw-rotated.

Referring to FIGS. 63 to 67, the surgical instrument 7000 according to the present disclosure may include the end tool 7100 including the first jaw 7101 and the second jaw 7102. Here, the end tool 7100 of the surgical instrument 7000 may be the end tool 5100 described with reference to FIG. 27. Alternatively, the end tool 7100 of the surgical instrument 7000 may be the end tool 5100 with at least some components changed or omitted.

The end tool 7100 of the surgical instrument 7000 may pitch-rotate around the pitch rotation axis (Y-axis) while yaw-rotating around the yaw direction rotation axis (Z-axis). In other words, the end tool 7100 of the surgical instrument 7000 may perform yaw rotation and pitch rotation simultaneously. In this case, the first jaw 7101 and the second jaw of the end tool 7100 may perform an actuation motion in a state in which the end tool 7100 is yaw-rotated and pitch-rotated.

Here, a rotation angle of the end tool 7100 may be variously set according to the ratio of pulleys.

Meanwhile, the end tool 7100 of the surgical instrument 7000 may roll-rotate around the roll rotation axis (X-axis) while pitch-rotating and yaw-rotating. At this time, the end tool 7100 may roll-rotate in a state in which the first jaw 7101 and the second jaw 7102 are spread apart from each other, and the first jaw 7101 and the second jaw 7102 may roll-rotate while performing an actuation motion.

Here, the end tool 7100 may rotate together with the rotation of the motor pack of the power generation part. When the motor pack of the power generation part roll-rotates, the power transmission part connected to the power generation part, the connection part connected to the power transmission part, and the end tool 7100 formed on one side of the connection part may rotate simultaneously.

As such, the surgical instrument 1000 according to the present disclosure is configured to enable simultaneous roll rotation of the motor pack 1510 (or 3510), the power transmission part 1300, and the end tool 1100, the end tool 1100 (or 5100), and thus, the problem of electric wires or wires being twisted inside the surgical instrument 1000 (or 3000) may not occur. This is of technical significance as it allows the surgical instrument 1000 (or 3000) to roll-rotate indefinitely.

For example, in conventional surgical instruments, only the connection part and the end tool roll-rotate, while the pulleys inside the power transmission part do not roll-rotate, causing the wires connecting the end tool to the power transmission part to be twisted inside the connection part. In this case, when the end tool and the connection part continue to roll-rotate, the wires will eventually break or become damaged.

In contrast, the surgical instrument 1000 (or 2000, 3000, 5000, 7000) according to the present disclosure allows the end tool 1100 (or 2100, 3100, 5100, 7100), the connection part 1400 (or 3400), and the pulleys 1320 and 1330 (or 3320, 3330, and 3340) inside the power transmission part 1300 (or 3300) to roll-rotate together. In other words, it may be said that the wires 1361, 1362, 1363, and 1364 (or 3361, 3362, 3363, 3364, 3365, and 3366) connecting the end tool 1100 (or 3100) to the pulleys 1320 and 1330 (or 3320, 3330, and 3340) of the power transmission part 1300 (or 3300) roll-rotate together at start and end points thereof. Thus, the wires 1361, 1362, 1363, and 1364 (or 3361, 3362, 3363, 3364, 3365, and 3366) are prevented from twisting inside the connection part 1400 (or 3400).

Figure 68:
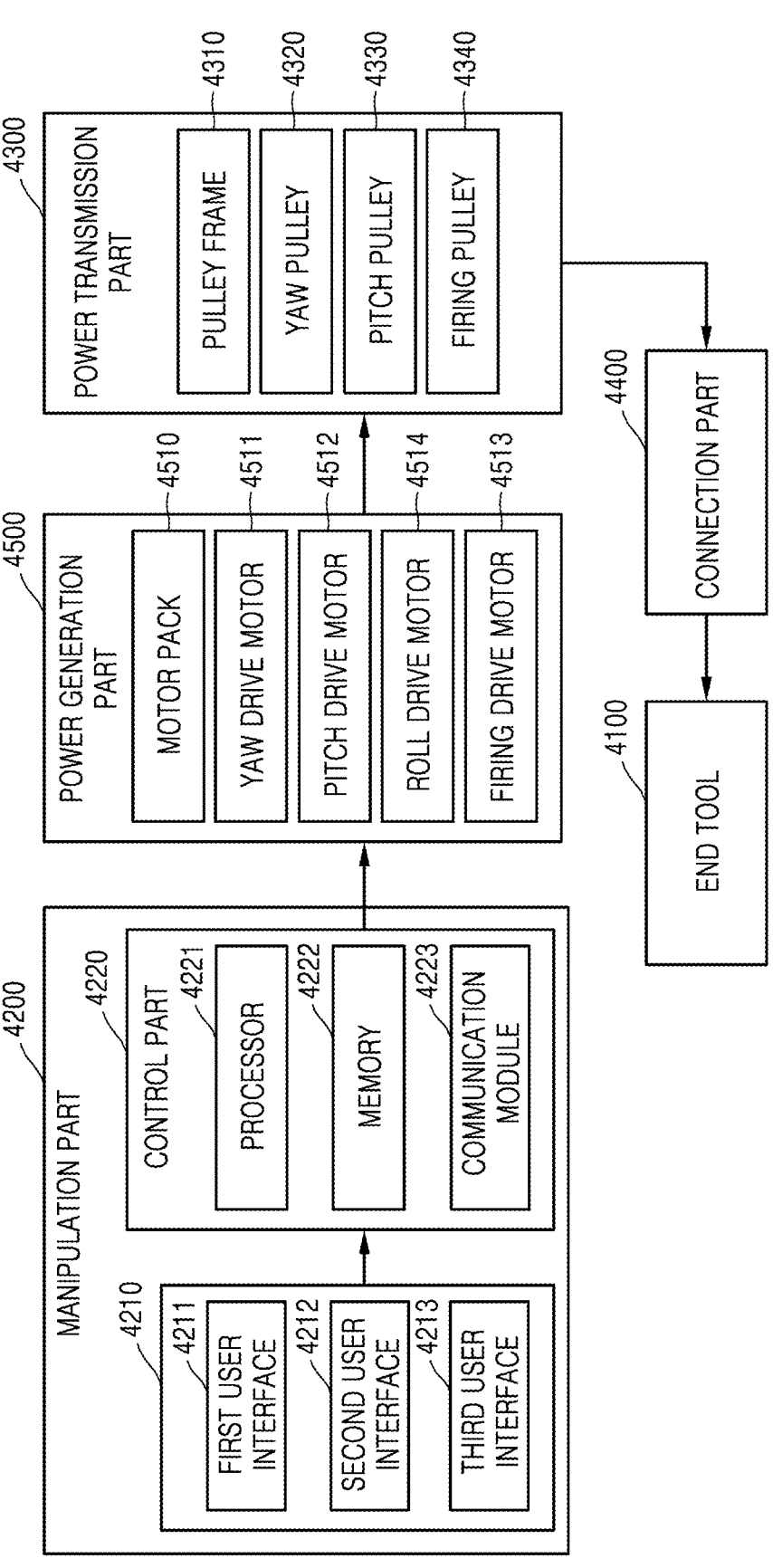
FIG. 68 is a block diagram for describing an example of an internal configuration of a surgical instrument according to an embodiment of the present disclosure.

FIG. 68 is a block diagram for describing an example of an internal configuration of a surgical instrument according to an embodiment of the present disclosure.

Referring to FIG. 68, a surgical instrument 4000 according to an embodiment of the present disclosure may include an end tool 4100, a manipulation part 4200, a power transmission part 4300, a connection part 4400, and a power generation part 4500. In addition, the manipulation part 4200 may include user interfaces 4211, 4212, and 4213 (collectively "4210"), and a control part 4220. In addition to the components illustrated in FIG. 68, the components that have been described herein as being included in the surgical instrument may be further included in the surgical instrument 4000. In addition, redundant descriptions of each component included in the surgical instrument 4000 will be omitted herein.

The manipulation part 4200 may receive user input (hereinafter, the user input may be used interchangeably with an input from a user) to change a posture of the end tool. In more detail, the user interfaces 4211, 4212, and 4213 included in the manipulation part 4200 may each receive user input to change the posture of the end tool 4100. For example, a first user interface 4211 may receive user input for a pitch rotation and a yaw rotation of the end tool 4100, and a second user interface 4212 may receive user input for a roll rotation of the end tool 4100.

The control part 4220 included in the manipulation part 4200 may be a device that controls motions of the end tool so that a target posture according to the user input is implemented. For example, the control part 4220 may be a device that generates a control value to change the posture of the end tool, based on a manipulation value according to user input.

In more detail, the control part 4220 (or, hereinafter, a device) may include a processor 4221, a memory 4222, and a communication module 4223. However, other general-purpose components may be further included in the control part 4220, and the processor 4221, the memory 4222, and the communication module 4223 may be implemented as independent devices.

The processor 4221 may process instructions of a computer program by performing a basic arithmetic operation, a logic operation, and an input/output operation. Here, the instructions may be provided from the memory 4222 or an external device (e.g., an external server (not shown) or the like). In addition, according to an embodiment, the processor 4221 may control overall operations of other components included in the surgical instrument 4000.

According to an embodiment, the processor 4221 may obtain a manipulation value according to user input to change a posture of the end tool included in the surgical instrument.

Here, the user input may include an input for at least one of a roll rotation, a pitch rotation, and a yaw rotation. That is, a user's manipulation value may be an input for each of the roll rotation, the pitch rotation, and the yaw rotation.

According to an embodiment, the processor 4221 may generate target posture information, which is posture information about a posture of the end tool to be changed, based on the user input.

For example, the processor 4221 may generate target orientation information about a target orientation of the end tool to be changed based on the user input. In addition, the processor 4221 may generate the target posture information based on the target orientation information of the end tool and a change in position of the surgical instrument.

According to an embodiment, the processor 4221 may obtain first posture information, which is information about a current posture of the end tool at the time of obtaining the user input.

For example, the processor 4221 may obtain first joint information that is information about a current joint of the end tool at the time of obtaining the user input, and compute the first posture information based on the first joint information.

According to an embodiment, the processor 4221 may control motions of the end tool to implement the target posture according to the user input, based on the manipulation value and the first posture information. For example, the processor 4221 may generate a control value to drive the joint of the end tool by comparing the target posture information and the first posture information.

Here, the control value may include at least one of a first control value for controlling a roll rotation of the end tool, a second control value for controlling a pitch rotation of the end tool, and a third control value for controlling a yaw rotation of the end tool.

As an example, the manipulation value according to user input may include at least one of a manipulation value for pitch rotation and a manipulation value for yaw rotation, and depending on the manipulation value, the control value may include a first control value for controlling a pitch rotation of the end tool and a second control value for controlling a yaw rotation of the end tool.

As another example, the manipulation value according to user input may include at least one of a manipulation value for pitch rotation and a manipulation value for yaw rotation, and depending on the manipulation value, the control value may include a first control value for controlling a pitch rotation of the end tool, a second control value for controlling a yaw rotation of the end tool, and a third control value for controlling a roll rotation of the end tool.

As another example, the manipulation value according to user input may include a manipulation value for roll rotation, and depending on the manipulation value, the control value may include a first control value for controlling the roll rotation of the end tool, a second control value for controlling a pitch rotation of the end tool, and a third control value for controlling a yaw rotation of the end tool.

Meanwhile, according to another embodiment, the processor 4221 may generate first posture difference information corresponding to a difference between the target posture information according to the user input and the first posture information, and compute the first posture difference information to generate first joint difference information related to the joint of the end tool. In addition, the processor 4221 may update the first joint information, which is information about a current joint of the end tool at the time of obtaining the user input, using the first joint difference information to generate second joint information, and generate a control value that causes the joint of the end tool to be driven according to the second joint information.

For example, in response to the first joint difference information being greater than a preset reference value, the processor 4221 may compute second posture information based on the second joint information, and compare the second posture information with the target posture information to determine joint information of the end tool for generating a control value.

In more detail, the processor 4221 may generate second posture difference information corresponding to a difference between the target posture information and the second posture information, and compute the second posture difference information to generate second joint difference information. In addition, in response to the second joint difference information being less than the preset reference value, the processor 4221 may update the second joint information using the second joint difference information to generate third joint information, and generate a control value that causes the joint of the end tool to be driven according to the third joint information.

Specific examples of the operation of the processor 4221 according to the embodiment will be described in more detail with reference to FIGS. 69 to 72.

The processor 4221 may be implemented as an array of a plurality of logic gates or may be implemented as a combination of a general-purpose microprocessor and a memory in which a program executable in the microprocessor is stored. For example, the processor 4221 may include a general-purpose processor, a central processing unit (CPU), a microprocessor, a digital signal processor (DSP), a controller, a microcontroller, a state machine, or the like. In some environments, the processor 4221 may include an application-specific semiconductor (ASIC), a programmable logic device (PLD), a field programmable gate array (FPGA), or the like. For example, the processor 4221 may refer to a combination of processing devices such as a combination of a DSP and a microprocessor, a combination of a plurality of microprocessors, a combination of one or more microprocessors in conjunction with a DSP core, or a combination of any other such configuration.

Meanwhile, according to an embodiment, the processor 4221 may correspond to the circuit plate 1570 or 3570 or the circuit unit 3600. Repeated descriptions will be omitted.

The memory 4222 may include any non-transitory computer-readable recording medium. In an example, the memory 4222 may include a permanent mass storage device such as a random access memory (RAM), a read-only memory (ROM), a disk drive, a solid state drive (SSD), a flash memory, or the like. In another example, the permanent mass storage device such as a ROM, SSD, a flash memory, a disk drive, or the like may be a separate permanent storage device which is distinguishable from the memory. In addition, an operating system (OS) and at least one program code (e.g., a code for the processor 4221 to perform operations to be described later with reference to FIGS. 69 to 72) may be stored in the memory 4222.

These software components may be loaded from a computer-readable recording medium separate from the memory 4222. The separate computer-readable recording medium may be a recording medium that may be directly connected to the control part 4220, and may include, for example, a computer-readable recording medium, such as a floppy drive, a disk, a tape, a DVD/CD-ROM drive, a memory card, or the like. The separate computer-readable recording medium may be non-transitory. Alternatively, the software components may be loaded into the memory 4222 through the communication module 4223 instead of the computer-readable recording medium. For example, at least one program may be loaded into the memory 4222 based on a computer program (for example, a computer program for performing, by the processor 4221, operations to be described later with reference to FIGS. 69 to 72) installed by the files provided through the communication module 4223 by developers or a computer file distribution system that distributes the installation files of applications.

The communication module 4223 may provide a configuration or function for external devices and the control part 4220 to communicate with each other through a network. In addition, the communication module 4223 may provide a configuration or function for the control part 4220 to communicate with another external device. For example, a control signal, a command, data, or the like provided according to the control of the processor 4221 may be transmitted to the external device through the communication module 4223 and the network.

According to an embodiment, the communication module 4223 may correspond to the slip ring 3700. Repeated descriptions will be omitted.

The power generation part 4500 may generate power to control the end tool 4100 in response to receiving user input. For example, the power generation part 4500 may include a motor pack 4510, a yaw drive motor 4511, a pitch drive motor 4512, a roll drive motor 4514, and a firing drive motor 4513. Repeated descriptions of each component will be omitted.

The power transmission part 4300 may transmit power generated by the power generation part 4500 to the end tool 4100. For example, the power transmission part 4300 may include a pulley frame 4310, a yaw pulley 4320, a pitch pulley 4330, and a firing pulley 4340. Repeated descriptions of each component will be omitted.

The power transmission part 4300 may be coupled to one end portion of the connection part 4400, and the end tool 4100 may be coupled to another end portion thereof, and thus the manipulation part 4200 may be connected to the end tool 4100.

The end tool 4100 may perform a surgical operation.

According to the embodiment of the present disclosure, the manipulation part 4200 may receive user input to change a posture of the end tool 4100, and the control part 4220 included in the manipulation part 4200 may use a user's manipulation value obtained based on the user input to generate a control value for controlling the end tool 4100. The power generation part 4500 may generate power based on the control value generated by the control part 4220, and the power transmission part 4300 may transmit the generated power to the end tool 4100 through the connection part 4400. Eventually, the end tool 4100 may use the received power to perform a motion to change a posture.

The end tool 4100 may perform a motion so that a target posture according to the user input is implemented independently of a current posture of the end tool at the time of obtaining the user input.

For example, even when a roll rotation angle included in first posture information is not an angle in an initial state (e.g., 0 degrees based on a coordinate system used by the end tool 4100), the end tool 4100 may implement the target posture to intuitively correspond to the movement of the manipulation part.

As another example, even when a pitch rotation angle or a yaw rotation angle included in the first posture information is not an angle in an initial state (e.g., 0 degrees based on the coordinate system used by the end tool 4100), the end tool 4100 may implement the target posture to intuitively correspond to the movement of the manipulation part.

Figure 69:
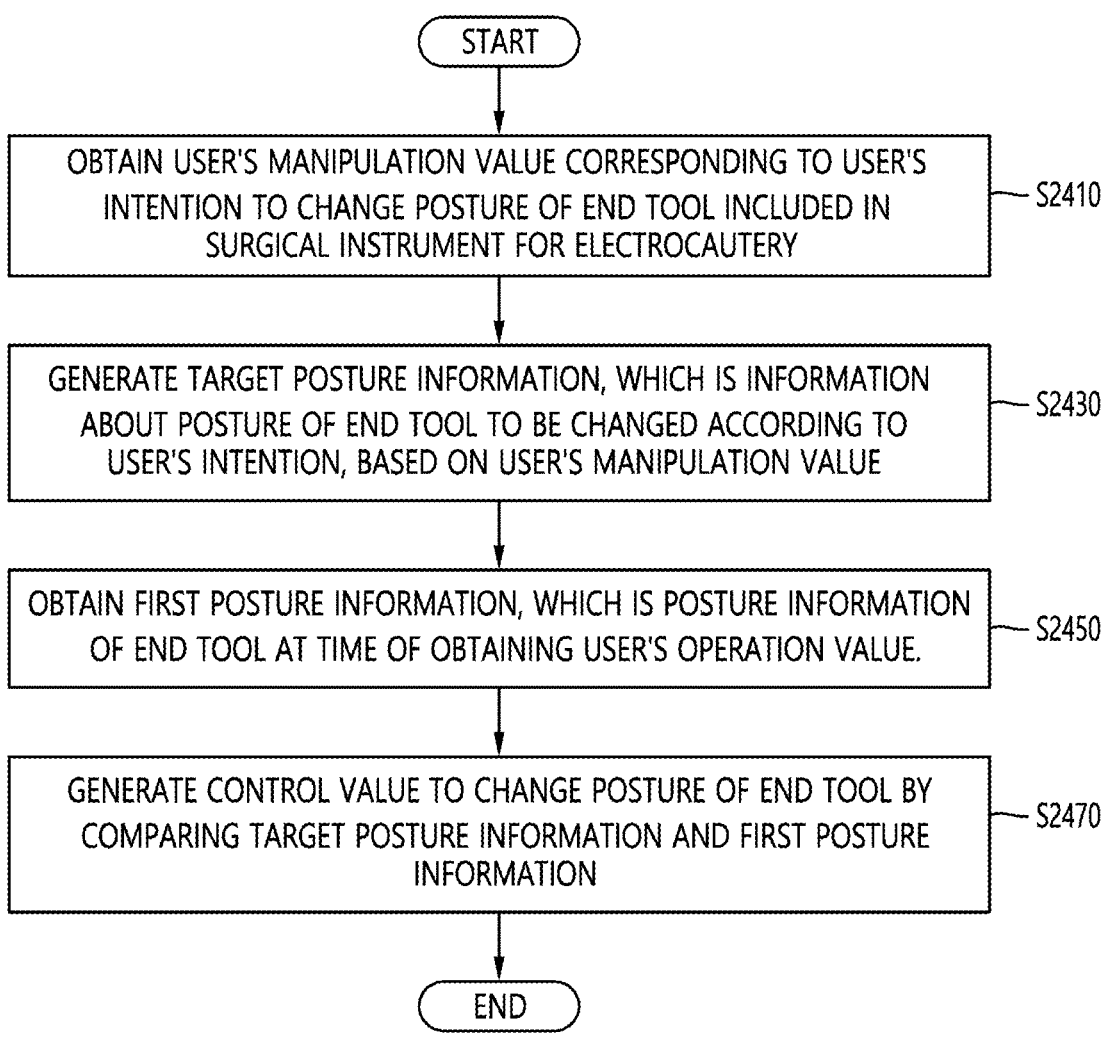
FIG. 69 is a flowchart for describing an example of a method of controlling a posture of the surgical instrument according to an embodiment.
Figure 70:
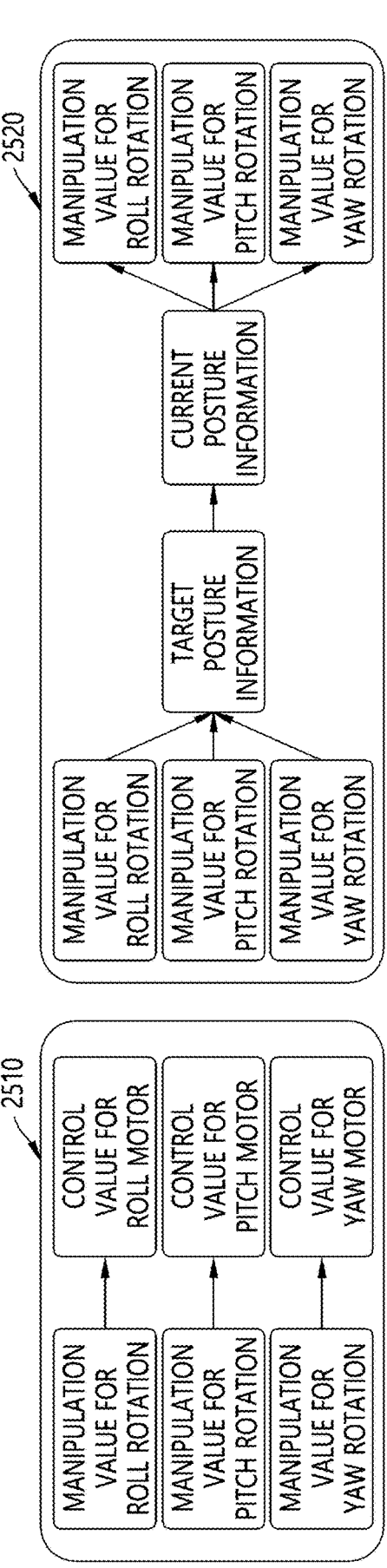
FIG. 70 is a conceptual diagram for describing the method of controlling a posture of the surgical instrument according to an embodiment.

FIG. 69 is a flowchart for describing an example of a method of controlling a posture of the surgical instrument according to an embodiment. FIG. 70 is a conceptual diagram for describing the method of controlling a posture of the surgical instrument according to an embodiment.

Referring to FIG. 69, the method of controlling a posture of the surgical instrument includes operations that are sequentially processed by the control part 4220 included in the surgical instrument illustrated in FIG. 68. However, since the control part 4220 controls the posture of the surgical instrument by exchanging information (e.g., user input and a motion control signal) with each component (the user interface, the power generation part, the power transmission part, the connection part, the end tool, or the like) included in the surgical instrument, the above description of each component (the user interface, the power generation part, the power transmission part, the connection part, the end tool, or the like) included in the surgical instrument may may include an angle for the roll rotation. However, the present disclosure is not limited thereto, and the control part 4220 may obtain a manipulation value for pitch rotation, a yaw rotation, and a roll rotation based on user input received through the first user interface 4211 and/or the second user interface 4212.

According to an embodiment, the control part 4220 may generate input information based on the user input. For example, the input information may include an angle $\theta_r$ for a roll rotation, an angle $\theta_g$ for a pitch rotation, and an angle $\theta_y$ for a yaw rotation.

According to an embodiment, in operation S2430, the control part 4220 may generate target posture information, which is posture information about a posture of the end tool to be changed, based on the user input.

For example, the control part 4220 may generate target orientation information about a target orientation of the end tool based on the user input. For example, the control part 4220 may generate information about an orientation of the end tool using Euler angles, quaternions, rotation matrices, or the like. For example, the control part 4220 may generate the target orientation information based on the user input, as shown in Equation 1 below,

[Equation 1]

$$R_{target} = \begin{bmatrix} \cos\theta_r\cos\theta_p & \cos\theta_r\sin\theta_p\sin\theta_y - \sin\theta_r\cos\theta_y & \cos\theta_r\sin\theta_p\cos\theta_y + \sin\theta_r\sin\theta_y \\ \sin\theta_r\cos\theta_p & \sin\theta_r\sin\theta_p\sin\theta_y + \cos\theta_r\cos\theta_y & \sin\theta_r\sin\theta_p\cos\theta_y - \cos\theta_r\sin\theta_y \\ -\sin\theta_p & \cos\theta_p\sin\theta_y & \cos\theta_p\cos\theta_y \end{bmatrix}$$

also be applied to the method of controlling a posture of the surgical instrument of FIG. 69, even when omitted herein.

First, in operation S2410, the control part 4220 may obtain a manipulation value according to user input to change a posture of the end tool included in the surgical instrument.

For example, the user interface 4210 included in the manipulation part 4200 may receive user input to change a posture of the end tool 4100 and transmit the received user input to the control part 4220. The control part 4220 may obtain a manipulation value based on the user input.

Here, the user input may include an input for at least one of a roll rotation, a pitch rotation, and a yaw rotation. As an example, the control part 4220 may obtain a manipulation value for pitch rotation and a yaw rotation based on user input received through the first user interface 4211 implewhere, $R_{target}$ refers to the target orientation information, and $\theta_r$, $\theta_p$, and $\theta_y$ refer to the angle for a roll rotation, the angle for a pitch rotation, and the angle for a yaw rotation, respectively.

According to an embodiment, the control part 4220 may generate the target posture information based on the target orientation information of the end tool and a change in position of the surgical instrument. Here, the user may directly change the position of the end tool without manipulating the manipulation part 4200, such as by bringing the surgical instrument or end tool closer to the patient or surgical site. Accordingly, the control part 4220 may set a user's manipulation value for the position information of the end tool to zero. In addition, the control part 4220 may generate the target posture information as shown in Equation 2 below,

[Equation 2]

$$T_{target} = \begin{bmatrix} R_{target} & 0 \\ 0 & 1 \end{bmatrix} = \begin{bmatrix} \cos\theta_r\cos\theta_p & \cos\theta_r\sin\theta_p\sin\theta_y - \sin\theta_r\cos\theta_y & \cos\theta_r\sin\theta_p\cos\theta_y + \sin\theta_r\sin\theta_y & 0 \\ \sin\theta_r\cos\theta_p & \sin\theta_r\sin\theta_p\sin\theta_y + \cos\theta_r\cos\theta_y & \sin\theta_r\sin\theta_p\cos\theta_y - \cos\theta_r\sin\theta_y & 0 \\ -\sin\theta_p & \cos\theta_p\sin\theta_y & \cos\theta_p\cos\theta_y & 0 \\ 0 & 0 & 0 & 1 \end{bmatrix}$$

mented in the form of a joystick. The manipulation value for the pitch rotation and the yaw rotation, which is obtained by the control part 4220, may include an angle for the pitch rotation and an angle for the yaw rotation. As another example, the control part 4220 may obtain a manipulation value for roll rotation based on user input received through the second user interface 4212. For example, a manipulation value for the roll rotation obtained by the control part 4220 where, $T_{target}$ refers to the target posture information.

Thereafter, in operation S2450, the control part 4220 may obtain first posture information, which is information about a current posture of the end tool at the time of obtaining the user input.

For example, in the embodiments of the surgical instrument described above, the surgical instrument may further include a plurality of joints that drive to change the posture of the end tool along various degrees of freedom (e.g., rotational degrees of freedom). For example, the surgical instrument may include a first joint that drives for a yaw rotation, a second joint that drives for a pitch rotation, and a third joint that drives for a roll rotation. Each joint may be disposed between the manipulation part 4200 and the connection part 4400, between the connection part 4400 and the end tool 4100, or in the end tool 4100. In addition, each joint may be configured to include a sensor capable of sensing a current state of the degree of freedom of the joint. For example, the sensor may be implemented as a sensor capable of measuring the amount of change in position or orientation of an object, such as a rotary encoder, a linear encoder, a potentiometer, or the like. For example, a first sensor included in the first joint may sense a current state (hereinafter, joint information) of the yaw rotation, a second sensor included in the second joint may sense a current state of the pitch rotation, and a third sensor included in the third joint may sense a current state of the roll rotation.

According to an embodiment, the control part 4220 may obtain first joint information, which is information about a current joint of the end tool at the time of obtaining the user's manipulation value. Here, the joint information may refer to state information of the joint for each degree of freedom, which is sensed by the sensor included in the surgical instrument 4000. For example, the joint information may include information about an angle and a position of each joint. For example, the control part 4220 may obtain the first joint information from the sensor included in the surgical instrument 4000.

According to an embodiment, the control part 4220 may compute the first posture information based on the first joint information. For example, the control part 4220 may compute the first posture information by performing forward kinematics (FK) computation on the first joint information.

In the present disclosure, forward kinematics computation may refer to a computation process of calculating the posture of the end tool based on the angle, direction, and position of the joint. For example, the control part 4220 may compute the first posture information by using the first joint information and the forward kinematics computation according to Equation 3 below, $$T_{curr} = FK(q_{curr})\qquad\text{[Equation 3]}$$

where, $T_{curr}$ refers to the first posture information, and $q_{curr}$ refers to the first joint information.

In operation S2470, the control part 4220 may control a motion of the end tool to implement the target posture according to the user input based on the manipulation value and the first posture information.

In more detail, the control part 4220 may compare the posture information (target posture information) about the posture of the end tool that is desired to change in response to the user input with the current posture information of the end tool at the time of obtaining the user input, i.e., at the time the user manipulates the manipulation part. Accordingly, the control part 4220 may obtain posture difference information about a difference between the two pieces of posture information, and generate a control value based on the corresponding posture difference information to cause the posture of the end tool to change, and more specifically, to cause the joint to be driven.

According to an embodiment, the control part 4220 may generate a control value that causes each joint related to each degree of freedom to be driven. In other words, the control value may include at least one of a first control value for controlling a roll rotation of the end tool, a second control value for controlling a pitch rotation of the end tool, and a third control value for controlling a yaw rotation of the end tool. That is, the joint performing the roll rotation of the end tool may be driven based on the first control value, the joint performing the pitch rotation of the end tool may be driven based on the second control value, and the joint performing the yaw rotation of the end tool may be driven based on the third control value.

Hereinafter, the differences between a typical method and the method of an embodiment of the present disclosure for controlling a posture of the surgical instrument based on user's manipulation values will be described with reference to FIG. 70.

FIG. 70 is a conceptual diagram for describing the method of controlling a posture of the surgical instrument according to an embodiment.

Referring to FIG. 70, in typical posture control method 2510, a motor control value is directly determined in response to user input. As an example, when a user intends to perform a roll rotation of the end tool and manipulates a manipulation device (e.g., the manipulation part) related to the roll rotation, the manipulation value according to user input may be directly converted into a control value for a joint that performs the roll rotation, and the corresponding joint may drive a motor according to the converted control value, thereby performing the roll rotation on the end tool. As another example, unlike the one shown in FIG. 70, when the user intends to perform a pitch rotation and a yaw rotation of the end tool and manipulates a manipulation device (e.g., a joystick) related to the pitch rotation and the yaw rotation, the manipulation value according to user input may be divided into a manipulation value for the pitch rotation and a manipulation value for the yaw rotation. Thereafter, each manipulation value is directly converted into a control value for a joint so that the joint performs the pitch rotation and the yaw rotation of the end tool according to the control value. In other words, in typical posture control method 2510, the manipulation value and the control value may have a one-to-one correspondence, and when a coordinate system used by the manipulation part and a coordinate system used by the end tool are different from each other, it may be inconvenient for the user to manipulate the manipulation part in consideration of the coordinate system difference.

In contrast, posture control method 2520 according to an embodiment of the present disclosure may generate new information called target posture information according to the user input, newly obtain posture difference information corresponding to a difference between the target posture information and current posture information, and generate a control value based on the corresponding posture difference information.

In other words, the posture control method 2520 may generate a control value for controlling a posture change of the end tool through a series of processes based on user input, in consideration of a transformation between the coordinate system used by the manipulation part and the coordinate system used by the end tool. That is, the manipulation value according to user input and the control value may not be in a one-to-one correspondence.

As an example, when the manipulation value according to user input includes at least one of a manipulation value for pitch rotation and a manipulation value for yaw rotation, the control value may include a first control value for controlling a pitch rotation of the end tool and a second control value for controlling a yaw rotation of the end tool.

As another example, when the manipulation value according to user input includes at least one of a manipulation value for pitch rotation and a manipulation value for yaw rotation, the control value may include a first control value for controlling a pitch rotation of the end tool, a second control value for controlling a yaw rotation of the end tool, and a third control value for controlling a roll rotation of the end tool.

As another example, the manipulation value according to user input may include a manipulation value for roll rotation, and the control value may include a first control value for controlling a roll rotation of the end tool, a second control value for controlling a pitch rotation of the end tool, and a third control value for controlling a yaw rotation of the end tool.

The posture control method 2520 according to an embodiment of the present disclosure generates the control value by automatically taking into account a coordinate system transformation, so that a user's intended posture change of the end tool intuitively corresponds to an end tool's actual posture change, allowing the user to have intuitive and efficient posture control.

FIG. 71 is a flowchart for describing another example of a method of controlling a posture of the surgical instrument according to an embodiment.

First, in operation S2610, the control part 4220 may generate first posture difference information corresponding to a difference between target posture information according to the user input and first posture information.

Here, the target posture information may be posture information about a posture of the end tool generated based on user input, as described with reference to FIG. 69. In addition, as described with reference to FIG. 69, the first posture information may be posture information of the end tool at the time of obtaining the user input.

Meanwhile, the target posture information and the first posture information may each be composed of a set of vectors and may be represented as a matrix. For example, the control part 4220 may generate first posture difference information by performing an operation between matrices (e.g., a subtraction operation between the matrices).

Thereafter, in operation S2620, the control part 4220 may compute the first posture difference information to generate first joint difference information regarding a joint of the end tool.

According to an embodiment, the control part 4220 may generate the first joint difference information by performing inverse kinematics (IK) computation on the first posture difference information.

In the present disclosure, the inverse kinematics computation may refer to a computation process of calculating an angle, a position, and the like that a joint should have, based on the position or orientation of the end tool. In other words, unlike the forward kinematics computation of calculating information about the posture of the end tool from the state information about the joint, the inverse kinematics computation may compute state information about the joint in reverse from the information about the posture of the end tool.

For example, the control part 4220 may compute the first joint difference information using the first posture difference information and the inverse kinematics computation according to Equation 4 below, $$q_{diff} = J^{+} T_{diff} \qquad \text{[Equation 4]}$$

where, $q_{diff}$ refers to the first joint difference information, and $T_{diff}$ refers to the first posture difference information. In addition, J may refer to a Jacobian matrix generally representing kinematic information of a robot, and addition (+) operation may refer to a pseudo-inverse operation. However, a detailed description of the Jacobian matrix and the pseudo-inverse operation is omitted in the present disclosure.

Thereafter, in operation S2630, the control part 4220 may generate second joint information by updating first joint information, which is information about a current joint of the end tool at the time of obtaining the user input, using the first joint difference information.

For example, the control part 4220 may update the first joint information into the second joint information by adding or subtracting the first joint difference information to or from the first joint information.

Thereafter, in operation S2640, the control part 4220 may compare the first joint difference information with a preset reference value and determine joint information of the end tool to generate a control value that causes the joint of the end tool to be driven.

Here, the preset reference value is a value set to determine whether the joint difference information has a value nearly zero, and may be set to any value nearly zero.

Meanwhile, as an example, in operation S2641, when it is determined that the first joint difference information is less than the preset reference value, the control part 4220 may generate a control value that causes the joint of the end tool to be driven according to the second joint information.

As another example, in operation S2650, when it is determined that the first joint difference information is greater than the preset reference value, the control part 4220 may compute second posture information based on the second joint information in response to the first joint difference information being greater than the preset reference value.

For example, the control part 4220 may compute the second posture information by performing forward kinematics computation on the second joint information.

Thereafter, the control part 4220 may repeatedly perform operations S2610 to S2630 based on the second posture information. In other words, the control part 4220 may compare the second posture information with the target posture information and determine joint information of the end tool to generate a control value that causes the joint of the end tool to be driven.

For example, in operation S2660, the control part 4220 may generate second posture difference information corresponding to a difference between the target posture information and the second posture information. For example, the control part 4220 may generate the second posture difference information by performing an operation between matrices (e.g., a subtraction operation between the matrices).

Thereafter, in operation S2670, the control part 4220 may compute the second posture difference information to generate second joint difference information. For example, the control part 4220 may generate the second joint difference information by performing inverse kinematics computation on the second posture difference information.

Thereafter, in operation S2680, the control part 4220 may generate third joint information by updating the second joint information using the second joint difference information.

Thereafter, in operation S2690, the control part 4220 may compare the second joint difference information with the preset reference value and determine joint information of the end tool to generate a control value that causes the joint of the end tool to be driven.

As an example, in operation S2691, when it is determined that the second joint difference information is less than the preset reference value, in response thereto, the control part 4220 may generate a control value that causes the joint of the end tool to be driven according to the third joint information.

As another example, in operation S2692, when it is determined that the second joint difference information is greater than the preset reference value, the control part 4220 may repeatedly perform operations 2650 to 2690, beginning with the computation of third posture information based on the third joint information.

Meanwhile, according to an embodiment, in a process of repeatedly performing an algorithm for generating the control value, the control part 4220 may repeatedly perform the algorithm within a preset time limit. For example, when the control part 4220 fails to generate a control value to drive the joint of the end tool within the preset time limit, this failure may initiate a process to handle the failure, as a result of the attempt to generate the control value based on user input. Here, the preset time limit may be set according to the performance of the control part 4220 (or the processor 4221), such as, 10 ms or the like.

Figure 72:
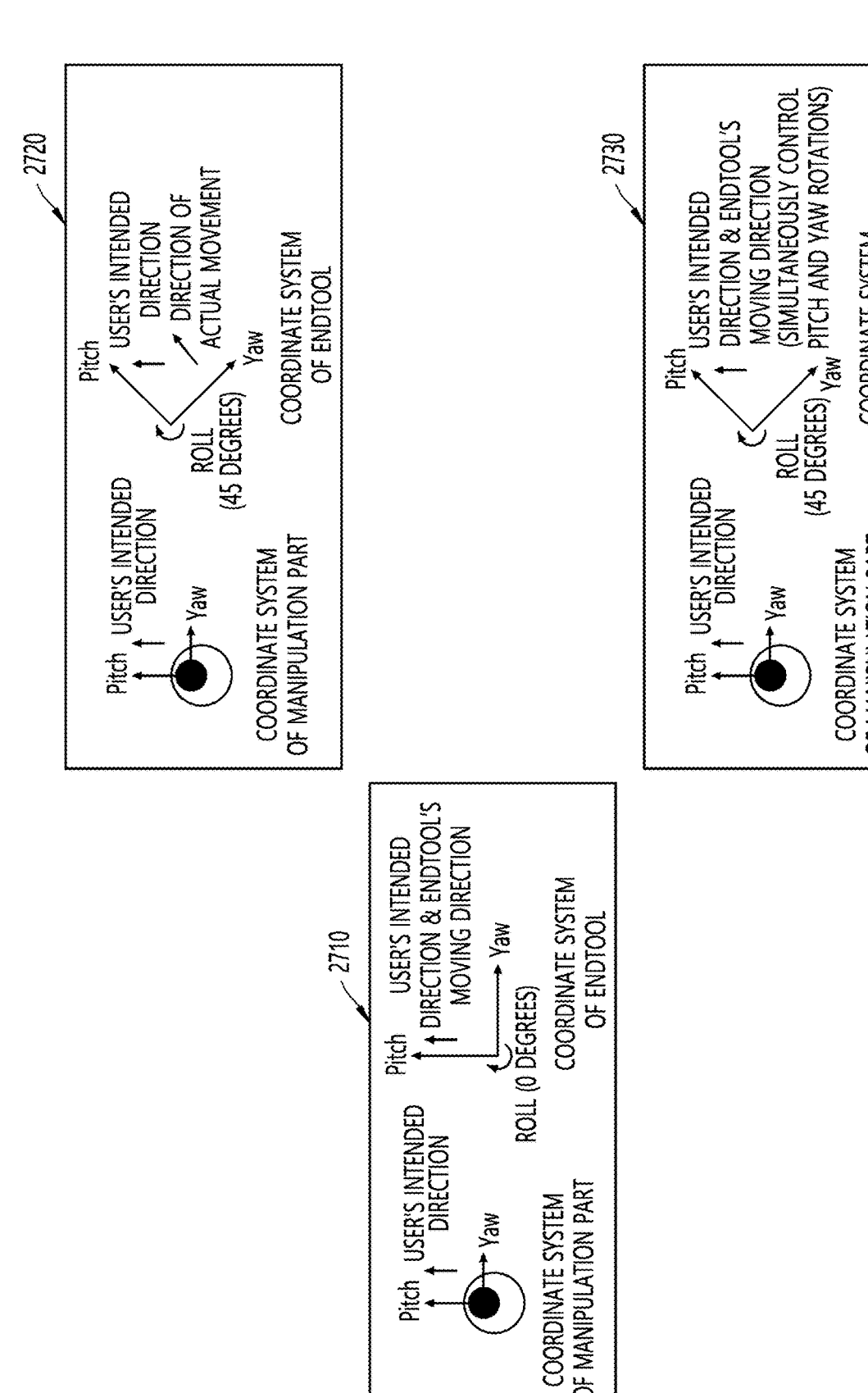
FIG. 72 is a diagram for describing an example of controlling the end tool according to a control value for controlling a posture of the surgical instrument according to an embodiment.

FIG. 72 is a diagram for describing an example of controlling the end tool according to a control value for controlling a posture of the surgical instrument according to an embodiment.

Referring to FIG. 72, an example is illustrated in which a posture of the end tool is changed based on a control value generated according to an embodiment of the present disclosure.

In a first manipulation example 2710 of FIG. 72, an axis (pitch direction rotation axis) centered on a pitch motion and an axis (yaw direction rotation axis) centered on a yaw motion are the same in a coordinate system (first coordinate system), which defines the movement of the manipulation part configured to receive user input, and in a coordinate system (second coordinate system) that defines the movement of the end tool. For example, it may be assumed that the first posture information of the end tool, more specifically, roll posture information (e.g., a roll direction rotation angle) included in the posture information of the end tool at the time of obtaining the user input is 0 degrees. In the first manipulation example 2710, a user may intend to change pitch posture information about a pitch rotation of the end tool (e.g., rotate the end tool in a pitch direction), and manipulate the manipulation part (e.g., a joystick) in the pitch direction based on the first coordinate system. In order to implement a target posture according to the user input, the end tool may change a posture thereof in the pitch direction based on the second coordinate system. In this case, posture change information about a posture change of the end tool generated based on the first coordinate system and based on the user input may be defined as first posture change information, posture change information about a posture change of the end tool generated based on the second coordinate system and based on the control value may be defined as second posture change information. Here, in the first manipulation example 2710, since the pitch direction rotation axis and the yaw direction rotation axis are the same in the coordinate system (first coordinate system), which defines the movement of the manipulation part configured to receive user input, and the coordinate system (second coordinate system) defining the movement of the end tool, the first posture change information of the end tool generated based on the first coordinate system and the second posture change information of the end tool generated based on the second coordinate system may be the same.

In a second manipulation example 2720 and a third manipulation example 2730 of FIG. 72, the axis (pitch direction rotation axis) centered on the pitch motion and the axis (yaw direction rotation axis) centered on the yaw motion in the first coordinate system and the second coordinate system are different from each other. For example, it may be assumed the roll posture information (e.g., the roll direction rotation angle) included in the first posture information of the end tool is 45 degrees.

First, a description is provided for the case of the second manipulation example 2720 in which the posture of the end tool is changed according to the manipulation value according to user input, i.e., the case in which the coordinate system transformation process is not performed between the manipulation value, and the control value for controlling the actual posture change of the end tool. In this case, the user intends to change the pitch posture information of the end tool (e.g., rotate the end tool in the pitch direction), and manipulates the manipulation part (e.g., a joystick) in the pitch direction based on the first coordinate system, but the end tool changes a posture thereof in the pitch direction (according to the user's manipulation value) based on the second coordinate system. As a result, the motion intended by the user (in other words, the first posture change information of the end tool generated based on the user input) is different from the motion of the end tool that actually changes the posture thereof (in other words, the second posture change information of the end tool generated based on the control value).

As an alternative case, a description will be provided for the third manipulation example 2730 in which the coordinate system transformation process is performed based on user input to generate a control value for controlling an actual posture change of the end tool, and the posture of the end tool is changed according to the generated control value. The user may intend to change the pitch posture information of the end tool (e.g., rotate the end tool in the pitch direction), and manipulate the manipulation part (e.g., a joystick) in the pitch direction based on the first coordinate system. For example, the first posture change information of the end tool generated based on the user input may include a 30-degree pitch direction rotation. In contrast, the second posture change information of the end tool, which is generated according to the control value generated based on the second coordinate system, may include a predetermined pitch direction rotation and a predetermined yaw direction rotation, rather than the 30-degree pitch direction rotation. However, even in this case, both the first posture change information and the second posture information are information for implementing the target posture.

In summary, according to the embodiment of the present disclosure, the first posture change information of the end tool generated based on the user input and the second posture change information of the end tool generated based on the control value may be information for implementing the target posture.

In addition, according to an embodiment of the present disclosure, even when the roll rotation angle included in the first posture information of the end tool, more specifically, the posture information of the end tool at the time of obtaining the user input, is not an angle in an initial state (e.g., 0 degrees), the target posture may be implemented in the end tool to intuitively correspond to the movement of the manipulation part. In other words, implementing the target posture in the end tool to intuitively correspond to the movement of the manipulation part means that when the user manipulates the manipulation part with the intention of rotating the end tool 30 degrees in the pitch direction, the end tool may perform this motion even when he end tool has already rotated a predetermined angle in the roll direction, as in the example described above.

In addition, according to an embodiment of the present disclosure, the manipulation value according to user input may include a manipulation value for roll rotation, and based on the manipulation value, the control value may include a first control value for controlling a roll rotation of the end tool, a second control value for controlling a pitch rotation of the end tool, and a third control value for controlling a yaw rotation of the end tool. In this case, the first posture change information of the end tool generated according to user input and the second posture change information of the end tool generated based on the control value may be information for implementing the target posture.

That is, even when the pitch rotation angle or the yaw rotation angle included in the first posture information of the end tool is not an angle in the initial state, the target posture may be implemented in the end tool to intuitively correspond to the movement of the manipulation part. In other words, implementing the target posture in the end tool to intuitively correspond to the movement of the manipulation part means that the end tool may rotate in the pitch and yaw directions as well as in the roll direction to implement the target posture when the user manipulates the manipulation part with the intention of rotating the end tool in the roll direction. However, even in this case, the target posture may be implemented such that the end tool moves according to the intention of the user's perspective, in other words, intuitively corresponds to the movement of the manipulation part. In addition, in this case, when the end tool performs a motion according to the second posture change information, the axis of the end tool before the roll rotation is performed and the axis of the end tool after the roll rotation is performed may be parallel to each other. In other words, the direction pointed by the reference axis (e.g., a longitudinal axis) of the roll rotation included in the first posture information of the end tool and the direction (e.g., a direction in which the end tool faces the surgical site, or the like) pointed by the reference axis of the roll rotation according to the second posture change information of the end tool in response to the control value may be parallel to each other.

The above-described method may be recorded as a program that may be executed on a computer, and may be implemented in a general-purpose digital computer operating the program using a computer-readable recording medium. In addition, the structure of the data used in the method described above may be recorded on a computer-readable recording medium through various means. Examples of the computer-readable recording medium include storage media such as magnetic storage media (e.g., ROM, floppy disks, hard disks, and the like), and optical read media (e.g., CD-ROMs, DVDs, and the like).

Meanwhile, the above-described method may be included and provided in a computer program product. The computer program product may be traded as a product between a seller and a buyer. The computer program product may be distributed in the form of a machine-readable storage medium (e.g., compact disc read-only memory (CD-ROM)), or be distributed (e.g., downloaded or uploaded) online via an application store (e.g., PlayStore™), or between two user devices (e.g., smart phones) directly. When distributed online, at least a part of the computer program product may be temporarily generated or at least temporarily stored in the machine-readable storage medium, such as memory of the manufacturer's server, a server of the application store, or a relay server.

It will be understood by those skilled in the art to which the present embodiment pertains that the present disclosure may be implemented in modified forms without departing from the spirit and scope of the present disclosure. Therefore, the disclosed methods are should be considered in an illustrative aspect rather than a restrictive aspect. The scope of the present disclosure should be defined by the claims rather than the above-mentioned description, and equivalents to the claims should be interpreted to fall within the present disclosure.

The invention claimed is:

1. A method of controlling a posture of a surgical instrument, the method comprising:
   obtaining a manipulation value according to user input to change a posture of an end tool included in the surgical instrument;
   obtaining first posture information about a current posture of the end tool at a time of obtaining the user input; and
   controlling a motion of the end tool based on the manipulation value and the first posture information to implement a target posture according to the user input,
   wherein the controlling of the motion of the end tool includes:
   generating first posture difference information corresponding to a difference between the target posture information according to the user input and the first posture information;
   generating first joint difference information regarding a joint of the end tool by computing the first posture difference information;
   generating second joint information by updating first joint information, which is information about a current joint of the end tool at the time of obtaining the user input, using the first joint difference information; and
   generating a control value to cause the joint of the end tool to be driven according to the second joint information.

2. The method of claim 1, further comprising:
   computing second posture information based on the second joint information in response to the first joint difference information being greater than a preset reference value; and
   determining joint information of the end tool to generate the control value by comparing the second posture information with the target posture information.

3. The method of claim 2,
   wherein the determining of the joint information includes:
   generating second posture difference information corresponding to a difference between the target posture information and the second posture information;
   generating second joint difference information by computing the second posture difference information;
   generating third joint information by updating the second joint information using the second joint difference information in response to the second joint difference information being less than the preset reference value; and
   generating another control value to cause the joint of the end tool to be driven according to the third joint information.

81

4. The method of claim 1,
wherein the control value includes at least one of a first
control value for controlling a roll rotation of the end
tool, a second control value for controlling a pitch
rotation of the end tool, and a third control value for
controlling a yaw rotation of the end tool.
5. The method of claim 1,
wherein the manipulation value according to the user
input includes at least one of a manipulation value for
pitch rotation and a manipulation value for yaw rota-
tion, and
wherein, depending on the manipulation value, the control
value includes a first control value for controlling a
pitch rotation of the end tool and a second control value
for controlling a yaw rotation of the end tool.
6. The method of claim 1,
wherein the manipulation value according to the user
input includes at least one of a manipulation value for
pitch rotation and a manipulation value for yaw rota-
tion, and
wherein, depending on the manipulation value, the control
value includes a first control value for controlling a
pitch rotation of the end tool, a second control value for
controlling a yaw rotation of the end tool, and a third
control value for controlling a roll rotation of the end
tool.
7. The method of claim 5,
wherein first posture change information of the end tool
generated based on the user input and second posture
change information of the end tool generated based on
the control value are pieces of information for imple-
menting the target posture,
wherein the first posture change information is generated
based on a first coordinate system defining a movement
of a manipulation part configured to receive the user
input, and
wherein the second posture change information is gener-
ated based on a second coordinate system defining a
movement of the end tool.
8. The method of claim 7,
wherein even when a roll rotation angle included in the
first posture information is not an angle in an initial
state, the target posture is implemented in the end tool
to intuitively correspond to the movement of the
manipulation part.
9. The method of claim 1,
wherein the manipulation value according to the user
input is a manipulation value for a roll rotation, and
wherein, depending on the manipulation value, the control
value includes a first control value for controlling the
roll rotation of the end tool, a second control value for
controlling a pitch rotation of the end tool, and a third
control value for controlling a yaw rotation of the end
tool.
10. The method of claim 9,
wherein first posture change information of the end tool
generated based on the user input and second posture
change information of the end tool generated based on
the control value are pieces of information for imple-
menting the target posture,
wherein the first posture change information is generated
based on a first coordinate system defining a movement
of a manipulation part configured to receive the user
input, and
wherein the second posture change information is gener-
ated based on a second coordinate system defining a
movement of the end tool.

82

11. The method of claim 10,
wherein, when the end tool performs a motion according
to the second posture change information, an axis of the
end tool before the roll rotation is performed and an
axis of the end tool after the roll rotation is performed
are parallel to each other.
12. The method of claim 1,
wherein the user input includes an input for at least one of
a roll rotation, a pitch rotation, and a yaw rotation.
13. The method of claim 1,
wherein the controlling of the motion of the end tool
includes:
generating target orientation information about a target
orientation of the end tool based on the user input; and
generating target posture information according to the
user input based on the target orientation information of
the end tool and a change in position of the surgical
instrument.
14. The method of claim 1,
wherein the obtaining of the first posture information
includes:
obtaining first joint information, which is information
about a current joint of the end tool at the time of
obtaining the user input; and
computing the first posture information based on the first
joint information.
15. A non-transitory computer-readable recording
medium having recorded thereon a program for executing
the method of claim 1 on a computer.
16. A device for controlling a posture of a surgical
instrument, the device comprising:
a memory configured to store at least one program; and
a processor configured to execute the at least one pro-
gram,
wherein the processor is further configured to:
obtain a manipulation value according to user input to
change a posture of an end tool included in the surgical
instrument;
obtain first posture information, which is information
about a current posture of the end tool at a time of
obtaining the user input;
control a motion of the end tool based on the manipulation
value and the first posture information to implement a
target posture according to the user input;
generate first posture difference information correspond-
ing to a difference between the target posture informa-
tion according to the user input and the first posture
information;
generate first joint difference information regarding a joint
of the end tool by computing the first posture difference
information;
generate second joint information by updating first joint
information, which is information about a current joint
of the end tool at the time of obtaining the user input,
using the first joint difference information; and
generate a control value to cause the joint of the end tool
to be driven according to the second joint information.
17. A surgical instrument comprising:
an end tool configured to perform a surgical operation;
a manipulation part configured to receive user input to
change a posture of the end tool;
a power generation part configured to generate power to
control the end tool in response to receiving the user
input;
a power transmission part configured to transmit the
power to the end tool;

a connection part connecting the manipulation part to the end tool by being coupled to the power transmission part at one end portion of the connection part and coupled to the end tool at another end portion of the connection part; and a control part configured to control a motion of the end tool based on a manipulation value according to the user input to implement a target posture, wherein the control part is configured to:

obtain the manipulation value according to the user input to change the posture of the end tool included in the surgical instrument;

obtain first posture information, which is information about a current posture of the end tool at a time of obtaining the user input;

control the motion of the end tool based on the manipulation value and the first posture information to implement the target posture according to the user input;

generate first posture difference information corresponding to a difference between the target posture information according to the user input and the first posture information;

generate first joint difference information regarding a joint of the end tool by computing the first posture difference information;

generate second joint information by updating first joint information, which is information about a current joint of the end tool at the time of obtaining the user input, using the first joint difference information; and generate a control value to cause the joint of the end tool to be driven according to the second joint information.

18. The surgical instrument of claim 17, wherein the manipulation part includes one or more user interfaces configured to receive one of the user input for a roll rotation of the end tool, the user input for a pitch rotation of the end tool, and the user input for a yaw rotation of the end tool.

19. The surgical instrument of claim 17, wherein the manipulation part includes a first user interface configured to receive the user input for a pitch rotation and a yaw rotation of the end tool, and a second user interface configured to receive the user input for a roll rotation of the end tool.

20. The surgical instrument of claim 19, wherein the first user interface includes a joystick, the first user interface being configured to receive the user input for the pitch rotation and the yaw rotation of the end tool over a range of 360 degrees.

21. The surgical instrument of claim 19, wherein the first user interface is attached to the manipulation part on a surface perpendicular to a direction in which the connection part extends.

22. The surgical instrument of claim 21, wherein the first user interface is attached to a front surface portion or a rear surface portion of the manipulation part.

23. The surgical instrument of claim 19, wherein the second user interface is attached to the manipulation part on a surface parallel to a direction in which the connection part extends.

24. The surgical instrument of claim 23, wherein the second user interface includes two switches capable of receiving the user input, the second user interface being attached to a side surface portion of the manipulation part.

25. The surgical instrument of claim 24, wherein, of the two switches included in the second user interface, one switch is disposed on one side surface portion of the manipulation part, and another switch is disposed symmetrically with the one switch on another side surface portion of the manipulation part.

26. A surgical instrument comprising:

a manipulation part configured to receive user input to change a posture of an end tool;

a control part configured to control a motion of the end tool based on a manipulation value according to the user input to implement a target posture;

a power generation part configured to generate power to change the posture of the end tool based on a control value of the control part;

a power transmission part configured to transmit the power to the end tool;

a connection part connecting the manipulation part to the end tool by being coupled to the power transmission part at one end portion of the connection part and coupled to the end tool at another end portion of the connection part; and the end tool configured to perform a motion to change a posture of the end tool by using the power, wherein the end tool is configured to perform a motion to implement a target posture according to the user input independently of a current posture of the end tool at a time of obtaining the user input, and wherein, when the end tool performs a motion according to second posture change information to implement the target posture based on the control value, an axis of the end tool before a roll rotation is performed and an axis of the end tool after the roll rotation is performed are parallel to each other.

27. The surgical instrument of claim 26, wherein even when a roll rotation angle included in the current posture of the end tool is not an angle in an initial state, the end tool is configured to implement the target posture to intuitively correspond to a movement of the manipulation part.

28. The surgical instrument of claim 26, wherein even when a pitch rotation angle or a yaw rotation angle included in the current posture of the end tool is not an angle in an initial state, the end tool is configured to implement the target posture to intuitively correspond to a movement of the manipulation part.

* * * * *